United States Patent
Thatcher et al.

(10) Patent No.: US 11,072,595 B2
(45) Date of Patent: Jul. 27, 2021

(54) BENZOTHIOPHENE-BASED SELECTIVE ESTROGEN RECEPTOR DOWNREGULATOR COMPOUNDS

(71) Applicant: The Board of Trustees of the University of Illinois, Urbana, IL (US)

(72) Inventors: Gregory R. Thatcher, Chicago, IL (US); Rui Xiong, Urbana, IL (US); Jiong Zhao, Urbana, IL (US); Debra A. Tonetti, Urbana, IL (US)

(73) Assignee: The Board of Trustees of lhe University of Illinois, Urbana, IL (US)

( * ) Notice: Subject to any disclaimer, the term of this patent is extended or adjusted under 35 U.S.C. 154(b) by 0 days.

(21) Appl. No.: 16/424,240

(22) Filed: May 28, 2019

(65) Prior Publication Data
US 2020/0123126 A1    Apr. 23, 2020

Related U.S. Application Data

(63) Continuation of application No. 15/375,049, filed on Dec. 9, 2016, now abandoned.

(60) Provisional application No. 62/322,878, filed on Apr. 15, 2016, provisional application No. 62/264,971, filed on Dec. 9, 2015.

(51) Int. Cl.
| | | |
|---|---|---|
| *A61K 35/00* | (2006.01) | |
| *C07D 333/64* | (2006.01) | |
| *A61P 35/00* | (2006.01) | |
| *A61P 19/10* | (2006.01) | |
| *C07D 409/06* | (2006.01) | |
| *C07D 409/12* | (2006.01) | |

(52) U.S. Cl.
CPC ............ *C07D 333/64* (2013.01); *A61P 19/10* (2018.01); *A61P 35/00* (2018.01); *C07D 409/06* (2013.01); *C07D 409/12* (2013.01)

(58) Field of Classification Search
CPC ..................................................... A61K 35/00
See application file for complete search history.

(56) References Cited

U.S. PATENT DOCUMENTS

| | | |
|---|---|---|
| 4,133,814 A | 1/1979 | Jones et al. |
| 4,418,068 A | 11/1983 | Jones |
| 4,659,516 A | 4/1987 | Bowler et al. |
| 5,393,763 A | 2/1995 | Black et al. |
| 5,457,117 A | 10/1995 | Black et al. |
| 5,478,847 A | 12/1995 | Draper |
| 5,491,123 A | 2/1996 | Hagen et al. |
| 5,780,497 A | 7/1998 | Miller et al. |
| 5,998,402 A | 12/1999 | Miller et al. |
| 6,005,102 A | 12/1999 | Raveendranath et al. |
| 6,326,392 B1 | 12/2001 | Gast et al. |
| 6,403,614 B1 | 6/2002 | Dodge et al. |
| 6,479,535 B1 | 11/2002 | Pickar et al. |
| 6,512,002 B2 | 1/2003 | Lee et al. |
| 6,583,170 B1 | 6/2003 | Pickar et al. |
| 6,632,834 B2 | 10/2003 | Thompson et al. |
| 6,756,401 B2 | 6/2004 | Day et al. |
| 6,777,424 B2 | 8/2004 | Littman et al. |
| 6,797,719 B2 | 9/2004 | Arbuthnot et al. |
| 6,821,989 B2 | 11/2004 | Rosati |
| 7,371,774 B2 | 5/2008 | Moinet |
| 8,030,330 B2 | 10/2011 | Arbuthnot et al. |
| 8,455,534 B2 | 6/2013 | Smith et al. |
| 8,642,632 B2 | 2/2014 | Miller |
| 8,703,810 B2 | 4/2014 | Kahraman et al. |
| 8,853,423 B2 | 10/2014 | Govek et al. |
| 9,078,871 B2 | 7/2015 | Kahraman et al. |
| 9,193,714 B2 | 11/2015 | Smith et al. |
| 9,475,798 B2 | 10/2016 | Govek et al. |
| 10,118,910 B2 * | 11/2018 | Thatcher ................. A61P 35/00 |
| 10,377,735 B2 * | 8/2019 | Thatcher ................. A61P 19/10 |
| 2001/0056099 A1 | 12/2001 | Day et al. |
| 2002/0013327 A1 | 1/2002 | Lee et al. |
| 2002/0016340 A1 | 2/2002 | Rosati |
| 2002/0128276 A1 | 9/2002 | Day et al. |
| 2004/0044059 A1 | 3/2004 | Pinney et al. |
| 2005/0240017 A1 | 10/2005 | Wallace |
| 2007/0112009 A1 | 5/2007 | Lafay et al. |
| 2012/0071535 A1 | 3/2012 | Caspers et al. |
| 2013/0116232 A1 | 5/2013 | Kahraman et al. |
| 2013/0178445 A1 | 7/2013 | Kushner et al. |
| 2014/0235660 A1 * | 8/2014 | Burks ................. C07D 409/12 514/274 |
| 2014/0378422 A1 | 12/2014 | Yovine et al. |
| 2015/0005286 A1 | 1/2015 | Smith et al. |
| 2015/0258080 A1 | 9/2015 | Hager et al. |

(Continued)

FOREIGN PATENT DOCUMENTS

| | | |
|---|---|---|
| EP | 752421 A1 | 1/1997 |
| EP | 802184 B1 | 6/2002 |

(Continued)

OTHER PUBLICATIONS

Guo et al., ZB716, a steroidal selective receptor degrader (SERD), is orally efficacious in blocking tumor growth in mouse xenograft models. Oncotarget, 2018, 9, 6924-6937.
Tria et al. Discovery of LSZ102, a Potent, Orally Bioavailable Selective Estrogen Receptor Degrader (SERD) for the Treatment of Estrogen Receptor Positive Breast Cancer. Journal of Medicinal Chemistry, 2018, 61, 2837-2864.
Abdelhamid et al. "Benzothiophene Selective Estrogen Receptor Modulators Provide Neuroprotection by a Novel GPR30-Dependent Mechanism" ACS Chem. Neuro., Mar. 15, 2011; 2: 256-268.
Bolton et al. "Potential Mechanisms of Estrogen Quinone Carcinogenesis" Chem. Res. Toxicol., Dec. 2007 ; 21: 93-101.
Bolton et al. "Quinoids Formed from Estrogens and Antiestrogens" Methods in Enzymology 2004; 378: 110-122.

(Continued)

*Primary Examiner* — John S Kenyon
(74) *Attorney, Agent, or Firm* — Knowles Intellectual Property Strategies, LLC

(57) ABSTRACT

This invention is benzothiophene-based estrogen receptor downregulators and their compositions and uses to treat estrogen-related medical disorders.

20 Claims, 19 Drawing Sheets

(56) References Cited

U.S. PATENT DOCUMENTS

| | | |
|---|---|---|
| 2015/0284357 A1 | 10/2015 | Thatcher et al. |
| 2015/0291552 A1 | 10/2015 | Thatcher et al. |
| 2016/0090377 A1 | 3/2016 | Govek et al. |
| 2016/0090378 A1 | 3/2016 | Kahraman et al. |
| 2016/0175284 A1 | 6/2016 | Labadie et al. |
| 2016/0175289 A1 | 6/2016 | Labadie et al. |
| 2016/0304450 A1 | 10/2016 | Liang et al. |
| 2016/0311805 A1 | 10/2016 | Kushner et al. |
| 2016/0347742 A1 | 12/2016 | Labadie et al. |
| 2016/0368911 A1 | 12/2016 | Campos et al. |
| 2017/0129855 A1 | 5/2017 | Liang et al. |
| 2019/0321332 A1 | 10/2019 | Strum et al. |
| 2020/0079752 A1* | 3/2020 | Thatcher .................. A61P 35/00 |
| 2021/0047286 A1* | 2/2021 | Thatcher .............. C07D 409/06 |

FOREIGN PATENT DOCUMENTS

| | | |
|---|---|---|
| EP | 1947085 A1 | 7/2008 |
| GB | 2483736 A | 3/2012 |
| WO | WO 1999/024027 A2 | 5/1999 |
| WO | WO 2002/003975 A2 | 1/2002 |
| WO | WO 2002/003976 A2 | 1/2002 |
| WO | WO 2002/003977 A2 | 1/2002 |
| WO | WO 2002/003986 A2 | 1/2002 |
| WO | WO 2002/003988 A2 | 1/2002 |
| WO | WO 2002/003989 A2 | 1/2002 |
| WO | WO 2002/003990 A2 | 1/2002 |
| WO | WO 2002/003991 A2 | 1/2002 |
| WO | WO 2002/003992 A2 | 1/2002 |
| WO | WO 2002/004418 A2 | 1/2002 |
| WO | WO 2002/013802 A2 | 2/2002 |
| WO | WO 2005/016929 A1 | 2/2005 |
| WO | WO 2006/078834 A1 | 7/2006 |
| WO | WO 2006/084338 A1 | 8/2006 |
| WO | WO 2007/087684 A1 | 8/2007 |
| WO | WO 2008/002490 A2 | 1/2008 |
| WO | WO 2009/013195 A1 | 1/2009 |
| WO | WO 2010/093578 A1 | 8/2010 |
| WO | WO 2010/127452 A1 | 11/2010 |
| WO | WO 2011/139769 A2 | 12/2011 |
| WO | WO 2011/156518 A2 | 12/2011 |
| WO | WO 2012/037410 A2 | 3/2012 |
| WO | WO 2012/037411 A2 | 3/2012 |
| WO | WO 2012/084711 A1 | 6/2012 |
| WO | WO 2013/083568 A1 | 6/2013 |
| WO | WO 2013/090829 A1 | 6/2013 |
| WO | WO 2013/090836 A1 | 6/2013 |
| WO | WO 2013/090921 A1 | 6/2013 |
| WO | WO 2013/142266 A1 | 9/2013 |
| WO | WO 2014/066692 A1 | 5/2014 |
| WO | WO 2014/066695 A1 | 5/2014 |
| WO | WO 2014/130310 A1 | 8/2014 |
| WO | WO 2014/151899 A1 | 9/2014 |
| WO | WO 2014/191726 A1 | 12/2014 |
| WO | WO 2014/203129 A1 | 12/2014 |
| WO | WO 2014/203132 A1 | 12/2014 |
| WO | WO 2014/205136 A1 | 12/2014 |
| WO | WO 2014/205138 A1 | 12/2014 |
| WO | WO 2015/000867 A1 | 1/2015 |
| WO | WO 2015/028409 A1 | 3/2015 |
| WO | WO 2015/092634 A1 | 6/2015 |
| WO | WO 2015/136016 A2 | 9/2015 |
| WO | WO 2015/136017 A1 | 9/2015 |
| WO | WO 2015/149045 A1 | 10/2015 |
| WO | WO 2016/097071 A1 | 6/2016 |
| WO | WO 2016/097072 A1 | 6/2016 |
| WO | WO 2016/097073 A1 | 6/2016 |
| WO | WO 2016/189011 A1 | 12/2016 |
| WO | WO 2016/202161 A1 | 12/2016 |
| WO | WO 2017/056115 A1 | 4/2017 |
| WO | WO 2017/059139 A1 | 4/2017 |
| WO | WO 2017/060326 A1 | 4/2017 |
| WO | WO 2017/072792 A1 | 5/2017 |
| WO | WO 2017/080338 A1 | 5/2017 |

OTHER PUBLICATIONS

Bolton et al. "Genotoxic Estrogen Pathway: Endogeneous and Equine Estrogen Hormone Replacement Therapy" The Chemical Biology of DNA Damage 2010; 185-199.

Chandrasena, et al. "Problematic Detoxification of Estrogen Quinones by NAD(P)H-Dependent Quinone Oxidoreductase and Gluthathione-S-transferase" Chem. Res. Toxicol 2008; 21: 1324-1329.

Dowers, et al. Bioactivation of Selective Estrogen Receptor Modulators (SERMs) Chem. Res. Toxicol. 2006; 19: 1125-1137.

Gherezghiher et al. "The Naphthol Selective Estrogen Receptor Modulator (SERM), LY2066948, is Oxidized to an o-quinone Analogous to the Naphthol Equine Estrogen, Equilenin" Chemico-Biological Interactions 196 (2012); 1-10.

Gutgesell et al. "Estrogen receptor ligands and their responses in de novo and tamoxifen resistant cell models" Poster Presented at AACR, Apr. 16-20, 2016; New Orleans, LA.

Gutgesell et al. "Combination therapy of targeted anticancer pathways and estrogen receptor ligands and their responses in de novo and tamoxifen resistant cell models" Poster Presented at San Antonio Breast Cancer Symposium, Dec. 8, 2016.

Hamilton et al. "A Phase 1 Study of AZD9496, a Novel Oral, Selective Estrogen Receptor Degrader (SERD) in Women with Estrogen Receptor Positive, HER-2 Negative Advanced Breast Cancer (ABC)" Poster Presented at San Antonio Breast Cancer Symposium, Dec. 6-10, 2016.

Hemachandra et al. Hops (Humulus lupulus) Inhibits Oxidative Estrogen Metabolism and Estrogen-Induced Malignant Transformation in Human Mammary Epithelial Cells (MCF-10A) Published OnlineFirst Oct. 13, 2011; DOI: 10.1158/1940-6207.CAPR-11-0348.

Hemachandra et al."SERMs Attenuate Estrogen-Induced Malignant Transformation of Human Mammary Epithelial Cells by Upregulating Detoxification of Oxidative Metabolites" Published OnlineFirst Mar. 5, 2014; DOI: 10.1158/1940-6207. CAPR-13-0296.

Huttunen, K., et al., "Prodrugs-from Serendipity to Rational Design." Pharmacological Reviews. (2011), vol. 63, pp. 750-771 (Year 2011).

International Search Report and Written Opinion for PCT/US2016/066026 dated Apr. 21, 2017.

Kastrati et al. "A Novel Aspirin Prodrug Inhibits NFkB Activity and Breast Cancer Stem Cell Properties" BMC Cancer (2015) 15:845.

Kastrati et al. "Estrogen-Induced Apoptosis of Breast Epithelial Cells Is Blocked by NO/cGMP and Mediated by Extranuclear Estrogen Receptors" Department of Medicinal Chemistry and Pharmacognosy, College of Pharmacy, University of Illinois at Chicago, Chicago, Illinois 60612.

Kastrati et al. "Raloxifene and Desmethylarzoxifene Block Estrogen-Induced Malignant Transformation of Human Breast Epithelial Cells" Department of Medicinal Chemistry and Pharmacognosy, College of Pharmacy, University of Illinois of Chicago, Illinois, United States.

Kim et al. "Click Synthesis of Estradiol-Cyclodextrin Conjugates as Cell Compartment Selective Estrogens" Bioorganic & Medicinal Chemistry 18 (2010) 809-821.

Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 162-173.

Liu et al. "Bioactivation of the Selective Estrogen Receptor Modulator Acolbifene e to Quinone Methides" Chem. Res. Toxicol. 2005, 18: 174-182.

Liu et al. "Analysis of Protein Covalent Modification by Xenobiotics Using a Covert Oxidatively Activated Tag: Raloxifene Proof-of-Principle Study" Chem. Res. Toxicol. 2005, 18: 1485-1496.

Liu et al. "Chemical Modification Modulates Estrogenic Activity, Oxidative Reactivity, and Metabolic Stability in 4'F-DMA, a New Benzothiophene Selective Estrogen Receptor Modulator" Chem. Res. Toxicol. 2006, 19: 779-787.

Liu et al. "Uterine Peroxidase-Catalyzed Formation of Diquinone Methides from the Selective Estrogen Receptor Modulators Raloxifene and Desmethylated Arzoxifene" Chem. Res. Toxicol. 207, 20: 1676-1684.

(56) References Cited

OTHER PUBLICATIONS

Michalsen et al. "Selective Estrogen Receptor Modulator (SERM) Lasofoxifene Forms Reactive Quinones Similar to Estradiol" Chem. Res. Toxicol. 2012, 25: 1472-1483.

Malloy et al. "Novel Selective Estrogen Mimics for the Treatment of Tamoxifen-Resistant Breast Cancer" Published OnlineFirst Sep. 9, 2014: DOI: 10.1158/1535-7163.MCT-14-0319.

Overk et al. "Structure-Activity Relationships for a Family of Benzothiophene Selective Estrogen Receptor Modulators Including Raloxifene and Arzoxifene" ChemMedChem 2007, 2: 1520-1526.

Patel et al. "A Chimeric SERM-Histone Deacetylase Inhibitor Approach to Breast Cancer Therapy" ChemMedChem 2014, 9: 602-613.

Peng et al. "Selective Estrogen Receptor Modulator Delivery of Quinone Warheads to DNA Triggering Apoptosis in Breast Cancer Cells" ACS Chemical Biology, 2009 vol. 4 No. 12, 1039-1049.

Peng et al. "Unexpected Hormonal Activity of a Catechol Equine Estrogen Metabolite Reveals Reversible Glutathione Conjugation" Chem. Res. Toxicol. 2010, 23: 1374-1383.

Pubchem: Substrnce Record for SID236885489. Feb. 13, 2015. [retrieved on Mar. 24, 2017]. Retrieved from internet. <URL:https://pubchem.ncbi.nlm.nih.gov/substance/236885489>.

Qin et al. "Structural Modulation of Oxidative Metabolism in Design of Improved Benzothiophene Selective Estrogen Receptor Modulators" Drug Metabolism and Disposition; vol. 37, No. 1.

Qin et al. "Benzothiophene Selective Estrogen Receptor Modulators with Modulated Oxidative Activity and Receptor Affinity" J. Med. Chem. 2007, 50: 2682-2692.

Ramagnoli et al. "Synthesis and Biological Evaluation of 2- and 3-Aminobenzo[b]thiophene Derivatives as Antimitotic Agents and Inhibitors of Tubulin Polymerization", J. Med. Chem. 2007, vol. 50, pp. 2273-2277.

Romagnoli et al. "Synthesis and biological evaluation of 2-(3',4',5'-trimethoxybenzoyl)-3-aryl/arylaminobenzo[b]thiophene derivatives as novel class of antiproliferative agents", Eur J Med Chem. 2010. vol. 45(12), pp. 5781-5791.

Svenson, S. "Carrier-Based Drug Delivery." (2004) American Chemical Society. (Year: 2004).

Thatcher et al. "Endocrine-independent ER+ breast cancer therapy: Benzothiophene SERMs, SERDs, MERDs, SEMs, and ShERPAs" PowerPoint presented at 252nd ACS National Meeting, Aug. 21, 2016.

Toader et al. "Nitrosation, Nitration, and Autoxidation of the Selective Estrogen Receptor Modulator Raloxifene by Nitric Oxide, Peroxynitrite, and Reactive Nitrogen/Oxygen Species" Chem. Res. Toxicol. 2003, 16: 1264-1276.

Vandevrede et al. "A NO Donor Approach to Neuroprotective and Procognitive Estrogen Therapy Overcomes Loss of NO Synthase Function and Potentially Thrombotic Risk" PLOS ONE, Aug. 2013, vol. 8, Issue 8.

Varma, K. "Excipients used in the Formulation of Tablets." Research and Reviews: Journal of Chemistry. (Jun. 2016), vol. 5, Issue 2, pp. 143-154. Available from: <http://www.rroij.com/open-access/excipients-used-in-the-formulation-of-tablets-.pdf > Accessed 13 Seotenber 2918 (Year 2016).

Wang et al. "Development of a Liquid Chromatography Electrospray Ionization Tandem Mass Spectrometry Method for Analysis of Stable 4-Hydroxyequilenin-DNA Adducts in Human Breast Cancer Cells" Chem. Res. Toxicol. 2009, 22: 1129-1136.

Wang et al. "Redox Cycling of Catechol Estrogens Generating Apurinic/Apyrimidinic Sites and 8-oxo-Deoxyguanosine via Reactive Oxygen Species Differentiates Equine and Human Estrogens" Chem. Res. Toxicol. 2010, 23: 1365-1373.

Wang et al. "Estrogen Receptor a Enhances the Rate of Oxidative DNA Damage by Targeting an Equine Estrogen Catechol Metabolite to the Nucleus" The Journal of Biological Chemistry vol. 284, No. 13, 8633-8642, Mar. 27, 2009.

Weir et al. "AZD9496: An Oral Estrogen Receptor Inhibitor That Blocks the Growth of ER-Positive and ESR1-Mutant Breast Tumors in Preclinical Models" Published OnlineFirst Mar. 28, 2016: DOI: 10.1158/0008-5472.Can-15-2357.

Xiong et al. "Selective Human Estrogen Receptor Partial Agonists (ShERPAs) for Tamoxifen-Resistant Breast Cancer" J. Med. Chem. 2016, 59: 219-237.

Xiong et al. "Novel Selective Estrogen Receptor Downregulators (SERDs) Developed against Treatment-Resistant Breast Cancer" J. Med. Chem. 2017, 60: 1325-1342.

Xiong et al. "Novel Selective Estrogen Receptor Downregulators (SERDs) for Advanced Breast Cancer" Poster Presented at UIC Cancer Center, Oct. 15, 2015.

Xiong et al. "Novel Selective Estrogen Receptor Downregulators (SERDs) for Advanced Breast Cancer" Poster Presented at UIC Research Day, Feb. 25, 2016.

Xiong et al. "Novel Selective Estrogen Receptor Downregulators Developed Using Endocrine-Independent Breast Cancer Cell Lines" Poster Presented at Yaoyuan Symposium, Mar. 25, 2016.

Xiong et al. "Novel Selective Estrogen Receptor Downregulators Developed Using Endocrine-Independent Breast Cancer Cell Lines" Poster Presented at AACR, Apr. 14, 2016.

Xiong, R., et al., "Novel Selective Estrogen Receptor Downregulators for Breast Cancer." Poster Presented at UIC Cancer Center (Feb. 25, 2016),.

Yu et al. "Comparative Methods for Analysis of Protein Covalent Modification by Electrophilic Quinoids Formed from Xenobiotics" Bioconjugate Chem. 2009, 20: 728-741.

Yu et al. "Structural Modulation of Reactivity/Activity in Design of Improved Benzothiophene Selective Estrogen Receptor Modulators: Induction of Chemopreventive Mechanisms" Mol. Cancer, Ther. 2007, 6(9), Sep. 2007.

* cited by examiner

BENZOTHIOPHENE-BASED SELECTIVE ESTROGEN RECEPTOR DOWNREGULATOR COMPOUNDS

CROSS-REFERENCE TO RELATED APPLICATIONS

This application is a continuation of U.S. patent application Ser. No. 15/375,049, filed Dec. 9, 2016, which claims the benefit of U.S. Provisional Application 62/264,971, filed Dec. 9, 2015, and U.S. Provisional Application 62/322,878, filed Apr. 15, 2016. The entirety of these applications is hereby incorporated by reference for all purposes.

STATEMENT OF GOVERNMENTAL INTEREST

This invention was made with government support under contract no. 1R01CA188017-01A1 awarded by the National Institutes of Health. The government has certain rights in this invention.

TECHNICAL FIELD

This invention provides compounds and compositions that include benzothiophene-based estrogen receptor ligands and uses of the compounds to treat estrogen-related medical disorders.

BACKGROUND OF THE INVENTION

Estrogens are the primary female hormones responsible for the development and regulation of the female reproductive system and secondary female sex characteristics. Estrogens also have pleotropic roles in protein synthesis, coagulation, lipid balance, fluid balance, melanin, gastrointestinal track function, lung function, cognition, immune response and heart disease, among others.

The estrogen receptor ("ER") is a ligand-activated transcriptional regulatory protein that mediates induction of the variety of biological effects through its interaction with endogenous estrogens, including 17β-estradiol and estrones. ER has been found to have two isoforms, ER-α and ER-β, and both receptors are involved in the regulation and development of the female reproductive tract.

ERs and estrogens regulate biological processes through several distinct pathways. The classical pathway involves the binding of a ligand-activated ER to a specific DNA sequence motif called an estrogen response element (ERE). ERs can also participate in non-classical pathways such as ERE-independent gene transcription via protein-protein interactions with other transcription factors, non-genomic pathways with rapid effects, and ligand-independent pathways that involve activation through other signaling pathways. This ER signaling is not only crucial for the development and maintenance of female reproductive organs, but also for bone metabolism and mass, lipid metabolism, cardiovascular protection, and central nervous system signaling.

Research in this area has confirmed the enormous complexity of estrogen and ER activities. A goal of drug development has been to create new compounds that modulate estrogen activity, either by acting as an antagonist or an agonist, or a partial antagonist or partial agonist.

One goal has been to identify complete anti-estrogens (complete antagonists) that have the effect of shutting down all estrogenic activity in the body. Fulvestrant is an example of a complete estrogen receptor antagonist with no agonist activity. It is a selective estrogen receptor downregulator (SERD). Fulvestrant was disclosed by Imperial Chemical Industries (ICI) in U.S. Pat. No. 4,659,516 and is sold by Astra Zeneca under the name Faslodex. It is indicated for the treatment of hormone receptor positive metastatic breast cancer in post-menopausal women with disease progression following anti-estrogen therapy. Fulvestrant has limited water solubility and requires monthly intramuscular (IM) injections. Fulvestrant's aqueous insolubility creates a challenge to achieve and maintain efficacious serum concentrations.

Another class of anti-estrogens are selective estrogen receptor modulators (SERMs) which act as antagonists or agonists in a gene-specific and tissue-specific fashion. A goal of SERM therapy is to identify drugs with mixed profiles that afford beneficial target anti-estrogenic activity and either avoid adverse off-target effects or exhibit incidental beneficial estrogenic side effects. An example of a SERM is tamoxifen, initially sold by AstraZeneca under the name Nolvadex. Tamoxifen was also disclosed by ICI in U.S. Pat. No. 4,659,516, (see also U.S. Pat. Nos. 6,774,122 and 7,456,160). Tamoxifen is a prodrug that is metabolized to 4-hydroxytamoxifen and N-desmethyl-4-hydroxytamoxifen which have high binding affinity to the estrogen receptor. Tamoxifen is indicated to prevent further breast cancer after breast cancer treatment and to treat node-positive breast cancer in women following mastectomy and radiation. Tamoxifen can affect bone health. In pre-menopausal women, tamoxifen can cause bone thinning, while it can be beneficial for bone health in post-menopausal woman. Serious side effects have been noted, including increased risk of uterine cancer in post-menopausal women and "tumor flares" in women with breast cancer that has spread to the bone. In addition to these side effects, some women who initially respond to tamoxifen experience acquired resistance over time, and in some cases ER positive breast cancer not only becomes resistant to tamoxifen, but tamoxifen becomes an agonist which induces tumor proliferation.

A third line of treatment for breast cancer includes steroidal and non-steroidal aromatase inhibitors that block the production of estrogen and therefore block ER-dependent growth. These drugs, which include letrozole, anastrozole, and exemestane, have the risk of removing all estrogens from women after menopause, increasing the risk of bone thinning, osteoporosis, and fractures.

A number of SERDs, SERMs, and aromatase inhibitors have been disclosed. The SERM raloxifene was disclosed by Eli Lilly in 1981 (U.S. Pat. Nos. 4,418,068; 5,478,847; 5,393,763; and 5,457,117) for prevention of breast cancer and treatment of osteoporosis. In June 2011, Aragon Pharmaceuticals disclosed benzopyran derivatives and acolbifene analogs for treatment of tamoxifen-resistant breast cancer (see WO2011/156518, U.S. Pat. Nos. 8,455,534 and 8,299,112). Aragon became Seragon in 2013, and was purchased by Genentech in 2014. See also U.S. Pat. Nos. 9,078,871; 8,853,423; 8,703,810; US 2015/0005286; and WO 2014/205138. Genentech is now developing Brilanstrant (GDC-0810, formerly ARN-810) for the treatment of locally advanced or metastatic estrogenic receptor positive breast cancer.

Genentech disclosed a series of tetrahydro-pyrido[3,4-b] indol-1-yl compounds with estrogen receptor modulation activity in US2016/0175289 and a combination therapy of three compounds, one of which was GDN-0810, for estrogen receptor modulation in US2015/0258080.

AstraZeneca is currently developing AZD9496, a novel, oral selective estrogen receptor downregulator in patients with estrogen receptor positive breast cancer (WO 2014/191726).

Additional anti-estrogenic compounds are disclosed in WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497 and 5,880,137.

J-Pharma is currently developing benzothiophene compounds for the treatment of disorders related to urate transportation. See for example WO 2012/048058.

Bionomics LTD is developing benzofurans, benzothiophenes, benzoselenophenes, and indoles for treatment of tubulin polymerization related disorders. See for example WO 2007/087684.

Additional benzothiophene compounds are disclosed in WO 2010/127452, WO 2010/093578, WO 2009/013195, EP1947085, JP 2005-129430, US 2007/0112009, WO 2005/016929, EP0752421, EP0622673, EP0551849, EP0545478, U.S. Pat. No. 5,491,123, and WO 2006/084338.

Given the often devastating effects of estrogen-modulated disorders, including cancer, tumors, and in particular breast cancer, there remains a strong need to create new drugs that have significant anti-estrogenic efficacy without unacceptable side effects.

SUMMARY OF THE INVENTION

Benzothiophene compounds and their pharmaceutically acceptable salts are provided that have advantageous selective estrogen receptor modulating activity, and in particular, anti-estrogenic activity. The compounds can be used for the treatment of a patient, typically a human, with an estrogen-related medical disorder, including but not limited to a cancer or a tumor by administering an effective amount to the patient in need thereof, optionally in a pharmaceutically acceptable carrier. In certain embodiments, the cancer is selected from breast, ovarian, endometrial, kidney, and uterine. In another embodiment the cancer is metastatic endocrine therapy resistant breast cancer. Alternatively, a compound or its pharmaceutically acceptable salt can be used to prevent an estrogen-mediated disorder, including but not limited to a cancer or a tumor including breast cancer. In some embodiments, the compound is used following chemotherapy or radiation treatment to avoid recurrence, or instead of chemotherapy or radiation as a primary treatment.

In one embodiment, a compound of the present invention is a selective estrogen downregulator (SERD). In another embodiment, a compound of the present invention can be a selective mixed estrogen receptor downregulator (SMERD). In one embodiment the compound antagonizes $E_2$ in breast epithelial cells and causes significant degradation of ERα.

In one aspect, a compound of the present invention or its pharmaceutically acceptable salt or prodrug, can be used to treat a hormone-related cancer or tumor that has metastasized to the brain, bone or other organ. In one embodiment of this aspect, the hormone-related cancer is estrogen mediated. In another embodiment, the estrogen mediated cancer is selected from breast, uterine, ovarian and endometrial. In other embodiments, a compound of the present invention or its pharmaceutically acceptable salt or prodrug, can be used to prevent a hormone-related cancer or tumor from metastasizing to the brain, bone or other organ, including a hormone-related cancer that is estrogen mediated, for example, breast, uterine, ovarian or endometrial.

In one aspect, this invention is a compound of Formula A, or a pharmaceutically acceptable salt thereof:

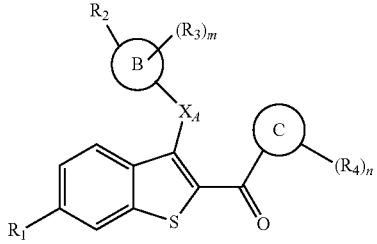

Formula A wherein:

m is 0, 1, 2, 3, or 4;

n is 0, 1, 2, 3, or 4;

$X_A$ is selected from —O—, —$CH_2$—, —S—, —$CF_2$—, and —$C_3$cycloalkyl-;

Ring B is phenyl, naphthyl, quinolinyl, 5- or 6-membered monocyclic heteroaryl or 7-, 8-, 9- or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

$R_1$ is selected from hydroxyl, —$OR_{17}$, hydrogen, halogen, —O($C_1$-$C_6$ alkyl), —OC(O)($C_1$-$C_6$ alkyl), —OC(O)$C_6H_5$, —OC(O)O($C_1$-$C_6$ alkyl), —OC(O)O$C_6H_5$ and —OSO$_2$($C_2$-$C_6$ alkyl);

$R_2$ is selected from —CH=CHC(O)$R_{16}$, —$NR_{17}$(CO)C(O)$R_{16}$, —C(O)$R_{16}$, $C_2$-$C_6$alkenylene-C(O)$R_{16}$, $C_2$-$C_6$alkylene-C(O)$R_{16}$, and $C_2$-$C_6$alkynylene-C(O)$R_{16}$;

$R_3$ is independently selected at each occurrence from hydrogen, halogen, —CN, —$NO_2$, $C_1$-$C_6$alkyl and $C_1$-$C_6$fluoroalkyl;

$R_4$ is independently selected at each occurrence from hydrogen, halogen, —$OR_{15}$, $C_1$-$C_6$alkyl, $C_1$-$C_6$fluoroalkyl, —CN, —O($C_1$-$C_6$ alkyl), and —O($C_1$-$C_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N($R_{15}$)$_2$, —$SR_{15}$, —$OR_{15}$; and $R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In another aspect, this invention includes a pharmaceutical composition that includes a compound of Formula A and a pharmaceutically acceptable carrier or excipient.

In another aspect, this invention is a method to treat or prevent cancer or a tumor that includes administering to a subject such as a human in need of such treatment a therapeutically effective amount of a compound of Formula A or a pharmaceutically acceptable salt thereof.

In another aspect, this invention is a compound of Formula B, or a pharmaceutically acceptable salt thereof:

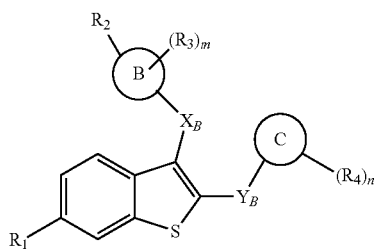

Formula B

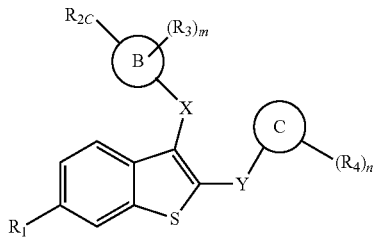

Formula C wherein:

m is 0, 1, 2, 3, or 4;

n is 0, 1, 2, 3, or 4;

$X_B$ is selected from —O—, —CH$_2$—, —S—, —NR$_{17}$—, —CF$_2$—, and C$_3$cycloalkyl;

$Y_B$ is selected from —C(O)—, —CF$_2$—, C$_3$cycloalkyl, and —CH$_2$—;

Ring B is phenyl, naphthyl, quinolinyl, 5- or 6-membered monocyclic heteroaryl or 7-, 8-, 9- or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

$R_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

$R_2$ is selected from —CH=CHC(O)R$_{16}$, —NR$_{17}$(CO)C(O)R$_{16}$, —C(O)R$_{16}$, C$_2$-C$_6$alkenylene-C(O)R$_{16}$ and C$_2$-C$_6$alkynylene-C(O)R$_{16}$;

$R_3$ is independently selected at each occurrence from hydrogen, halogen, —CN, —NO$_2$, C$_1$-C$_6$alkyl and C$_1$-C$_6$fluoroalkyl;

$R_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes a compound of Formula B and a pharmaceutically acceptable carrier or excipient.

In another aspect, this invention is a method to treat or prevent cancer or a tumor that includes administering to a subject such as a human in need of such treatment a therapeutically effective amount of a compound of Formula B or a pharmaceutically acceptable salt thereof.

In another aspect, this invention provides a compound of Formula C:

wherein:

m is 0, 1, 2, 3, or 4;

n is 0, 1, 2, 3, or 4;

X is selected from —O—, —C(O)—, —CH$_2$—, —S—, —NH—, —NMe-, —CF$_2$—, and C$_3$cycloalkyl;

Y is selected from —C(O)—, —O—, —CF$_2$—, or C$_3$cycloalkyl, —CH$_2$—, —S—, —NH—, and —NMe;

Ring B is phenyl, naphthyl, quinolinyl, 5- or 6-membered monocyclic heteroaryl, cycloalkyl, or 7-, 8-, 9- or 10-membered bicyclic heterocyclyl;

Ring C is phenyl, thiophenyl (i.e., thienyl), 5- or 6-membered monocyclic heteroaryl, cycloalkyl or 7-, 8-, 9- or 10-membered bicyclic heterocyclyl;

$R_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

$R_{2C}$ is selected from —CH=CHC(O)R$_{16}$, —NR$_{17}$(CO)C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;

$R_3$ is independently selected at each occurrence from hydrogen, halogen, —CN, —NO$_2$, C$_1$-C$_6$alkyl and C$_1$-C$_6$fluoroalkyl;

$R_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes one or more compounds of Formula C and a pharmaceutically acceptable carrier or excipient.

In another aspect, this invention is a method to treat or prevent cancer or a tumor that includes administering to a subject such as a human in need of such treatment a therapeutically effective amount of a compound of Formula C or a pharmaceutically acceptable salt thereof.

In one aspect, this invention provides a compound of Formula D:

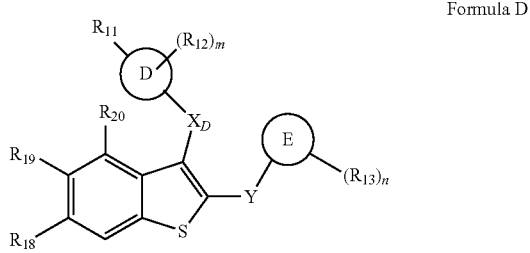

Formula D wherein:
m is 0, 1, 2, 3, or 4;
n is 0, 1, 2, 3, or 4;
$X_D$ is selected from —O—, —CH$_2$—, —S—, —NR$_{17}$—, —CHF—, —CF$_2$—, and cycloalkyl;
Y is selected from —C(O)—, —O—, —CF$_2$—, or C$_3$cycloalkyl, —CH$_2$—, —S—, —NH—, and —NMe;
Ring D is phenyl, naphthyl, quinolinyl, 5- or 6-membered monocyclic heteroaryl, cycloalkyl, or 7-, 8-, 9- or 10 membered bicyclic heterocyclyl;
Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
one of $R_{18}$, $R_{19}$ and $R_{20}$ is $R_{10}$ and the other two are $R_{14}$;
$R_{10}$ is selected from —OR$_{17}$, —SR$_{17}$, —N(R$_{17}$)$_2$ hydrogen, halogen, —OC(S)(C$_1$-C$_6$ alkyl), —OC(O)C$_6$H$_5$, —OC(S)C$_6$H$_5$, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, —OC(S)OC$_6$H$_5$, —OS(O)C$_2$-C$_6$ alkyl, and —OSO$_2$(C$_2$-C$_6$ alkyl);
$R_{11}$ is selected from —CH═CHCOOR$_{17}$, —NR$_{17}$(CO)COOR$_{17}$, —COOR$_{17}$, cycloalkyl-COOR$_{17}$, —C$_2$-C$_6$alkenylene-COOR$_{17}$, —C$_2$-C$_6$alkynylene-COOR$_{17}$, —CH═CHC(O)R$_{16}$, —NR$_{17}$(CO)C(O)R$_{16}$, —C(O)R$_{16}$, -cycloalkyl-C(O)R$_{16}$, —C$_2$-C$_6$alkenylene-C(O)R$_{16}$ and —C$_2$-C$_6$alkynylene-C(O)R$_{16}$;
$R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$R$_{16}$, —NHSO$_2$OR$_{15}$, —NHSO$_2$R$_{16}$, —N(alkyl)SO$_2$R$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months in solid form under ambient conditions.

In another aspect, this invention includes a pharmaceutical composition comprising one or more compounds of Formula D and a pharmaceutically acceptable carrier or excipient.

In another aspect, this invention is a method to treat or prevent cancer or a tumor that includes administering to a subject such as a human in need of such treatment a therapeutically effective amount of a compound of Formula D or a pharmaceutically acceptable salt thereof.

In another aspect, this invention provides a compound of Formula E:

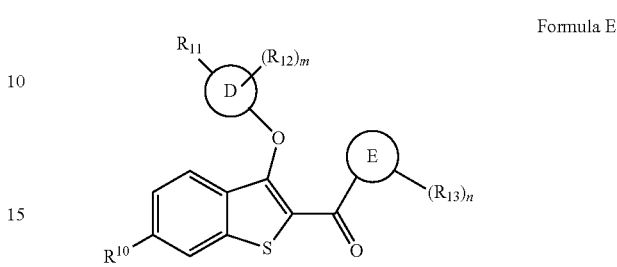

Formula E wherein:
m is 0, 1, 2, 3, or 4;
n is 0, 1, 2, 3, or 4;
Ring D is phenyl, naphthyl, quinolinyl, 5- or 6-membered monocyclic heteroaryl, cycloalkyl, or 7-, 8-, 9- or 10 membered bicyclic heterocyclyl;
Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
$R_{10}$ is selected from —OR$_{17}$, —SR$_{17}$, —N(R$_{17}$)$_2$, hydrogen, halogen, —OC(S)(C$_1$-C$_6$ alkyl), —OC(O)C$_6$H$_5$, —OC(S)C$_6$H$_5$, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, —OC(S)OC$_6$H$_5$, —OS(O)C$_2$-C$_6$ alkyl, and —OSO$_2$(C$_2$-C$_6$ alkyl);
$R_{11}$ is selected from —CH═CHCOOR$_{17}$, —NR$_{17}$(CO)COOR$_{17}$, —COOR$_{17}$, cycloalkyl-COOR$_{17}$, —C$_2$-C$_6$alkenylene-COOR$_{17}$, —C$_2$-C$_6$alkynylene-COOR$_{17}$, —CH═CHC(O)R$_{16}$, —NR$_{17}$(CO)C(O)R$_{16}$, —C(O)R$_{16}$, -cycloalkyl-C(O)R$_{16}$, —C$_2$-C$_6$alkenylene-C(O)R$_{16}$ and —C$_2$-C$_6$alkynylene-C(O)R$_{16}$;
$R_{12}$ and $R_{13}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{10}$, —OSO$_2$R$_{15}$, —OSO$_2$R$_{16}$, —NHSO$_2$OR$_{15}$, —NHSO$_2$R$_{16}$, —N(alkyl)SO$_2$R$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months under ambient conditions.

In another aspect, this invention includes a pharmaceutical composition comprising one or more compounds of Formula E and a pharmaceutically acceptable carrier or excipient.

In another aspect, this invention is a method to treat or prevent cancer or a tumor that includes administering to a subject such as a human in need of such treatment a therapeutically effective amount of a compound of Formula E or a pharmaceutically acceptable salt thereof.

In another aspect, this invention provides a compound of Formula F:

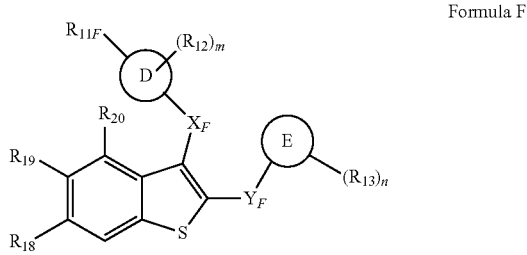

Formula F wherein:
m is 0, 1, 2, 3, or 4;
n is 0, 1, 2, 3, or 4;
one of $R_{18}$, $R_{19}$ and $R_{20}$ is $R_{10}$ and the other two are $R_{14}$;
$X_F$ is selected from —O—, —C(O), —CH$_2$—, —S—, —NR$_{17}$—, —CHF—, —CF$_2$—, and cycloalkyl;
$Y_F$ is selected from —C(O)—, —O, —S, —NR$_{17}$—, CF$_2$—, cycloalkyl, —CH$_2$—, and —CHF—;
Ring D is phenyl, naphthyl, quinolinyl, 5- or 6-membered monocyclic heteroaryl, cycloalkyl, or 7-, 8-, 9- or 10 membered bicyclic heterocyclyl;
Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
$R_{10}$ is selected from —OR$_{17}$, —SR$_{17}$, —N(R$_{17}$)$_2$ hydrogen, halogen, —OC(S)(C$_1$-C$_6$ alkyl), —OC(O)C$_6$H$_5$, —OC(S)C$_6$H$_5$, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, —OC(S)OC$_6$H$_5$, —OS(O)C$_2$-C$_6$ alkyl, and —OSO$_2$(C$_2$-C$_6$ alkyl);
$R_{11F}$ is selected from —CH=CHCOOR$_{17}$, —NR$_{17}$(CO)COOR$_{17}$, cycloalkyl-COOR$_{17}$, —C$_2$-C$_6$alkenylene-COOR$_{17}$, —C$_2$-C$_6$alkynylene-COOR$_{17}$, —CH=CHC(O)R$_{16}$, —NR$_{17}$(CO)C(O)R$_{16}$, -cycloalkyl-C(O)R$_{16}$, —C$_2$-C$_6$alkenylene-C(O)R$_{16}$ and —C$_2$-C$_6$alkynylene-C(O)R$_{16}$;
$R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months in solid form under ambient conditions.

In another aspect, this invention includes a pharmaceutical composition comprising one or more compounds of Formula F and a pharmaceutically acceptable carrier or excipient.

In another aspect, this invention is a method to treat or prevent cancer or a tumor that includes administering to a subject such as a human in need of such treatment a therapeutically effective amount of a compound of Formula F or a pharmaceutically acceptable salt thereof.

In one aspect, this invention is a compound of Formula G, or a pharmaceutically acceptable salt thereof:

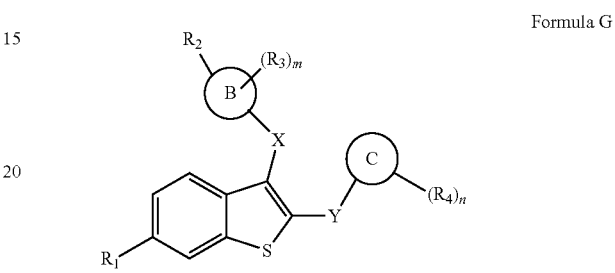

Formula G wherein:
m is 0, 1, 2, 3, or 4;
n is 0, 1, 2, 3, or 4;
X is selected from —O—, —C(O)—, —CH$_2$—, —S—, —CF$_2$—, and —C$_3$cycloalkyl;
Y is selected from —C(O)—, —O—, —CF$_2$—, or —C$_3$cycloalkyl, —CH$_2$—, —S—, and —NR$_{17}$—;
Ring B is phenyl, naphthyl, quinolinyl, 5- or 6-membered monocyclic heteroaryl or 7-, 8-, 9- or 10 membered bicyclic heterocyclyl;
Ring C is phenyl, thiophenyl (i.e., thienyl), 5- or 6-membered monocyclic heteroaryl or 7-, 8-, 9- or 10-membered bicyclic heterocyclyl;
$R_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);
$R_2$ is selected from —CH=CHC(O)R$_{16}$, —NR$_{17}$(CO)C(O)R$_{16}$, —C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;
$R_3$ is independently selected at each occurrence from hydrogen, halogen, —CN, —NO$_2$, C$_1$-C$_6$alkyl and C$_1$-C$_6$fluoroalkyl;
$R_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes one or more compounds of Formula G and a pharmaceutically acceptable carrier or excipient.

In another aspect, this invention is a method to treat or prevent cancer or a tumor that includes administering to a subject such as a human in need of such treatment a therapeutically effective amount of a compound of Formula G or a pharmaceutically acceptable salt thereof.
In certain embodiments, the compound has the structure, or is a pharmaceutically acceptable salt thereof:
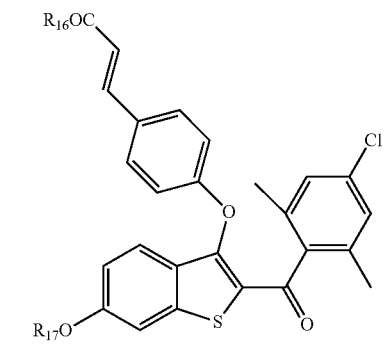
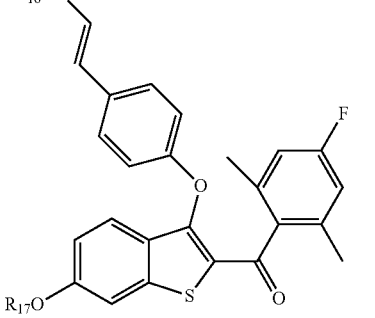
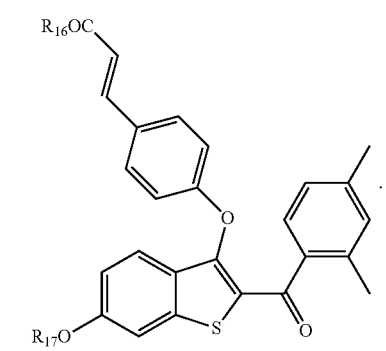
and
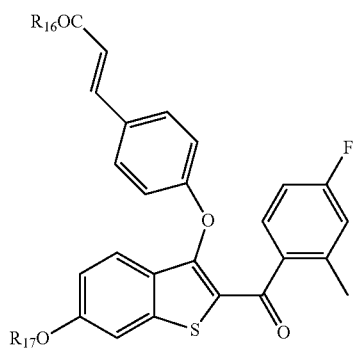
In other embodiments, the compound is selected from the following, or a pharmaceutically acceptable salt thereof:
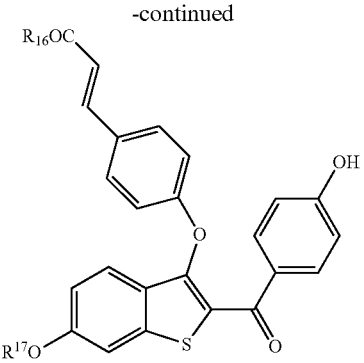
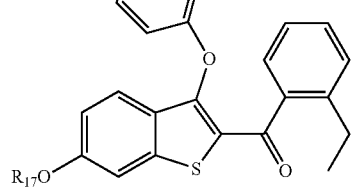
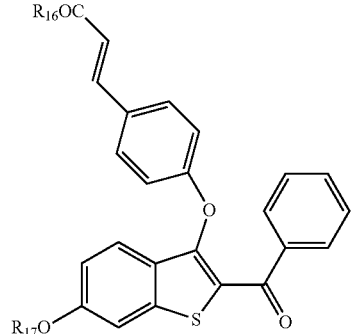
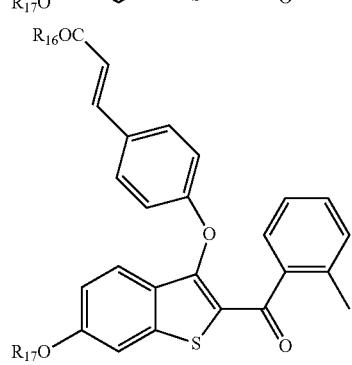
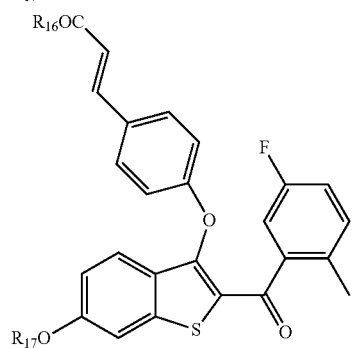

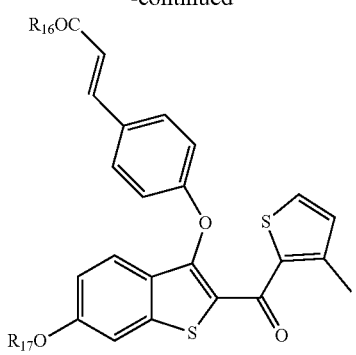
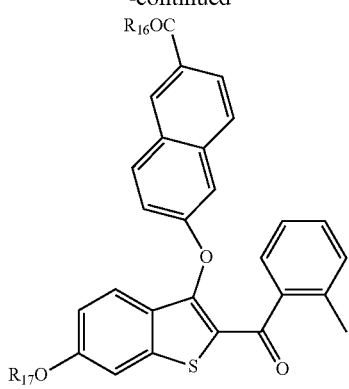
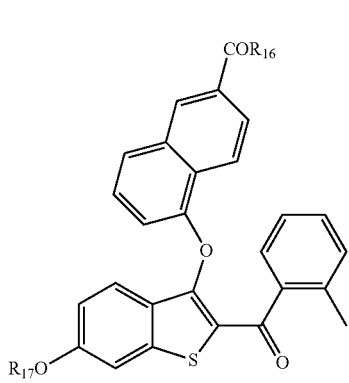
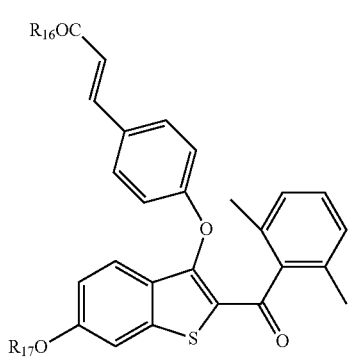
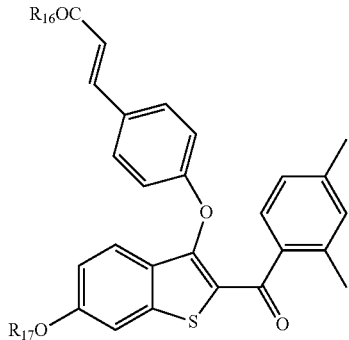

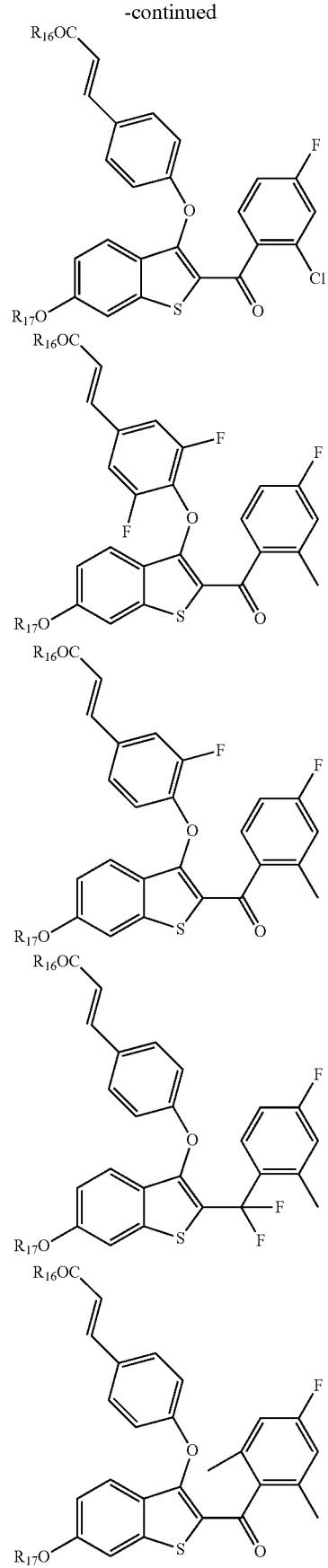
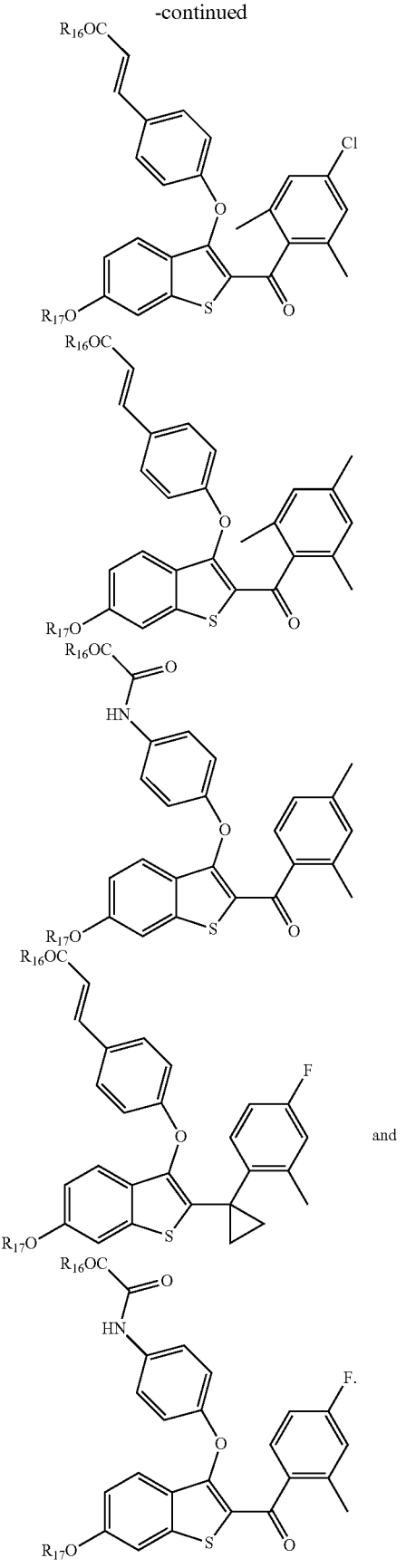

The present invention thus includes at least the following features:

(a) a compound as described herein, or a pharmaceutically acceptable salt or prodrug thereof;

(b) a compound as described herein, or a pharmaceutically acceptable salt or prodrug thereof that is useful in the treatment or prevention of an estrogen-related disorder, including without limitation a tumor or cancer;

(c) use of a compound as described herein, or a pharmaceutically acceptable salt or prodrug thereof in the manufacture of a medicament for the treatment or prevention of an estrogen-related disorder, including but not limited to a tumor or cancer;

(d) a method for manufacturing a medicament for the therapeutic use to treat or prevent a disorder of abnormal cellular proliferation including but not limited to a tumor or cancer, characterized in that a compound of the present invention or its salt or prodrug as described herein is used in the manufacture;

(e) a compound as described herein or its pharmaceutically acceptable salt or prodrug for use in the treatment or prevention of breast, kidney, uterine, ovarian or endometrial cancer;

(f) use of a compound as described herein or a pharmaceutically acceptable salt or prodrug thereof in the manufacture of a medicament for the treatment or prevention of breast, kidney, uterine, ovarian or endometrial cancer;

(g) a method for manufacturing a medicament for the therapeutic use in treating or preventing breast, kidney, uterine, ovarian or endometrial cancer, characterized in that a compound as described herein or its pharmaceutically acceptable salt or prodrug is used in the manufacture;

(h) a compound as described herein or a pharmaceutically acceptable salt or prodrug thereof for use in the treatment or prevention of hormone receptor positive metastatic breast cancer;

(i) use of a compound as described herein or a pharmaceutically acceptable salt or prodrug thereof in the manufacture of a medicament for the treatment or prevention of a hormone receptor positive metastatic breast cancer tumor;

(j) a method for manufacturing a medicament for treatment or prevention of a hormone receptor positive metastatic breast cancer, characterized in that a compound as described herein or its pharmaceutically acceptable salt or prodrug is used in the manufacture;

(k) a compound as described herein or a pharmaceutically acceptable salt or prodrug thereof for use to treat or prevent bone loss, including osteoporosis;

(l) use of a compound as described herein or a pharmaceutically acceptable salt or prodrug thereof in the manufacture of a medicament for the treatment or prevention of bone loss, including osteoporosis;

(m) a method for manufacturing a medicament for use to treat or prevent bone loss, including osteoporosis, characterized in that a compound as described herein is used in the manufacture;

(n) a pharmaceutical formulation comprising an effective treatment or prevention amount of a compound of a compound as described herein or a pharmaceutically acceptable salt or prodrug thereof together with a pharmaceutically acceptable carrier or diluent;

(o) a compound as described herein, or its pharmaceutically acceptable salt or prodrug as a mixture of enantiomers or diastereomers (as relevant), including as a racemate;

(p) a compound of the present invention as described herein in enantiomerically or diastereomerically (as relevant) enriched form, including as an isolated enantiomer or disastereomer (i.e., greater than 85, 90, 95, 97 or 99% pure);

(q) a process for the preparation of a therapeutic product that contain an effective amount of a compound as described herein, or its pharmaceutically acceptable salt or prodrug;

(r) a compound as described herein isotopically substituted with deuterium; and (s) an isotopic derivative of a compound as described herein.

DETAILED DESCRIPTION OF THE INVENTION

Definitions

Figure 1A:
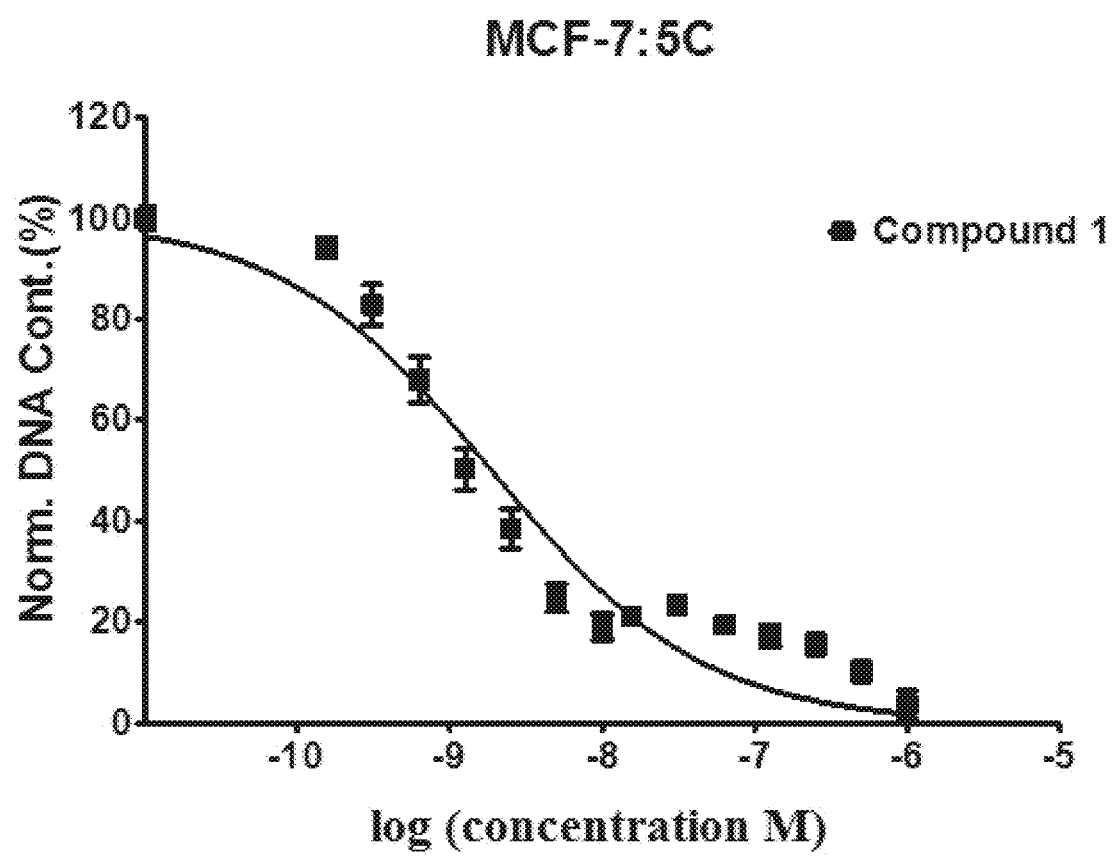
FIG. 1A, FIG. 1B, FIG. 1C, FIG. 1D, and FIG. 1E are graphs of the efficacy of Compounds 1, 5, 11, and 12 compared to known compound GDN-0810 against tamoxifen-resistant MCF-7:5C cells. The y-axis is normalized DNA content in percent and the x-axis is the concentration of compound measured in log(molar) units. The graph shows that representative compounds have sub-nanomolar efficacy in tamoxifen-resistant MCF-7:5C cells using DNA content assay.

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$ alkyl indicate the same functionality; similarly arylalkyl and -alkylaryl indicate the same functionality.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" is a branched or straight chain saturated aliphatic hydrocarbon group. In several non-limiting embodiments, the alkyl group contains from 1 to about 12 carbon atoms, more generally from 1 to about 6 carbon atoms, from 1 to about 4 carbon atoms, or 1 to 3 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. In several non-limiting embodiments, the alkenyl group contains from 2 to about 12 carbon atoms, more generally from 2 to about 6 carbon atoms, from 2 to about 4 carbon atoms, or 2 to 3 carbon atoms. In one non-limiting embodiment, the alkenyl contains from 2 to about 8 carbon atoms. In certain embodiments, the alkenyl is $C_2$, $C_2$-$C_3$, $C_2$-$C_4$, $C_2$-05, or $C_2$-$C_6$. The specified ranges as used herein indicate an alkenyl group having each member of the range described as an independent species. For example, the term $C_2$-$C_6$ alkenyl as used herein indicates a straight or branched alkenyl group having 2, 2, 3, 4, 5, or 6 carbon atoms and is intended to mean that each of these is described as an independent species. For example, the term $C_2$-$C_4$ alkenyl as used herein indicates a straight or branched alkenyl group having from 2, 3, or 4 carbon atoms and is intended to mean that each of these is described as an independent species. Examples of alkenyl include, but are not limited to, ethylene, propylene, n-butylene, isobutylene, n-pentylene, and isopentylene, In an alternative embodiment, the alkenyl group is optionally substituted. The term "Alkenyl" also encompasses cycloalkenyl groups. For example, when a term is used that includes "alken" then "cycloalkenyl'" can be considered part of the definition, unless unambiguously excluded by the context. For example and without limitation, the term alkenyl, can be considered to include the cyclic forms of alkenyl, unless unambiguously excluded by context. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. In several non-limiting embodiments, the alkynyl group contains from 2 to about 12 carbon atoms, more generally from 2 to about 6 carbon atoms, from 2 to about 4 carbon atoms, or 2 to 3 carbon atoms. In one non-limiting embodiment, the alkynyl contains from 2 to about 8 carbon atoms. In certain embodiments, the alkynyl is $C_2$, $C_2$-$C_3$, $C_2$-$C_4$, $C_2$-$C_5$, or $C_2$-$C_6$. The specified ranges as used herein indicate an alkynyl group having each member of the range described as an independent species. For example, the term $C_2$-$C_6$ alkynyl as used herein indicates a straight or branched alkynyl group having 1, 2, 3, 4, 5, or 6 carbon atoms and is intended to mean that each of these is described as an independent species. For example, the term $C_2$-$C_4$ alkynyl as used herein indicates a straight or branched alkynyl group having from 2, 3, or 4 carbon atoms and is intended to mean that each of these is described as an independent species. In an alternative embodiment, the alkynyl group is optionally substituted. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-14 aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

"Cyano" and "nitrile" mean a —CN group.

"Halo" or "halogen" means —Cl, —Br, —I or —F. In certain embodiments, "halo" or "halogen" refers to —Cl or —F.

"Haloalkyl" is a branched or straight-chain alkyl groups substituted with 1 or more halo atoms described above, up to the maximum allowable number of halogen atoms. In several non-limiting embodiments, the haloalkyl group contains from 1 to about 12 carbon atoms, more generally from 1 to about 6 carbon atoms, from 1 to about 4 carbon atoms, or 1 to 3 carbon atoms. In one non-limiting embodiment, the haloalkyl contains from 1 to about 8 carbon atoms. In certain embodiments, the haloalkyl is $C_1$-$C_2$, $C_2$-$C_3$, $C_2$-$C_4$, $C_2$-$C_5$, or $C_2$-$C_6$. The specified ranges as used herein indicate a haloalkyl group having each member of the range described as an independent species. For example, the term $C_1$-$C_6$ haloalkyl as used herein indicates a straight or branched haloalkyl group having 1, 2, 3, 4, 5, or 6 carbon atoms and is intended to mean that each of these is described as an independent species. For example, the term $C_1$-$C_4$ haloalkyl as used herein indicates a straight or branched alkynyl group having from 1, 2, 3, or 4 carbon atoms and is intended to mean that each of these is described as an independent species. In an alternative embodiment, the haloalkyl group is optionally substituted. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted with 1 to 3 substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

Heterocyclo groups also include radicals where heterocyclic radicals are fused/condensed with aryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

"Arylalkyl" is an aryl group as defined herein attached through an alkyl group. Non-limiting examples of arylalkyl groups include:

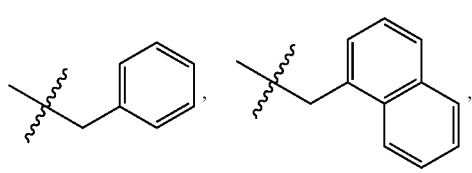

-continued

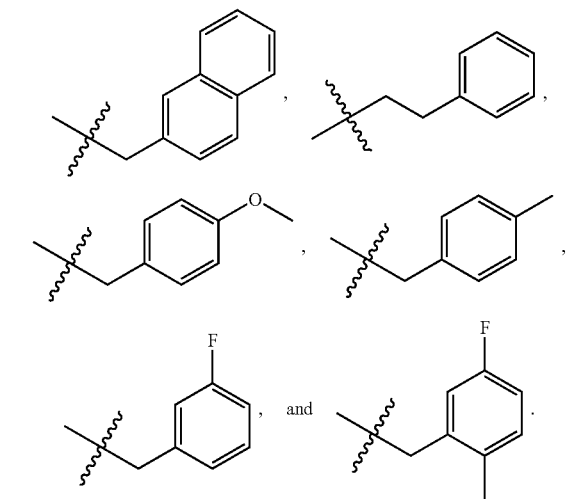

"Heteroarylalkyl" is a heteroaryl group as defined herein attached through an alkyl group. Non-limiting examples of heteroarylalkyl groups include:

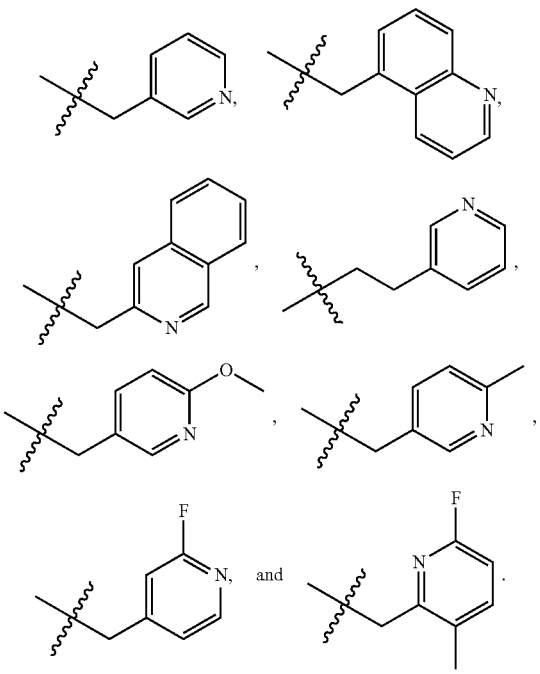

"Aryloxy" is an aryl group as defined herein attached through a —O-linker. Non-limiting examples of aryloxy groups include:

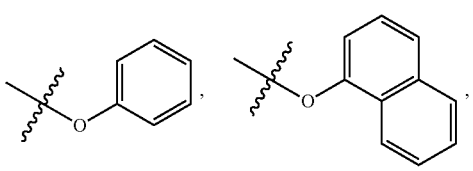

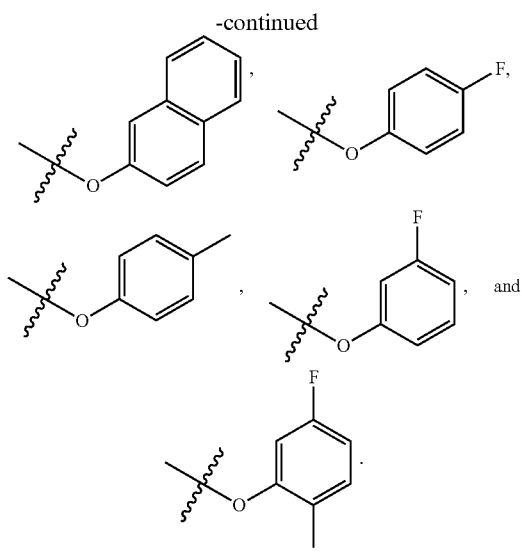

"Saturated" means the referenced chemical structure does not contain any multiple carbon-carbon bonds. For example, a saturated cycloalkyl group as defined herein includes cyclohexyl, cyclopropyl, and the like.

"Unsaturated" means the referenced chemical structure contains at least one multiple carbon-carbon bond. For example, a unsaturated cycloalkyl group as defined herein includes cyclohexenyl, cyclopentenyl, cyclohexadienyl, and the like.

"Pharmaceutically acceptable salt" refers to both acid and base addition salts.

"Modulating" or "modulate" refers to the treating, prevention, suppression, enhancement or induction of a function, condition or disorder.

"Treating" or "treatment" refer to the treatment of a disease or disorder described herein, in a subject, preferably a human, and includes:

i. inhibiting a disease or disorder, i.e., arresting its development;
  ii. relieving a disease or disorder, i.e., causing regression of the disorder;
  iii. slowing progression of the disorder; and/or
  iv. inhibiting, relieving, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

The present invention includes compounds of Formula A, Formula B, Formula C, Formula D, Formula E, Formula F, Formula G, Formula H, Formula I, Formula J, Formula K, Formula L, Formula M, Formula N, Formula O, Formula P, Formula Q, Formula R, Formula S, Formula T, Formula U, Formula V, and Formula W with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any of Formula A, Formula B, Formula C, Formula D, Formula E, Formula F, Formula G, Formula H, Formula I, Formula J, Formula K, Formula L, Formula M, Formula N, Formula O, Formula P, Formula Q, Formula R, Formula S, Formula T, Formula U, Formula V, or Formula W. In one non-limiting embodiment, the substitution of a hydrogen atom for a deuterium atom occurs within a group selected from any of X, $X_A$, $X_B$, Y, $Y_B$, B, C, D, E, F, $R_1$, $R_2$, $R_{2C}$, $R_3$, $R_4$, $R_5$, $R_6$, $R_7$, $R_8$, $R_9$, $R_{10}$, $R_{11}$, $R_{11F}$, $R_{12}$, $R_{13}$, $R_{14}$, $R_{15}$, $R_{16}$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

Compounds

Benzothiophene based estrogen receptor ligands of the invention includes compounds of Formula A, or a pharmaceutically acceptable salt thereof:

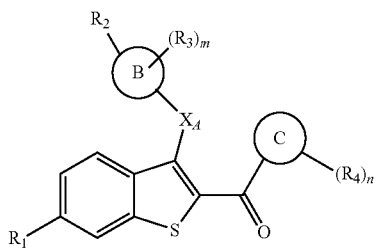

Formula A wherein:

m is 0, 1, 2, 3, or 4;

n is 0, 1, 2, 3, or 4;

$X_A$ is selected from —O—, —CH$_2$—, —S—, —CF$_2$—, and —C$_3$cycloalkyl-;

Ring B is phenyl, naphthyl, quinolinyl, 5- or 6-membered monocyclic heteroaryl or 7-, 8-, 9- or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

$R_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

$R_2$ is selected from —CH═CHC(O)R$_{16}$, —NR$_{17}$(CO)C(O)R$_{16}$, —C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;

$R_3$ is independently selected at each occurrence from hydrogen, halogen, —CN, —NO$_2$, C$_1$-C$_6$alkyl and C$_1$-C$_6$fluoroalkyl;

$R_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes a compound of Formula A and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula A or a pharmaceutically acceptable salt or prodrug thereof.

In another aspect, this invention is a compound of Formula B, or a pharmaceutically acceptable salt thereof:

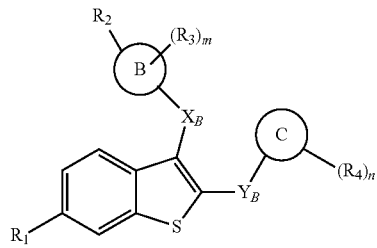

Formula B wherein:

m is 0, 1, 2, 3, or 4;

n is 0, 1, 2, 3, or 4;

$X_B$ is selected from —O—, —CH$_2$—, —S—, —NR$_{17}$—, —CF$_2$—, and C$_3$cycloalkyl;

$Y_B$ is selected from —C(O)—, —CF$_2$—, C$_3$cycloalkyl, and —CH$_2$—;

Ring B is phenyl, naphthyl, quinolinyl, 5- or 6-membered monocyclic heteroaryl or 7-, 8-, 9- or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

$R_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

$R_2$ is selected from —CH═CHC(O)R$_{16}$, —NR$_{17}$(CO)C(O)R$_{16}$, —C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;

$R_3$ is independently selected at each occurrence from hydrogen, halogen, —CN, —NO$_2$, C$_1$-C$_6$alkyl and C$_1$-C$_6$fluoroalkyl;

$R_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes a compound of Formula B and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula B or a pharmaceutically acceptable salt or prodrug thereof.

In another aspect, this invention provides a compound of Formula C:

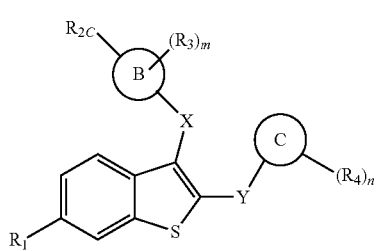

Formula C

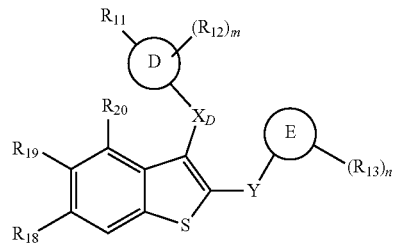

Formula D wherein:
  m is 0, 1, 2, 3, or 4;
  n is 0, 1, 2, 3, or 4;
  X is selected from —O—, —C(O)—, —CH$_2$—, —S—, —NH—, —CF$_2$—, and C$_3$cycloalkyl;
  Y is selected from —C(O)—, —O—, —CF$_2$—, or C$_3$cycloalkyl, —CH$_2$—, —S—, —NH—, and —NMe;
  Ring B is phenyl, naphthyl, quinolinyl, 5- or 6-membered monocyclic heteroaryl, cycloalkyl, or 7-, 8-, 9- or 10-membered bicyclic heterocyclyl;
  Ring C is phenyl, thiophenyl (i.e., thienyl), 5- or 6-membered monocyclic heteroaryl, cycloalkyl or 7-, 8-, 9- or 10-membered bicyclic heterocyclyl;
  R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);
  R$_{2C}$ is selected from —CH=CHC(O)R$_{16}$, —NR$_{17}$(CO)C(O)R$_{16}$, C$_2$-C$_6$alkylene-C(O)R$_{16}$, C$_2$-C$_6$alkenylene-C(O)R$_{16}$ and C$_2$-C$_6$alkynylene-C(O)R$_{16}$;
  R$_3$ is independently selected at each occurrence from hydrogen, halogen, —CN, —NO$_2$, C$_1$-C$_6$alkyl and C$_1$-C$_6$fluoroalkyl;
  R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);
  R$_{15}$ is independently selected at each occurrence from hydrogen, alkyl, alkenyl, alkynyl, cycloalkyl, aryl, arylalkyl, heteroaryl, and heteroarylalkyl;
  R$_{16}$ is independently selected at each occurrence from —N(R$_{15}$)$_2$, —SR$_{15}$, —OR$_{15}$; and
  R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition that includes one or more compounds of Formula C and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula C or a pharmaceutically acceptable salt or prodrug thereof.

In one aspect, this invention provides a compound of Formula D:

wherein:
  m is 0, 1, 2, 3, or 4;
  n is 0, 1, 2, 3, or 4;
  X$_D$ is selected from —O—, —CH$_2$—, —S—, —NR$_{17}$—, —CHF—, —CF$_2$—, and cycloalkyl;
  Y is selected from —C(O)—, —O—, —CF$_2$—, or C$_3$cycloalkyl, —CH$_2$—, —S—, —NH—, and —NMe;
  Ring D is phenyl, naphthyl, quinolinyl, 5- or 6-membered monocyclic heteroaryl, cycloalkyl, or 7-, 8-, 9- or 10-membered bicyclic heterocyclyl;
  Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
  one of R$_{18}$, R$_{19}$ and R$_{20}$ is R$_{10}$ and the other two are R$_{14}$;
  R$_{10}$ is selected from —OR$_{17}$, —SR$_{17}$, —N(R$_{17}$)$_2$ hydrogen, halogen, —OC(S)(C$_1$-C$_6$ alkyl), —OC(O)C$_6$H$_5$, —OC(S)C$_6$H$_5$, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, —OC(S)OC$_6$H$_5$, —OS(O)C$_2$-C$_6$ alkyl, and —OSO$_2$(C$_2$-C$_6$ alkyl);
  R$_{11}$ is selected from —CH=CHCOOR$_{17}$, —NR$_{17}$(CO)COOR$_{17}$, —COOR$_{17}$, cycloalkyl-COOR$_{17}$, —C$_2$-C$_6$alkenylene-COOR$_{17}$, —C$_2$-C$_6$alkynylene-COOR$_{17}$, —CH=CHC(O)R$_{16}$, —NR$_{17}$(CO)C(O)R$_{16}$, —C(O)R$_{16}$, -cycloalkyl-C(O)R$_{16}$, —C$_2$-C$_6$alkenylene-C(O)R$_{16}$ and —C$_2$-C$_6$alkynylene-C(O)R$_{16}$;
  R$_{12}$, R$_{13}$, and R$_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;
  R$_{15}$ is independently selected at each occurrence from hydrogen, alkyl, alkenyl, alkynyl, cycloalkyl, aryl, arylalkyl, heteroaryl, and heteroarylalkyl;
  R$_{16}$ is independently selected at each occurrence from —N(R$_{15}$)$_2$, —SR$_{15}$, —OR$_{15}$; and
  R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months in solid form under ambient conditions.

In another aspect, this invention includes a pharmaceutical composition comprising one or more compounds of Formula D and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula D or a pharmaceutically acceptable salt or prodrug thereof.

In another aspect, this invention provides a compound of Formula E:

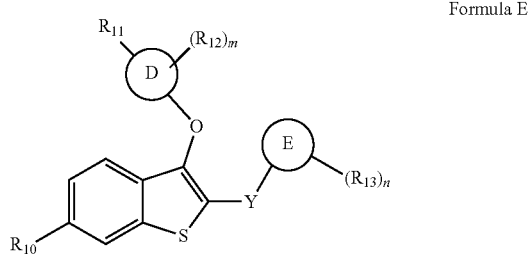

Formula E wherein:
m is 0, 1, 2, 3, or 4;
n is 0, 1, 2, 3, or 4;
Ring D is phenyl, naphthyl, quinolinyl, 5- or 6-membered monocyclic heteroaryl, cycloalkyl, or 7-, 8-, 9- or 10 membered bicyclic heterocyclyl;
Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
$R_{10}$ is selected from hydroxyl, hydrogen, halogen, —O($C_1$-$C_6$ alkyl), —S($C_1$-$C_6$ alkyl), aryloxy, —OC(O)($C_1$-$C_6$ alkyl), —OC(S)($C_1$-$C_6$ alkyl), —OC(O)$C_6H_5$, —OC(S)$C_6H_5$, —OC(O)aryl, —OC(S)aryl, —OC(O)heteroaryl, —OC(S)heteroaryl, —OC(O)O($C_1$-$C_6$ alkyl), —OC(S)O($C_1$-$C_6$ alkyl), —OC(O)O$C_6H_5$, OC(S)O$C_6H_5$, amino, aminoalkyl, —SH, and —OSO$_2$($C_2$-$C_6$ alkyl);
$R_{11}$ is selected from —CH=CHCOOR$_{17}$, —NR$_{17}$(CO)COOR$_{17}$, —COOR$_{17}$, cycloalkyl-COOR$_{17}$, —$C_2$-$C_6$alkenylene-COOR$_{17}$, —$C_2$-$C_6$alkynylene-COOR$_{17}$, —CH=CHC(O)R$_{16}$, —NR$_{17}$(CO)C(O)R$_{16}$, —C(O)R$_{16}$, -cycloalkyl-C(O)R$_{16}$, —$C_2$-$C_6$alkenylene-C(O)R$_{16}$ and —$C_2$-$C_6$alkynylene-C(O)R$_{16}$;
$R_{12}$ and $R_{13}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and $C_1$-$C_6$fluoroalkyl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months in solid form under ambient conditions.

In another aspect, this invention includes a pharmaceutical composition comprising one or more compounds of Formula E and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula E or a pharmaceutically acceptable salt or prodrug thereof.

In another aspect, this invention provides a compound of Formula F:

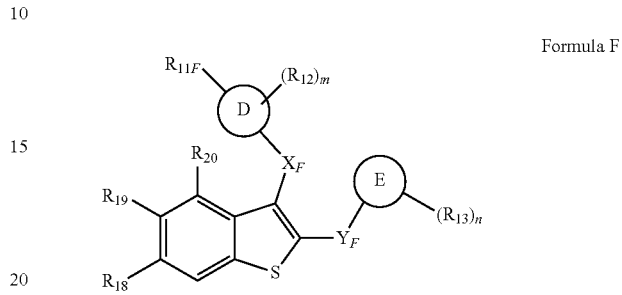

Formula F wherein:
m is 0, 1, 2, 3, or 4;
n is 0, 1, 2, 3, or 4;
one of $R_{18}$, $R_{19}$ and $R_{20}$ is $R_{10}$ and the other two are $R_{14}$;
$X_F$ is selected from —O—, —C(O), —CH$_2$—, —S—, —NR$_{17}$—, —CHF—, —CF$_2$—, and cycloalkyl;
$Y_F$ is selected from —C(O)—, —O, —S, —NR$_{17}$—, CF$_2$—, cycloalkyl, —CH$_2$—, and —CHF—;
Ring D is phenyl, naphthyl, quinolinyl, 5- or 6-membered monocyclic heteroaryl, cycloalkyl, or 7-, 8-, 9- or 10 membered bicyclic heterocyclyl;
Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;
$R_{10}$ is selected from —OR$_{17}$, —SR$_{17}$, —N(R$_{17}$)$_2$ hydrogen, halogen, —OC(S)($C_1$-$C_6$ alkyl), —OC(O)$C_6H_5$, —OC(S)$C_6H_5$, —OC(S)aryl, —OC(O)heteroaryl, —OC(S)heteroaryl, —OC(O)O($C_1$-$C_6$ alkyl), —OC(S)O($C_1$-$C_6$ alkyl), —OC(O)O$C_6H_5$, —OC(S)O$C_6H_5$, —OS(O)$C_2$-$C_6$ alkyl, and —OSO$_2$($C_2$-$C_6$ alkyl);
$R_{11F}$ is selected from —CH=CHCOOR$_{17}$, —NR$_{17}$(CO)COOR$_{17}$, cycloalkyl-COOR$_{17}$, —$C_2$-$C_6$alkenylene-COOR$_{17}$, —$C_2$-$C_6$alkynylene-COOR$_{17}$, —CH=CHC(O)R$_{16}$, —NR$_{17}$(CO)C(O)R$_{16}$, -cycloalkyl-C(O)R$_{16}$, —$C_2$-$C_6$alkenylene-C(O)R$_{16}$ and —$C_2$-$C_6$alkynylene-C(O)R$_{16}$;
$R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and $C_1$-$C_6$fluoroalkyl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N(R$_{15}$)$_2$, —SR$_{15}$, —OR$_{15}$; and
$R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment, the variables above are selected such that a stable compound results with a shelf life of at least three months in solid form under ambient conditions.

In another aspect, this invention includes a pharmaceutical composition comprising one or more compounds of Formula F and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula F or a pharmaceutically acceptable salt or prodrug thereof.

In one embodiment, Ring D is phenyl, naphthyl or quinolinyl and Ring E is phenyl or thienyl.

In one embodiment, Ring E is phenyl.

In one embodiment,

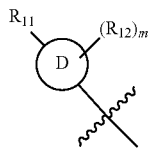

is selected from:

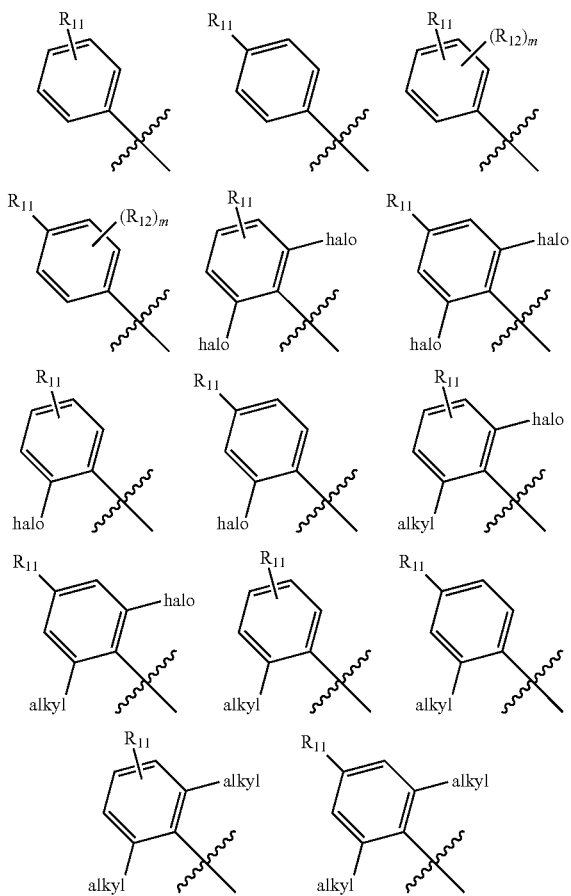

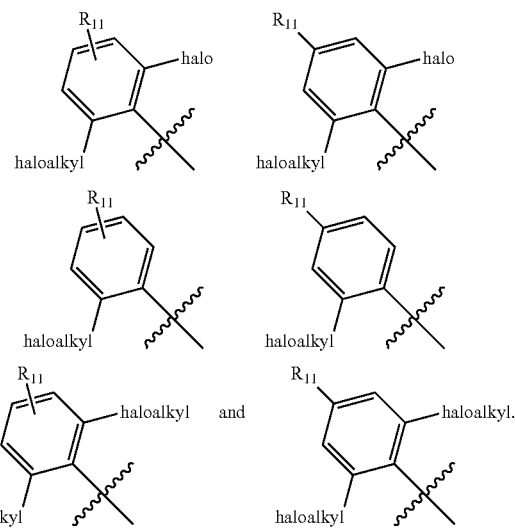

In one embodiment of the above D-ring embodiments, alkyl is methyl. In another embodiment of the above D-ring embodiments, alkyl is independently methyl, ethyl, propyl or cyclopropyl. In one embodiment of the above D-ring embodiments, halo is fluoro. In one embodiment of the above D-ring embodiments, haloalkyl is independently mono-, di- or trifluoro-methyl.

In another embodiment,

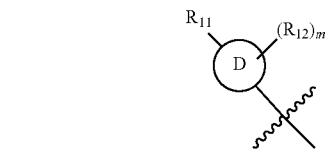

is selected from:

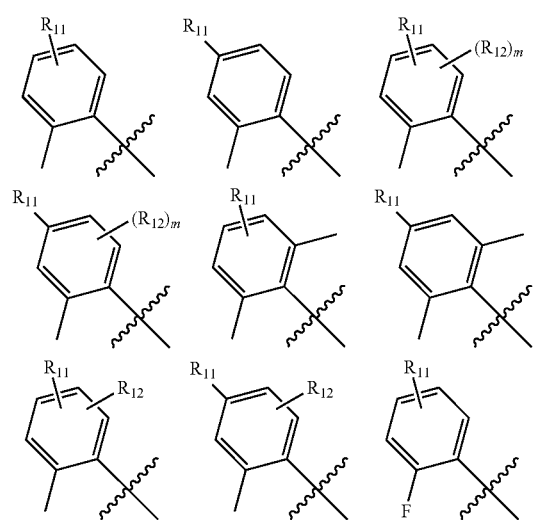

-continued
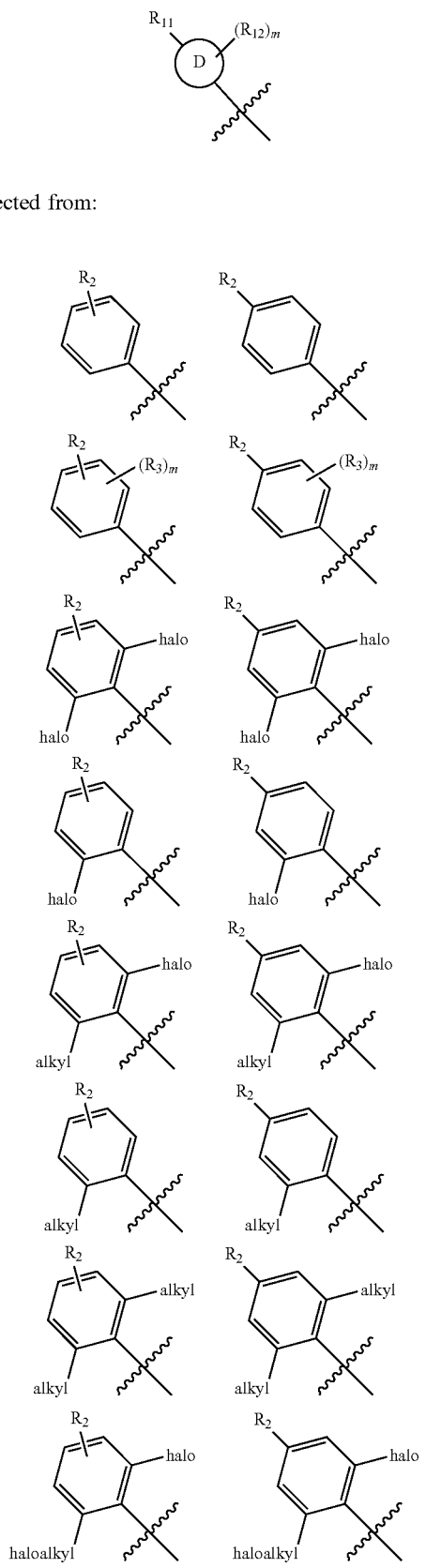
In another embodiment,
is selected from:

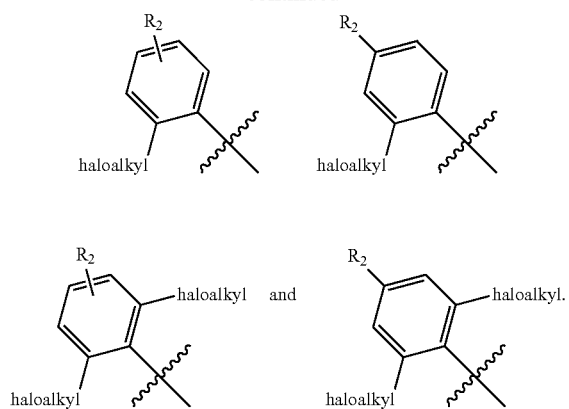

In one embodiment of the above D-ring embodiments, alkyl is methyl. In another embodiment of the above D-ring embodiments, alkyl is independently methyl, ethyl, propyl or cyclopropyl. In one embodiment of the above D-ring embodiments, halo is fluoro. In one embodiment of the above D-ring embodiments, haloalkyl is independently mono-, di- or trifluoro-methyl.

In another embodiment,

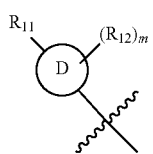

is selected from:

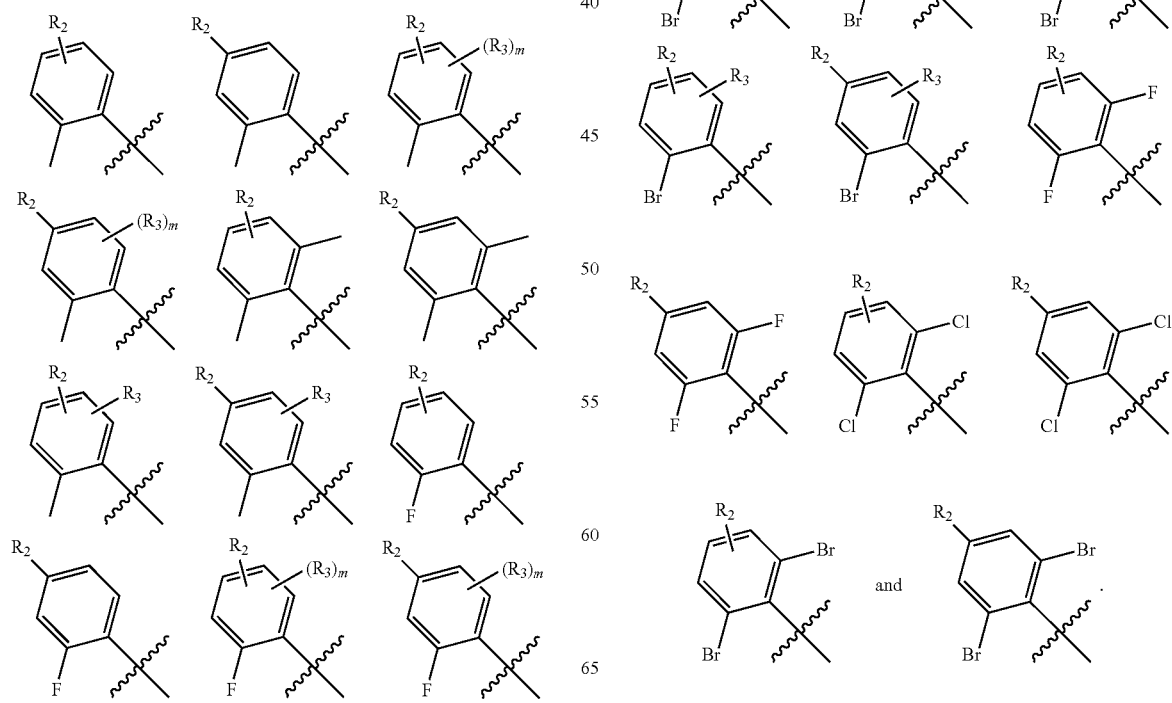

In one embodiment,

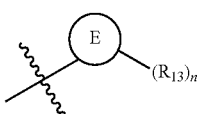

is selected from:

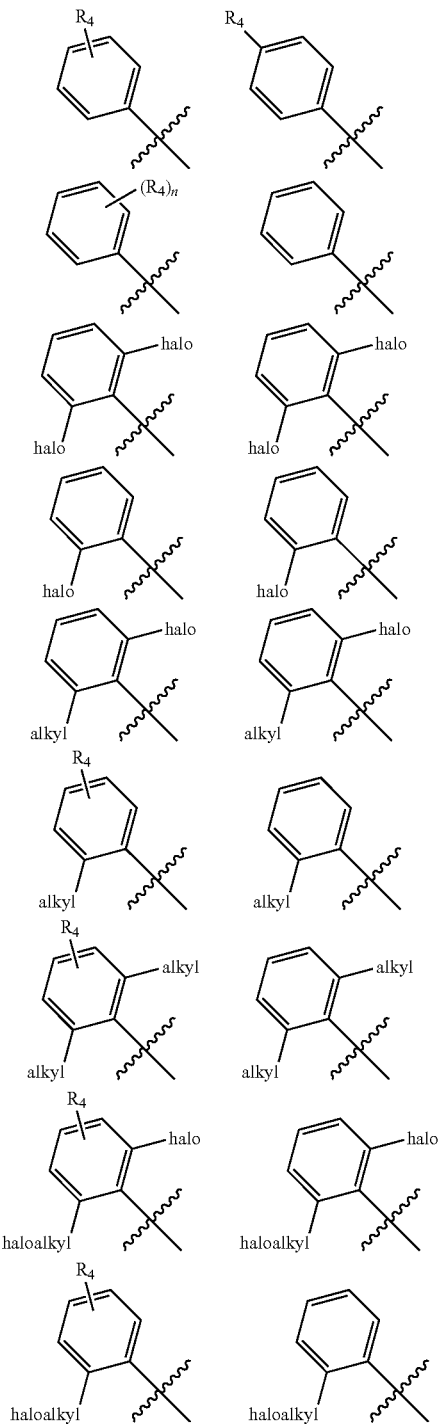

-continued

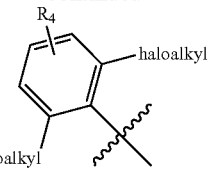

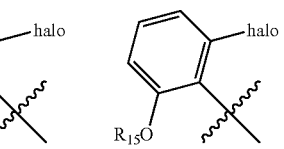

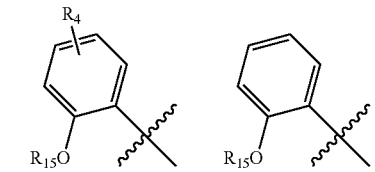

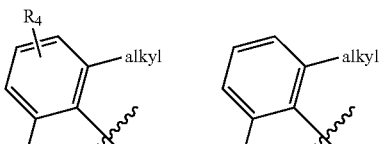

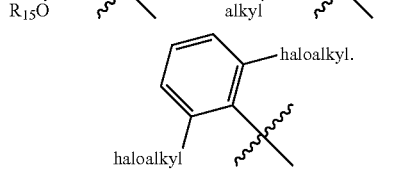

and

In one embodiment of the above E-ring embodiments, alkyl is methyl. In another embodiment of the above E-ring embodiments, alkyl is independently methyl, ethyl, propyl or cyclopropyl. In one embodiment of the above E-ring embodiments, halo is fluoro. In one embodiment of the above E-ring embodiments, haloalkyl is independently mono-, di- or trifluoro-methyl.

In one embodiment,

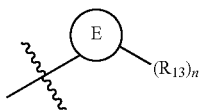

is selected from:

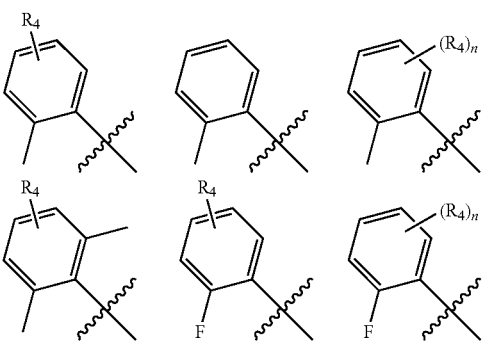

-continued

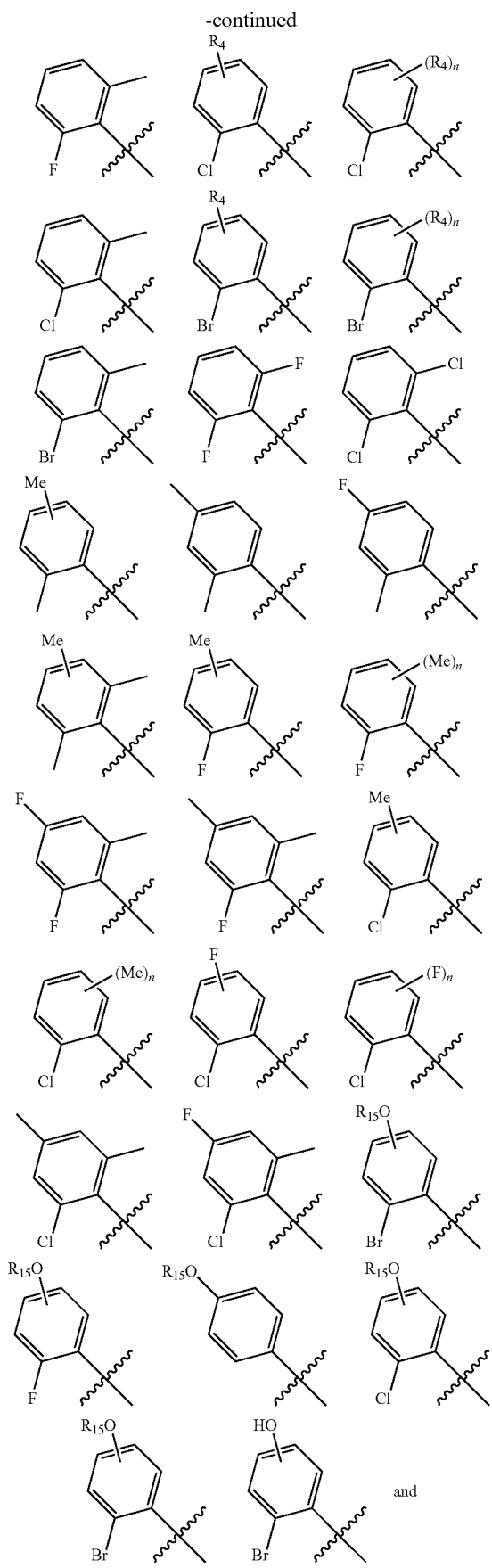

-continued

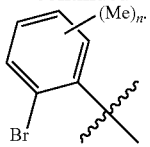

and

In one aspect, this invention is a compound of Formula G, or a pharmaceutically acceptable salt thereof:

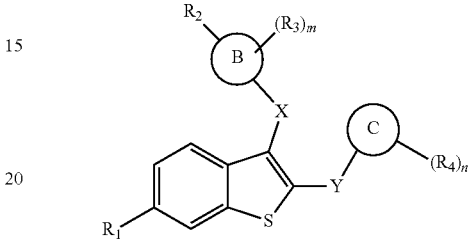

Formula G wherein:
m is 0, 1, 2, 3, or 4;
n is 0, 1, 2, 3, or 4;
X is selected from —O—, —C(O)—, —CH$_2$—, —S—, —CF$_2$—, and C$_3$cycloalkyl;
Y is selected from —C(O)—, —O—, —CF$_2$—, or C$_3$cycloalkyl, —CH$_2$—, —S—, and —NR$_{17}$;
Ring B is phenyl, naphthyl, quinolinyl, 5- or 6-membered monocyclic heteroaryl or 7-, 8-, 9- or 10 membered bicyclic heterocyclyl;
Ring C is phenyl, thiophenyl (i.e., thienyl), 5- or 6-membered monocyclic heteroaryl or 7-, 8-, 9- or 10-membered bicyclic heterocyclyl;
R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);
R$_2$ is selected from —CH=CHC(O)R$_{16}$, —NR$_{17}$(CO)C(O)R$_{16}$, —C(O)R$_{16}$, C$_2$-C$_6$alkylene-C(O)R$_{16}$, C$_2$-C$_6$alkenylene-C(O)R$_{16}$, and C$_2$-C$_6$alkynylene-C(O)R$_{16}$;
R$_3$ is independently selected at each occurrence from hydrogen, halogen, —CN, —NO$_2$, C$_1$-C$_6$alkyl and C$_1$-C$_6$fluoroalkyl;
R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);
R$_{15}$ is independently selected at each occurrence from hydrogen, alkyl, alkenyl, alkynyl, cycloalkyl, aryl, arylalkyl, heteroaryl, and heteroarylalkyl;
R$_{16}$ is independently selected at each occurrence from —N(R$_{15}$)$_2$, —SR$_{15}$, —OR$_{15}$; and
R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another aspect, this invention includes a pharmaceutical composition comprising one or more compounds of Formula G and a pharmaceutically acceptable carrier or excipient.

In another aspect, this invention is a method of treating or preventing cancer (including breast, ovarian, uterine, kidney, or endometrial) or a tumor comprising administering to a subject such as a human in need of such treatment a therapeutically effective amount of a compound of Formula G or a pharmaceutically acceptable salt or prodrug thereof.

In one embodiment of the present invention, X is —O—.

In another embodiment, Y is —C(O)—.

In a further embodiment X is —O— and Y is —C(O)—.

In one embodiment, $R_1$ is selected from hydroxyl and —O($C_1$-$C_6$ alkyl).

In one embodiment, $R_2$ is selected from —COOH, —NH(CO)COOH and —CH=CHCOOH.

In one embodiment, Ring B is phenyl, naphthyl or quinolinyl and Ring C is phenyl or thienyl.

In one embodiment, Ring C is phenyl.

In one embodiment,

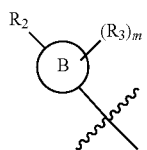

is selected from:

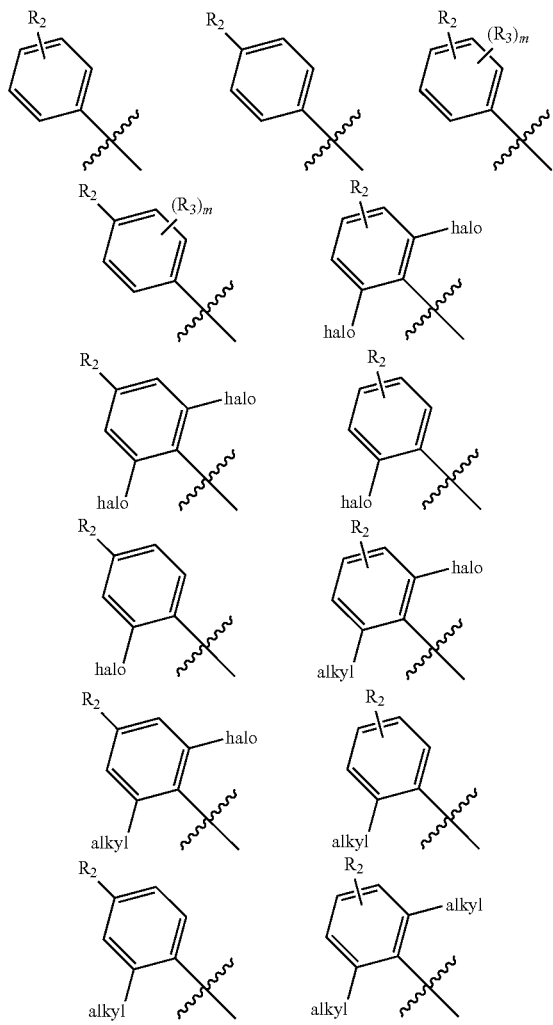

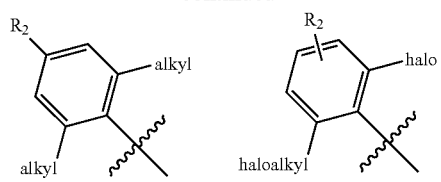

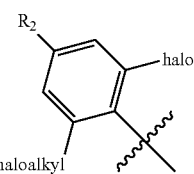

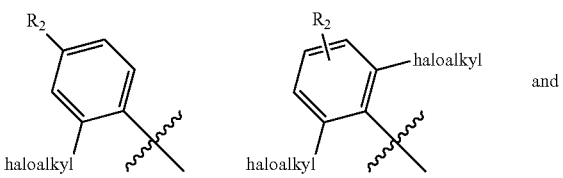

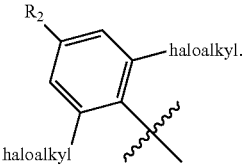 and

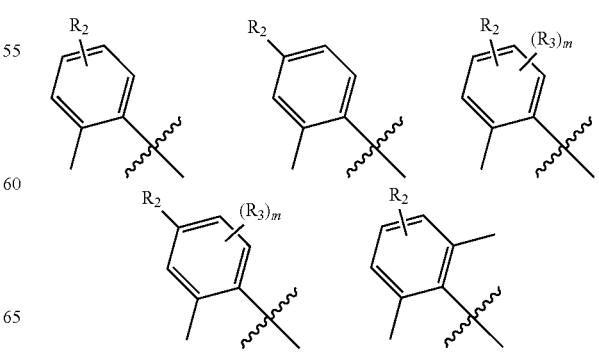

In one embodiment of the above B-ring embodiments, alkyl is methyl. In another embodiment of the above B-ring embodiments, alkyl is independently, methyl, ethyl, propyl or cyclopropyl. In one embodiment of the above B-ring embodiments, halo is fluoro. In another embodiment of the above B-rings, halo is independently fluoro or chloro, including wherein one halo is fluoro and the other is chloro. In one embodiment of the above B-ring embodiments, haloalkyl is independently mono-, di- or trifluoro-methyl.

In another embodiment,

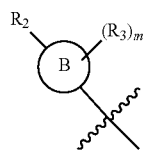

is selected from:

-continued
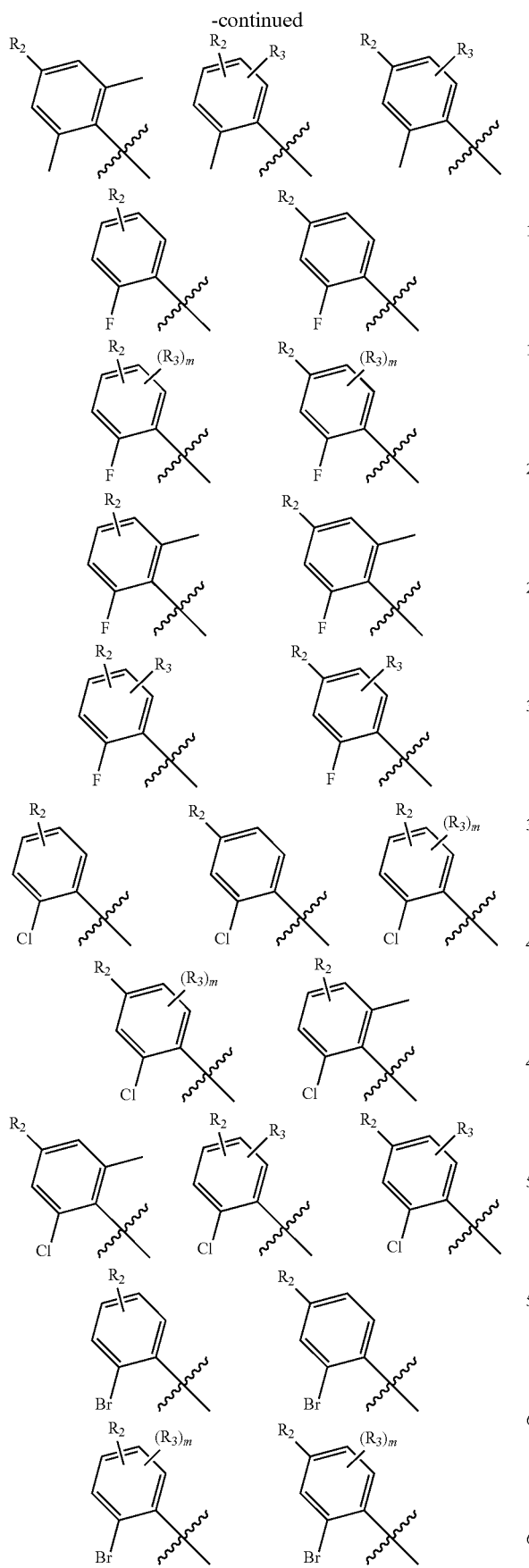
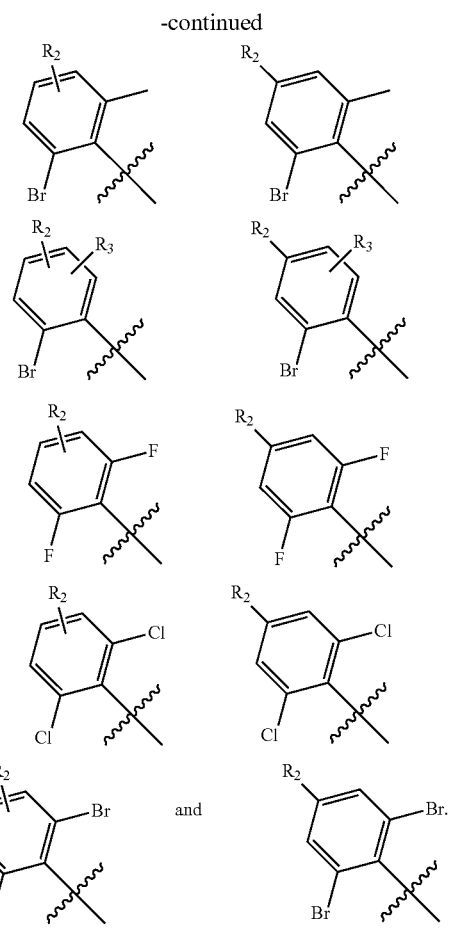
In one embodiment,
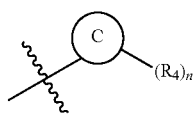
is selected from:
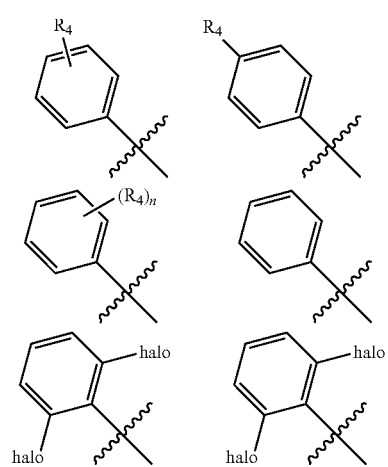

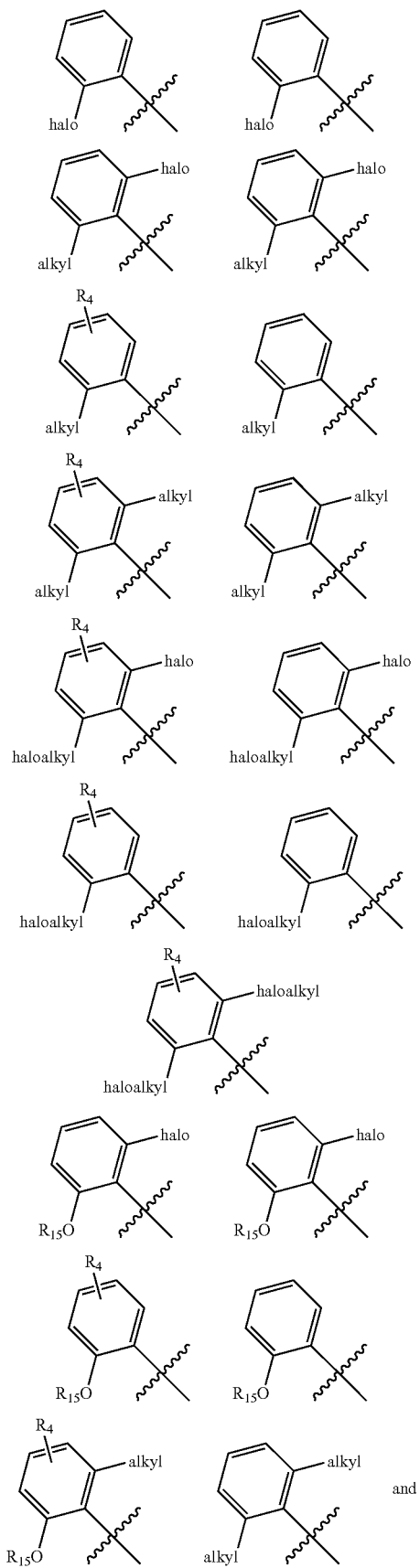
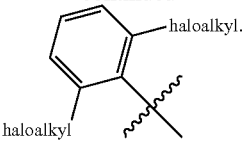

In one embodiment of the above C-ring embodiments, alkyl is methyl. In another embodiment of the above C-ring embodiments, alkyl is independently, methyl, ethyl, propyl or cyclopropyl. In one embodiment of the above C-ring embodiments, halo is fluoro. In another embodiment of the above C-rings, halo is independently fluoro or chloro, including wherein one halo is fluoro and the other is chloro. In one embodiment of the above C-ring embodiments, haloalkyl is independently mono-, di- or trifluoro-methyl.

In another embodiment,

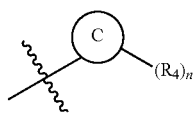

is selected from:

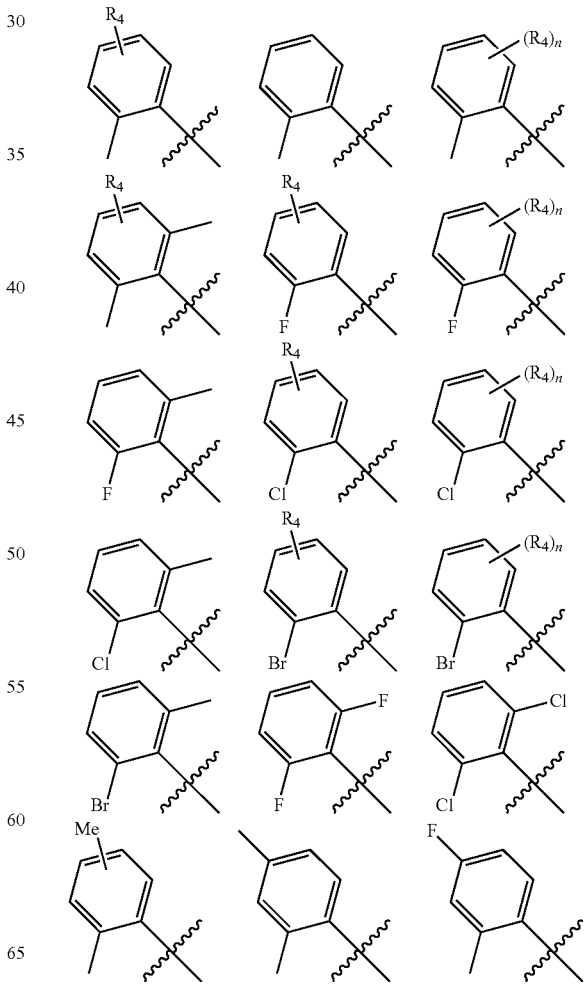

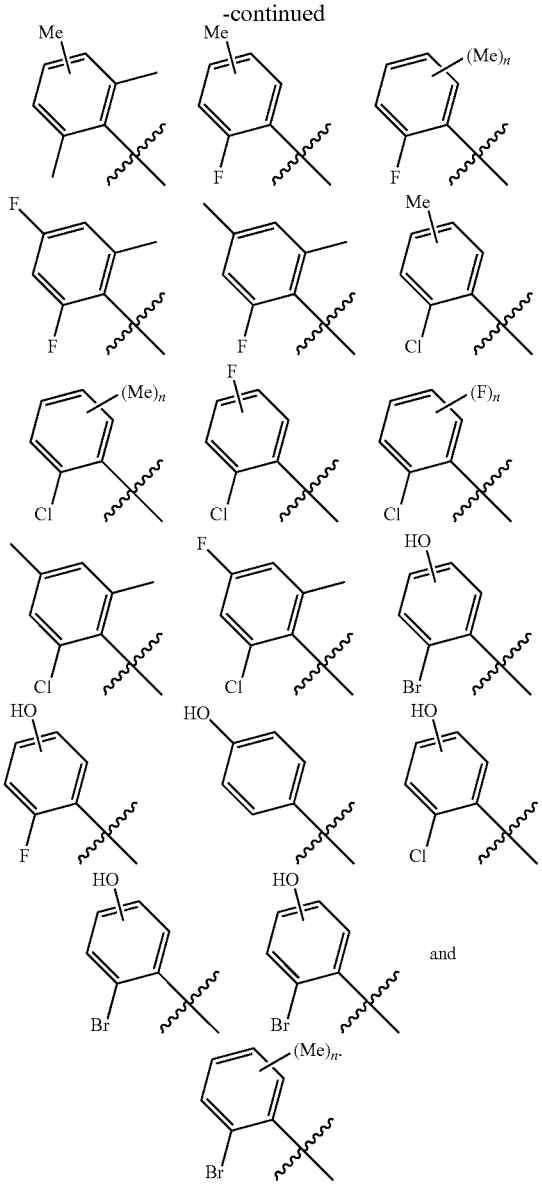

In another embodiment, the compound of Formula G has Formula H:

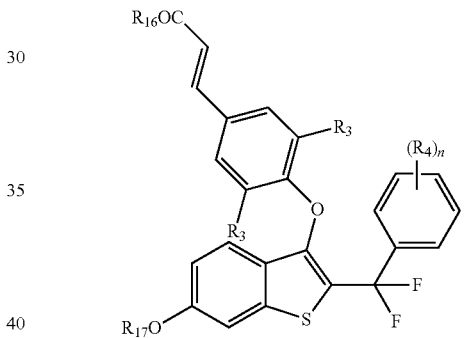

wherein:

n is 0, 1, 2, 3, or 4;

$R_3$ is independently selected at each occurrence from hydrogen, halogen, —CN, —NO$_2$, $C_1$-$C_6$alkyl and $C_1$-$C_6$fluoroalkyl;

$R_4$ is independently selected at each occurrence from hydrogen, halogen, hydroxyl, $C_1$-$C_6$alkyl, $C_1$-$C_6$fluoroalkyl, —CN, —O($C_1$-$C_6$ alkyl), and —O($C_1$-$C_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N($R_{15}$)$_2$, —S$R_{15}$, —O$R_{15}$; and $R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_3$ is independently selected at each occurrence from hydrogen, halogen, methyl and —CN.

In one embodiment $R_{16}$ is hydroxyl.

In one embodiment $R_{17}$ is hydrogen.

In another embodiment, the compound of Formula G has Formula I:

Formula I wherein n is 0, 1, 2, 3, or 4;

$R_3$ is independently selected at each occurrence from hydrogen, halogen, —CN, —NO$_2$, $C_1$-$C_6$alkyl and $C_1$-$C_6$fluoroalkyl;

$R_4$ is independently selected at each occurrence from hydrogen, halogen, hydroxyl, $C_1$-$C_6$alkyl, $C_1$-$C_6$fluoroalkyl, —CN, —O($C_1$-$C_6$ alkyl), and —O($C_1$-$C_6$fluoroalkyl);

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N($R_{15}$)$_2$, —S$R_{15}$, —O$R_{15}$; and $R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_{16}$ is hydroxyl.

In one embodiment $R_{17}$ is hydrogen.

In one embodiment $R_3$ is independently selected at each occurrence from hydrogen, halogen, methyl and —CN.

In another embodiment, the compound of Formula G has Formula J:

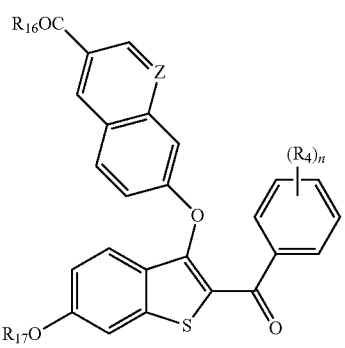

Formula J wherein:
Z is CH or N;
n is 0, 1, 2, 3, or 4;
$R_4$ is independently selected at each occurrence from hydrogen, halogen, hydroxyl, $C_1$-$C_6$alkyl, $C_1$-$C_6$fluoroalkyl, —CN, —O($C_1$-$C_6$ alkyl), and —O($C_1$-$C_6$fluoroalkyl);
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N($R_{15}$)$_2$, —S$R_{15}$, —O$R_{15}$; and
$R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_{16}$ is hydroxyl.
In one embodiment $R_{17}$ is hydrogen.
In another embodiment, the compound of Formula G has Formula K:

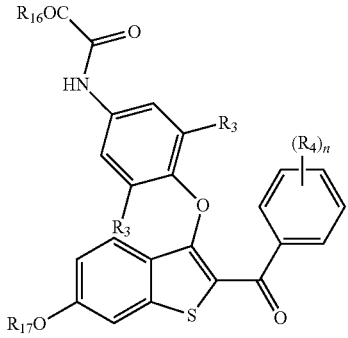

Formula K wherein:
n is 0, 1, 2, 3, or 4;
$R_3$ is independently selected at each occurrence from hydrogen, halogen, —CN, —NO$_2$, $C_1$-$C_6$alkyl and $C_1$-$C_6$fluoroalkyl;
$R_4$ is independently selected at each occurrence from hydrogen, halogen, hydroxyl, $C_1$-$C_6$alkyl, $C_1$-$C_6$fluoroalkyl, —CN, —O($C_1$-$C_6$ alkyl), and —O($C_1$-$C_6$fluoroalkyl);
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N($R_{15}$)$_2$, —S$R_{15}$, —O$R_{15}$; and
$R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_{16}$ is hydroxyl.
In one embodiment $R_{17}$ is hydrogen.
In one embodiment $R_3$ is independently selected at each occurrence from hydrogen, halogen, methyl and —CN.
In another embodiment, a compound of Formula L is provided:

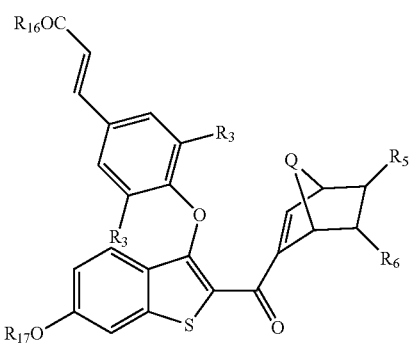

Formula L wherein:
Q is selected from O, S, CH$_2$, NH and S(O);
$R_5$ and $R_6$ are independently selected from CN, halogen and COO$R_7$;
$R_3$ is independently selected at each occurrence from hydrogen, halogen, methyl and —CN;
$R_7$ is selected from haloalkyl, alkyl, cycloalkyl, aryl and heteroaryl;
$R_{15}$ is independently selected at each occurrence from hydrogen, alkyl, alkenyl, alkynyl, cycloalkyl, aryl, arylalkyl, heteroaryl, and heteroarylalkyl;
$R_{16}$ is independently selected at each occurrence from —N($R_{15}$)$_2$, —S$R_{15}$, —O$R_{15}$; and
$R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_{16}$ is hydroxyl.
In one embodiment $R_{17}$ is hydrogen.
In an additional embodiment, a compound of Formula M is provided:

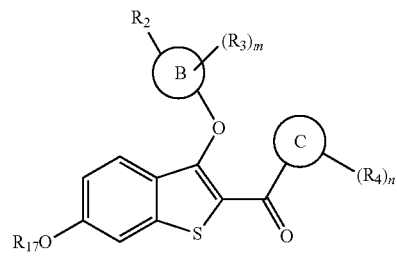

Formula M wherein:
m is 0, 1, 2, 3, or 4;
n is 0, 1, 2, 3, or 4;
Ring B is phenyl, naphthyl, quinolinyl, 5- or 6-membered monocyclic heteroaryl or 7-, 8-, 9- or 10 membered bicyclic heterocyclyl;
Ring C is phenyl, thiophenyl (i.e., thienyl), 5- or 6-membered monocyclic heteroaryl or 7-, 8-, 9- or 10-membered bicyclic heterocyclyl;

R$_2$ is selected from —CH=CHC(O)R$_{16}$, —NR$_{17}$(CO)C(O)R$_{16}$, —C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;

R$_3$ is independently selected at each occurrence from hydrogen, halogen, —CN, —NO$_2$, C$_1$-C$_6$alkyl and C$_1$-C$_6$fluoroalkyl;

R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{16}$ is hydroxyl.

In one embodiment R$_{17}$ is hydrogen.

In an additional embodiment, a compound of Formula N is provided:

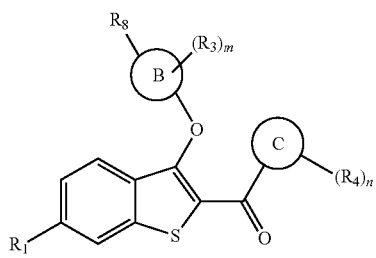

Formula N wherein:

m is 0, 1, 2, 3, or 4;

n is 0, 1, 2, 3, or 4;

Ring B is phenyl, naphthyl, quinolinyl, 5- or 6-membered monocyclic heteroaryl or 7-, 8-, 9- or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

R$_8$ is selected from —CH=CHC(O)R$_{16}$, —NR$_{17}$(CO)C(O)R$_{16}$, —C(O)R$_{16}$, C$_2$-C$_6$alkenylene-C(O)R$_{16}$ and C$_2$-C$_6$alkynylene-C(O)R$_{16}$;

R$_3$ is independently selected at each occurrence from hydrogen, halogen, —CN, —NO$_2$, C$_1$-C$_6$alkyl and C$_1$-C$_6$fluoroalkyl;

R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In an additional embodiment, a compound of Formula O is provided:

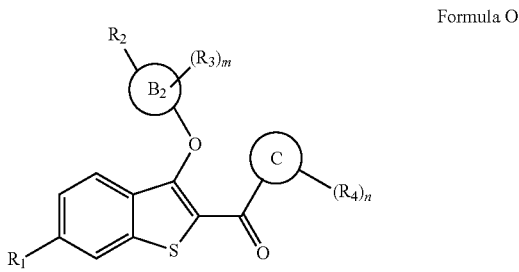

Formula O wherein:

m is 0, 1, 2, 3, or 4;

n is 0, 1, 2, 3, or 4;

Ring B$_2$ is naphthyl, quinolinyl, or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

R$_2$ is selected from —CH=CHC(O)R$_{16}$, —NR$_{17}$(CO)C(O)R$_{16}$, —C(O)R$_{16}$, C$_2$-C$_6$alkenylene-C(O)R$_{16}$, C$_2$-C$_6$alkylene-C(O)R$_{16}$, and C$_2$-C$_6$alkynylene-C(O)R$_{16}$;

R$_3$ is independently selected at each occurrence from hydrogen, halogen, —CN, —NO$_2$, C$_1$-C$_6$alkyl and C$_1$-C$_6$fluoroalkyl;

R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In an additional embodiment, a compound of Formula P is provided:

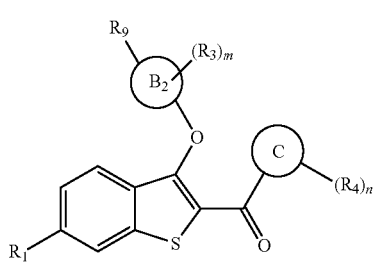

Formula P wherein:

m is 0, 1, 2, 3, or 4;

n is 0, 1, 2, 3, or 4;

Ring B$_2$ is naphthyl, quinolinyl, or 10 membered bicyclic heterocyclyl;

Ring C is phenyl, thiophenyl (i.e., thienyl), 5- or 6-membered monocyclic heteroaryl or 7-, 8-, 9- or 10-membered bicyclic heterocyclyl;

R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

R$_9$ is —C(O)R$_{16}$.

R$_3$ is independently selected at each occurrence from hydrogen, halogen, —CN, —NO$_2$, C$_1$-C$_6$alkyl and C$_1$-C$_6$fluoroalkyl;

R$_4$ is independently selected at each occurrence from hydrogen, halogen, —OR$_{15}$, C$_1$-C$_6$alkyl, C$_1$-C$_6$fluoroalkyl, —CN, —O(C$_1$-C$_6$ alkyl), and —O(C$_1$-C$_6$fluoroalkyl);

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In another embodiment, the compound of Formula D has Formula Q:

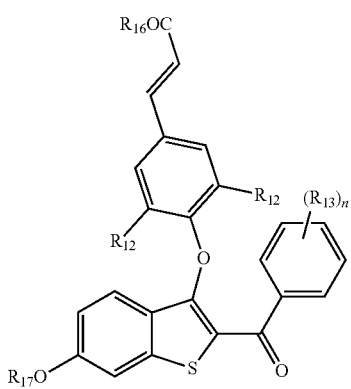

Formula Q wherein:
n is 0, 1, 2, 3, or 4;

R$_{12}$ and R$_{13}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{12}$ is independently selected at each occurrence from hydrogen, halogen, methyl and —CN.

In one embodiment R$_{16}$ is hydroxyl.

In one embodiment R$_{17}$ is hydrogen.

In another embodiment, the compound of Formula D has Formula R:

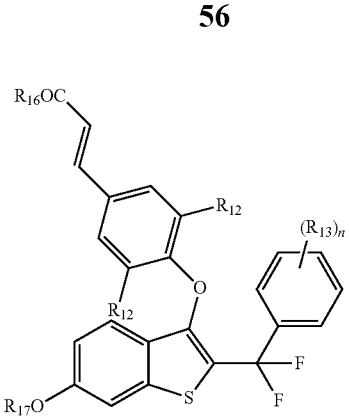

Formula R wherein
n is 0, 1, 2, 3, or 4;

R$_{12}$ and R$_{13}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{12}$ is independently selected at each occurrence from hydrogen, halogen, methyl and —CN.

In one embodiment R$_{16}$ is hydroxyl.

In one embodiment R$_{17}$ is hydrogen.

In another embodiment, the compound of Formula D has Formula S:

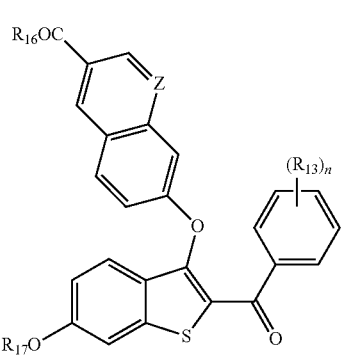

Formula S wherein:
Z is CH or N;
n is 0, 1, 2, 3, or 4; and

R$_{13}$ is selected at each occurrence from hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl;

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{16}$ is hydroxyl.

In one embodiment R$_{17}$ is hydrogen.

In another embodiment, the compound of Formula D has Formula T:

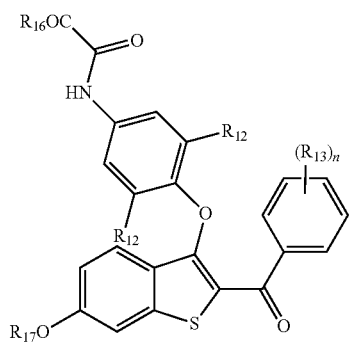

Formula T wherein:

n is 0, 1, 2, 3, or 4;

R$_{12}$ and R$_{13}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, alkyl, arylalkyl, aryloxy, heteroarylalkyl, and C$_1$-C$_6$fluoroalkyl;

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{12}$ is independently selected at each occurrence from hydrogen, halogen, methyl and —CN.

In one embodiment R$_{16}$ is hydroxyl.

In one embodiment R$_{17}$ is hydrogen.

In another embodiment, the compound of Formula D has Formula U:

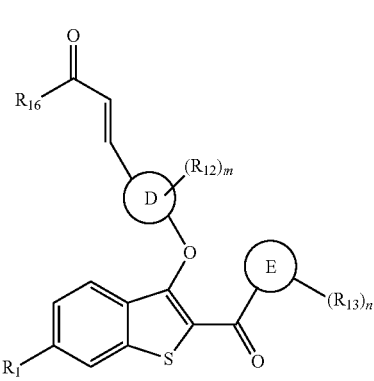

Formula U wherein:

m is 0, 1, 2, 3, or 4;

n is 0, 1, 2, 3, or 4;

Ring D is phenyl, naphthyl, quinolinyl, 5- or 6-membered monocyclic heteroaryl, cycloalkyl, or 7-, 8-, 9- or 10 membered bicyclic heterocyclyl;

Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;

R$_1$ is selected from hydroxyl, —OR$_{17}$, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);

R$_{12}$ and R$_{13}$ are independently selected at each occurrence from —OR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, alkyl, arylalkyl, aryloxy, heteroarylalkyl, and C$_1$-C$_6$fluoroalkyl;

R$_{15}$ is independently selected at each occurrence from hydrogen, alkyl, alkenyl, alkynyl, cycloalkyl, aryl, arylalkyl, heteroaryl, and heteroarylalkyl;

R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In one embodiment R$_{16}$ is hydroxyl.

In another embodiment, the compound of Formula D has Formula V:

Formula V

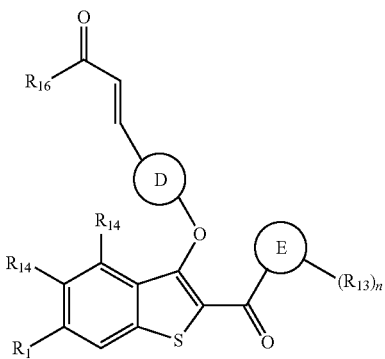

wherein:

n is 0, 1, 2, 3, or 4;

Ring D is phenyl, naphthyl, quinolinyl, 5- or 6-membered monocyclic heteroaryl, cycloalkyl, or 7-, 8-, 9- or 10-membered bicyclic heterocyclyl;

Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;

$R_1$ is selected from hydroxyl, —$OR_{17}$, hydrogen, halogen, —O($C_1$-$C_6$ alkyl), —OC(O)($C_1$-$C_6$ alkyl), —OC(O)$C_6H_5$, —OC(O)O($C_1$-$C_6$ alkyl), —OC(O)O$C_6H_5$ and —O$SO_2$($C_2$-$C_6$ alkyl);

$R_{13}$ and $R_{14}$ are independently selected at each occurrence from hydrogen, aryl, heteroaryl, halogen, —CN, —$NO_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —$SF_5$, —B(OH)$_2$, —B(O$R_{15}$)$_2$, —C(O)O$R_{15}$, —C(O)$R_{16}$, —C(S)O$R_{15}$, —C(S)$R_{16}$, —O$SO_2$O$R_{15}$, —O$SO_2R_{16}$, —NH$SO_2$O$R_{15}$, —NH$SO_2R_{16}$, —N(alkyl)$SO_2$O$R_{15}$, —N(alkyl)$SO_2R_{16}$, —OP(O)(O$R_{15}$)$_2$, —OP(O)($R_{16}$)$_2$, —P(O)(O$R_{15}$)$_3$, —P(O)($R_{16}$)$_3$, —P(O)O$R_{15}$, —P(O)$R_{16}$, —$SO_2R_{16}$, —$SO_2$O$R_{15}$, alkyne, alkene, alkyl, arylalkyl, aryloxy, heteroarylalkyl, and $C_1$-$C_6$fluoroalkyl;

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N($R_{15}$)$_2$, —S$R_{15}$, —O$R_{15}$; and $R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment $R_{16}$ is hydroxyl.

In an alternative embodiment, a compound of Formula W is provided:

Formula W

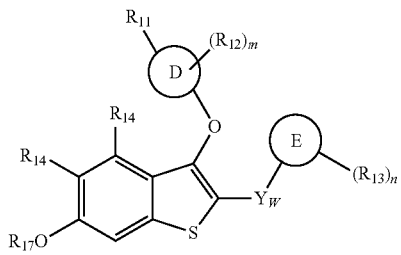

wherein:

m is 0, 1, 2, 3, or 4;
n is 0, 1, 2, 3, or 4;

$X_D$ is selected from —O—, —$CH_2$—, —S—, —$NR_{17}$—, —CHF—, —$CF_2$—, and cycloalkyl;

$Y_W$ is $C_2$-$C_6$alkynylene;

Ring D is phenyl, naphthyl, quinolinyl, 5- or 6-membered monocyclic heteroaryl, cycloalkyl, or 7-, 8-, 9- or 10-membered bicyclic heterocyclyl;

Ring E is phenyl, heteroaryl, thiophenyl (i.e., thienyl), 5- or 6-membered monocyclic heteroaryl, cycloalkyl or 7-, 8-, 9- or 10-membered bicyclic heterocyclyl;

$R_{11}$ is selected from —CH═CHCOO$R_{17}$, —$NR_{17}$(CO)COO$R_{17}$, —COO$R_{17}$, cycloalkyl-COO$R_{17}$, —$C_2$-$C_6$alkenylene-COO$R_{17}$, —$C_2$-$C_6$alkynylene-COO$R_{17}$, —CH═CHC(O)$R_{16}$, —$NR_{17}$(CO)C(O)$R_{16}$, —C(O)$R_{16}$, -cycloalkyl-C(O)$R_{16}$, —$C_2$-$C_6$alkenylene-C(O)$R_{16}$ and —$C_2$-$C_6$alkynylene-C(O)$R_{16}$;

$R_{12}$, $R_{13}$, and $R_{14}$ are independently selected at each occurrence from —O$R_{15}$, —S$R_{15}$, —N($R_{15}$)$_2$, hydrogen, aryl, heteroaryl, halogen, —CN, —$NO_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —$SF_5$, —B(OH)$_2$, —B(O$R_{15}$)$_2$, —C(O)O$R_{15}$, —C(O)$R_{16}$, —C(S)O$R_{15}$, —C(S)$R_{16}$, —O$SO_2$O$R_{15}$, —O$SO_2R_{16}$, —NH$SO_2$O$R_{15}$, —NH$SO_2R_{16}$, —N(alkyl)$SO_2$O$R_{15}$, —N(alkyl)$SO_2R_{16}$, OP(O)(O$R_{15}$)$_2$, OP(O)(O$R_{16}$)$_2$, —P(O)(O$R_{15}$)$_3$, —P(O)($R_{16}$)$_3$, —P(O)O$R_{15}$, —P(O)$R_{16}$, —$SO_2R_{16}$, —$SO_2$O$R_{15}$, alkyne, alkene, arylalkyl, aryloxy, heteroarylalkyl, and $C_1$-$C_6$fluoroalkyl;

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N($R_{15}$)$_2$, —S$R_{15}$, —O$R_{15}$; and $R_{17}$ is independently selected at each occurrence from hydrogen, alkyl, alkenyl, alkynyl, cycloalkyl, aryl, —C(O)$R_{15}$, —C(S)$R_{15}$, —C(O)$R_{16}$, —C(S)$R_{16}$, and heteroaryl.

In one embodiment, the variables above are selected such that a stable compound results with a shelf life of at least three months in solid form under ambient conditions.

In one embodiment the compound is selected from Formula G and $R_1$ is hydroxyl, halogen, or —O($C_1$-$C_6$ alkyl).

In one embodiment the compound is selected from Formula A and $R_1$ is hydroxyl, halogen, or —O($C_1$-$C_6$ alkyl).

In one embodiment the compound is selected from Formula B and $R_1$ is hydroxyl, halogen, or —O($C_1$-$C_6$ alkyl).

In one embodiment the compound is selected from Formula C and $R_1$ is hydroxyl, halogen, or —O($C_1$-$C_6$ alkyl).

In one embodiment the compound is selected from Formula D and $R_{10}$ is hydroxyl, halogen, or —O($C_1$-$C_6$ alkyl).

In one embodiment the compound is selected from Formula E and $R_{10}$ is hydroxyl, halogen, or —O($C_1$-$C_6$ alkyl).

In one embodiment the compound is selected from Formula F and $R_{10}$ is hydroxyl, halogen, or —O($C_1$-$C_6$ alkyl).

In one embodiment $R_2$ is —COOH or —C(O)$R_{16}$.

In one embodiment $R_2$ is

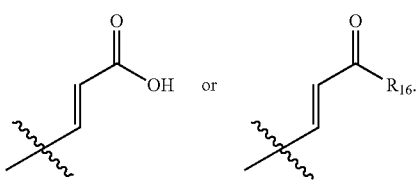

In one embodiment the compound is selected from Formula G and $R_2$ is

In one embodiment the compound is selected from Formula A and R$_2$ is

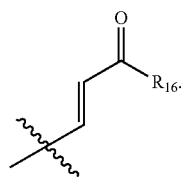

In one embodiment the compound is selected from Formula B and R$_2$ is

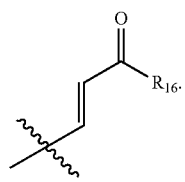

In one embodiment the compound is selected from Formula C and R$_2$ is

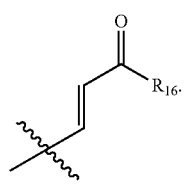

In one embodiment the compound is selected from Formula D and R$_{11}$ is

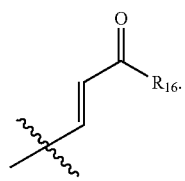

In one embodiment the compound is selected from Formula E and R$_{11}$

In one embodiment the compound is selected from Formula G and R$_2$ is

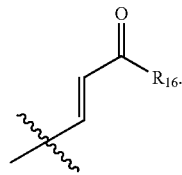

In one embodiment the compound is selected from Formula G and R$_2$ is

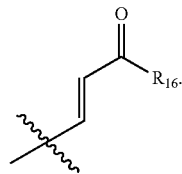

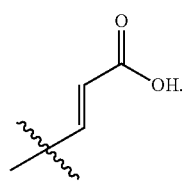 [SMILES: */C=C/C(=O)O]

In one embodiment the compound is selected from Formula A and R$_2$ is —COR$_{16}$.
In one embodiment the compound is selected from Formula B and R$_2$ is —COR$_{16}$.
In one embodiment the compound is selected from Formula C and R$_2$ is —COR$_{16}$.
In one embodiment the compound is selected from Formula D and R$_2$ is —COR$_{16}$.
In one embodiment the compound is selected from Formula E and R$_2$ is —COR$_{16}$.
In one embodiment the compound is selected from Formula A and R$_2$ is COOH or

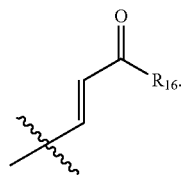

In one embodiment the compound is selected from Formula B and R$_2$ is —COOH or

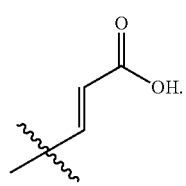 [SMILES: */C=C/C(=O)O]

In one embodiment the compound is selected from Formula C and $R_2$ is —COOH or

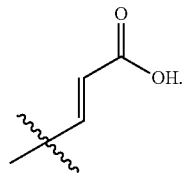 [SMILES: */C=C/C(=O)O]

In one embodiment the compound is selected from Formula D and $R_{11}$ is —COOH or

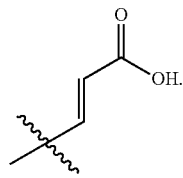 [SMILES: */C=C/C(=O)O]

In one embodiment the compound is selected from Formula E and $R_{11}$ is —COOH or

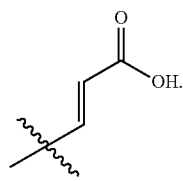 [SMILES: */C=C/C(=O)O]

In one embodiment the compound is selected from Formula G and $R_2$ is —COOH or

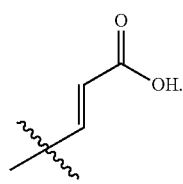 [SMILES: */C=C/C(=O)O]

In one embodiment $R_3$ is fluorine.
In one embodiment $R_3$ is chlorine.
In one embodiment $R_3$ is methyl.
In one embodiment the compound is selected from Formula A and $R_3$ is halogen or $C_1$-$C_6$alkyl, including methyl, ethyl, propyl, and isopropyl.
In one embodiment the compound is selected from Formula B and $R_3$ is halogen or $C_1$-$C_6$alkyl, including methyl, ethyl, propyl, and isopropyl.
In one embodiment the compound is selected from Formula C and $R_3$ is halogen or $C_1$-$C_6$alkyl, including methyl, ethyl, propyl, and isopropyl.
In one embodiment the compound is selected from Formula D and $R_{12}$ is halogen or $C_1$-$C_6$alkyl, including methyl, ethyl, propyl, and isopropyl.
In one embodiment the compound is selected from Formula E and $R_{12}$ is halogen or $C_1$-$C_6$alkyl, including methyl, ethyl, propyl, and isopropyl.
In one embodiment the compound is selected from Formula F and $R_{12}$ is halogen or $C_1$-$C_6$alkyl, including methyl, ethyl, propyl, and isopropyl.
In one embodiment the compound is selected from Formula G and $R_3$ is halogen or $C_1$-$C_6$alkyl, including methyl, ethyl, propyl, and isopropyl.
In one embodiment $R_4$ is halogen.
In one embodiment $R_4$ is $C_1$-$C_6$alkyl.
In one embodiment $R_4$ is hydroxyl.
In one embodiment $R_4$ is $OR_{15}$.
In one embodiment the compound is selected from Formula A and $R_4$ is halogen, $C_1$-$C_6$alkyl, or hydroxyl.
In one embodiment the compound is selected from Formula B and $R_4$ is halogen, $C_1$-$C_6$alkyl, or hydroxyl.
In one embodiment the compound is selected from Formula C and $R_4$ is halogen, $C_1$-$C_6$alkyl, or hydroxyl.
In one embodiment the compound is selected from Formula D and $R_{13}$ is halogen, $C_1$-$C_6$alkyl, or hydroxyl.
In one embodiment the compound is selected from Formula E and $R_{13}$ is halogen, $C_1$-$C_6$alkyl, or hydroxyl.
In one embodiment the compound is selected from Formula F and $R_{13}$ is halogen, $C_1$-$C_6$alkyl, or hydroxyl.
In one embodiment the compound is selected from Formula G and $R_4$ is halogen, $C_1$-$C_6$alkyl, or hydroxyl.
In one embodiment the compound is selected from Formula A and $R_4$ is $OR_{15}$.
In one embodiment the compound is selected from Formula B and $R_4$ is $OR_{15}$.
In one embodiment the compound is selected from Formula C and $R_4$ is $OR_{15}$.
In one embodiment the compound is selected from Formula D and $R_4$ is $OR_{15}$.
In one embodiment the compound is selected from Formula E and $R_4$ is $OR_{15}$.
In one embodiment the compound is selected from Formula F and $R_4$ is $OR_{15}$.
In one embodiment the compound is selected from Formula G and $R_4$ is $OR_{15}$.
In one embodiment m is 0.
In one embodiment m is 1.
In one embodiment m is 2
In one embodiment the compound is selected from Formula A and m is 0, 1, or 2.
In one embodiment the compound is selected from Formula B and m is 0, 1, or 2.
In one embodiment the compound is selected from Formula C and m is 0, 1, or 2.
In one embodiment the compound is selected from Formula D and m is 0, 1, or 2.
In one embodiment the compound is selected from Formula E and m is 0, 1, or 2.
In one embodiment the compound is selected from Formula F and m is 0, 1, or 2.
In one embodiment the compound is selected from Formula G and m is 0, 1, or 2.
In one embodiment n is 0.
In one embodiment n is 1.
In one embodiment n is 2
In one embodiment the compound is selected from Formula A and n is 0, 1, or 2.
In one embodiment the compound is selected from Formula B and n is 0, 1, or 2.
In one embodiment the compound is selected from Formula C and n is 0, 1, or 2.
In one embodiment the compound is selected from Formula D and n is 0, 1, or 2.

In one embodiment the compound is selected from Formula E and n is 0, 1, or 2.

In one embodiment the compound is selected from Formula F and n is 0, 1, or 2.

In one embodiment the compound is selected from Formula G and n is 0, 1, or 2.

In one embodiment X is —O—.

In one embodiment the compound is selected from Formula B and X is —O—.

In one embodiment the compound is selected from Formula C and X is —O—.

In one embodiment the compound is selected from Formula D and X is —O—.

In one embodiment the compound is selected from Formula F and X is —O—.

In one embodiment the compound is selected from Formula G and X is —O—.

In one embodiment Y is —CO—.

In one embodiment the compound is selected from Formula B and Y is —CO—.

In one embodiment the compound is selected from Formula C and Y is —CO—.

In one embodiment the compound is selected from Formula D and Y is —CO—.

In one embodiment the compound is selected from Formula F and Y is —CO—.

In one embodiment the compound is selected from Formula G and Y is —CO—.

In one embodiment Ring B is phenyl.

In one embodiment Ring B is napthyl.

In one embodiment Ring B is quinolinyl.

In one embodiment the compound is selected from Formula A and Ring B is phenyl, napthyl, or quinolinyl.

In one embodiment the compound is selected from Formula B and Ring B is phenyl, napthyl, or quinolinyl.

In one embodiment the compound is selected from Formula C and Ring B is phenyl, napthyl, or quinolinyl.

In one embodiment the compound is selected from Formula D and Ring D is phenyl, napthyl, or quinolinyl.

In one embodiment the compound is selected from Formula E and Ring D is phenyl, napthyl, or quinolinyl.

In one embodiment the compound is selected from Formula F and Ring D is phenyl, napthyl, or quinolinyl.

In one embodiment the compound is selected from Formula G and Ring B is phenyl, napthyl, or quinolinyl.

In one embodiment Ring C is phenyl.

In one embodiment the compound is selected from Formula A and Ring C is phenyl.

In one embodiment the compound is selected from Formula B and Ring C is phenyl.

In one embodiment the compound is selected from Formula C and Ring C is phenyl.

In one embodiment the compound is selected from Formula D and Ring E is phenyl.

In one embodiment the compound is selected from Formula E and Ring E is phenyl.

In one embodiment the compound is selected from Formula F and Ring E is phenyl.

In one embodiment m and n are 0.

In one embodiment m is 0 and n is 1.

In one embodiment m is 0 and n is 2.

In one embodiment m is 1 and n is 0.

In one embodiment m is 1 and n is 1.

In one embodiment m is 1 and n is 2.

In one embodiment m is 2 and n is 0.

In one embodiment m is 2 and n is 1.

In one embodiment m is 2 and n is 2.

In one embodiment X is —O— and Y is —C(O)—.

In one embodiment $R_1$ is hydroxyl, X is —O—, and Y is —C(O).

In one embodiment $R_1$ is hydroxyl, X is —O—, Y is —C(O), and $R_2$ is

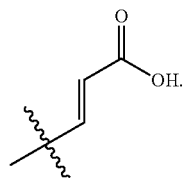 [SMILES: */C=C/C(=O)O]

In one embodiment $R_1$ is hydroxyl, X is —O—, Y is —C(O), and $R_2$ is

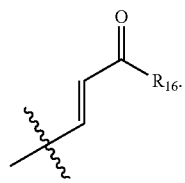

In one embodiment $R_1$ is hydroxyl, X is —O—, Y is —C(O), and n is 0.

In one embodiment $R_1$ is hydroxyl, X is —O—, Y is —C(O), and m is 0.

In one embodiment $R_1$ is hydroxyl, X is —O—, Y is —C(O), Ring B is phenyl and $R_2$ is

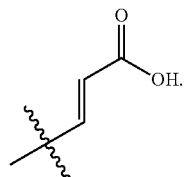 [SMILES: */C=C/C(=O)O]

In one embodiment $R_1$ is hydroxyl, X is —O—, Y is —C(O), Ring B is phenyl and $R_2$ is

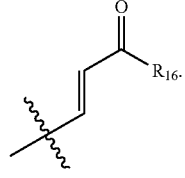

In one embodiment $R_1$ is hydroxyl, X is —O—, Y is —C(O), and Ring B is napthyl, and $R_2$ is —COOH.

In one embodiment $R_1$ is hydroxyl, X is —O—, Y is —C(O), and Ring B is quinolinyl, and $R_2$ is —COOH.

Non-limiting examples of compounds of the present invention include:

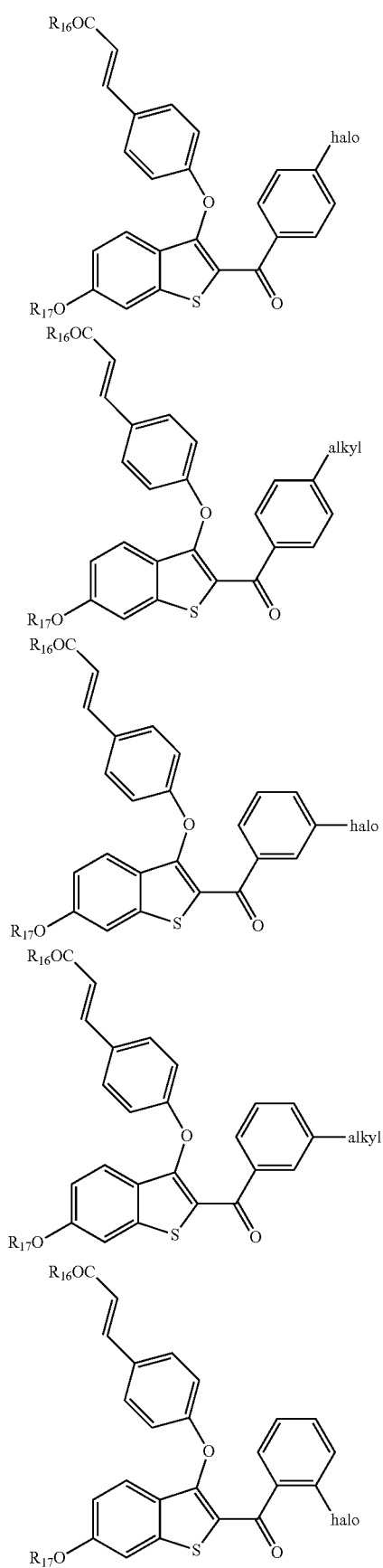
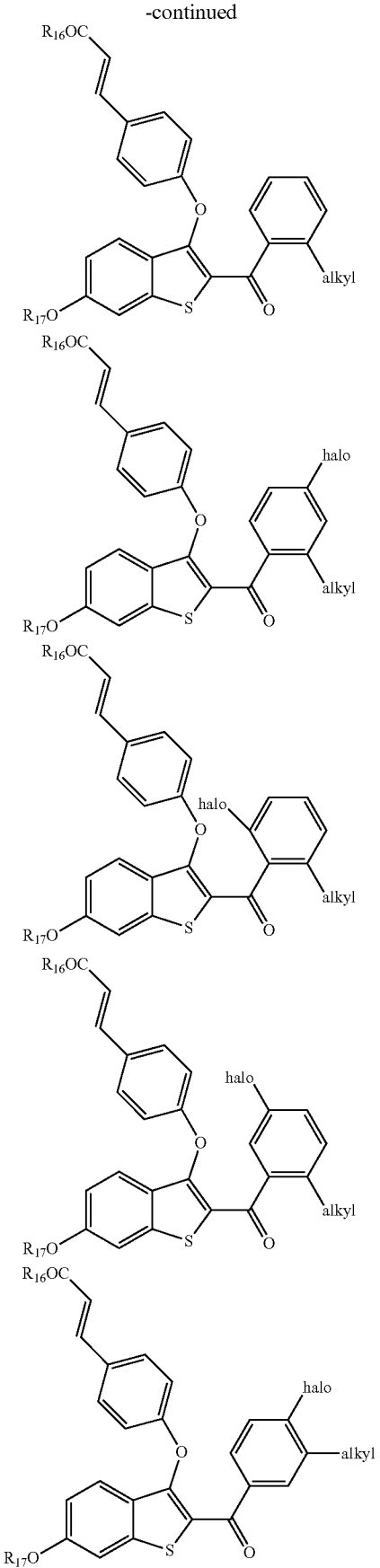
-continued

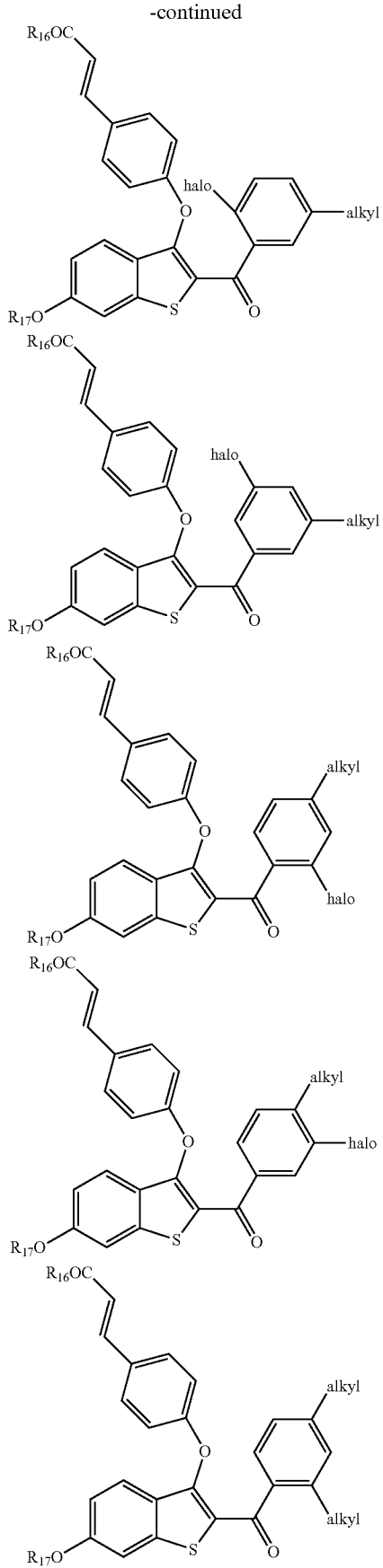
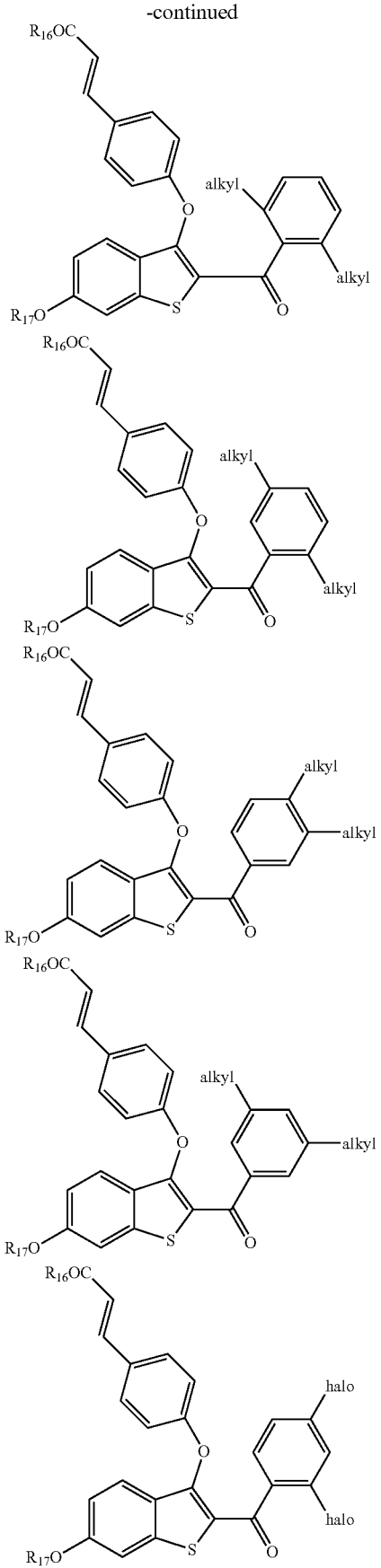

-continued

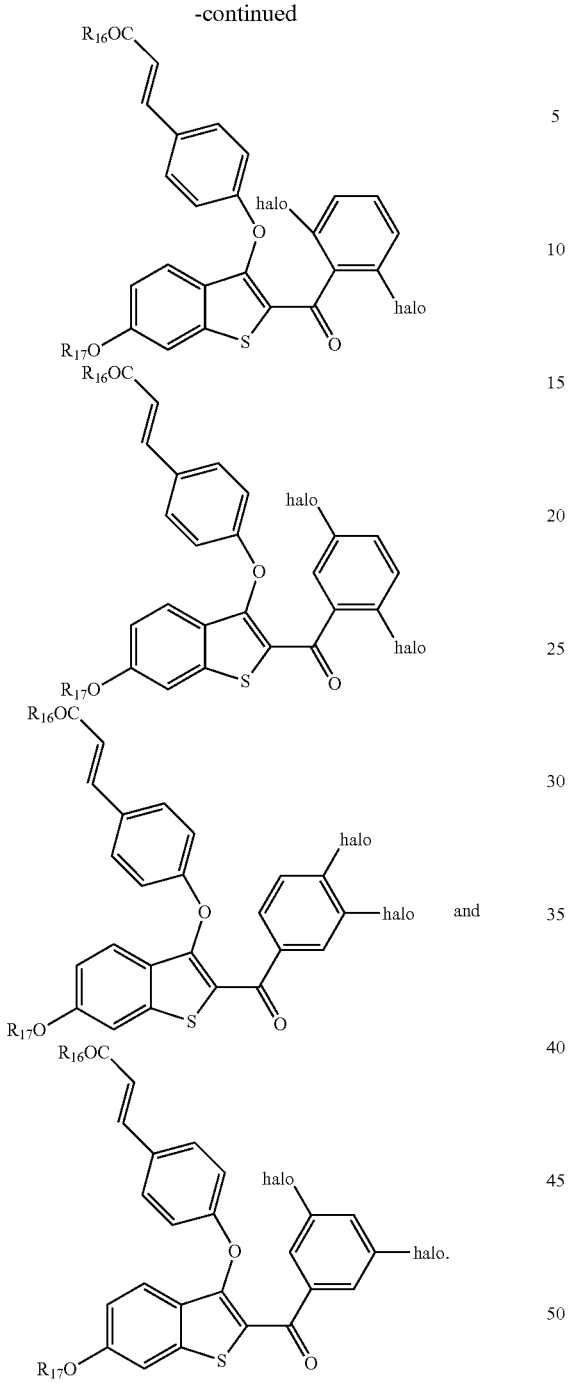

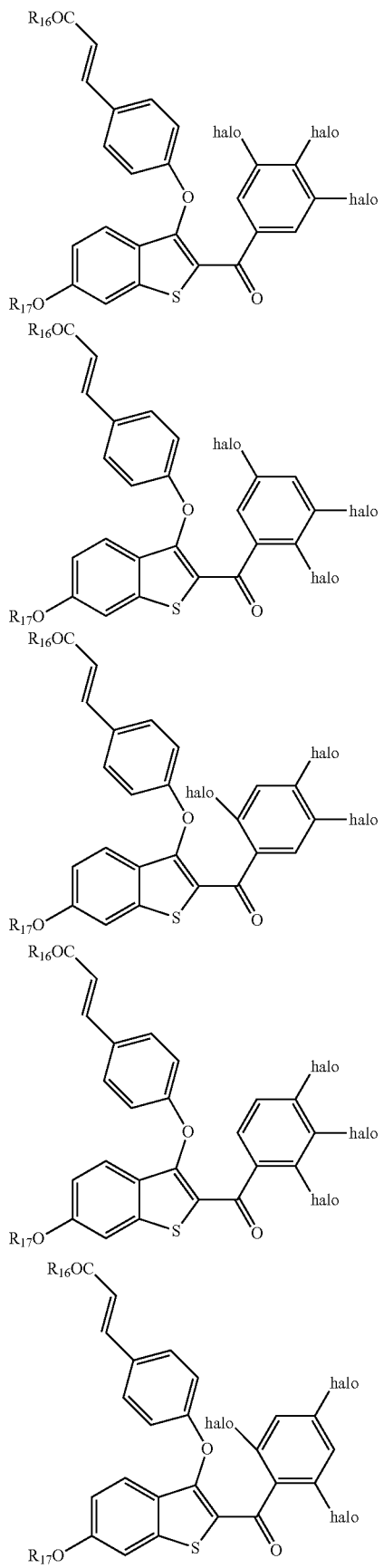

In certain embodiments of the above structures, alkyl is methyl. In other embodiments of the above structures embodiments, alkyl is independently methyl, ethyl, propyl or cyclopropyl. In some embodiments of the above embodiments, halo is fluoro. In some embodiments, haloalkyl is independently mono-, di- or trifluoro-methyl. In certain embodiments where the benzene ring has two halos, the halos can be one fluoro one chloro, two fluoros, or two chloros. In certain embodiments where the benzene ring has three halos, the halos can be one fluoro two chloros, two fluoros one chloro, three fluoros, or three chloros.

Additional non-limiting examples of compounds of the present invention include:

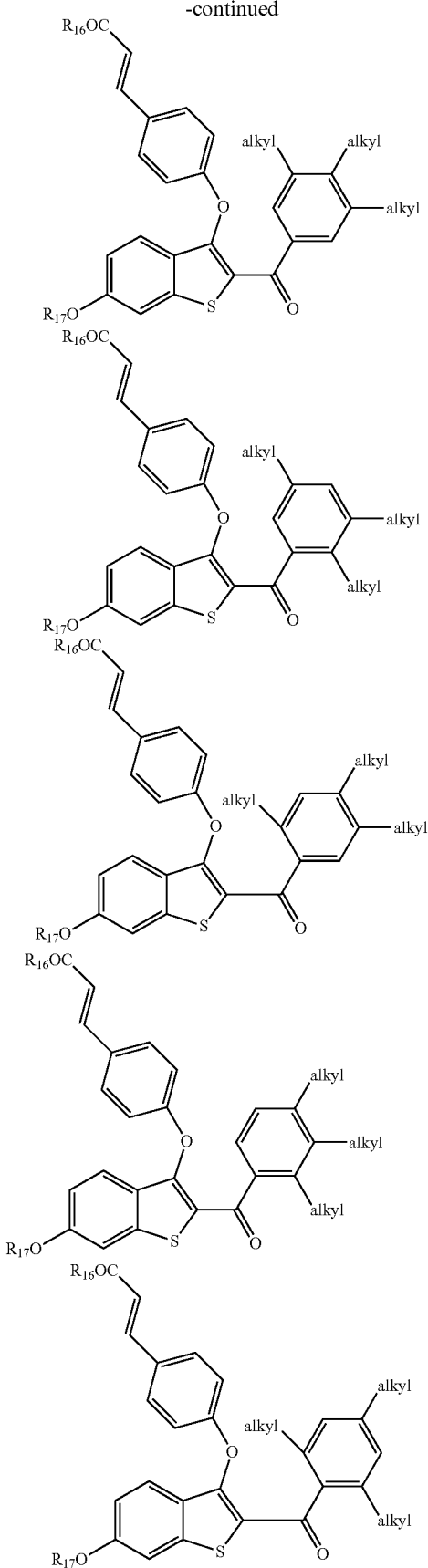
Additional non-limiting examples of compounds of the present invention include:
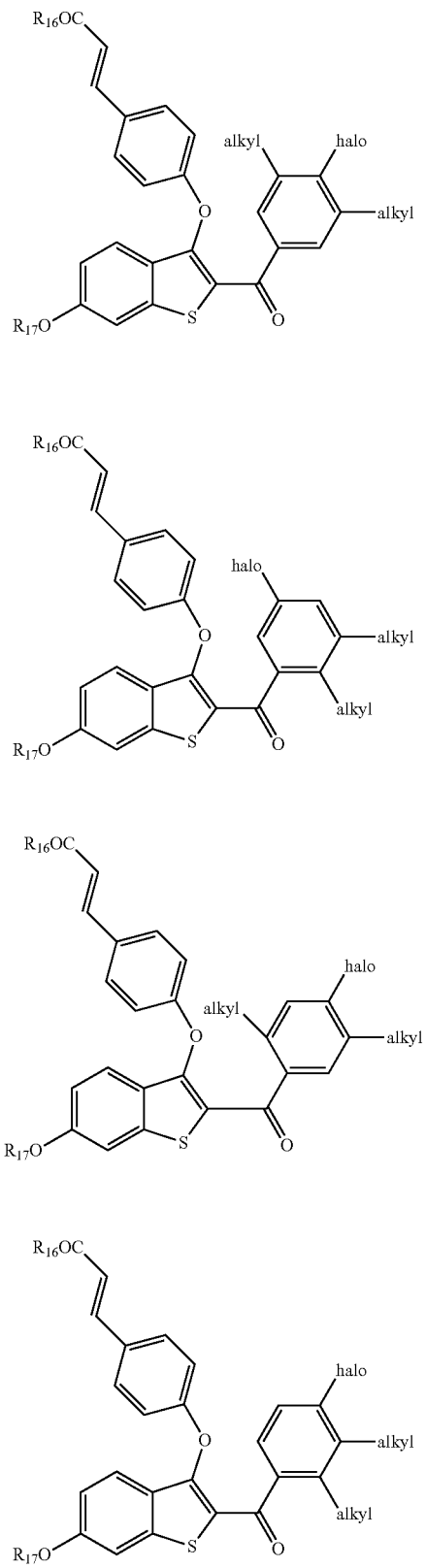
and -continued
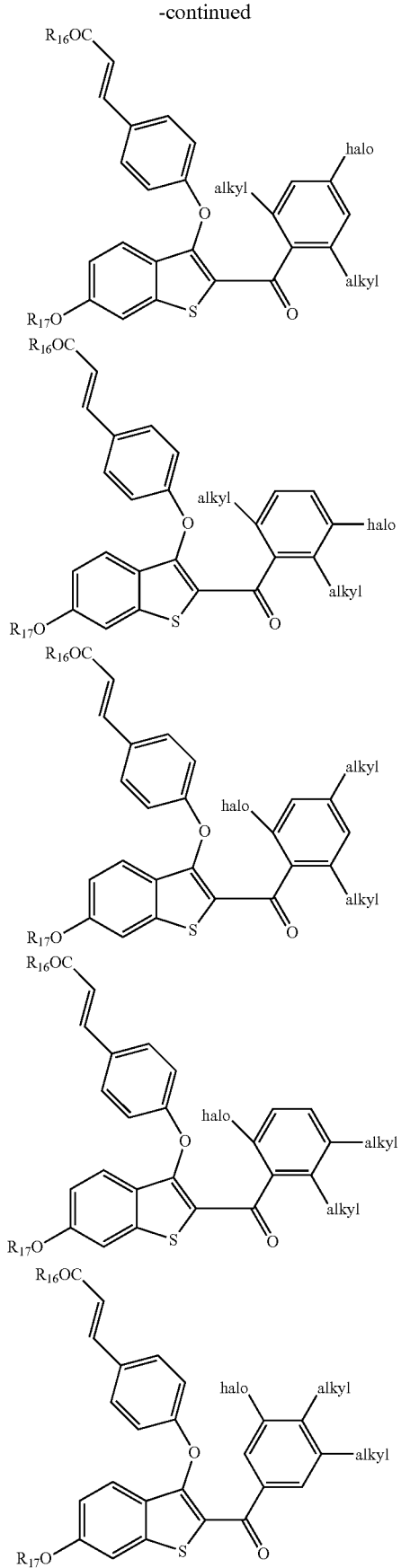
-continued
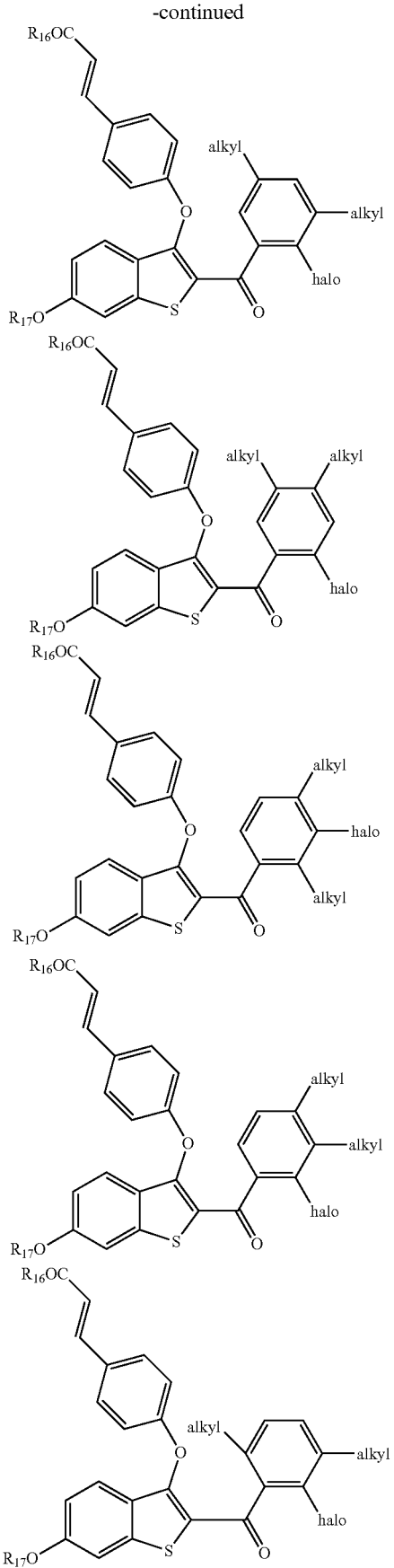

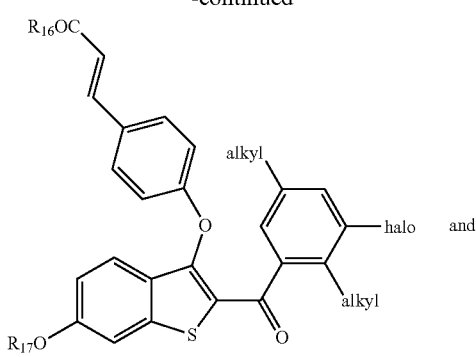
and
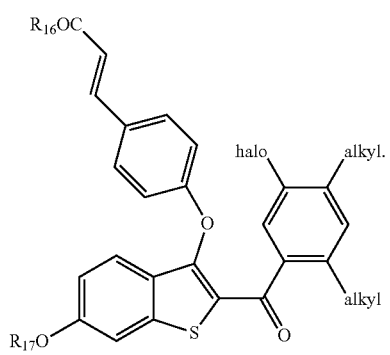
Additional non-limiting examples of compounds of the present invention include:
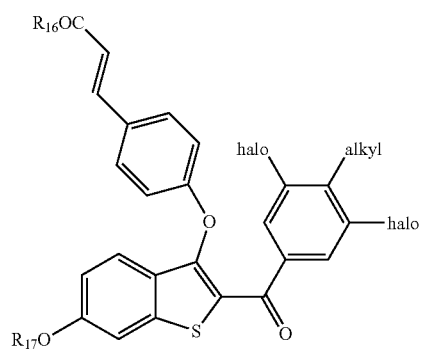
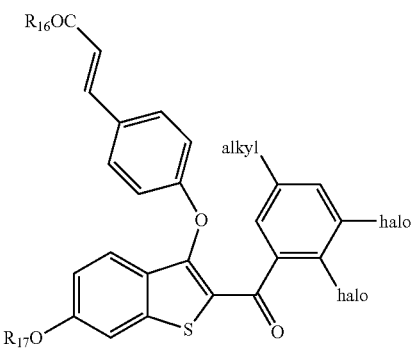
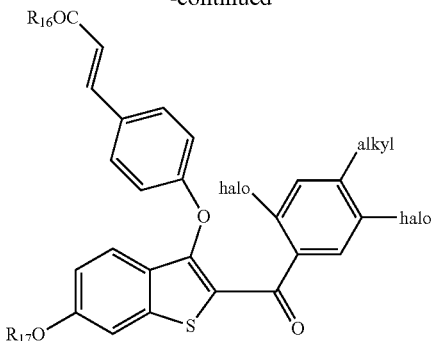
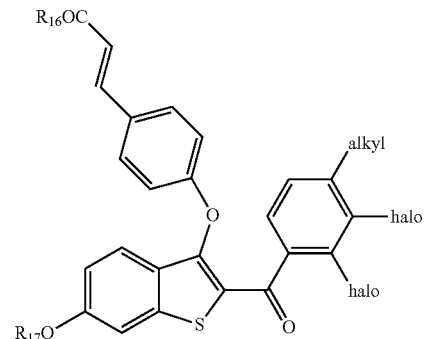
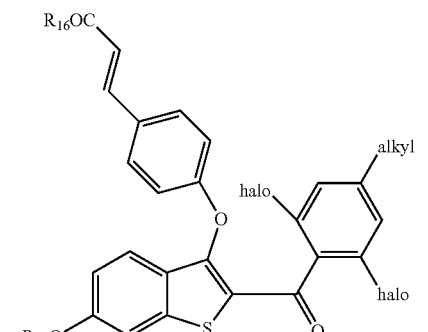
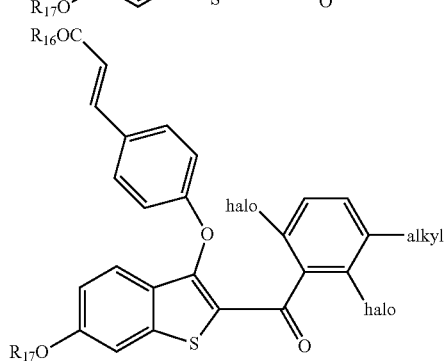
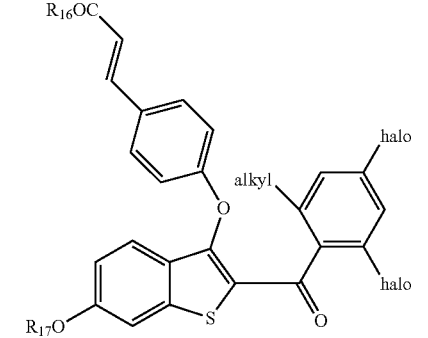

-continued
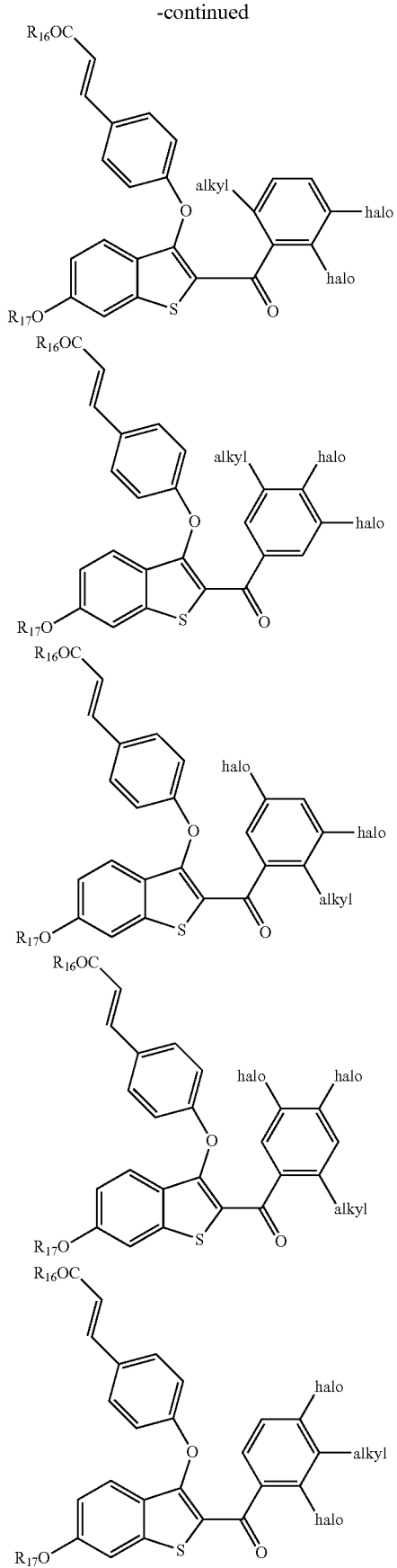
-continued
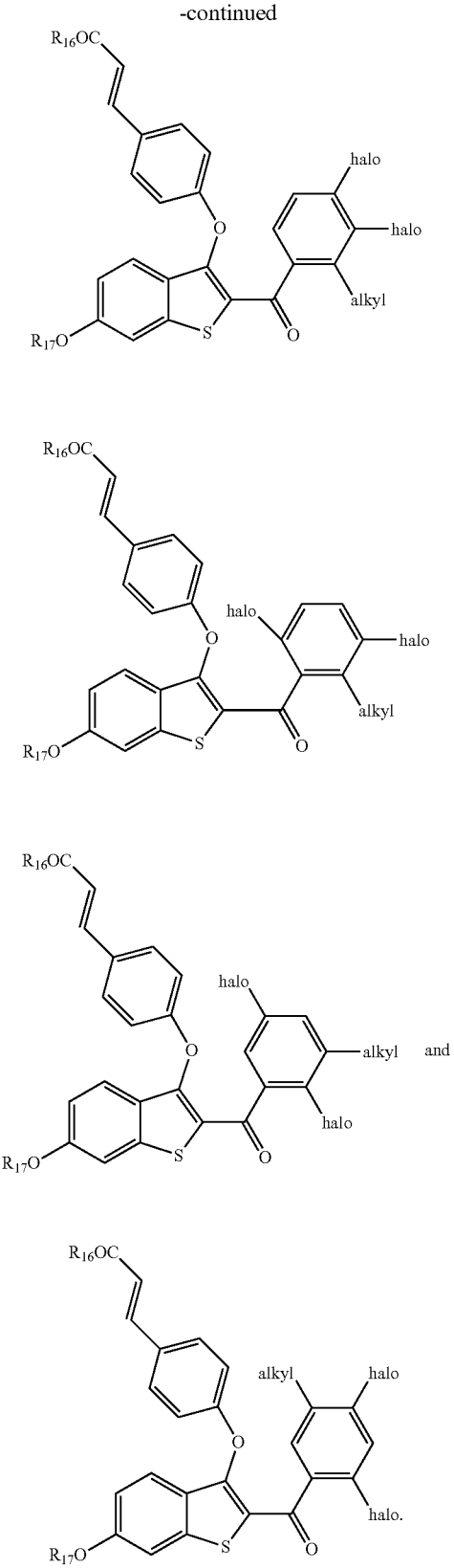
Additional non-limiting examples of compounds of the present invention include:

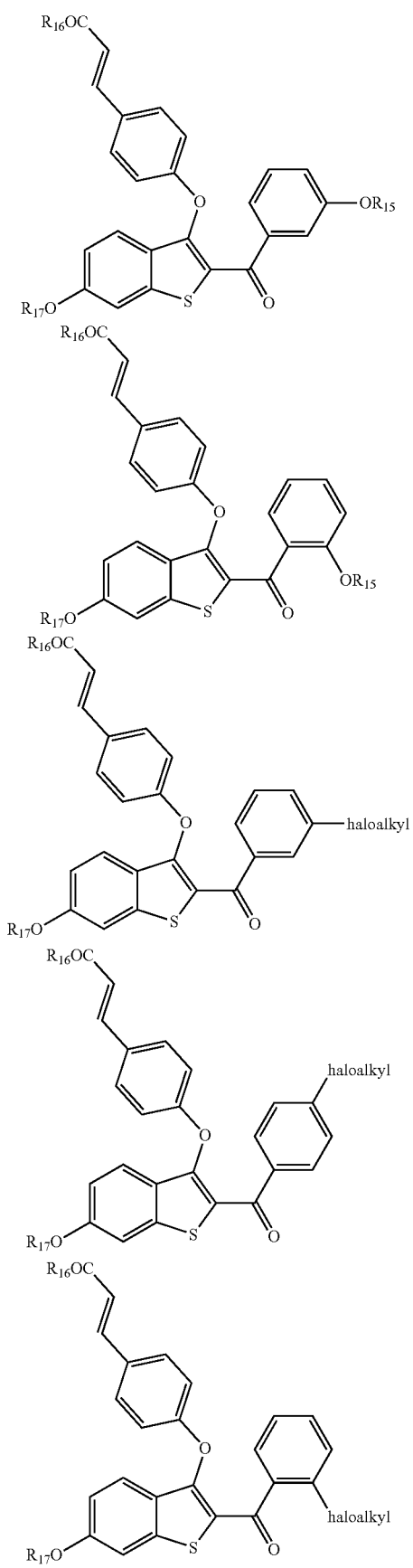

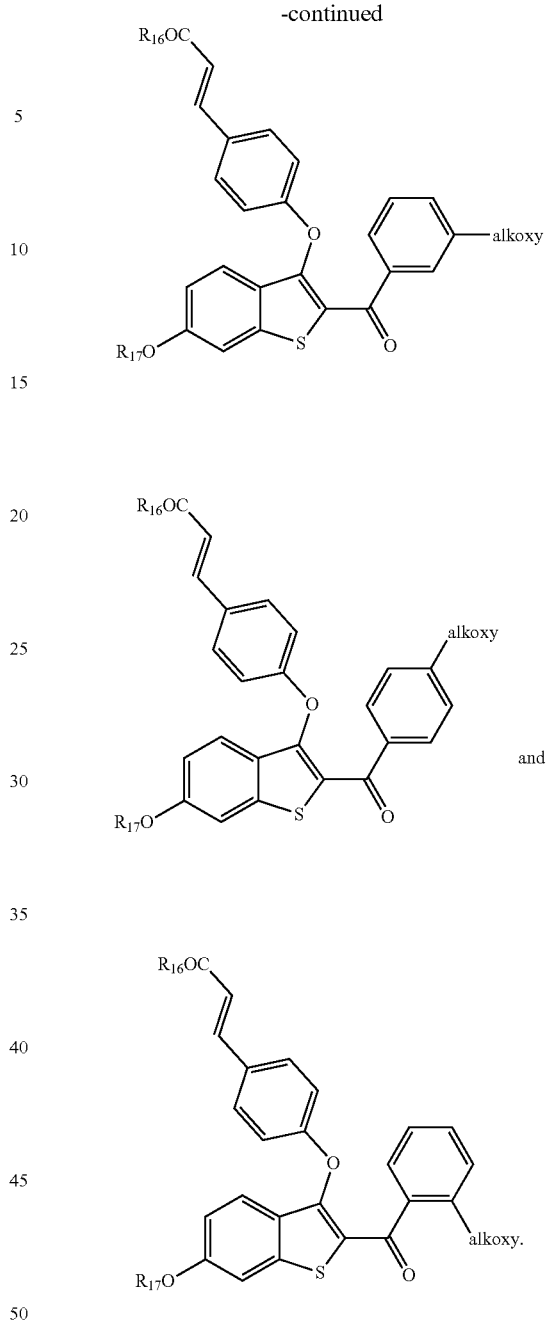

In certain embodiments of the above structures, alkyl is methyl. In other embodiments of the above structures embodiments, alkyl is independently methyl, ethyl, propyl or cyclopropyl. In some embodiments of the above embodiments, halo is fluoro. In some embodiments, haloalkyl is independently mono-, di- or trifluoro-methyl. In certain embodiments where the benzene ring has two halos, the halos can be one fluoro one chloro, two fluoros, or two chloros. In certain embodiments where the benzene ring has three halos, the halos can be one fluoro two chloros, two fluoros one chloro, three fluoros, or three chloros.

Representative compounds of the invention include, but are not limited to compounds of formula:

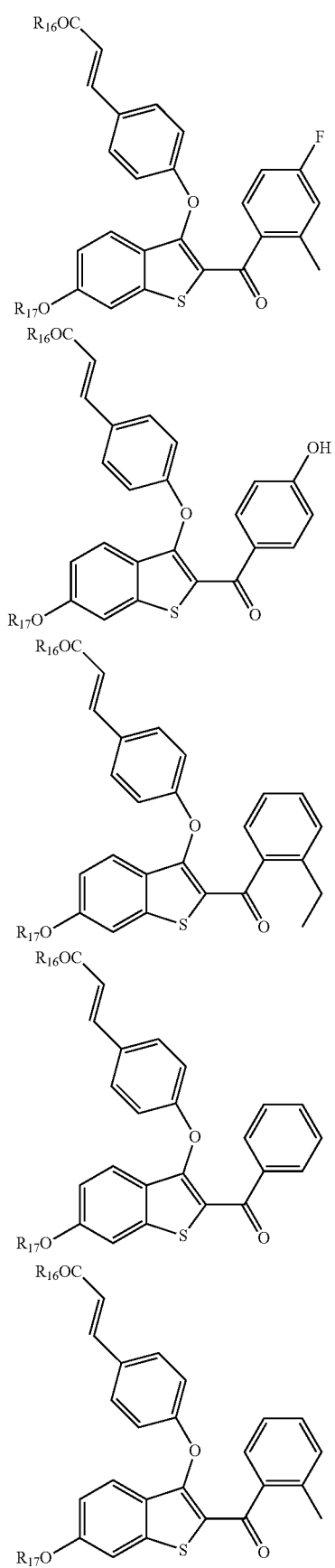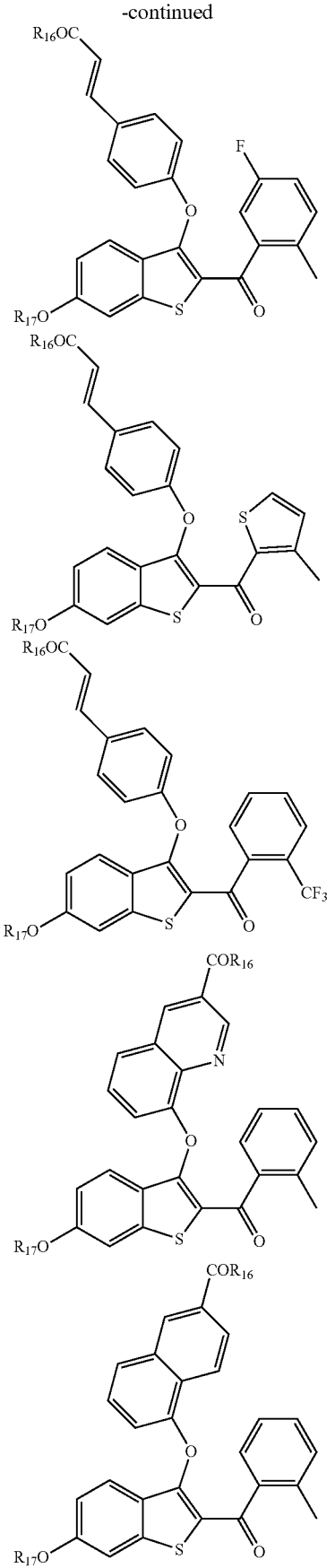

85
-continued
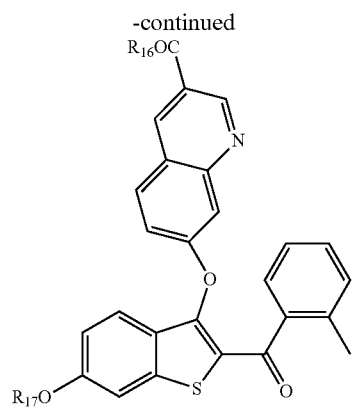
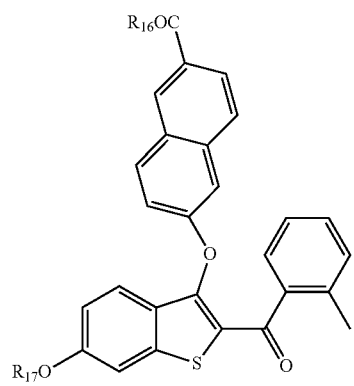
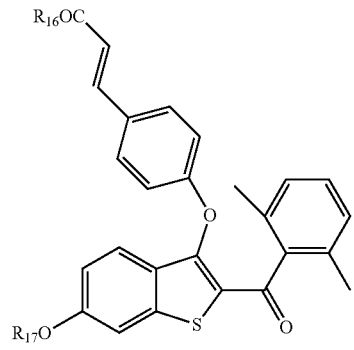
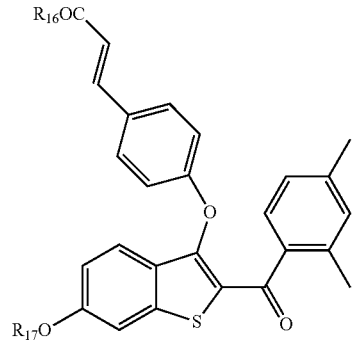
86
-continued
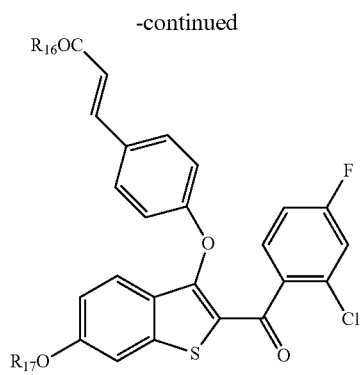
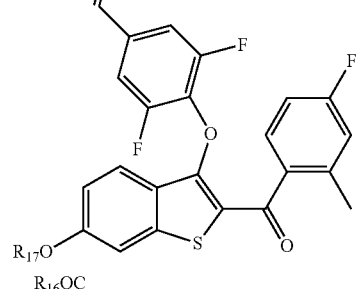
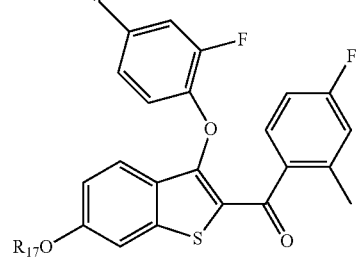
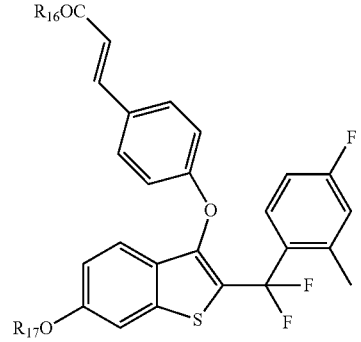
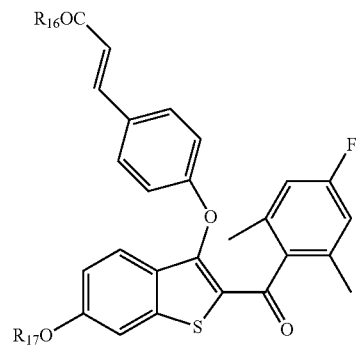

87
-continued
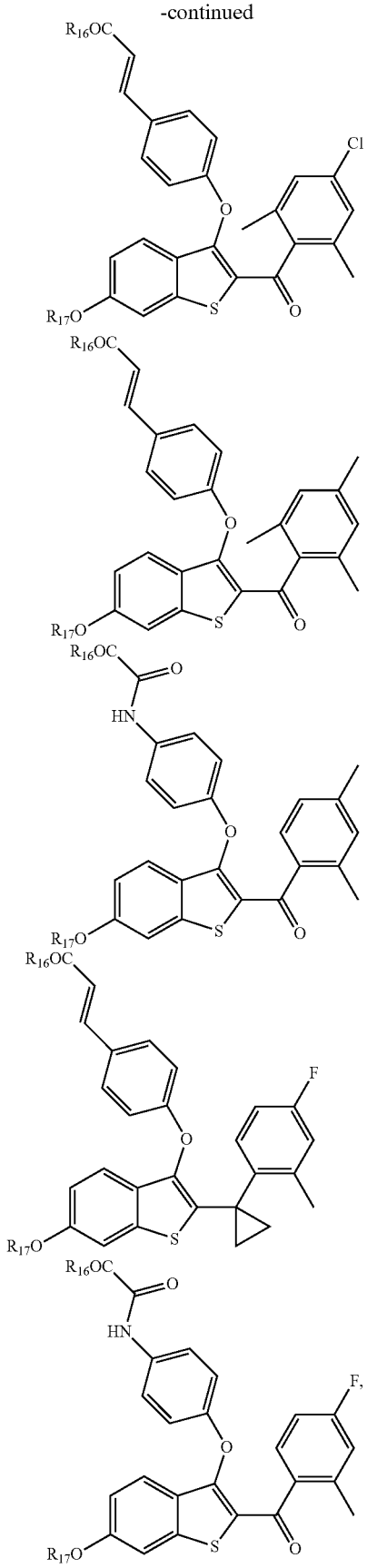
or a pharmaceutically acceptable salt thereof.
88
Additional representative compounds of the invention include, but are not limited to compounds of formula:
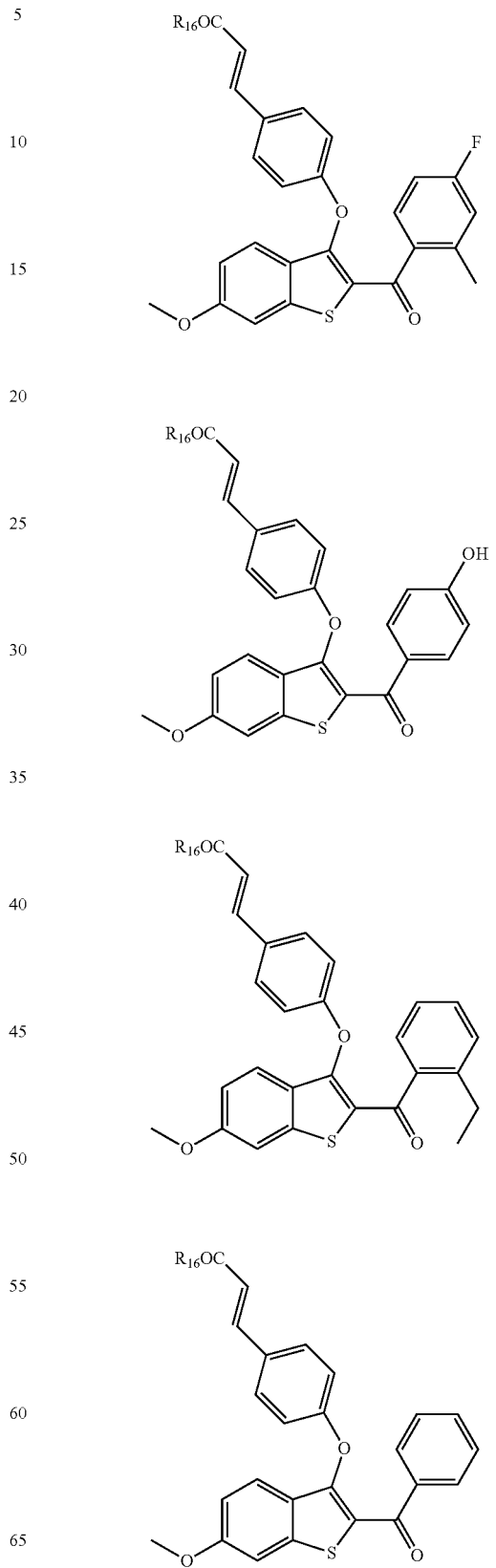
and

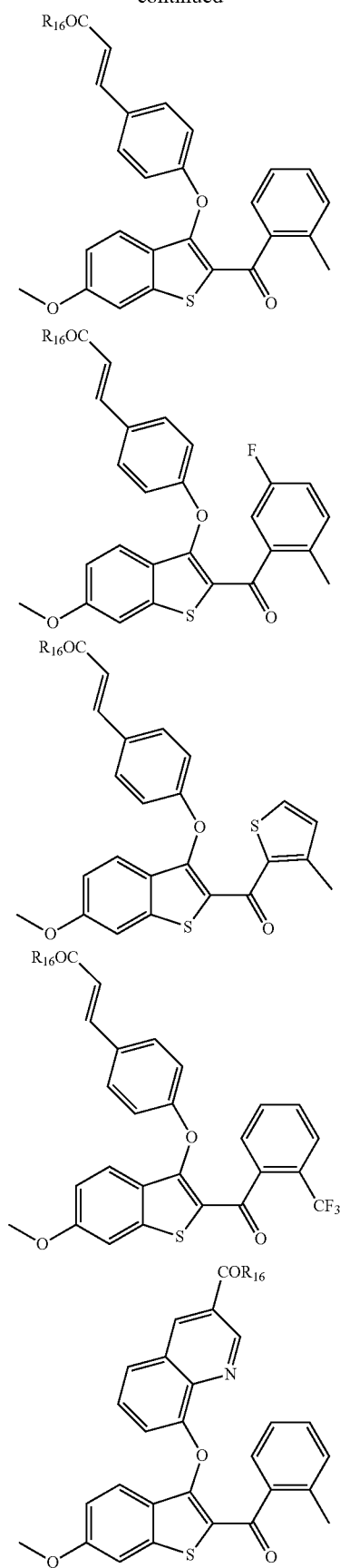
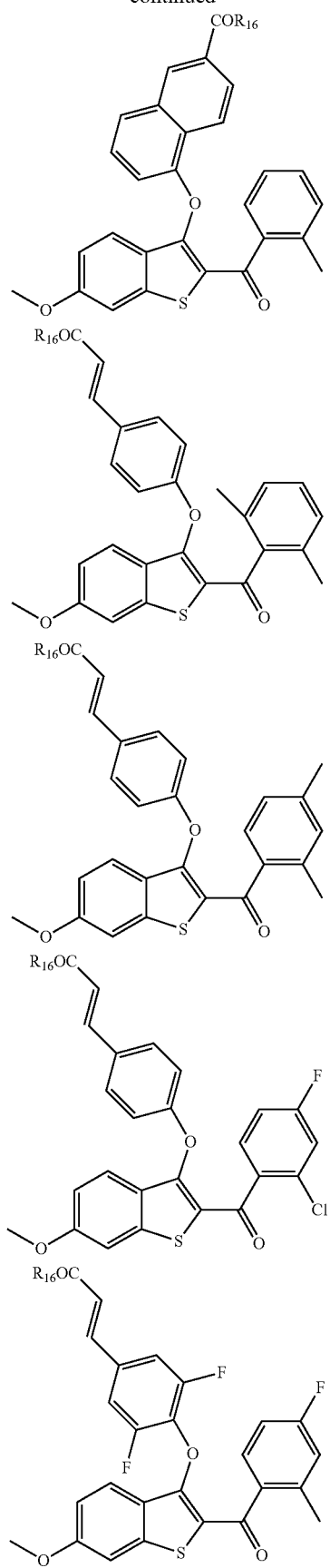

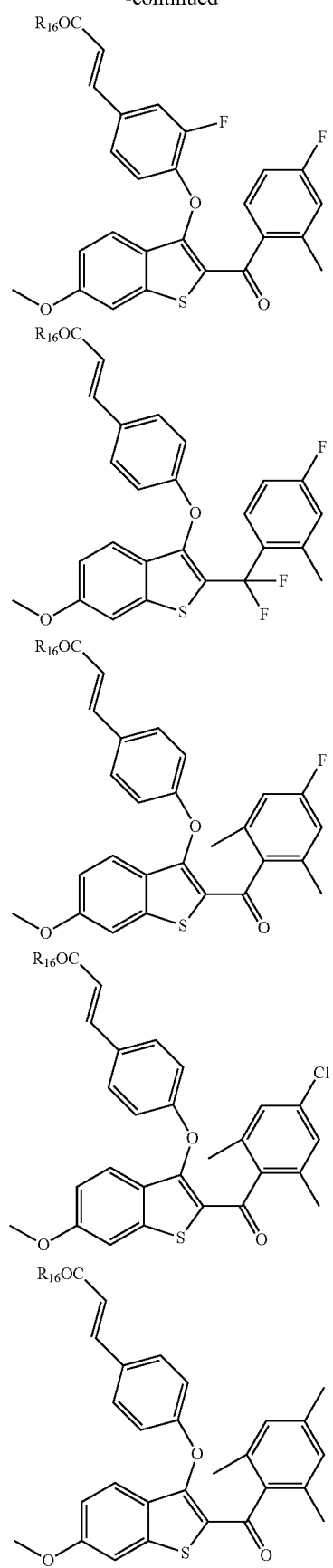
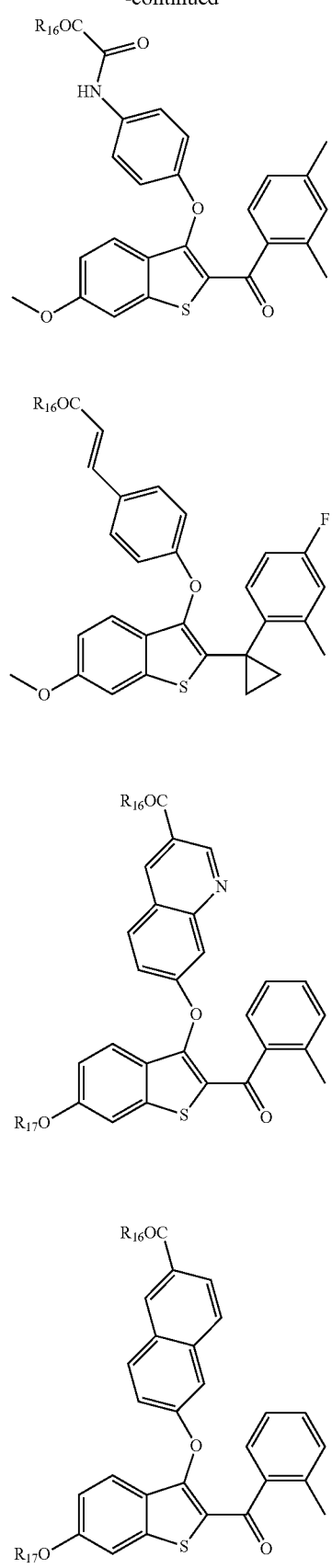

-continued
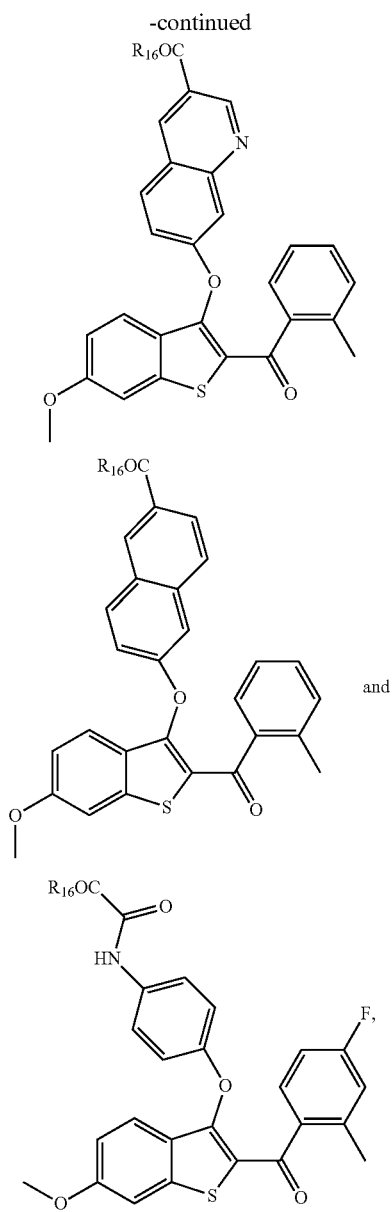
or a pharmaceutically acceptable salt thereof.
Additional representative compounds of the invention include, but are not limited to compounds of formula:
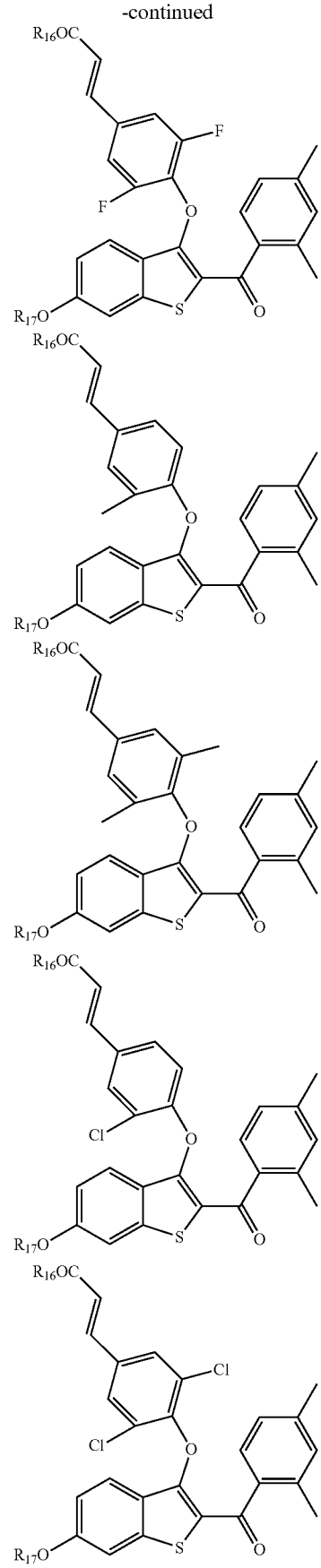

-continued
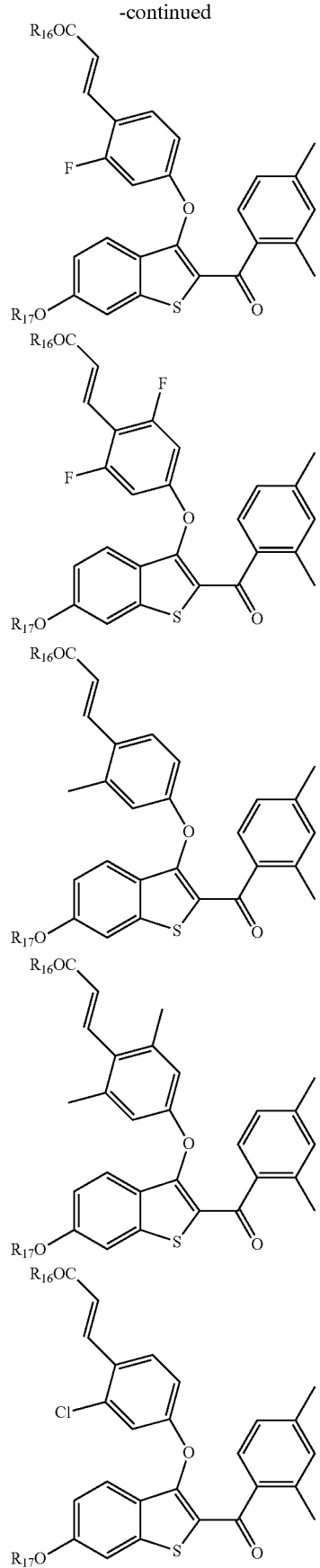
-continued
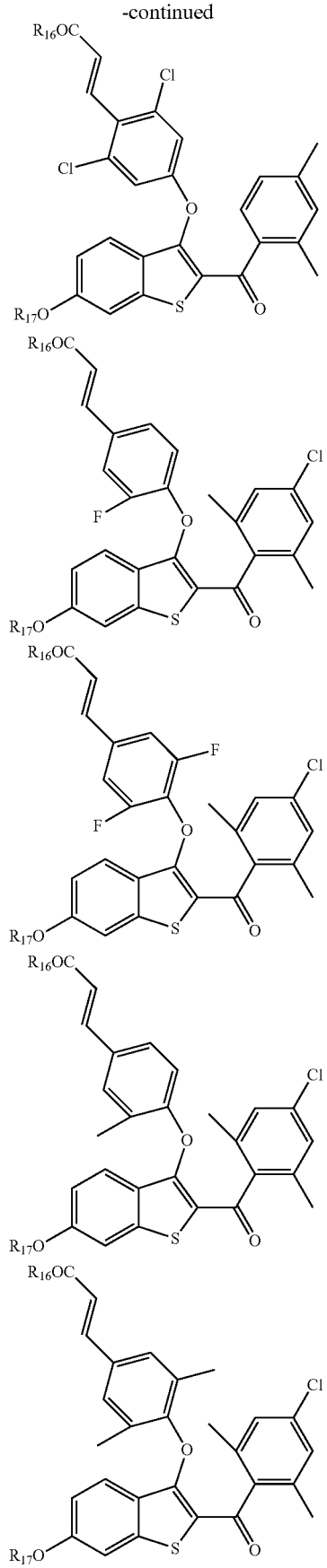

-continued
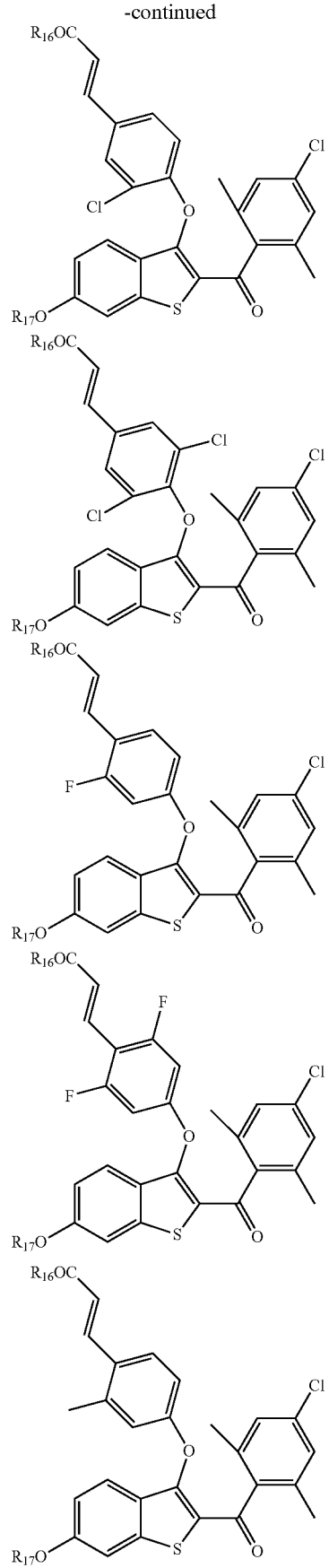
-continued
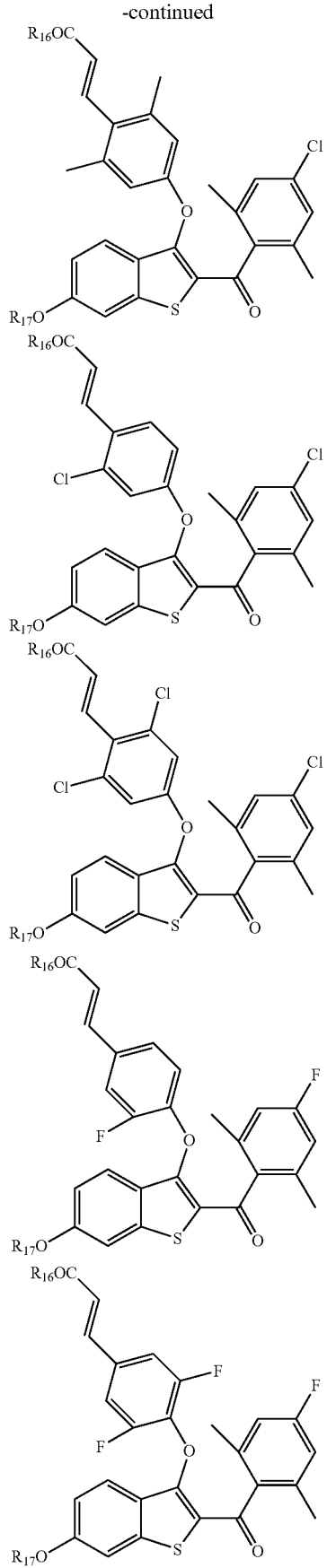

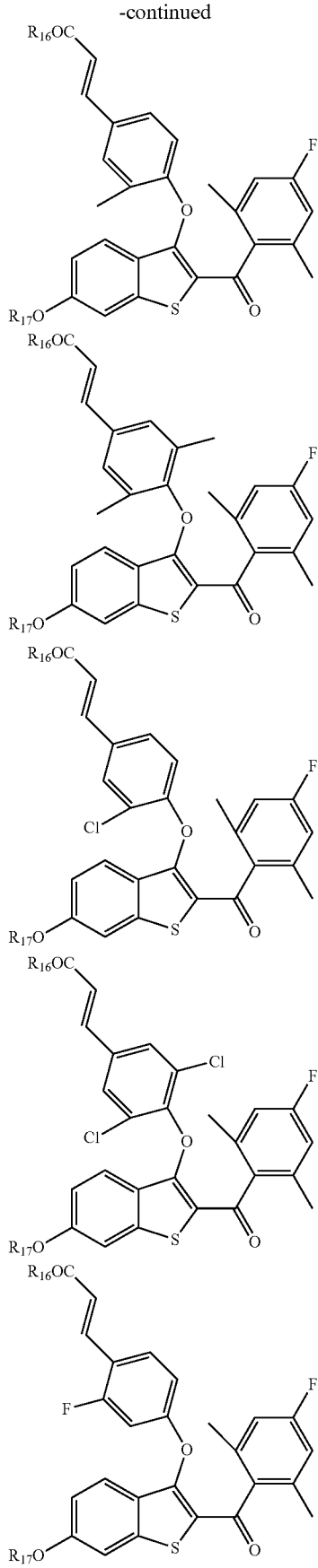
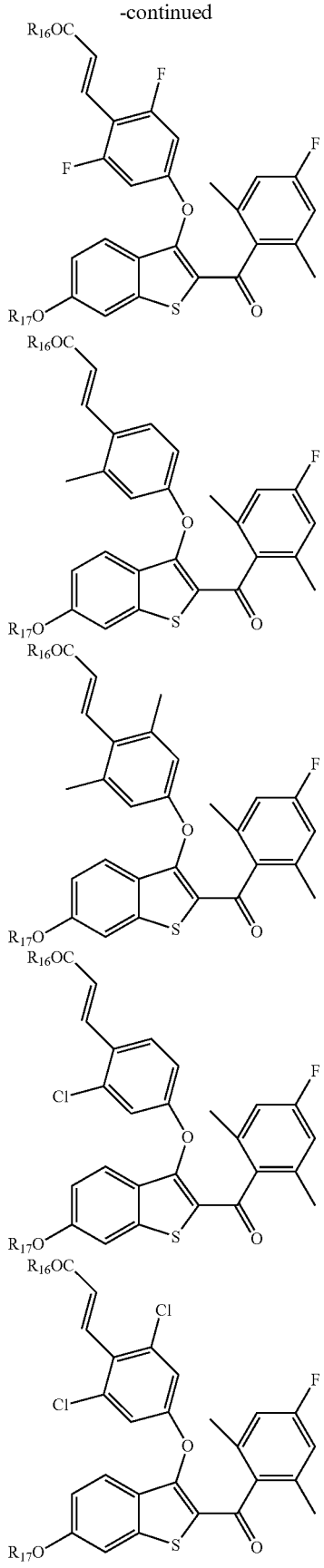
or a pharmaceutically acceptable salt thereof.

Additional representative compounds of the invention include, but are not limited to compounds of formula:
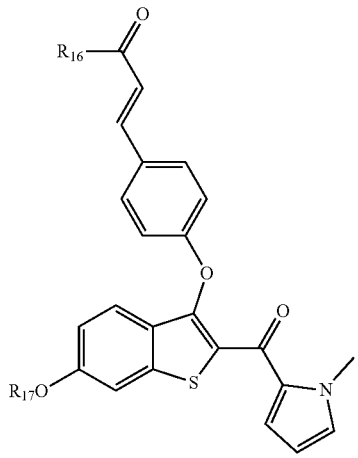
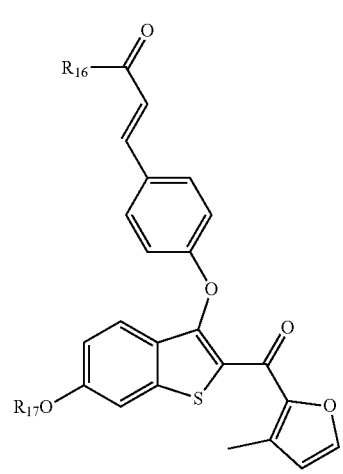
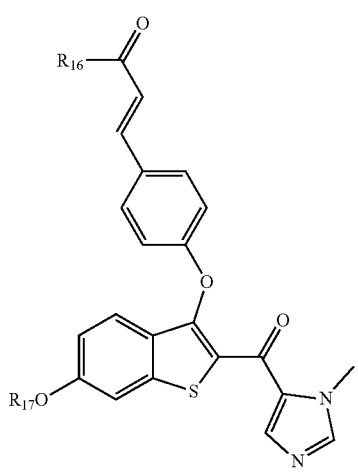
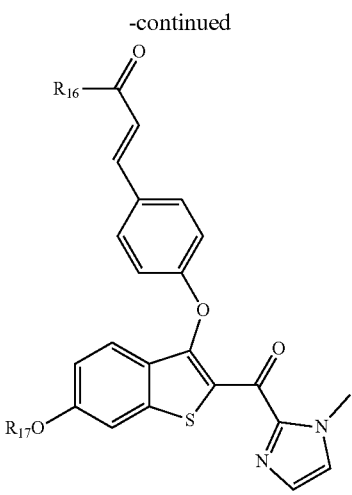
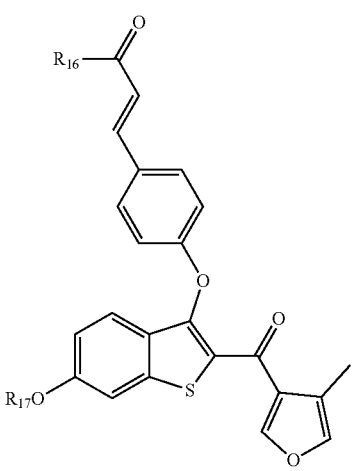
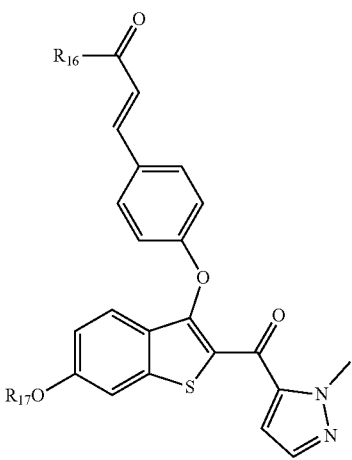

-continued

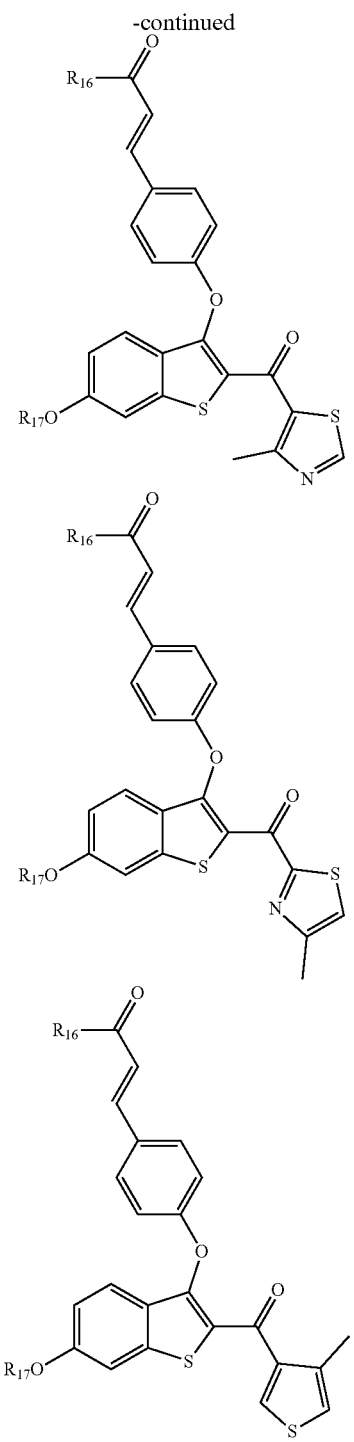

Pharmaceutical Compositions and Dosage Forms

In other aspects, this invention is a pharmaceutical composition comprising a therapeutically effective amount of a compound of Formula A, Formula B, Formula C, Formula D, Formula E, Formula F, Formula G, Formula H, Formula I, Formula J, Formula K, Formula L, Formula M, Formula N, Formula O, Formula P, Formula Q, Formula R, Formula S, Formula T, Formula U, Formula V, or Formula W as described herein, and one or more pharmaceutically acceptable diluents, preservatives, solubilizers, emulsifiers, adjuvants, excipients, or carriers. Such excipients include liquids such as water, saline, glycerol, polyethylene glycol, hyaluronic acid, ethanol, and the like.

The term "pharmaceutically acceptable carrier" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Methods of Treatment

The compounds and compositions of the invention may be used in methods for treatment or prevention of estrogen-related medical disorders, for example, cancer. The cancer may be a breast cancer, a uterine cancer, an ovarian cancer, a prostate cancer, and a lung cancer. Particularly, the breast cancer may be a tamoxifen resistant breast cancer or a triple negative breast cancer.

In one embodiment "cancer" refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In one embodiment, the cancer or tumor is estrogen-mediated. In an alternative embodiment, the cancer or tumor is not estrogen-mediated. In variable embodiments, the cancer or tumor is not hormone-mediated. Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The method of treatment may prevent or reduce the risk of cancer. The method of treatment may cause partial or complete regression of cancer in a subject.

The method of treatment may cause partial or complete regression of a tamoxifen resistant cancer or tumor. The method of treatment may cause partial or complete regression of a triple negative breast cancer.

In some embodiments, compounds disclosed herein are used to treat or prevent cancer or a tumor in a mammal, such as a human. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In one embodiment a compound of the present invention is used for hormone therapy.

The foregoing may be better understood by reference to the following Examples, which are presented for purposes of illustration and are not intended to limit the scope of the invention.

Checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combination thereof.

In one embodiment, the checkpoint inhibitor is a PD-1 inhibitor that blocks the interaction of PD-1 and PD-L1 by binding to the PD-1 receptor, and in turn inhibits immune suppression. In one embodiment, the checkpoint inhibitor is a PD-1 checkpoint inhibitor selected from nivoluniab, pembrolizumab, pidilizumab, AMP-224 (AstraZeneca and MedImmune), H-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.).

In one embodiment, the checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, avelumab, atezolizumab, durvalumab, KN035, and BMS-936559 (Bristol-Myers Squibb).

In one aspect of this embodiment, the checkpoint inhibitor is a CTLA-4 checkpoint inhibitor that binds to CTLA-1-4 and inhibits immune suppression. CTLA-4 inhibitors include, but are not limited to, ipilimumab, tremelimumab (AstraZeneca and MedImmune), AGEN1884 and AGEN2041 (Agenus).

In another embodiment, the checkpoint inhibitor is a LAG-3 checkpoint inhibitor. Examples of LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics), In yet another aspect of this embodiment, the checkpoint inhibitor is a TIM-3 checkpoint inhibitor. A specific TIM-3 inhibitor includes, but is not limited to, TSR-022 (Tesaro).

In one aspect, a compound of the present invention or its pharmaceutically acceptable salt or prodrug, can be used to treat a hormone-related cancer or tumor that has metastasized to the brain, bone or other organ. In one embodiment of this aspect, the hormone-related cancer is estrogen mediated. in another embodiment, the estrogen mediated cancer is selected from breast, uterine, ovarian and endometrial. In oilier embodiments, a compound of the present invention or its pharmaceutically acceptable salt or prodrug, can be used to prevent a hormone-related cancer or tumor from metastasizing to the brain, bone or other organ, including a hormone-related cancer that is estrogen mediated, for example, breast, uterine, ovarian or endometrial.

Combination Therapy

In one aspect, a method for the treatment of a disorder of abnormal cellular proliferation in a host such as a human is provided that includes administering an effective amount of a combination of one or more of the active compounds described herein in combination or alternation with another active compound.

In one aspect of this embodiment, the second active compound is an immune modulator, including but not limited to a checkpoint inhibitor. Checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combination thereof.

In one embodiment, the checkpoint inhibitor is a PD-1 inhibitor that blocks the interaction of PD-1 and PD-L1 by binding to the PD-1 receptor, and in turn inhibits immune suppression. In one embodiment, the checkpoint inhibitor is a PD-1 checkpoint inhibitor selected from nivolumab, pembrolizumab, pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.).

In one embodiment, the checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, avelumab, atezolizumab, durvalumab, KN035, and BMS-936559 (Bristol-Myers Squibb).

In one aspect of this embodiment, the checkpoint inhibitor is a CTLA-4 checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In another embodiment, the checkpoint inhibitor is a LAG-3 checkpoint inhibitor. Examples of LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the checkpoint inhibitor is a TIM-3 checkpoint inhibitor. A specific TIM-3 inhibitor includes, but is not limited to, TSR-022 (Tesaro).

In yet another embodiment, one of the active compounds described herein is administered in an effective amount for the treatment of abnormal tissue of the female reproductive system such as breast, ovarian, kidney, endometrial, or uterine cancer, in combination or alternation with an effective amount of an estrogen inhibitor including but not limited to a SERM (selective estrogen receptor modulator), a SERD (selective estrogen receptor downregulator), a complete estrogen receptor downregulator, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to AstraZeneca. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

In another embodiment, one of the active compounds described herein is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor downregulator and/or degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one aspect, a treatment regimen is provided comprising the administration of a compound of the present invention in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of a compound of the present invention in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-(0-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8 S,14 S,17 S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N-[4-(4, 6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4, 5h]isochromen-10-yl] acetate (also known as sonolisib)).

In one embodiment, the compound of the present invention is combined in a single dosage form with the PIk3 inhibitor.

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, *Journal of Hematology & Oncology,* 2013, 6:59, the entirety of which is incorporated herein by reference. In one embodiment, the compound of the present invention is combined in a single dosage form with the BTK inhibitor.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'4(5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), YM193306 (see Singh et al. Discovery and Development of Spleen Tyrosine Kinase (SYK) Inhibitors, *J. Med. Chem.* 2012, 55, 3614-3643), 7-azaindole, piceatannol, ER-27319 (see Singh et al. Discovery and Development of Spleen Tyrosine Kinase (SYK) Inhibitors, *J. Med. Chem.* 2012, 55, 3614-3643 incorporated in its entirety herein), Compound D (see Singh et al. Discovery and Development of Spleen Tyrosine Kinase (SYK) Inhibitors, *J. Med. Chem.* 2012, 55, 3614-3643 incorporated in its entirety herein), PRT060318 (see Singh et al. Discovery and Development of Spleen Tyrosine Kinase (SYK) Inhibitors, *J. Med. Chem.* 2012, 55, 3614-3643 incorporated in its entirety herein), luteolin (see Singh et al. Discovery and Development of Spleen Tyrosine Kinase (SYK) Inhibitors, *J. Med. Chem.* 2012, 55, 3614-3643 incorporated in its entirety herein), apigenin (see Singh et al. Discovery and Development of Spleen Tyrosine Kinase (SYK) Inhibitors, *J. Med. Chem.* 2012, 55, 3614-3643 incorporated in its entirety herein), quercetin (see Singh et al. Discovery and Development of Spleen Tyrosine Kinase (SYK) Inhibitors, *J. Med. Chem.* 2012, 55, 3614-3643 incorporated in its entirety herein), fisetin (see Singh et al. Discovery and Development of Spleen Tyrosine Kinase (SYK) Inhibitors, *J. Med. Chem.* 2012, 55, 3614-3643 incorporated in its entirety herein), myricetin (see Singh et al. Discovery and Development of Spleen Tyrosine Kinase (SYK) Inhibitors, *J. Med. Chem.* 2012, 55, 3614-3643 incorporated in its entirety herein), morin (see Singh et al. Discovery and Development of Spleen Tyrosine Kinase (SYK) Inhibitors, *J. Med. Chem.* 2012, 55, 3614-3643 incorporated in its entirety herein). In one embodiment, the compound of the present invention is combined in a single dosage form with the Syk inhibitor.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, the compound of the present invention is combined in a single dosage form with the at least one BCL-2 inhibitor.

The compound of the present invention or its pharmaceutically active salt can be combined with an immunotherapy. As discussed in more detail below, the compound of the present invention can be conjugated to an antibody, radioactive agent, or other targeting agent that directs the compound to the diseased or abnormally proliferating cell.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs, which bind to cell surface growth factor receptors, prevent the targeted receptors from sending their normal growth-promoting signals. They may also trigger apoptosis and activate the immune system to destroy tumor cells.

In some embodiments, the combination can be administered to the subject in further combination with other chemotherapeutic agents. If convenient, the combination described herein can be administered at the same time as another chemotherapeutic agent in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus (Deforolimus), and sirolimus. Examples of MEK inhibitors include but are not limited to trametinib/GSK1120212 (N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2 S)-piperidin-2-yl]azetidin-3-ol), refametinib/BAY869766/RDEA119 (N-(3, 4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-dihydroxypropoxy]-3,4-difluoro-2-[(2-fluoro-4-iodophenyl)amino]-benzamide), TAK733 ((R)-3-(2,3-dihydroxypropyl)-6-fluoro-5-(2-fluoro-4-iodophenylamino)-8-methylpyrido[2,3 d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-fluoro-2-(methyl sulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, a compound of the present invention described herein can be combined with a chemotherapeutic selected from, but are not limited to, Imatinib mesylate (Gleevec®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™) Examples of additional suitable chemotherapeutic agents include but are not limited to 1-dehydrotestosterone, 5-fluorouracil, dacarbazine, 6-mercaptopurine, 6-thioguanine, actinomycin D, adriamycin, alkylating agents, allopurinol sodium, altretamine, amifostine, anastrozole, anthramycin (AMC)), anti-mitotic agents, cis-dichlorodiamine platinum (II) (DDP) cisplatin, diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicine, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunorubicin HCl, daunorubicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptopurine, Mesna, methotrexate, methyltestosterone, mithramycin, mitomycin C, mitotane, mitoxantrone, nilutamide, octreotide acetate, ondansetron HCl, paclitaxel, pamidronate disodium, pentostatin, pilocarpine HCl, plicamycin, polifeprosan 20 with carmustine implant, porfimer sodium, procaine, procarbazine HCl, propranolol, sargramostim, streptozotocin, tamoxifen, taxol, teniposide, teniposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include 2-methoxyestradiol or 2ME2, finasunate, vatalanib, volociximab, etaracizumab (MEDI-522), cilengitide, dovitinib, figitumumab, atacicept, rituximab, alemtuzumab, aldesleukin, atlizumab, tocilizumab, lucatumumab, dacetuzumab, HLL1, huN901-DM1, atiprimod, natalizumab, bortezomib, marizomib, tanespimycin, saquinavir mesylate, ritonavir, nelfinavir mesylate, indinavir sulfate, belinostat, panobinostat, mapatumumab, lexatumumab, dulanermin, plitidepsin, talmapimod, P276-00, enzastaurin, tipifarnib, lenalidomide, thalidomide, pomalidomide, simvastatin, and celecoxib.

In one aspect of the present invention, a compound described herein can be combined with at least one immunosuppressive agent. The immunosuppressive agent in one embodiment is selected from the group consisting of a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, methotrexate, dexamethasone, ISAtx-247, SDZ ASM 981 (pimecrolimus, Elidel®), CTLA41g, Abatacept, belatacept, LFA31g, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, aspirin, and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

Synthetic Methods

The compounds described herein can be prepared by methods known by those skilled in the art. In one non-limiting example the disclosed compounds can be prepared using the schemes.

As used herein alkenylene can encompass both cis and trans isomers of alkenes, unless indicated otherwise. In one embodiment the isomer is cis. In a preferred embodiment the isomer is trans. In one embodiment $R_2$ is $—C_2$-$C_6$alkenylene-$COOR_{17}$ and the alkene group is cis. In a preferred embodiment $R_2$ is $—C_2$-$C_6$alkenylene-$COOR_{17}$ and the alkene group is trans.

Some of the compounds described herein can have a chiral center, and the compound can exist in isomeric or diastereomeric form. When multiple chiral variables are present on formulas of the present invention, the formula further encompasses every possible diastereomer unless indicated otherwise. For example (R,R), (S,R), (S,S), and (R,S) for a molecule with two chiral centers. One skilled in the art will recognize that pure enantiomers, diastereomers, and cis/trans isomers can be prepared by methods known in the art. Examples of methods to obtain optically active materials include at least the following.

i) Physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) Simultaneous crystallization—a technique whereby the individual enantiomers are separately crystallized from a solution of the racemate, possible only if the latter is a conglomerate in the solid state;

iii) Enzymatic resolutions—a technique whereby partial or complete separation of a racemate by virtue of differing rates of reaction for the enantiomers with an enzyme;

iv) Enzymatic asymmetric synthesis—a synthetic technique whereby at least one step of the synthesis uses an enzymatic reaction to obtain an enantiomerically pure or enriched synthetic precursor of the desired enantiomer;

v) Chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) Diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) First- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) Kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) Enantiospecific synthesis from non-racemic precursors—a synthetic technique whereby the desired enantiomer is obtained from non-chiral starting materials and where the stereochemical integrity is not or is only minimally compromised over the course of the synthesis;

x) Chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) Chiral gas chromatography—a technique whereby the racemate is volatilized and enantiomers are separated by virtue of their differing interactions in the gaseous mobile phase with a column containing a fixed non-racemic chiral adsorbent phase;

xii) Extraction with chiral solvents—a technique whereby the enantiomers are separated by virtue of preferential dissolution of one enantiomer into a particular chiral solvent;

xiii) Transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) Simulated moving bed chromatography, is used in one embodiment. A wide variety of chiral stationary phases are commercially available.

General Synthetic Route 1:
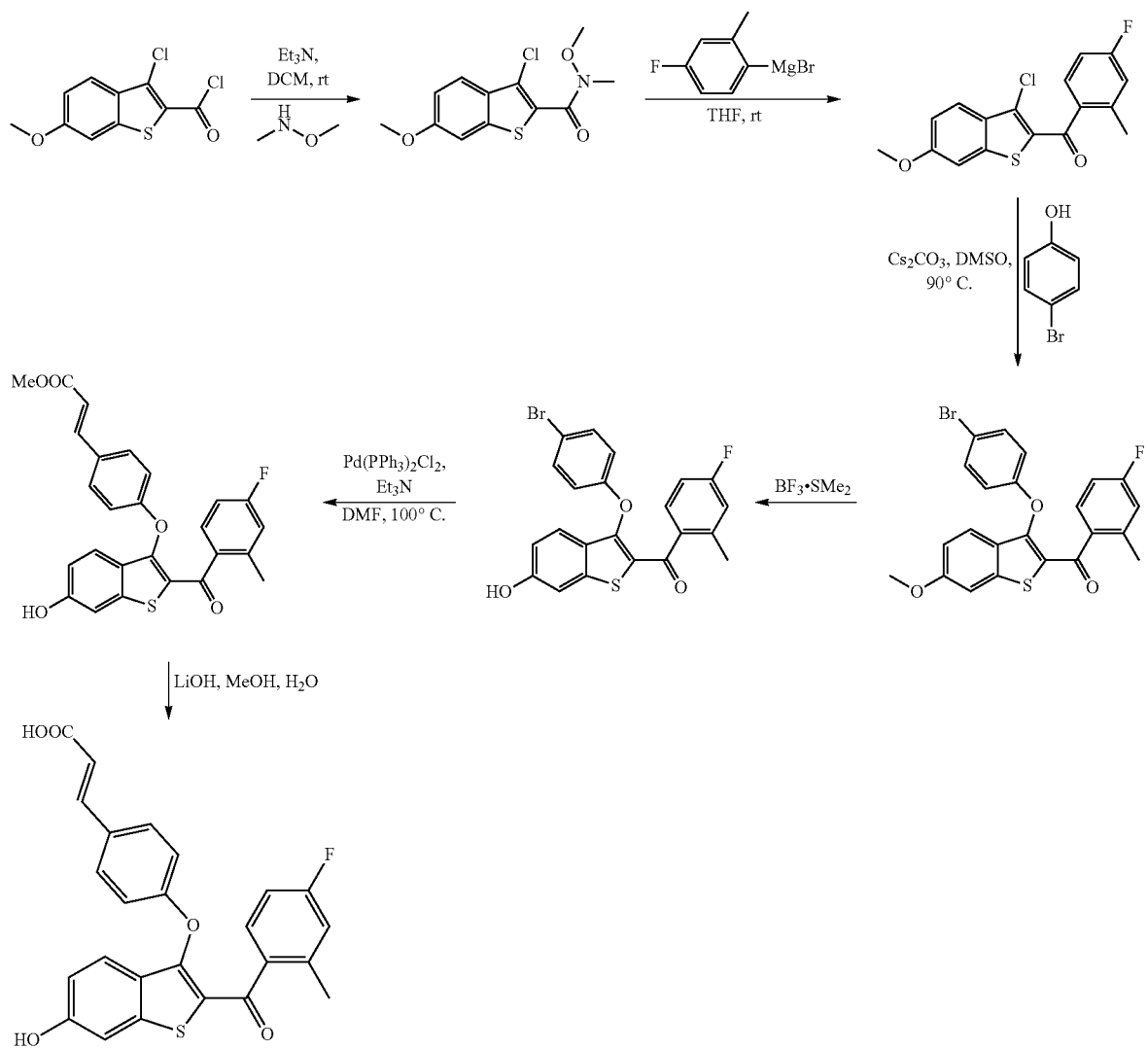
General Synthetic Route 2:
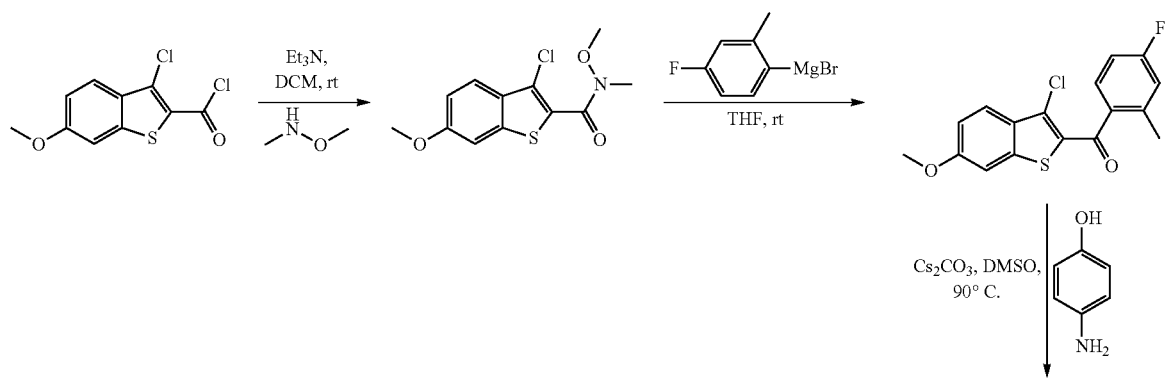

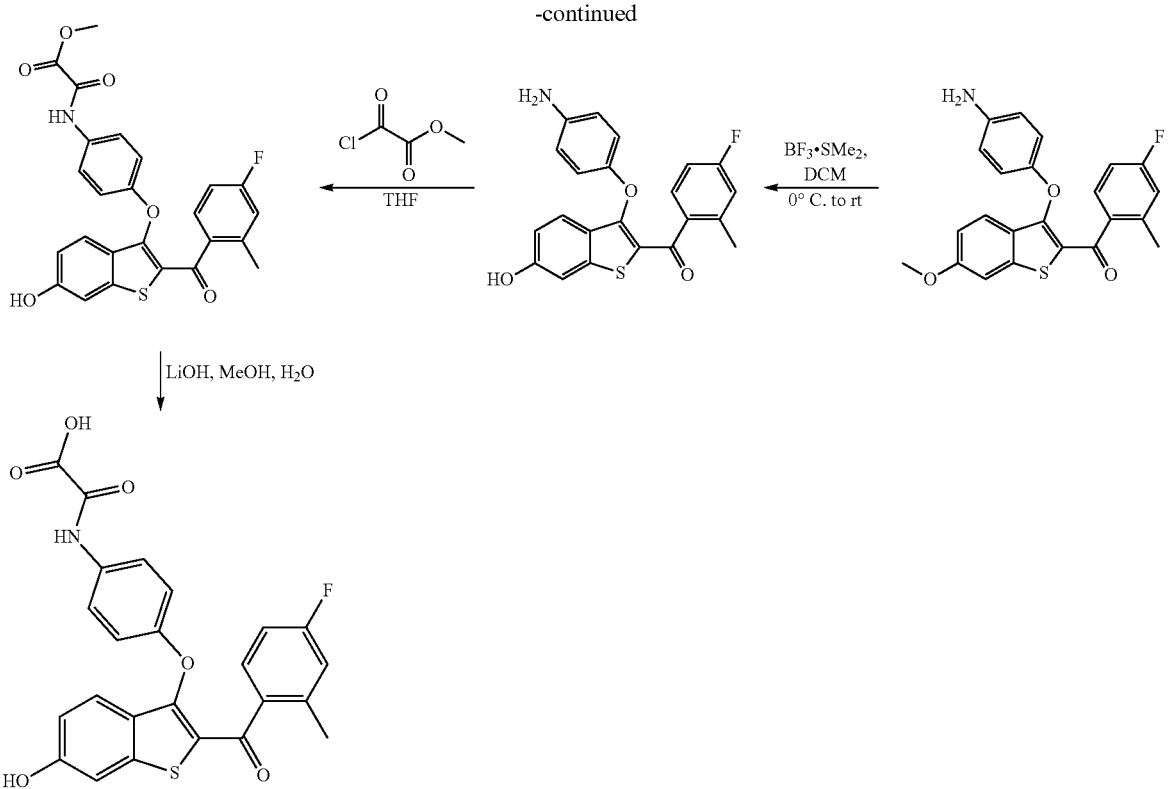
General Synthetic Route 3:
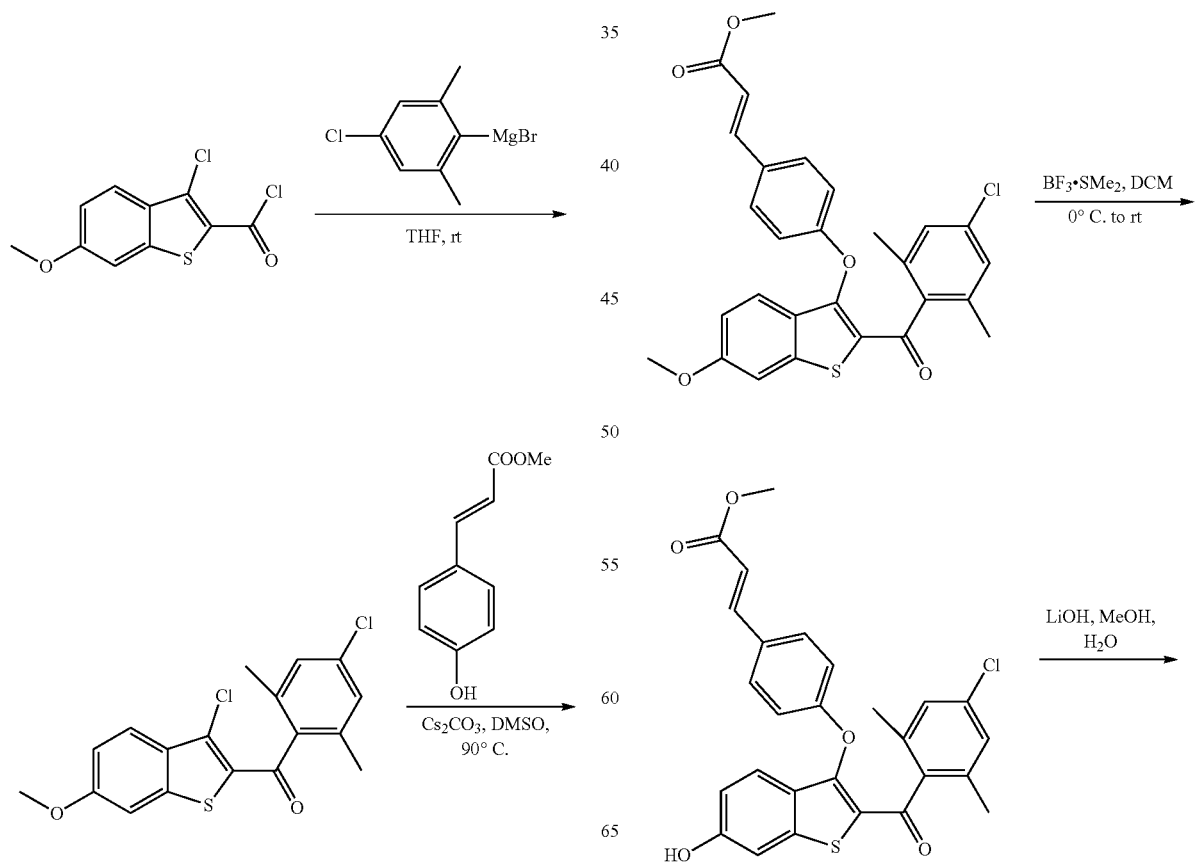

-continued
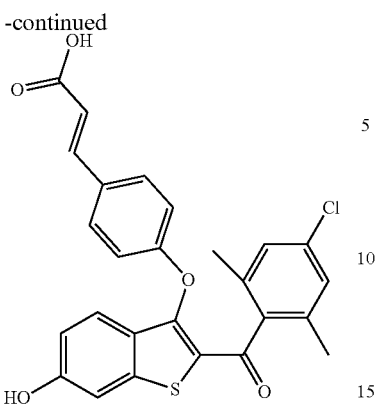
General Synthetic Route 4:
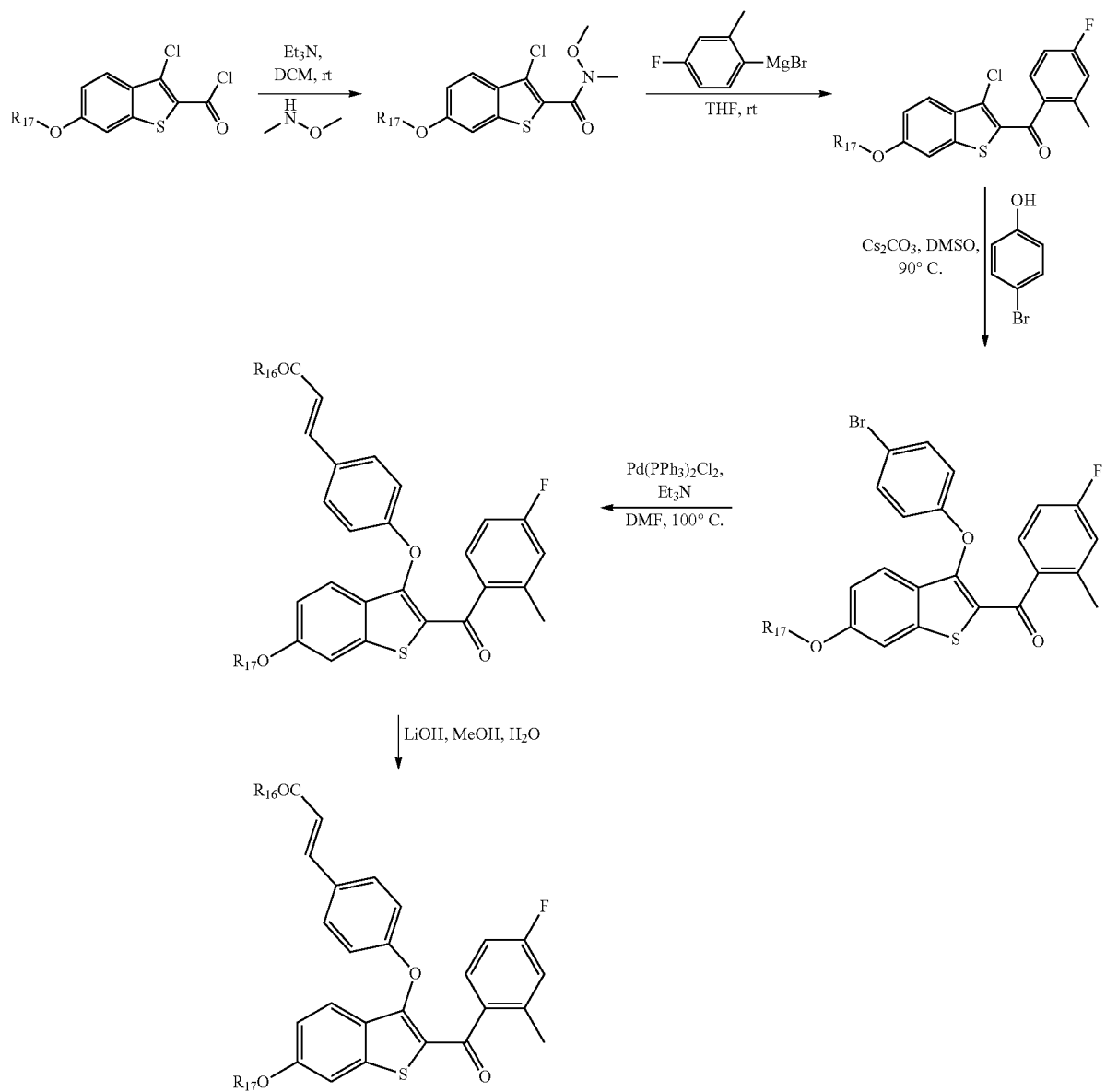

General Synthetic Route 5:
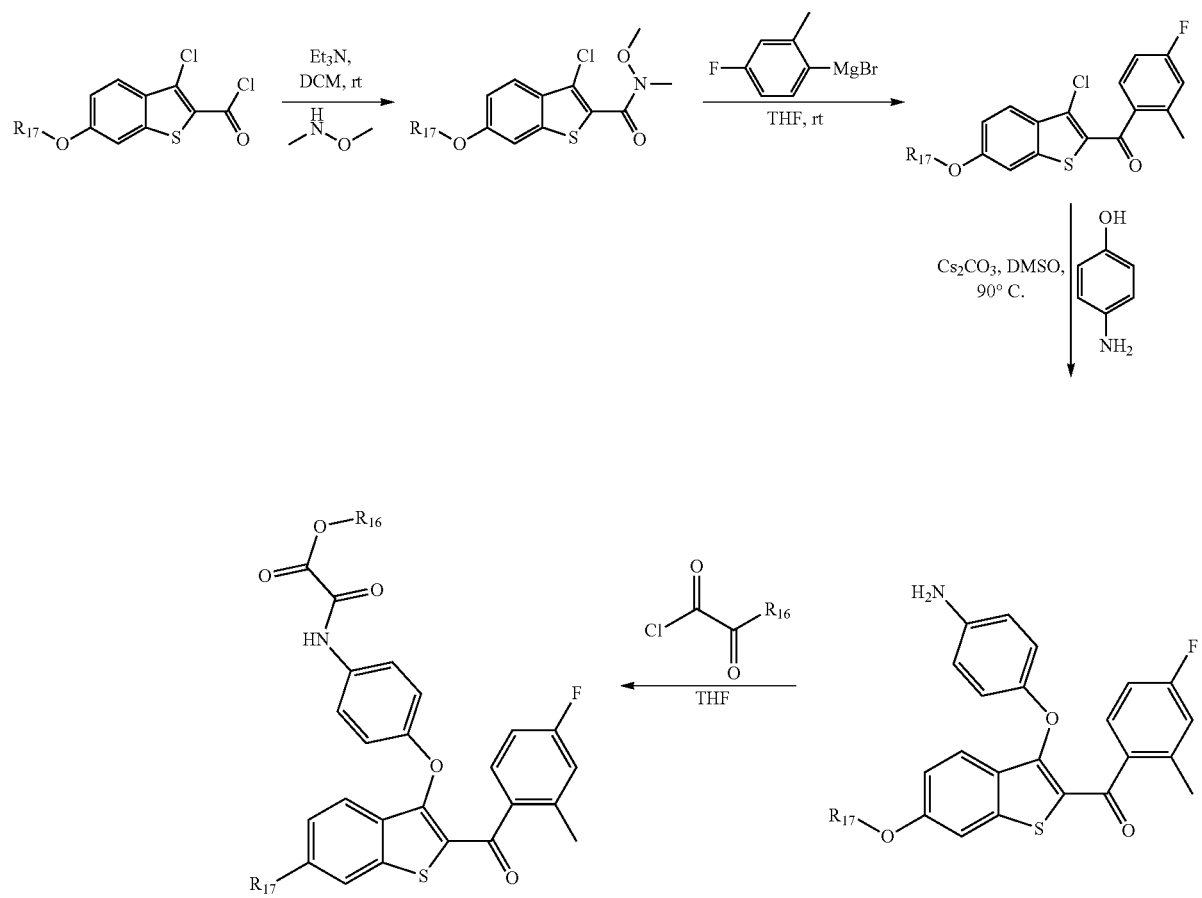
General Synthetic Route 6:
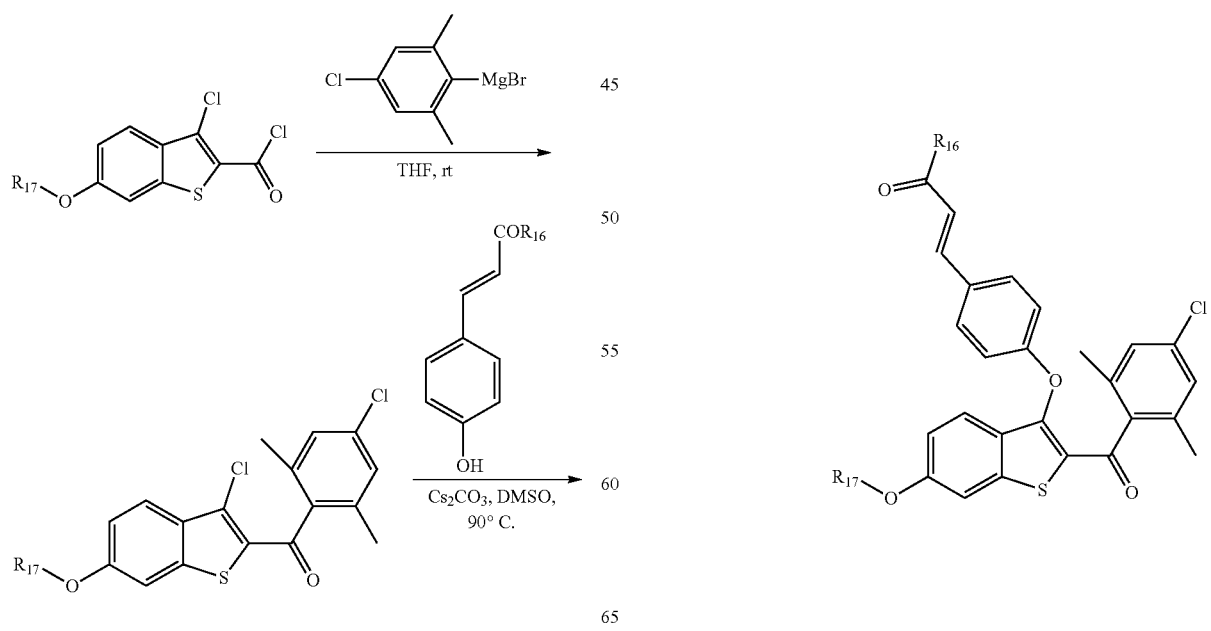

General Synthetic Route 7:

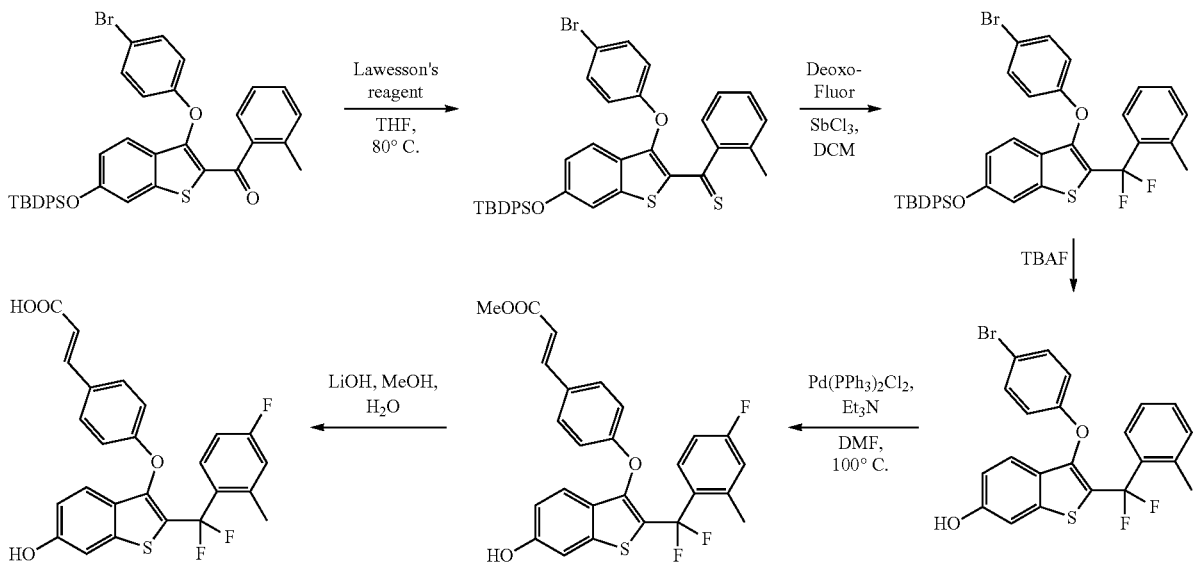

General Synthetic Route 8:

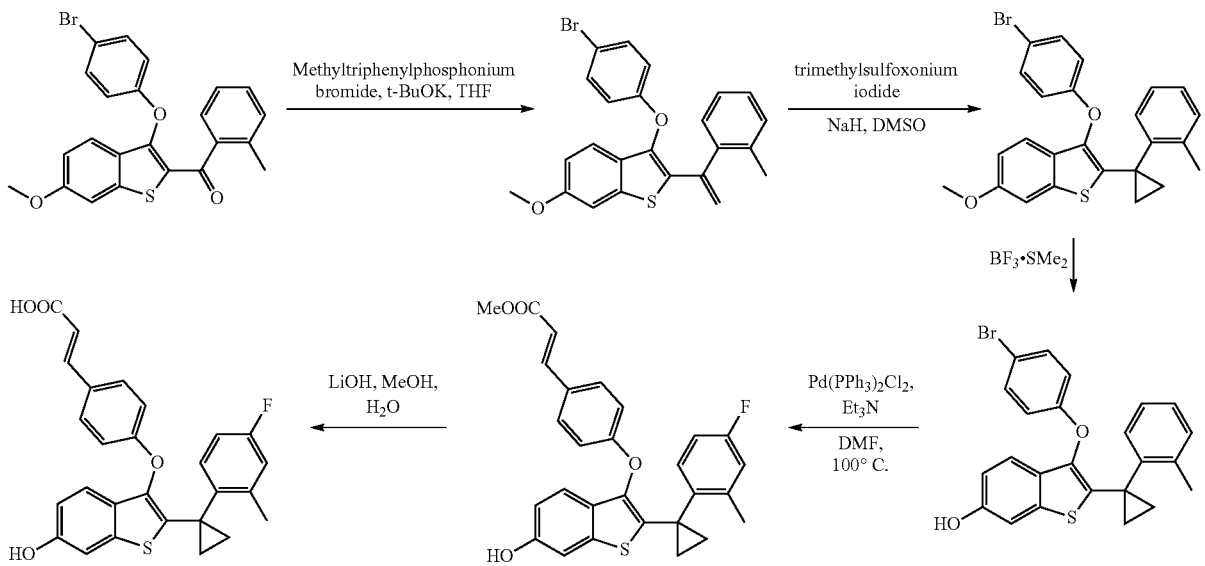

Intermediate 1: 3-Chloro-N,6-dimethoxy-N-methyl-benzo[b]thiophene-2-carboxamide

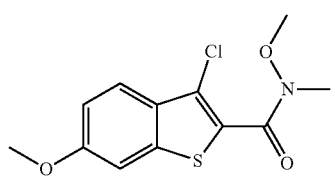

In an oven-dried round-bottom flask, 3-chloro-6-methoxybenzo[b]thiophene-2-carbonyl chloride (8.9 g, 34.9 mmol) was dissolved in 50 mL of anhydrous dichlorometh-ane under argon atmosphere and N,O-dimethylhydroxylam-ine hydrochloride (3.75 g, 38.4 mmol) was added in one portion. After stirring for 10 minutes, $Et_3N$ (17.6 g, 174.5 mmol) was added dropwise. The reaction mixture was stirred overnight until TLC indicated consumption of all starting materials. The reaction was quenched by ice water, the solution was extracted with ethyl acetate, and washed with brine. The organic extracts were combined, dried over anhydrous $Na_2SO_4$, concentrated in vacuum, and purified by flash chromatography (5%-50% ethyl acetate in hexane) to afford 7.6 g as a white solid (76%). $^1$H NMR (400 MHz, $CDCl_3$) δ 7.82 (d, J=8.9 Hz, 1H), 7.23 (s, 1H), 7.10 (dd, J=8.9, 2.3 Hz, 1H), 3.90 (s, 3H), 3.73 (s, 3H), 3.39 (s, 3H). $^{13}$C NMR (100 MHz, $CDCl_3$) δ 162.04, 159.88, 140.35, 130.23, 124.19, 116.09, 104.29, 62.04, 55.87, 33.75.

Intermediate 2: (3-Chloro-6-methoxybenzo[b]thiophen-2-yl)(4-fluoro-2-methylphenyl)methanone

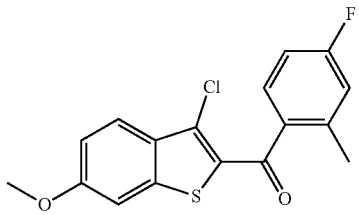 [SMILES: COc1ccc2c(Cl)c(C(=O)c3ccc(F)cc3C)sc2c1]

To a solution of intermediate (1) (500 mg, 1.75 mmol) in THF under argon atmosphere was added a 0.5 M solution of (4-fluoro-2-methylphenyl)magnesium bromide (4 mL, 2 mmol) dropwise. The reaction mixture was stirred overnight and quenched by 1 N HCl/ice water. The solution was extracted with ethyl acetate and washed with brine. The organic extracts were combined, dried over anhydrous $Na_2SO_4$, concentrated in vacuum, and purified by flash chromatography (1%-15% ethyl acetate in hexane) to afford 550 mg of a white solid (94%).

The following intermediates were made by an analogous procedure utilizing the appropriate Grignard reagent:

| Structure | Name | NMR |
|---|---|---|
| 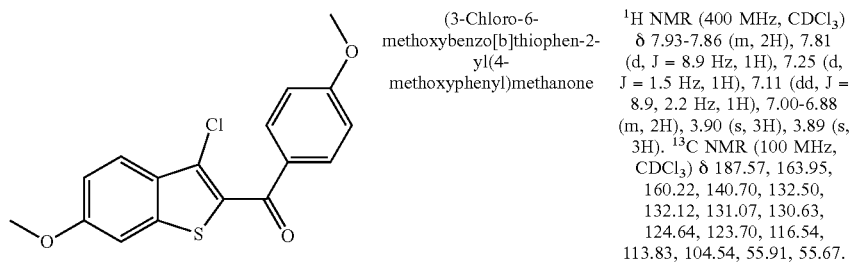 | (3-Chloro-6-methoxybenzo[b]thiophen-2-yl)(4-methoxyphenyl)methanone | $^1$H NMR (400 MHz, CDCl$_3$) δ 7.93-7.86 (m, 2H), 7.81 (d, J = 8.9 Hz, 1H), 7.25 (d, J = 1.5 Hz, 1H), 7.11 (dd, J = 8.9, 2.2 Hz, 1H), 7.00-6.88 (m, 2H), 3.90 (s, 3H), 3.89 (s, 3H). $^{13}$C NMR (100 MHz, CDCl$_3$) δ 187.57, 163.95, 160.22, 140.70, 132.50, 132.12, 131.07, 130.63, 124.64, 123.70, 116.54, 113.83, 104.54, 55.91, 55.67. |
| 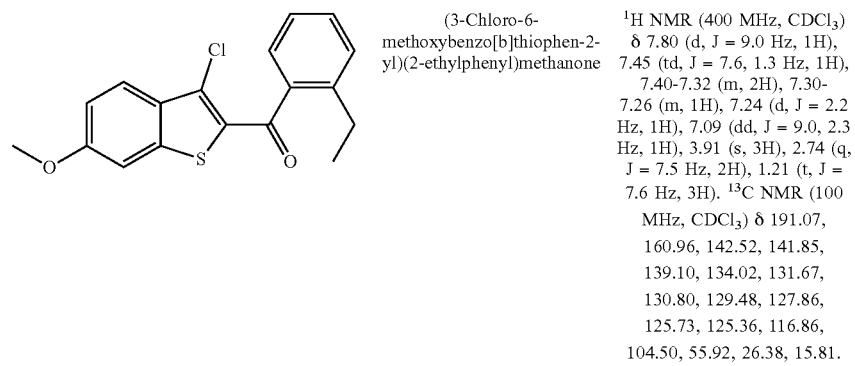 | (3-Chloro-6-methoxybenzo[b]thiophen-2-yl)(2-ethylphenyl)methanone | $^1$H NMR (400 MHz, CDCl$_3$) δ 7.80 (d, J = 9.0 Hz, 1H), 7.45 (td, J = 7.6, 1.3 Hz, 1H), 7.40-7.32 (m, 2H), 7.30-7.26 (m, 1H), 7.24 (d, J = 2.2 Hz, 1H), 7.09 (dd, J = 9.0, 2.3 Hz, 1H), 3.91 (s, 3H), 2.74 (q, J = 7.5 Hz, 2H), 1.21 (t, J = 7.6 Hz, 3H). $^{13}$C NMR (100 MHz, CDCl$_3$) δ 191.07, 160.96, 142.52, 141.85, 139.10, 134.02, 131.67, 130.80, 129.48, 127.86, 125.73, 125.36, 116.86, 104.50, 55.92, 26.38, 15.81. |
| 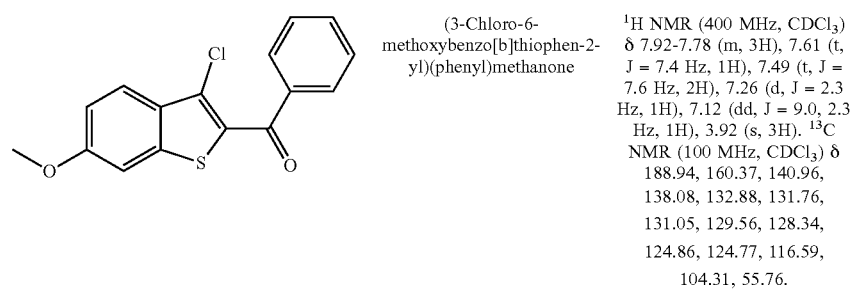 | (3-Chloro-6-methoxybenzo[b]thiophen-2-yl)(phenyl)methanone | $^1$H NMR (400 MHz, CDCl$_3$) δ 7.92-7.78 (m, 3H), 7.61 (t, J = 7.4 Hz, 1H), 7.49 (t, J = 7.6 Hz, 2H), 7.26 (d, J = 2.3 Hz, 1H), 7.12 (dd, J = 9.0, 2.3 Hz, 1H), 3.92 (s, 3H). $^{13}$C NMR (100 MHz, CDCl$_3$) δ 188.94, 160.37, 140.96, 138.08, 132.88, 131.76, 131.05, 129.56, 128.34, 124.86, 124.77, 116.59, 104.31, 55.76. |
| 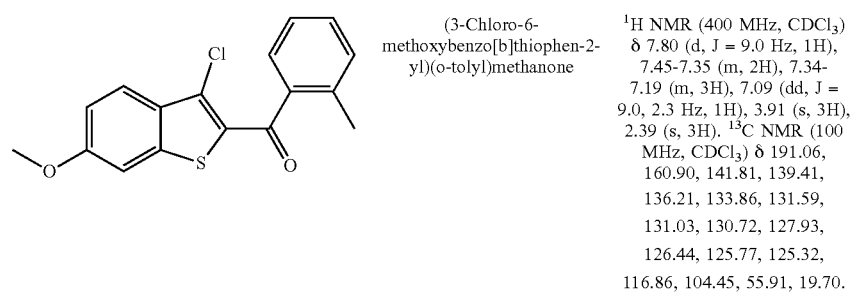 | (3-Chloro-6-methoxybenzo[b]thiophen-2-yl)(o-tolyl)methanone | $^1$H NMR (400 MHz, CDCl$_3$) δ 7.80 (d, J = 9.0 Hz, 1H), 7.45-7.35 (m, 2H), 7.34-7.19 (m, 3H), 7.09 (dd, J = 9.0, 2.3 Hz, 1H), 3.91 (s, 3H), 2.39 (s, 3H). $^{13}$C NMR (100 MHz, CDCl$_3$) δ 191.06, 160.90, 141.81, 139.41, 136.21, 133.86, 131.59, 131.03, 130.72, 127.93, 126.44, 125.77, 125.32, 116.86, 104.45, 55.91, 19.70. |

| Structure | Name | NMR |
|---|---|---|
| 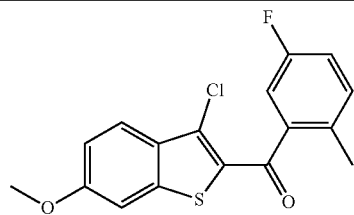 | (3-chloro-6-methoxybenzo[b]thiophen-2-yl)(5-fluoro-2-methylphenyl)methanone | ¹H NMR (400 MHz, CDCl₃) δ 7.81 (d, J = 9.0 Hz, 1H), 7.26-7.23 (m, 2H), 7.13-7.08 (m, 3H), 3.92 (s, 3H), 2.32 (s, 3H). ¹³C NMR (100 MHz, CDCl₃) δ 189.59, 161.17, 160.92 (d, J = 245.5 Hz), 142.07, 140.77 (d, J = 6.3 Hz), 133.30, 132.55 (d, J = 7.4 Hz), 131.64 (d, J = 3.5 Hz), 131.58, 127.03, 125.48, 117.45 (d, J = 21.0 Hz), 117.06, 114.61 (d, J = 23.0 Hz), 104.52, 55.95, 18.84. |
| 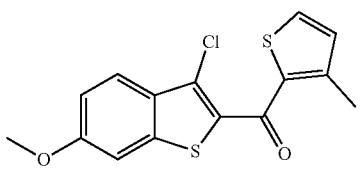 | (3-chloro-6-methoxybenzo[b]thiophen-2-yl)(3-methylthiophen-2-yl)methanone | ¹H NMR (400 MHz, CDCl₃) δ 7.82 (d, J = 8.9 Hz, 1H), 7.54 (d, J = 4.9 Hz, 1H), 7.26 (d, J = 2.2 Hz, 1H), 7.12 (dd, J = 8.9, 2.2 Hz, 1H), 6.99 (d, J = 4.9 Hz, 1H), 3.91 (s, 3H), 2.50 (s, 3H). ¹³C NMR (100 MHz, CDCl₃) δ 181.18, 160.26, 146.19, 140.41, 135.96, 132.23, 132.15, 131.81, 130.83, 124.63, 124.02, 116.64, 104.52, 55.89, 16.40. |
| 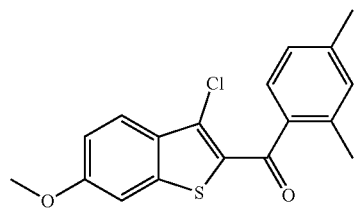 | (3-chloro-6-methoxybenzo[b]thiophen-2-yl)(2,4-dimethylphenyl)methanone | ¹H NMR (400 MHz, CDCl₃) δ 7.76 (d, J = 9.0 Hz, 1H), 7.33 (d, J = 7.7 Hz, 1H), 7.20 (d, J = 2.0 Hz, 1H), 7.10-7.00 (m, 3H), 3.87 (s, 3H), 2.37 (s, 6H). |

Intermediate 3: (3-Chloro-6-methoxybenzo[b]thiophen-2-yl)(2-(trifluoromethyl)phenyl)methanone

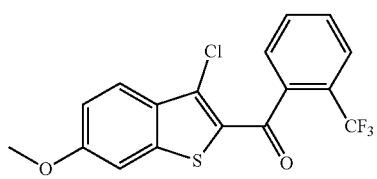 [SMILES: COc1ccc2c(Cl)c(C(=O)c3ccccc3C(F)(F)F)sc2c1]

To a solution of 3-chloro-6-methoxybenzo[b]thiophene-2-carbonyl chloride (1.04 g, 4 mmol) in THF under argon atmosphere was added a freshly prepared solution of (2-(trifluoromethyl)phenyl)magnesium bromide (5 mmol) dropwise. The reaction mixture was stirred overnight and quenched by 1 N HCl/ice water. The solution was extracted with ethyl acetate and washed with brine. The organic extracts were combined, dried over anhydrous Na₂SO₄, concentrated in vacuum, and purified by flash chromatography (1%-15% ethyl acetate in hexane) to afford 350 mg of a white solid (19%). ¹H NMR (400 MHz, CDCl₃) δ 7.77 (t, J=8.3 Hz, 2H), 7.70-7.57 (m, 2H), 7.47 (d, J=6.4 Hz, 1H), 7.24 (s, 1H), 7.07 (dd, J=9.0, 1.9 Hz, 1H), 3.90 (s, 3H). ¹³C NMR (100 MHz, CDCl₃) δ 187.86, 161.27, 142.29, 138.58 (q, J=2.1 Hz), 133.23, 131.99, 131.49, 130.20, 127.88, 127.75, 127.69 (q, J=32.3 Hz), 126.89 (q, J=4.5 Hz), 125.49, 123.70 (q, J=274.0 Hz), 117.07, 104.41, 55.91. ¹⁹F NMR (400 MHz, CDCl₃) δ−58.46.

The following intermediates were made by an analogous procedure utilizing the appropriate Grignard reagent:

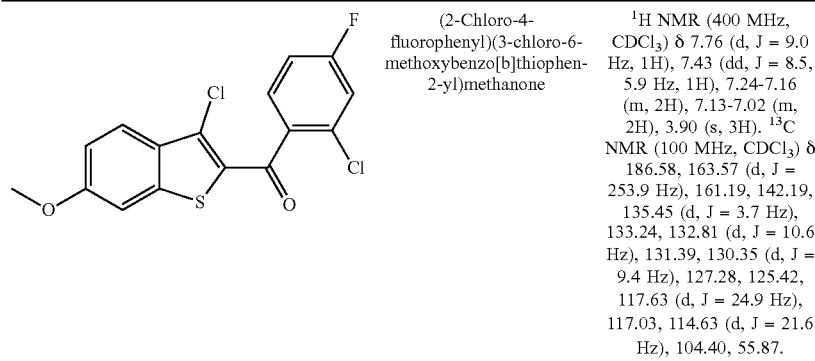

| Structure | Name | NMR |
|---|---|---|
| 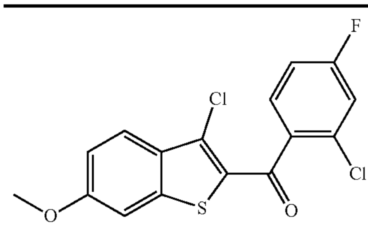 | (2-Chloro-4-fluorophenyl)(3-chloro-6-methoxybenzo[b]thiophen-2-yl)methanone | ¹H NMR (400 MHz, CDCl₃) δ 7.76 (d, J = 9.0 Hz, 1H), 7.43 (dd, J = 8.5, 5.9 Hz, 1H), 7.24-7.16 (m, 2H), 7.13-7.02 (m, 2H), 3.90 (s, 3H). ¹³C NMR (100 MHz, CDCl₃) δ 186.58, 163.57 (d, J = 253.9 Hz), 161.19, 142.19, 135.45 (d, J = 3.7 Hz), 133.24, 132.81 (d, J = 10.6 Hz), 131.39, 130.35 (d, J = 9.4 Hz), 127.28, 125.42, 117.63 (d, J = 24.9 Hz), 117.03, 114.63 (d, J = 21.6 Hz), 104.40, 55.87. |

| | | |
|---|---|---|
| 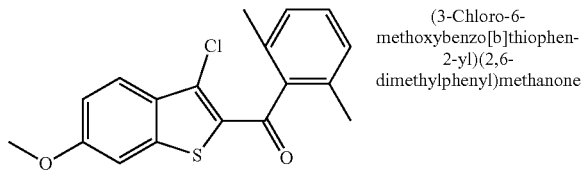 | (3-Chloro-6-methoxybenzo[b]thiophen-2-yl)(2,6-dimethylphenyl)methanone | $^{1}$H NMR (400 MHz, CDCl$_3$) δ 7.79 (d, J = 9.0 Hz, 1H), 7.26-7.18 (m, 2H), 7.12-7.02 (m, 3H), 3.90 (s, 3H), 2.22 (s, 6H). $^{13}$C NMR (100 MHz, CDCl$_3$) δ 192.58, 161.14, 142.18, 140.22, 134.18, 131.75, 129.31, 127.84, 126.81, 125.55, 116.91, 104.53, 55.91, 19.31. |

Compound I-4: (3-(4-Bromophenoxy)-6-methoxy-benzo[b]thiophen-2-yl)(4-fluoro-2-methylphenyl)methanone

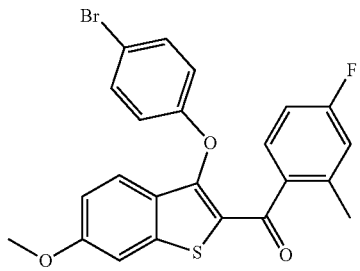 [SMILES: COc1ccc2c(Oc3ccc(Br)cc3)c(C(=O)c3ccc(F)cc3C)sc2c1]

Cs$_2$CO$_3$ (1.52 g, 4.67 mmol) was added in one portion to a solution of intermediate 2 (520 mg, 1.56 mmol) and 4-bromophenol in 5 mL DMF. The reaction mixture was raised to 50° C. and after stirring overnight, the reaction mixture was quenched with ice water, extracted with ethyl acetate, and washed with brine. The organic extracts were combined, dried over anhydrous Na$_2$SO$_4$, concentrated in vacuum, and purified by flash chromatography (1%-15% ethyl acetate in hexane) to afford 490 mg white solid (67%). $^{1}$H NMR (400 MHz, CDCl$_3$) δ 7.43 (d, J=8.9 Hz, 1H), 7.34-7.27 (m, 2H), 7.22-7.17 (m, 2H), 6.96 (dd, J=8.9, 2.2 Hz, 1H), 6.80-6.76 (m, 2H), 6.40-6.33 (m, 2H), 3.91 (s, 3H), 2.16 (s, 3H). $^{13}$C NMR (100 MHz, CDCl$_3$) δ 189.34, 163.72 (d, J=250.2 Hz), 161.07, 157.45, 148.25, 142.21, 139.63 (d, J=8.6 Hz), 135.29 (d, J=3.1 Hz), 132.38, 130.24 (d, J=9.2 Hz), 126.82, 127.48, 124.57, 117.45 (d, J=21.4 Hz), 116.74, 116.55, 115.09, 112.19 (d, J=21.7 Hz), 105.19, 55.89, 19.53 (d, J=1.3 Hz).

The following Compounds were made by an analogous procedure utilizing the appropriate starting materials:

| | | |
|---|---|---|
| 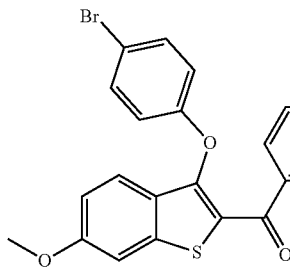 | (3-(4-Bromophenoxy)-6-methoxybenzo[b]thiophen-2-yl)(4-methoxyphenyl)methanone | $^{1}$H NMR (400 MHz, CDCl$_3$) δ 7.76 (d, J = 8.9 Hz, 2H), 7.47 (d, J = 8.9 Hz, 1H), 7.28 (d, J = 2.1 Hz, 1H), 7.21 (d, J = 9.0 Hz, 2H), 6.98 (dd, J = 8.9, 2.2 Hz, 1H), 6.86 (d, J = 8.9 Hz, 2H), 6.54 (d, J = 9.0 Hz, 2H), 3.91 (s, 3H), 3.86 (s, 3H). $^{13}$C NMR (100 MHz, CDCl$_3$) δ $^{13}$C NMR (100 MHz, CDCl$_3$) δ 187.33, 163.49, 160.43, 157.45, 146.58, 141.29, 132.47, 131.84, 130.92, 126.71, 125.99, 124.18, 117.46, 116.23, 115.05, 113.43, 105.08, 55.87, 55.64. |
| 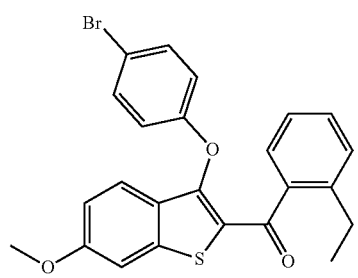 [SMILES: CCc1ccccc1C(=O)c1sc2cc(OC)ccc2c1Oc1ccc(Br)cc1] | (3-(4-Bromophenoxy)-6-methoxybenzo[b]thiophen-2-yl)(2-ethylphenyl)methanone | $^{1}$H NMR (400 MHz, CDCl$_3$) δ 7.39 (d, J = 8.9 Hz, 1H), 7.29-7.24 (m, 3H), 7.17-7.13 (m, 3H), 7.07 (t, J = 7.5 Hz, 1H), 6.94 (dd, J = 8.9, 2.2 Hz, 1H), 6.35-6.29 (m, 2H), 3.91 (s, 3H), 2.50 (q, J = 7.5 Hz, 2H), 1.06 (t, J = 7.6 Hz, 3H). $^{13}$C NMR (100 MHz, CDCl$_3$) δ 190.68, 160.98, 157.30, 148.30, 142.19, 142.15, 138.95, 132.27, 130.35, 128.91, 128.06, 127.55, 126.90, 125.21, 124.66, 116.93, 116.46, 114.91, 105.22, 55.89, 26.21, |

15.62.

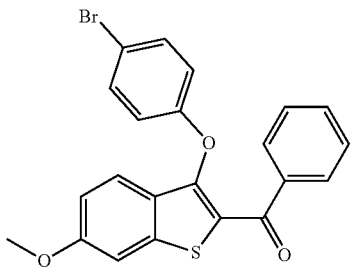 [SMILES: COc1ccc2c(Oc3ccc(Br)cc3)c(C(=O)c3ccccc3)sc2c1]

(3-(4-Bromophenoxy)-6-methoxybenzo[b]thiophen-2-yl)(phenyl)methanone $^1$H NMR (400 MHz, CDCl$_3$) δ 7.72-7.65 (m, 2H), 7.52-7.44 (m, 2H), 7.34 (t, J = 7.7 Hz, 2H), 7.28 (d, J = 2.1 Hz, 1H), 7.21-7.15 (m, 2H), 6.97 (dd, J = 8.9, 2.2 Hz, 1H), 6.49-6.43 (m, 2H), 3.92 (s, 3H). $^{13}$C NMR (100 MHz, CDCl$_3$) δ 188.95, 160.72, 157.40, 147.59, 141.76, 138.49, 132.47, 132.40, 129.02, 128.09, 126.72, 125.92, 124.44, 117.33, 116.40, 115.07, 105.10, 55.88.

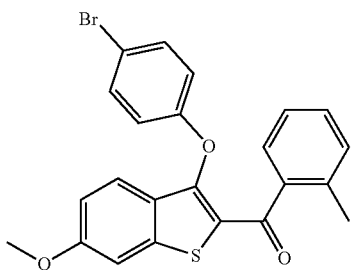

(3-(4-Bromophenoxy)-6-methoxybenzo[b]thiophen-2-yl)(o-tolyl)methanone $^1$H NMR (400 MHz, CDCl$_3$) δ 7.42 (d, J = 8.9 Hz, 1H), 7.29-7.20 (m, 3H), 7.18-7.12 (m, 2H), 7.11-7.04 (m, 2H), 6.95 (dd, J = 8.9, 2.2 Hz, 1H), 6.37-6.26 (m, 2H), 3.91 (s, 3H), 2.16 (s, 3H). $^{13}$C NMR (100 MHz, CDCl$_3$) δ 190.66, 160.99, 157.45, 148.38, 142.20, 139.30, 135.92, 132.27, 130.63, 130.28, 127.74, 127.63, 126.92, 125.25, 124.60, 116.86, 116.48, 114.92, 105.20, 55.89, 19.36.

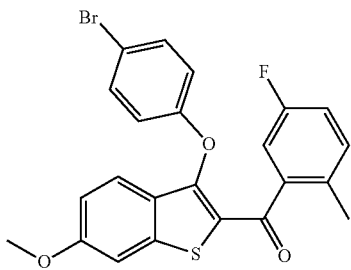

(3-(4-Bromophenoxy)-6-methoxybenzo[b]thiophen-2-yl)(5-fluoro-2-methylphenyl)methanone $^1$H NMR (400 MHz, CDCl$_3$) δ 7.41 (d, J = 8.9 Hz, 1H), 7.28 (d, J = 2.1 Hz, 1H), 7.19 (d, J = 9.0 Hz, 2H), 7.04-6.91 (m, 4H), 6.38 (d, J = 9.0 Hz, 2H), 3.91 (s, 3H), 2.11 (s, 3H). $^{13}$C NMR (100 MHz, CDCl$_3$) δ 189.11, 161.19, 160.60 (d, J = 245.3 Hz), 157.28, 148.76, 142.47, 140.60 (d, J = 6.3 Hz), 132.42, 132.06 (d, J = 7.4 Hz), 131.36 (d, J = 3.5 Hz), 127.15, 126.70, 124.75, 116.90 (d, J = 20.9 Hz), 116.76, 116.64, 115.15, 114.34 (d, J = 23.0 Hz), 105.22, 55.90, 18.56.

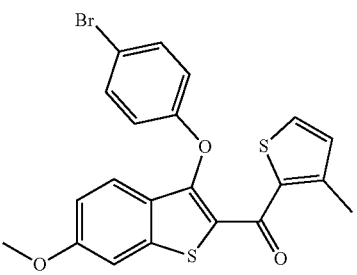

(3-(4-Bromophenoxy)-6-methoxybenzo[b]thiophen-2-yl)(3-methylthiophen-2-yl)methanone $^1$H NMR (400 MHz, CDCl$_3$) δ 7.52 (d, J = 8 9 Hz, 1H), 7.42 (d, J = 4.9 Hz, 1H), 7.28-7.23 (m, 3H), 6.99 (dd, J = 8.9, 2.2 Hz, 1H), 6.87 (d, J = 4.9 Hz, 1H), 6.67-6.59 (m, 2H), 3.91 (s, 3H), 2.34 (s, 3H). $^{13}$C NMR (101 MHz, DMSO) δ 181.10, 160.50, 157.62, 147.31, 145.02, 140.99, 135.76, 132.50, 131.63, 130.84, 126.58, 125.44, 124.19, 117.62, 116.31, 115.25, 104.96, 55.87, 15.94.

-continued

| | | |
|---|---|---|
| 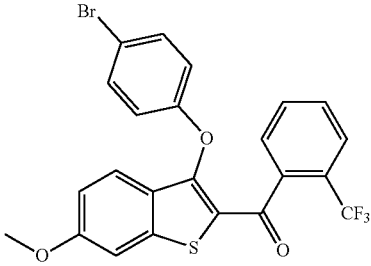 [SMILES: COc1ccc2c(Oc3ccc(Br)cc3)c(C(=O)c3ccccc3C(F)(F)F)sc2c1] | (3-(4-Bromophenoxy)-6-methoxybenzo[b]thiophen-2-yl)(2-(trifluoromethyl)phenyl)methanone | $^1$H NMR (400 MHz, CDCl$_3$) δ 7.59 (d, J = 7.7 Hz, 1H), 7.43 (t, J = 7.5 Hz, 1H), 7.37 (t, J = 7.3 Hz, 1H), 7.33-7.28 (m, 1H), 7.27-7.21 (m, 2H), 7.18 (d, J = 8.9 Hz, 2H), 6.89 (dd, J = 8.9, 2.2 Hz, 1H), 6.33 (d, J = 8.9 Hz, 2H), 3.89 (s, 3H). |
| 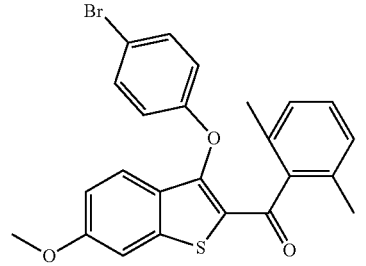 | (3-(4-Bromophenoxy)-6-methoxybenzo[b]thiophen-2-yl)(2,6-dimethylphenyl)methanone | $^1$H NMR (400 MHz, CDCl$_3$) δ 7.34 (d, J = 8.9 Hz, 1H), 7.28 (d, J = 2.1 Hz, 1H), 7.17 (d, J = 8.9 Hz, 2H), 7.04 (t, J = 7.6 Hz, 1H), 6.92 (dd, J = 8.9, 2.2 Hz, 1H), 6.86 (d, J = 7.7 Hz, 2H), 6.34 (d, J = 8.9 Hz, 2H), 3.88 (s, 3H), 2.11 (s, 6H). $^{13}$C NMR (100 MHz, CDCl$_3$) δ 192.08, 160.94, 156.72, 148.28, 142.22, 140.16, 133.71, 131.95, 128.73, 128.49, 127.35, 126.59, 124.67, 116.52, 116.40, 114.74, 105.22, 55.75, 19.18. |
| 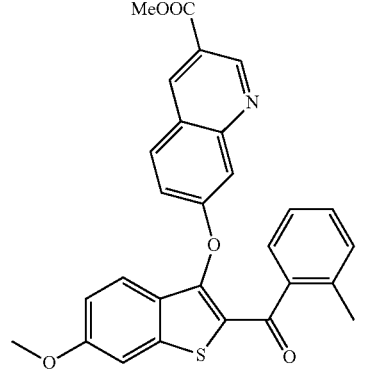 | Methyl 7-((6-methoxy-2-(2-methylbenzoyl)benzo[b]thiophen-3-yl)oxy)quinoline-3-carboxylate | $^1$H NMR (400 MHz, CDCl$_3$) δ 9.29 (d, J = 1.7 Hz, 1H), 8.71 (s, 1H), 7.64 (d, J = 9.0 Hz, 1H), 7.45 (d, J = 8.9 Hz, 1H), 7.30 (d, J = 1.8 Hz, 1H), 7.25 (d, J = 7.3 Hz, 1H), 7.16 (t, J = 7.3 Hz, 1H), 7.08 (d, J = 1.9 Hz, 1H), 6.99-6.88 (m, 3H), 6.83 (dd, J = 8.9, 2.3 Hz, 1H), 3.98 (s, 3H), 3.91 (s, 3H), 2.04 (s, 3H). $^{13}$C NMR (100 MHz, CDCl$_3$) δ 190.40, 165.93, 161.07, 160.98, 150.88, 150.81, 147.66, 142.34, 139.30, 138.37, 135.65, 130.48, 130.41, 130.14, 128.07, 127.33, 126.64, 125.14, 124.40, 122.83, 121.83, 118.87, 116.73, 111.31, 105.15, 55.89, 52.53, 19.22. |
| 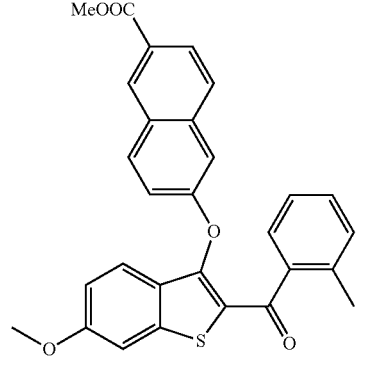 | Methyl 6-((6-methoxy-2-(2-methylbenzoyl)benzo[b]thiophen-3-yl)oxy)-2-naphthoate | $^1$H NMR (400 MHz, CDCl$_3$) δ 8.48 (s, 1H), 7.96 (dd, J = 8.6, 1.5 Hz, 1H), 7.64 (d, J = 9.0 Hz, 1H), 7.50 (d, J = 8.7 Hz, 1H), 7.47 (d, J = 8.9 Hz, 1H), 7.32-7.27 (m, 2H), 7.16 (t, J = 7.5 Hz, 1H), 6.98 (t, J = 7.5 Hz, 1H), 6.95-6.86 (m, 2H), 6.77 (d, J = 2.2 Hz, 1H), 6.73 (dd, J = 8.9, 2.5 Hz, 1H), 3.93 (s, 3H), 3.86 (s, 3H), 1.99 (s, 3H). $^{13}$C NMR (100 MHz, CDCl$_3$) δ 190.43, 167.05, 160.88, 158.00, 148.20, 142.08, 139.06, 136.21, 135.72, 131.02, 130.70, 130.36, 130.05, 128.52, 127.67, 127.47, 127.05, 126.85, |

-continued

| | | |
|---|---|---|
| | | 126.09, 126.02, 125.04, 124.43, 117.70, 116.38, 109.49, 105.09, 55.69, 52.11, 19.06. |
| 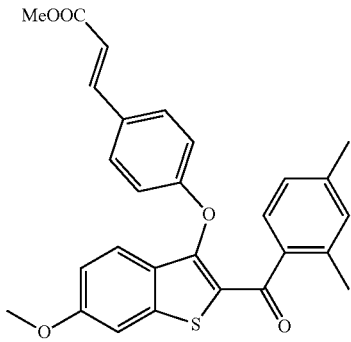 | Methyl (E)-3-(4-((2-(2,4-dimethylbenzoyl)-6-methoxybenzo[b]thiophen-3-yl)oxy)phenyl)acrylate | $^1$H NMR (400 MHz, CDCl$_3$) δ 7.57 (d, J = 16.0 Hz, 1H), 7.46 (d, J = 8.9 Hz, 1H), 7.28 (d, J = 2.1 Hz, 1H), 7.23 (t, J = 8.9 Hz, 3H), 6.96 (dd, J = 8.9, 2.2 Hz, 1H), 6.85 (d, J = 11.2 Hz, 2H), 6.47 (d, J = 8.8 Hz, 2H), 6.27 (d, J = 16.0 Hz, 1H), 3.91 (s, 3H), 3.79 (s, 3H), 2.29 (s, 3H), 2.09 (s, 3H). $^{13}$C NMR (100 MHz, CDCl$_3$) δ 190.48, 167.65, 160.87, 160.01, 147.81, 144.09, 141.92, 140.64, 136.30, 136.22, 131.40, 129.33, 128.91, 128.29, 127.79, 127.05, 125.79, 124.43, 116.48, 116.43, 115.58, 105.11, 55.87, 51.79, 21.47, 19.38. |
| 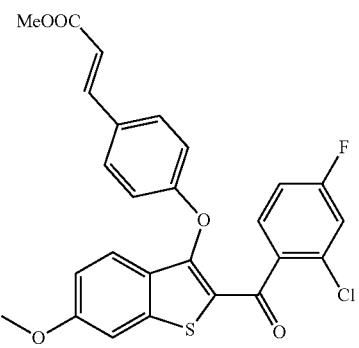 [SMILES: COC(=O)/C=C/c1ccc(Oc2c(C(=O)c3ccc(F)cc3Cl)sc3cc(OC)ccc23)cc1] | Methyl (E)-3-(4-((2-(2-chloro-4-fluorobenzoyl)-6-methoxybenzo[b]thiophen-3-yl)oxy)phenyl)acrylate | $^1$H NMR (400 MHz, CDCl$_3$) δ 7.58 (d, J = 16.0 Hz, 1H), 7.37 (d, J = 9.0 Hz, 1H), 7.28 (t, J = 8.8 Hz, 3H), 7.20 (dd, J = 8.5, 5.9 Hz, 1H), 7.00 (dd, J = 8.6, 2.3 Hz, 1H), 6.93 (dd, J = 9.0, 2.2 Hz, 1H), 6.81 (td, J = 8.3, 2.4 Hz, 1H), 6.55 (d, J = 8.7 Hz, 2H), 6.29 (d, J = 16.0 Hz, 1H), 3.91 (s, 3H), 3.79 (s, 3H). $^{13}$C NMR (100 MHz, CDCl$_3$) δ 186.10, 167.53, 163.16 (d, J = 253.1 Hz), 161.27, 159.30, 148.85, 143.81, 142.73, 135.48 (d, J = 3.7 Hz), 132.49 (d, J = 10.6 Hz), 129.79 (d, J = 9.3 Hz), 129.56, 129.36, 127.18, 126.36, 124.83, 117.18 (d, J = 24.9 Hz), 116.91, 116.72, 115.45, 113.83 (d, J = 21.6 Hz), 105.22, 55.91, 51.82. |

Compound I-5: (3-(4-Bromophenoxy)-6-hydroxy-benzo[b]thiophen-2-yl)(4-fluoro-2-methylphenyl)methanone

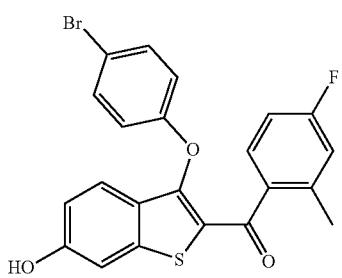 [SMILES: Cc1cc(F)ccc1C(=O)c1sc2cc(O)ccc2c1Oc1ccc(Br)cc1]

Compound I-4 (480 mg, 1 mmol) was dissolved in 10 mL of anhydrous dichloromethane at room temperature and BF$_3$.SMe$_2$ (1.2 ml, 5 mmol) was added dropwise to this solution. The reaction mixture was stirred until starting material, as monitored by TLC, was consumed. The reaction was then quenched with saturated NaHCO$_3$/ice water, extracted with ethyl acetate, and washed with brine. The organic extracts were combined, dried over anhydrous Na$_2$SO$_4$, concentrated in vacuum, and purified by flash chromatography (5%-60% ethyl acetate in hexane) to afford 390 mg as a white powder (85%). $^1$H NMR (400 MHz, MeOD) δ 7.38 (d, J=8.8 Hz, 1H), 7.35-7.28 (m, 1H), 7.28-7.20 (m, 3H), 6.90 (dd, J=8.8, 2.1 Hz, 1H), 6.87-6.80 (m, 2H), 6.46-6.38 (m, 2H), 2.13 (s, 3H).

The following compounds were made by an analogous procedure utilizing appropriate starting materials:

| | | |
|---|---|---|
| 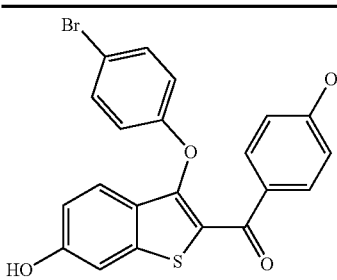 | (3-(4-Bromophenoxy)-6-hydroxybenzo[b]thiophen-2-yl) (4-hydroxyphenyl)methanone | ¹H NMR (400 MHz, Acetone) δ 7.71 (d, J = 8.7 Hz, 2H), 7.47 (d, J = 8.7 Hz, 1H), 7.41 (d, J = 2.0 Hz, 1H), 7.35 (d, J = 9.0 Hz, 2H), 7.02 (dd, J = 8.8, 2.1 Hz, 1H), 6.86 (d, J = 8.7 Hz, 2H), 6.68 (d, J = 9.0 Hz, 2H). |
| 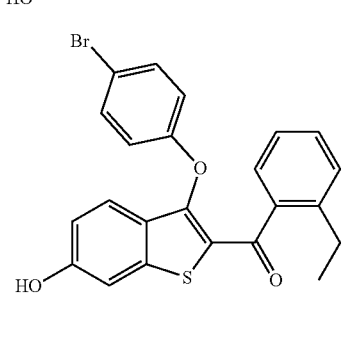 | (3-(4-Bromophenoxy)-6-hydroxybenzo[b]thiophen-2-yl) (2-ethylphenyl)methanone | ¹H NMR (400 MHz, Acetone) δ 9.25 (s, 1H), 7.44-7.38 (m, 2H), 7.35-7.26 (m, 4H), 7.19 (d, J = 7.5 Hz, 1H), 7.12 (t, J = 7.5 Hz, 1H), 6.99 (dd, J = 8.8, 2.2 Hz, 1H), 6.52-6.44 (m, 2H), 2.49 (q, J = 7.5 Hz, 2H), 1.04 (t, J = 7.6 Hz, 3H). ¹³C NMR (101 MHz, CDCl₃) δ 190.58, 159.88, 158.26, 149.03, 142.77, 142.50, 140.15, 133.10, 130.97, 129.63, 128.13, 128.05, 126.79, 126.01, 125.59, 118.04, 117.20, 115.18, 108.98, 26.72, 15.95. |
| 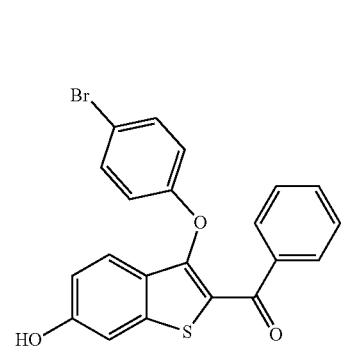 [SMILES: O=C(c1ccccc1)c1sc2cc(O)ccc2c1Oc1ccc(Br)cc1] | (3-(4-Bromophenoxy)-6-hydroxybenzo[b]thiophen-2-yl)(phenyl)methanone | ¹H NMR (400 MHz, MeOD) δ 7.62 (d, J = 7.2 Hz, 2H), 7.51 (t, J = 7.5 Hz, 1H), 7.44-7.32 (m, 3H), 7.25-7.21 (m, 3H), 6.91 (dd, J = 8.8, 2.1 Hz, 1H), 6.49 (d, J = 9.0 Hz, 2H). ¹³C NMR (101 MHz, MeOD) δ 190.76, 160.50, 158.77, 149.54, 143.24, 139.95, 133.47, 133.38, 129.69, 129.14, 126.80, 125.81, 125.53, 118.42, 117.39, 115.88, 108.74. |
| 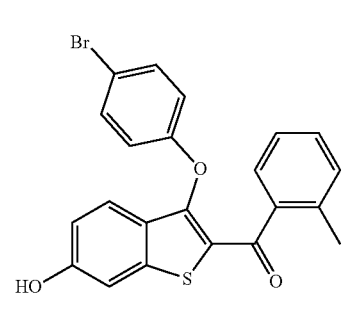 [SMILES: Cc1ccccc1C(=O)c1sc2cc(O)ccc2c1Oc1ccc(Br)cc1] | (3-(4-Bromophenoxy)-6-hydroxybenzo[b]thiophen-2-yl) (o-tolyl)methanone | ¹H NMR (400 MHz, MeOD) δ 7.36 (d, J = 8.8 Hz, 1H), 7.30-7.17 (m, 5H), 7.09 (t, J = 7.4 Hz, 2H), 6.89 (dd, J = 8.8, 2.1 Hz, 1H), 6.41-6.32 (m, 2H), 2.11 (s, 3H). ¹³C NMR (100 MHz, MeOD) δ 192.45, 160.86, 158.79, 150.45, 143.73, 140.77, 136.58, 133.33, 131.53, 131.27, 128.38, 127.60, 126.95, 126.34, 125.74, 117.99, 117.49, 115.77, 108.88, 19.29. |
| 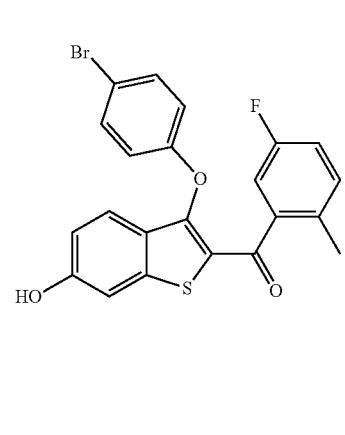 [SMILES: Cc1ccc(F)cc1C(=O)c1sc2cc(O)ccc2c1Oc1ccc(Br)cc1] | (3-(4-Bromophenoxy)-6-hydroxybenzo[b]thiophen-2-yl) (5-fluoro-2-methylphenyl)methanone | ¹H NMR (400 MHz, Acetone) δ 7.44-7.41 (m, 2H), 7.33 (d, J = 9.0 Hz, 2H), 7.18-7.13 (m, 1H), 7.09 (dd, J = 8.9, 2.7 Hz, 1H), 7.05-6.99 (m, 2H), 6.54 (d, J = 9.0 Hz, 2H), 2.11 (s, 3H). ¹³C NMR (101 MHz, CDCl₃) δ 189.08, 161.39 (d, J = 243.4 Hz), 160.11, 158.23, 149.48, 143.09, 142.07 (d, J = 6.4 Hz), 133.24, 132.96 (d, J = 7.6 Hz), 131.83 (d, J = 3.4 Hz), 127.43, 126.60, 125.72, 117.91, 117.34, 117.29 (d, J = 21.3 Hz), 115.39, 114.60 (d, J = 23.2 Hz), 109.04, 18.45. |

| | | |
|---|---|---|
| 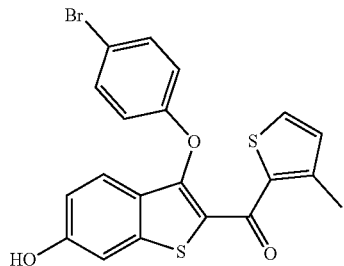 [SMILES: Cc1ccsc1C(=O)c1sc2cc(O)ccc2c1Oc1ccc(Br)cc1] | (3-(4-Bromophenoxy)-6-hydroxybenzo[b]thiophen-2-yl)(3-methylthiophen-2-yl)methanone | $^1$H NMR (400 MHz, Acetone-d6) δ 9.19 (s, 1H), 7.65 (d, J = 4.9 Hz, 1H), 7.54 (d, J = 8.8 Hz, 1H), 7.42 (d, J = 2.1 Hz, 1H), 7.39-7.32 (m, 2H), 7.04 (dd, J = 8.8, 2.1 Hz, 1H), 6.97 (d, J = 4.9 Hz, 1H), 6.74-6.65 (m, 2H), 2.29 (s, 3H). $^{13}$C NMR (100 MHz, Acetone-d6) δ 181.07, 159.40, 158.68, 147.89, 144.79, 141.57, 136.57, 133.26, 132.38, 131.63, 126.53, 125.63, 124.95, 118.55, 117.13, 115.47, 108.74, 15.70. |
| 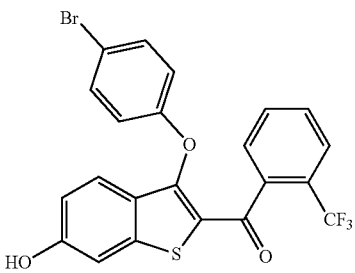 [SMILES: O=C(c1ccccc1C(F)(F)F)c1sc2cc(O)ccc2c1Oc1ccc(Br)cc1] | (3-(4-Bromophenoxy)-6-hydroxybenzo[b]thiophen-2-yl) (2-(trifluoromethyl)phenyl)methanone | $^1$H NMR (400 MHz, MeOD) δ 7.58 (d, J = 7.8 Hz, 1H), 7.43 (t, J = 7.5 Hz, 1H), 7.36 (t, J = 7.3 Hz, 1H), 7.31 (d, J = 7.2 Hz, 1H), 7.23 (d, J = 2.0 Hz, 1H), 7.19-7.09 (m, 3H), 6.80 (dd, J = 8.9, 2.1 Hz, 1H), 6.31 (d, J = 9.0 Hz, 2H). |
| 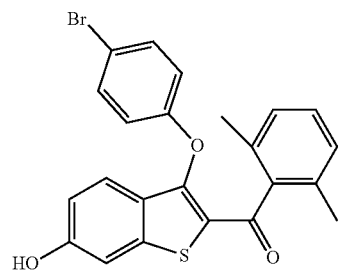 [SMILES: Cc1cccc(C)c1C(=O)c1sc2cc(O)ccc2c1Oc1ccc(Br)cc1] | (3-(4-Bromophenoxy)-6-hydroxybenzo[b]thiophen-2-yl)(2,6-dimethylphenyl)methanone | $^1$H NMR (400 MHz, Acetone) δ 9.29 (s, 1H), 7.43 (d, J = 2.1 Hz, 1H), 7.35 (d, J = 8.8 Hz, 1H), 7.29 (d, J = 9.0 Hz, 2H), 7.06 (t, J = 7.6 Hz, 1H), 6.98 (dd, J = 8.8, 2.1 Hz, 1H), 6.90 (d, J = 7.5 Hz, 2H), 6.46 (d, J = 8.9 Hz, 2H), 2.08 (s, 6H). $^{13}$C NMR (100 MHz, Acetone) δ 191.96, 159.98, 157.87, 149.06, 142.90, 141.45, 134.37, 132.90, 129.46, 128.64, 128.13, 126.65, 125.75, 117.72, 117.26, 115.12, 109.12, 19.29. |

Compound I-6: Methyl (E)-3-(4-((2-(4-fluoro-2-methylbenzoyl)-6-hydroxybenzo[b]thiophen-3-yl)oxy)phenyl)acrylate

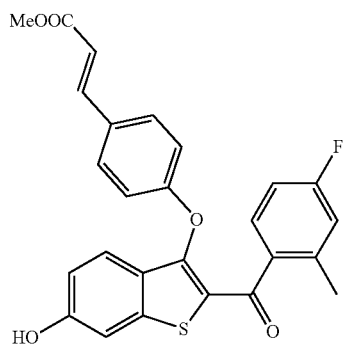 [SMILES: COC(=O)/C=C/c1ccc(Oc2c(C(=O)c3ccc(F)cc3C)sc3cc(O)ccc23)cc1]

In a sealed tube, Compound I-5 (200 mg, 0.46 mmol), methyl acrylate (240 mg, 2.76 mmol), and Pd(PPh$_3$)$_2$Cl$_2$ were suspended in DMF (2 ml) and triethylamine (235 mg, 2.3 mmol). The reaction was heated at 110° C. for 6 hours. The reaction mixture was quenched by water and extracted with ethyl acetate. The organic layers was collected and purified by flash chromatography (5%-60% ethyl acetate in hexane) to afford 170 mg as a white powder (85%). $^1$H NMR (400 MHz, MeOD) δ 7.57 (d, J=16.0 Hz, 1H), 7.40-7.36 (m, 3H), 7.32 (dd, J=8.8, 6.0 Hz, 1H), 7.27 (d, J=1.8 Hz, 1H), 6.89 (m J=8.9, 1.9 Hz, 1H), 6.83-6.78 (m, 2H), 6.52 (d, J=8.7 Hz, 2H), 6.37 (d, J=16.0 Hz, 1H), 3.76 (s, 3H), 2.10 (s, 3H). $^{13}$C NMR (100 MHz, MeOD) δ 191.09, 169.17, 164.95 (d, J=248.7 Hz), 161.19, 160.91, 150.13, 145.22, 143.71, 140.41 (d, J=8.6 Hz), 136.86 (d, J=3.0 Hz), 131.11 (d, J=9.2 Hz), 130.77, 130.47, 127.59, 126.92, 125.70, 118.13 (d, J=21.8 Hz), 117.55, 117.48, 116.47, 113.11 (d, J=21.9 Hz), 108.89, 52.09, 19.41.

The following compounds were made by an analogous procedure utilizing appropriate starting materials:

| | | |
|---|---|---|
| 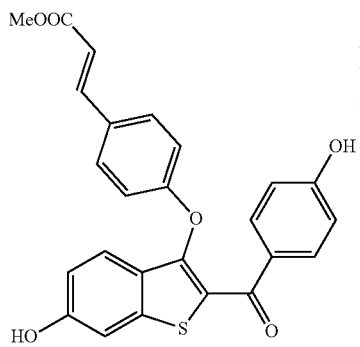 | Methyl (E)-3-(4-((6-hydroxy-2-(4-hydroxybenzoyl)benzo[b]thiophen-3-yl)oxy)phenyl)acrylate | $^1$H NMR (400 MHz, MeOD) δ 7.61 (d, J = 8.7 Hz, 2H), 7.55 (d, J = 16.0 Hz, 1H), 7.42 (d, J = 8.8 Hz, 1H), 7.39 (d, J = 8.8 Hz, 2H), 7.26 (d, J = 2.0 Hz, 1H), 6.91 (dd, J = 8.8, 2.1 Hz, 1H), 6.74 (d, J = 8.7 Hz, 2H), 6.66 (d, J = 8.8 Hz, 2H), 6.35 (d, J = 16.0 Hz, 1H), 3.74 (s, 3H). |
| 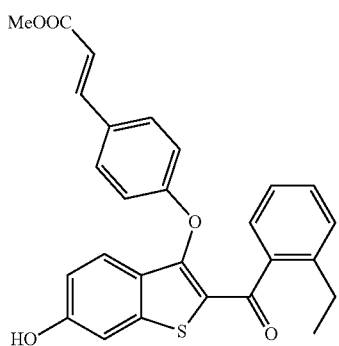 | Methyl (E)-3-(4-((2-(2-ethylbenzoyl)-6-hydroxybenzo[b]thiophen-3-yl)oxy)phenyl)acrylate | $^1$H NMR (400 MHz, MeOD) δ 7.57 (d, J = 16.0 Hz, 1H), 7.40-7.20 (m, 6H), 7.14 (d, J = 7.7 Hz, 1H), 7.06 (t, J = 7.5 Hz, 1H), 6.88 (dd, J = 8.8, 2.1 Hz, 1H), 6.47 (d, J = 8.8 Hz, 2H), 6.36 (d, J = 16.0 Hz, 1H), 3.76 (s, 3H), 2.46 (q, J = 7.5 Hz, 2H), 1.02 (t, J = 7.6 Hz, 3H). 13C NMR (101 MHz, CDCl$_3$) δ 192.46, 169.17, 161.00, 160.81, 150.20, 145.31, 143.66, 142.87, 140.35, 131.30, 130.70, 130.29, 129.89, 128.29, 127.97, 126.89, 126.30, 125.79, 117.47, 117.31, 116.67, 108.90, 52.09, 27.10, 15.96. |
| 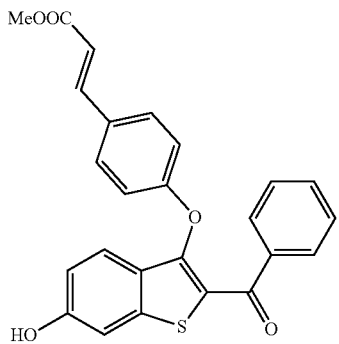 | Methyl (E)-3-(4-((2-benzoyl-6-hydroxybenzo[b]thiophen-3-yl)oxy)phenyl)acrylate | $^1$H NMR (400 MHz, DMSO) δ 10.39 (s, 1H), 7.65 (d, J = 7.9 Hz, 2H), 7.56-7.52 (m, 4H), 7.39-7.34 (m, 4H), 6.93 (d, J = 8.8 Hz, 1H), 6.66 (d, J = 8.5 Hz, 2H), 6.47 (d, J = 16.1 Hz, 1H), 3.69 (s, 3H). $^{13}$C NMR (101 MHz, DMSO) δ 187.95, 166.69, 159.08, 158.90, 147.19, 143.62, 141.00, 138.11, 132.27, 130.10, 128.67, 128.32, 128.03, 124.63, 124.32, 124.29, 116.55, 116.51, 115.66, 108.03, 51.37. |
| 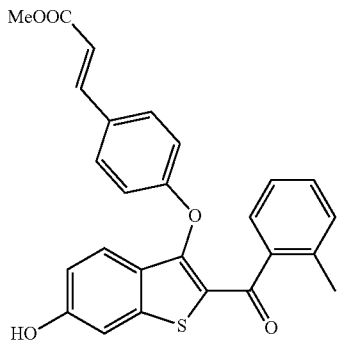 [SMILES: COC(=O)/C=C/c1ccc(Oc2c(C(=O)c3ccccc3C)sc3cc(O)ccc23)cc1] | Methyl (E)-3-(4-((6-hydroxy-2-(2-methylbenzoyl)benzo[b]thiophen-3-yl)oxy)phenyl)acrylate | $^1$H NMR (400 MHz, MeOD) δ 7.56 (d, J= 16.0 Hz, 1H), 7.35 (d, J = 8.6 Hz, 3H), 7.28-7.21 (m, 3H), 7.10-7.01 (m, 2H), 6.88 (dd, J = 8.8, 2.1 Hz, 1H), 6.46 (d, J = 8.7 Hz, 2H), 6.35 (d, J = 16.0 Hz, 1H), 3.76 (s, 3H), 2.09 (s, 3H). $^{13}$C NMR (100 MHz, MeOD) δ 192.43, 169.18, 161.17, 160.84, 150.28, 145.31, 143.69, 140.72, 136.56, 131.51, 131.25, 130.70, 130.31, 128.36, 127.69, 126.95, 126.32, 125.73, 117.49, 117.33, 116.58, 108.90, 52.09, 19.31. |

| | | |
|---|---|---|
| 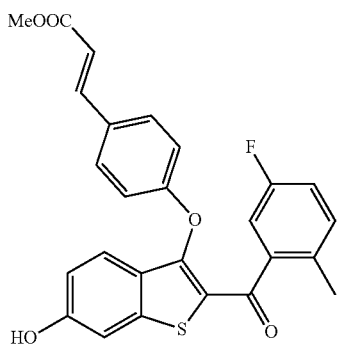 [SMILES: COC(=O)/C=C/c1ccc(Oc2c(C(=O)c3cc(F)ccc3C)sc3cc(O)ccc23)cc1] | Methyl (E)-3-(4-((2-(5-fluoro-2-methylbenzoyl)-6-hydroxybenzo[b]thiophen-3-yl)oxy)phenyl)acrylate | $^1$H NMR (400 MHz, MeOD) δ 7.55 (d, J = 16.0 Hz, 1H), 7.38-7.31 (m, 3H), 7.26 (d, J = 2.1 Hz, 1H), 7.09-7.00 (m, 1H), 6.99-6.92 (m, 2H), 6.87 (dd, J = 8.9, 2.1 Hz, 1H), 6.50 (d, J = 8.7 Hz, 2H), 6.35 (d, J = 16.0 Hz, 1H), 3.75 (s, 3H), 2.06 (s, 3H). $^{13}$C NMR (100 MHz, MeOD) δ 190.64, 169.15, 161.89 (d, J = 244.5 Hz), 161.01, 160.96, 150.54, 145.21, 143.94, 142.19 (d, J = 6.4 Hz), 133.17 (d, J = 7.5 Hz), 132.14 (d, J = 3.4 Hz), 130.80, 130.47, 127.31, 126.75, 125.87, 117.62 (d, J = 21.3 Hz), 117.60, 117.45, 116.49, 114.83 (d, J = 23.3 Hz), 108.94, 52.09, 18.49. |
| 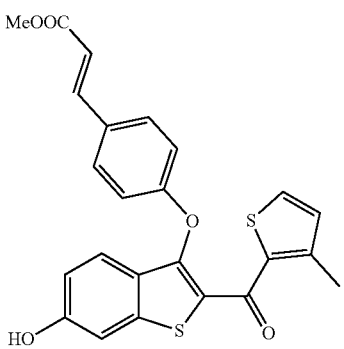 [SMILES: COC(=O)/C=C/c1ccc(Oc2c(C(=O)c3sccc3C)sc3cc(O)ccc23)cc1] | Methyl (E)-3-(4-((6-hydroxy-2-(3-methylthiophene-2-carbonyl)benzo[b]thiophen-3-yl)oxy)phenyl)acrylate | $^1$H NMR (400 MHz, MeOD) δ 7.61-7.55 (m, 2H), 7.50 (d, J = 8.8 Hz, 1H), 7.42 (d, J = 8.7 Hz, 2H), 7.28 (d, J = 2.1 Hz, 1H), 6.98-6.87 (m, 2H), 6.71 (d, J = 8.7 Hz, 2H), 6.38 (d, J = 16.0 Hz, 1H), 3.77 (s, 3H), 2.24 (s, 3H). $^{13}$C NMR (100 MHz, MeOD) δ 182.78, 169.15, 161.50, 160.27, 148.90, 145.52, 145.28, 142.40, 136.89, 132.55, 132.19, 130.85, 130.50, 126.82, 125.53, 125.13, 117.39, 117.09, 108.64, 52.09, 15.67. |
| 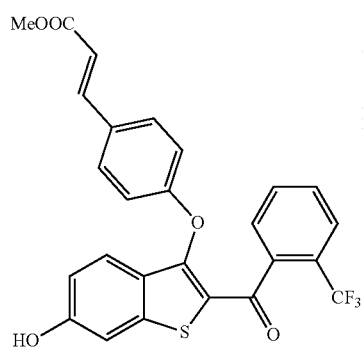 [SMILES: COC(=O)/C=C/c1ccc(Oc2c(C(=O)c3ccccc3C(F)(F)F)sc3cc(O)ccc23)cc1] | Methyl (E)-3-(4-((6-hydroxy-2-(2-(trifluoromethyl)benzoyl)benzo[b]thiophen-3-yl)oxy)phenyl)acrylate | $^1$H NMR (400 MHz, MeOD) δ 7.58 (d, J = 7.8 Hz, 1H), 7.52 (d, J = 16.0 Hz, 1H), 7.43 (t, J = 7.3 Hz, 1H), 7.38-7.21 (m, 5H), 7.17 (d, J = 8.8 Hz, 1H), 6.80 (dd, J = 8.8, 2.0 Hz, 1H), 6.42 (d, J = 8.7 Hz, 2H), 6.30 (d, J = 16.0 Hz, 1H), 3.71 (s, 3H). $^{13}$C NMR (100 MHz, MeOD) δ 188.88, 169.00, 160.87, 160.11, 150.85, 145.06, 143.97, 139.62 (q, J = 1.9 Hz), 132.62, 130.84, 130.65, 130.39, 128.51, 127.81 (q, J = 32.0 Hz), 127.29, 127.26 (q, J = 4.5 Hz), 126.13, 126.02, 125.02 (q, J = 273.4 Hz), 117.48, 117.42, 116.64, 109.01, 52.10. $^{19}$F NMR (400 MHz, MeOD) δ -57.84. |
| 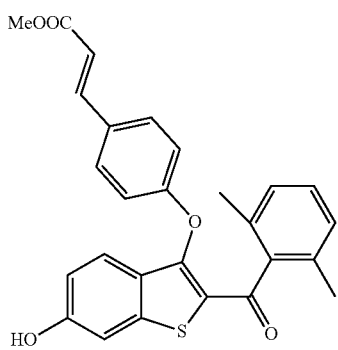 [SMILES: COC(=O)/C=C/c1ccc(Oc2c(C(=O)c3c(C)cccc3C)sc3cc(O)ccc23)cc1] | Methyl (E)-3-(4-((2-(2,6-dimethylbenzoyl)-6-hydroxybenzo[b]thiophen-3-yl)oxy)phenyl)acrylate | $^1$H NMR (400 MHz, MeOD) δ 7.57 (d, J = 16.0 Hz, 1H), 7.35 (d, J = 8.7 Hz, 2H), 7.30-7.24 (m, 2H), 7.03 (t, J = 7.6 Hz, 1H), 6.88-6.80 (m, 3H), 6.45 (d, J = 8.7 Hz, 2H), 6.36 (d, J = 16.0 Hz, 1H), 3.75 (s, 3H), 2.06 (s, 6H). $^{13}$C NMR (100 MHz, MeOD) δ 194.05, 169.17, 160.99, 160.62, 150.45, 145.33, 143.89, 141.52, 134.80, 130.57, 130.30, 129.92, 128.47, 126.75, 125.99, 117.57, 117.27, 116.42, 109.04, 52.10, 19.34. |

Example 1: Synthetic Procedures for Representative Compounds (E)-3-(4-((2-(4-Fluoro-2-methylbenzoyl)-6-hydroxybenzo[b]thiophen-3-yl)oxy)phenyl)acrylic acid (Compound 1)

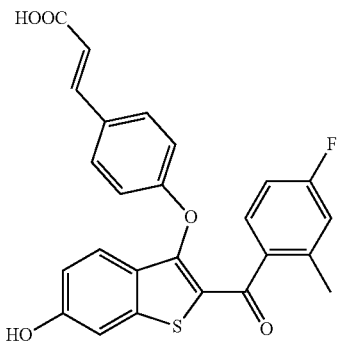 [SMILES: Cc1cc(F)ccc1C(=O)c1sc2cc(O)ccc2c1Oc1ccc(/C=C/C(=O)O)cc1]

To a solution of Compound I-6 (75 mg, 0.16 mmol) in methanol (2 ml) was added 10% LiOH solution (2 ml) dropwise. The reaction was monitored by TLC and once TLC indicated consumption of starting materials, the reaction was quenched by 1 N HCl/ice water. After stirring for 10 minutes, the mixture was extracted with ethyl acetate. The organic layers were collected and purified by C18 chromatography (5%-60% ethyl methanol in water) to afford 71 mg as a white powder (99%). $^1$H NMR (400 MHz, CDCl$_3$) δ 7.58 (d, J=16.0 Hz, 1H), 7.37 (d, J=9.0 Hz, 1H), 7.28 (t, J=8.8 Hz, 3H), 7.20 (dd, J=8.5, 5.9 Hz, 1H), 7.00 (dd, J=8.6, 2.3 Hz, 1H), 6.93 (dd, J=9.0, 2.2 Hz, 1H), 6.81 (td, J=8.3, 2.4 Hz, 1H), 6.55 (d, J=8.7 Hz, 2H), 6.29 (d, J=16.0 Hz, 1H), 3.91 (s, 3H), 3.79 (s, 3H). $^{13}$C NMR (100 MHz, CDCl$_3$) δ 186.10, 167.53, 163.16 (d, J=253.1 Hz), 161.27, 159.30, 148.85, 143.81, 142.73, 135.48 (d, J=3.7 Hz), 132.49 (d, J=10.6 Hz), 129.79 (d, J=9.3 Hz), 129.56, 129.36, 127.18, 126.36, 124.83, 117.18 (d, J=24.9 Hz), 116.91, 116.72, 115.45, 113.83 (d, J=21.6 Hz), 105.22, 55.91, 51.82.

Compounds 2-8 and 11-22 were made via an analogous procedure for the synthesis of Compound 1 utilizing appropriate starting materials. Characterization for these compounds is shown below in Table 1.

Compound 9: 5-((6-Hydroxy-2-(2-methylbenzoyl)benzo[b]thiophen-3-yl)oxy)-2-naphthoic Acid Compound 4 (100 mg, 0.21 mmol) was dissolved in 3 mL of anhydrous dichloromethane at room temperature under argon atmosphere. The solution was cooled using an ice water bath and BF$_3$.SMe$_2$ (1 ml, 4.2 mmol) was added dropwise. After stirring for 30 minutes, the solution was allowed to warm to 35° C. The reaction mixture was stirred until starting material was consumed, as monitored by TLC, and then quenched by saturated NaHCO$_3$/ice water. The reaction mixture was extracted with ethyl acetate and washed with brine. The organic extracts were combined, dried over anhydrous Na$_2$SO$_4$, concentrated in vacuum, and purified by flash chromatography (5%-60% ethyl acetate in hexane) to afford 37 mg white powder (38%). $^1$H NMR (400 MHz, MeOD) δ 8.47 (s, 1H), 7.93 (d, J=8.4 Hz, 1H), 7.72 (d, J=8.9 Hz, 1H), 7.56 (d, J=8.4 Hz, 1H), 7.40 (d, J=8.8 Hz, 1H), 7.30 (d, J=1.9 Hz, 1H), 7.28-7.08 (m, 2H), 7.01 (t, J=7.4 Hz, 1H), 6.94 (d, J=7.6 Hz, 1H), 6.88 (dd, J=8.8, 2.1 Hz, 1H), 6.79 (s, 1H), 6.74 (dd, J=8.9, 2.4 Hz, 1H), 1.95 (s, 3H). $^{13}$C NMR (100 MHz, MeOD) δ 192.50, 169.84, 160.87, 159.24, 150.50, 143.78, 140.65, 137.54, 136.54, 132.21, 131.70, 131.42, 131.18, 130.09, 128.34, 128.08, 127.69, 127.38, 127.05, 126.27, 125.78, 118.69, 117.51, 110.58, 108.92, 19.19. ESI-HRMS (m/z): [M+H]$^+$ calcd. for C$_{27}$H$_{18}$O$_5$S: 455.0953; observed, 455.0939.

Compound 10: 8-((6-Hydroxy-2-(2-methylbenzoyl)benzo[b]thiophen-3-yl)oxy)quinoline-3-carboxylic Acid Compound 24 was prepared following the procedure for the synthesis of Compound 9 to afford 33 mg (57%). $^1$H NMR (400 MHz, MeOD) δ 9.20 (s, 1H), 8.85 (s, 1H), 7.83 (d, J=9.0 Hz, 1H), 7.44 (d, J=8.8 Hz, 1H), 7.31 (s, 1H), 7.27-7.13 (m, 2H), 7.04-6.81 (m, 5H), 1.97 (s, 3H). $^{13}$C NMR (100 MHz, MeOD with TFA vapor) δ 192.08, 165.75, 162.47, 161.00, 151.79, 151.11, 149.43, 143.78, 140.53, 140.32, 136.47, 132.26, 131.43, 131.32, 128.29, 127.90, 126.64, 126.32, 125.56, 124.53, 119.98, 117.75, 110.96, 108.96, 19.21. ESI-HRMS (m/z): [M+H]$^+$ calcd. for C$_{26}$H$_{17}$NO$_5$S: 456.0906; observed, 456.0893.

TABLE 1

| | | | | |
|---|---|---|---|---|
| | | Characterization and Biological Data of Compounds 1-24 | | |
| Cmpd # | Structure | Name/Physical Data | MCF-7:5C IC$_{50}$ (nM) | MCF-7WS8 IC$_{50}$ (nM) |
| 1 | HOOC structure | $^1$H NMR (400 MHz, CDCl$_3$) δ 7.58 (d, J = 16.0 Hz, 1H), 7.37 (d, J = 9.0 Hz, 1H), 7.28 (t, J = 8.8 Hz, 3H), 7.20 (dd, J = 8.5, 5.9 Hz, 1H), 7.00 (dd, J = 8.6, 2.3 Hz, 1H), 6.93 (dd, J = 9.0, 2.2 Hz, 1H), 6.81 (td, J = 8.3, 2.4 Hz, 1H), 6.55 (d, J = 8.7 Hz, 2H), 6.29 (d, J = 16.0 Hz, 1H), 3.91 (s, 3H), 3.79 (s, 3H). $^{13}$C NMR (100 MHz, CDCl$_3$) δ 186.10, 167.53, 163.16 (d, J = 253.1 Hz), 161.27, 159.30, 148.85, 143.81, 142.73, 135.48 (d, J = 3.7 Hz), 132.49 (d, J = 10.6 Hz), 129.79 (d, J = 9.3 Hz), 129.56, 129.36, | 1.0 +/− 0.05 | 0.4 +/− 0.07 |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| | | 127.18, 126.36, 124.83, 117.18 (d, J = 24.9 Hz), 116.91, 116.72, 115.45, 113.83 (d, J = 21.6 Hz), 105.22, 55.91, 51.82. | | |
| 2 | 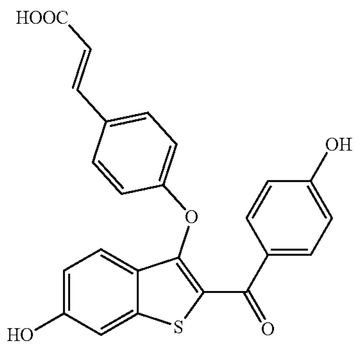 [SMILES: O=C(O)/C=C/c1ccc(Oc2c(C(=O)c3ccc(O)cc3)sc3cc(O)ccc23)cc1] | (E)-3-(4-((6-Hydroxy-2-(4-hydroxybenzoyl)benzo[b]thiophen-3-yl)oxy)phenyl) acrylic acid $^1$H NMR (400 MHz, MeOD) δ 7.61 (d, J = 8.7 Hz, 2H), 7.55 (d, J = 16.0 Hz, 1H), 7.43 (d, J = 8.8 Hz, 1H), 7.39 (d, J = 8.7 Hz, 2H), 7.26 (d, J = 2.1 Hz, 1H), 6.92 (dd, J = 8.8, 2.1 Hz, 1H), 6.74 (d, J = 8.7 Hz, 2H), 6.67 (d, J = 8.7 Hz, 2H), 6.31 (d, J = 16.0 Hz, 1H). $^{13}$C NMR (100 MHz, MeOD) δ 189.36, 170.39, 163.61, 161.20, 160.04, 148.16, 145.39, 142.57, 132.95, 130.77, 130.74, 130.42, 126.91, 125.84, 125.15, 118.03, 117.20, 117.05, 115.87, 108.68. 24 | 3.9 +/− 0.06 (54% Emax) | No Inhiibition |
| 3 | 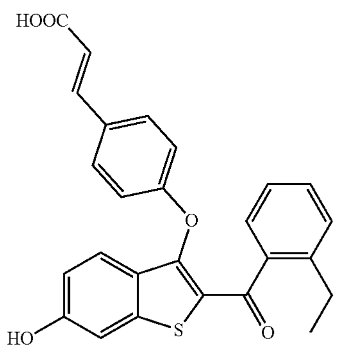 [SMILES: CCc1ccccc1C(=O)c1sc2cc(O)ccc2c1Oc1ccc(/C=C/C(=O)O)cc1] | (E)-3-(4-((2-(2-Ethylbenzoyl)-6-hydroxybenzo[b]thiophen-3-yl)oxy)phenyl) acrylic acid $^1$H NMR (400 MHz, MeOD) δ 7.55 (d, J = 16.0 Hz, 1H), 7.42-7.26 (m, 5H), 7.24 (d, J = 7.6 Hz, 1H), 7.15 (d, J = 7.7 Hz, 1H), 7.07 (t, J = 7.5 Hz, 1H), 6.88 (dd, J = 8.8, 2.1 Hz, 1H), 6.47 (d, J = 8.7 Hz, 2H), 6.32 (d, J = 16.0 Hz, 1H), 2.47 (q, J = 7.6 Hz, 2H), 1.02 (t, J = 7.6 Hz, 3H). $^{13}$C NMR (101 MHz, MeOD) δ 192.52, 170.42, 160.94, 160.82, 150.26, 145.35, 143.68, 142.88, 140.37, 131.31, 130.64, 130.43, 129.91, 128.29, 127.98, 126.92, 126.31, 125.81, 118.08, 117.47, 116.67, 108.91, 27.10, 15.95. | 1.2 +/− 0.04 | 0.9 +/− 0.04 |
| 4 | 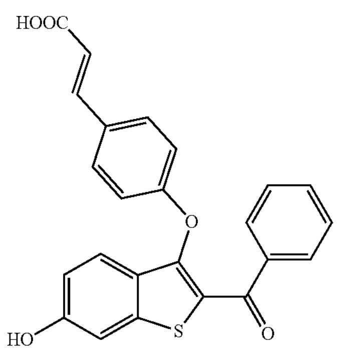 [SMILES: O=C(O)/C=C/c1ccc(Oc2c(C(=O)c3ccccc3)sc3cc(O)ccc23)cc1] | (E)-3-(4-((2-Benzoyl-6-hydroxybenzo[b]thiophen-3-yl)oxy)phenyl) acrylic acid $^1$H NMR (400 MHz, MeOD) δ 7.66-7.58 (m, 2H), 7.55 (d, J = 16.0 Hz, 1H), 7.50 (d, J = 7.4 Hz, 1H), 7.43-7.34 (m, 5H), 7.28 (d, J = 2.0 Hz, 1H), 6.92 (dd, J = 8.8, 2.1 Hz, 1H), 6.61 (d, J = 8.8 Hz, 2H), 6.32 (d, J = 16.0 Hz, 1H). $^{13}$C NMR (100 MHz, MeOD) δ 190.76, 170.39, 161.08, 160.51, 149.38, 145.33, 143.23, 139.90, 133.38, 130.77, 130.47, 129.70, 129.13, 126.82, 125.95, 125.55, 118.13, 117.38, 116.96, 108.75 | 13 +/− 0.08 | 2.2 +/− 0.1 |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 5 | 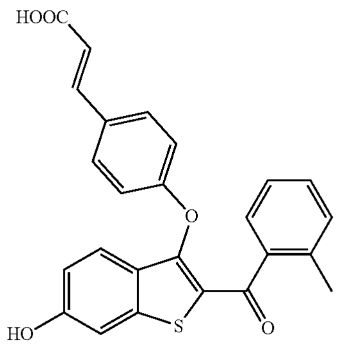 [SMILES: Cc1ccccc1C(=O)c1sc2cc(O)ccc2c1Oc1ccc(/C=C/C(=O)O)cc1] | (E)-3-(4-((6-Hydroxy-2-(2-methylbenzoyl)benzo[b]thiophen-3-yl)oxy)phenyl) acrylic acid <br> $^1$H NMR (400 MHz, MeOD) δ 7.54 (d, J = 16.0 Hz, 1H), 7.32 (dd, J = 8.7, 6.0 Hz, 3H), 7.28-7.2 (m, 3H), 7.06-7.03 (m, 2H), 6.87 (dd, J = 8.8, 2.0 Hz, 1H), 6.44 (d, J = 8.7 Hz, 2H), 6.30 (d, J = 16.0 Hz, 1H), 2.07 (s, 3H). $^{13}$C NMR (100 MHz, MeOD) δ 192.43, 170.39, 161.05, 160.78, 150.29, 145.35, 143.66, 140.66, 136.53, 131.49, 131.22, 130.61, 130.37, 128.35, 127.64, 126.93, 126.29, 125.73, 118.02, 117.47, 116.54, 108.90, 19.32. | 1.3 +/− 0.06 | 0.9 +/− 0.09 |
| 6 | 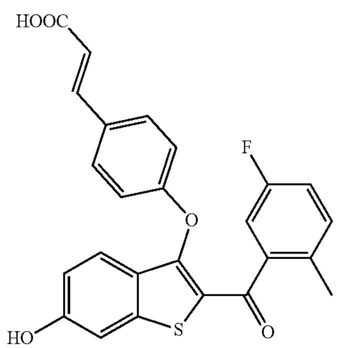 [SMILES: Cc1ccc(F)cc1C(=O)c1sc2cc(O)ccc2c1Oc1ccc(/C=C/C(=O)O)cc1] | (E)-3-(4-((2-(5-Fluoro-2-methylbenzoyl)-6-hydroxybenzo[b]thiophen-3-yl)oxy)phenyl) acrylic acid <br> $^1$H NMR (400 MHz, MeOD) δ 7.56 (d, J = 16.0 Hz, 1H), 7.41-7.34 (m, 3H), 7.27 (d, J = 2.0 Hz, 1H), 7.10-7.06 (m, 1H), 7.02-6.93 (m, 2H), 6.89 (dd, J = 8.9, 2.1 Hz, 1H), 6.53 (d, J = 8.8 Hz, 2H), 6.33 (d, J = 16.0 Hz, 1H), 2.08 (s, 3H). $^{13}$C NMR (100 MHz, MeOD) δ 190.69, 170.37, 161.92 (d, J = 244.8 Hz), 161.03, 160.90, 150.60, 145.27, 143.95, 142.21 (d, J = 6.5 Hz), 133.18 (d, J = 7.5 Hz), 132.15 (d, J = 3.4 Hz), 130.74, 130.62, 127.31, 126.78, 125.88, 118.21, 117.63 (d, J = 21.3 Hz), 117.59, 116.48, 114.82 (d, J = 23.3 Hz), 108.93, 18.48. | 4.7 +/− 0.04 | 0.7 +/− 0.3 |
| 7 | 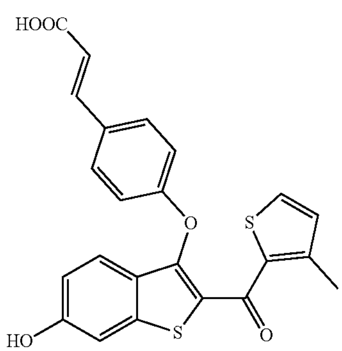 [SMILES: Cc1ccsc1C(=O)c1sc2cc(O)ccc2c1Oc1ccc(/C=C/C(=O)O)cc1] | (E)-3-(4-((6-Hydroxy-2-(3-methylthiophene-2-carbonyl)benzo[b]thiophen-3-yl)oxy)phenyl) acrylic acid <br> $^1$H NMR (400 MHz, MeOD) δ 7.59-7.51 (m, 2H), 7.49 (d, J = 8.8 Hz, 1H), 7.40 (d, J = 8.7 Hz, 2H), 7.26 (d, J = 2.1 Hz, 1H), 6.93 (dd, J = 8.8, 2.1 Hz, 1H), 6.90 (d, J = 4.9 Hz, 1H), 6.70 (d, J = 8.7 Hz, 2H), 6.32 (d, J = 16.0 Hz, 1H), 2.23 (s, 3H). $^{13}$C NMR (100 MHz, MeOD) δ 182.84, 170.46, 161.42, 160.27, 148.95, 145.51, 145.27, 142.41, 136.91, 132.55, 132.20, 130.78, 130.65, 126.84, 125.52, 125.14, 118.24, 117.38, 117.08, 108.63, 15.66. | 12.5 +/− 0.01 | 2.8 +/− 0.16 |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 8 | 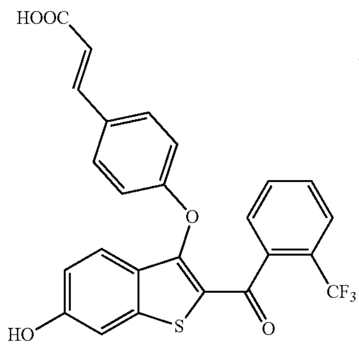 | (E)-3-(4-((6-Hydroxy-2-(2-(trifluoromethyl)benzoyl)benzo[b]-thiophen-3-yl)oxy)phenyl) acrylic acid $^1$H NMR (400 MHz, Acetone) δ 7.69 (d, J = 7.9 Hz, 1H), 7.62-7.53 (m, 2H), 7.53-7.46 (m, 4H), 7.45 (d, J = 1.9 Hz, 1H), 7.31 (d, J = 8.8 Hz, 1H), 6.97 (dd, J = 8.9, 2.1 Hz, 1H), 6.57 (d, J = 8.8 Hz, 2H), 6.39 (d, J = 16.0 Hz, 1H). $^{13}$C NMR (100 MHz, Acetone) $^{13}$C NMR (101 MHz, CDCl$_3$) δ 187.60, 167.78, 160.17, 159.68, 149.95, 144.51, 143.23, 139.58, 132.63, 130.73, 130.49, 130.33, 128.38, 127.45, 127.24 (q, J = 31.9 Hz), 127.11 (q, J = 4.6 Hz), 126.14, 125.91, 124.85 (q, J = 273.3 Hz), 118.10, 117.32, 116.51, 109.12. | 2.7 +/− 0.11 (61% Emax) | 1.2 +/− 0.08 (65% Emax) |
| 9 | 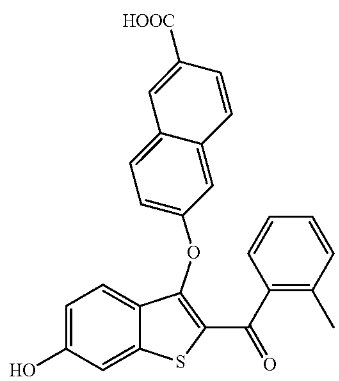 [SMILES: Cc1ccccc1C(=O)c1sc2cc(O)ccc2c1Oc1ccc2cc(C(=O)O)ccc2c1] | $^1$H NMR (400 MHz, MeOD) δ 8.47 (s, 1H), 7.93 (d, J = 8.4 Hz, 1H), 7.72 (d, J = 8.9 Hz, 1H), 7.56 (d, J = 8.4 Hz, 1H), 7.40 (d, J = 8.8 Hz, 1H), 7.30 (d, J = 1.9 Hz, 1H), 7.28-7.08 (m, 2H), 7.01 (t, J = 7.4 Hz, 1H), 6.94 (d, J = 7.6 Hz, 1H), 6.88 (dd, J = 8.8, 2.1 Hz, 1H), 6.79 (s, 1H), 6.74 (dd, J = 8.9, 2.4 Hz, 1H), 1.95 (s, 3H). $^{13}$C NMR (100 MHz, MeOD) δ 192.50, 169.84, 160.87, 159.24, 150.50, 143.78, 140.65, 137.54, 136.54, 132.21, 131.70, 131.42, 131.18, 130.09, 128.34, 128.08, 127.69, 127.38, 127.05, 126.27, 125.78, 118.69, 117.51, 110.58, 108.92, 19.19. ESI-HRMS (m/z): [M + H]$^+$ calcd. for C$_{27}$H$_{18}$O$_5$S: 455.0953; observed, 455.0939. | 4.8 +/− 0.06 | 2.4 +/− 0.12 |
| 10 | 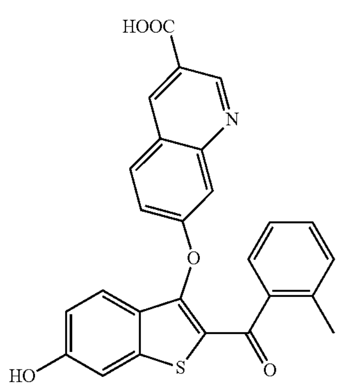 [SMILES: Cc1ccccc1C(=O)c1sc2cc(O)ccc2c1Oc1ccc2cc(C(=O)O)cnc2c1] | $^1$H NMR (400 MHz, MeOD) δ 9.20 (s, 1H), 8.85 (s, 1H), 7.83 (d, J = 9.0 Hz, 1H), 7.44 (d, J = 8.8 Hz, 1H), 7.31 (s, 1H), 7.27-7.13 (m, 2H), 7.04-6.81 (m, 5H), 1.97 (s, 3H). $^{13}$C NMR (100 MHz, MeOD with TFA vapor) δ 192.08, 165.75, 162.47, 161.00, 151.79, 151.11, 149.43, 143.78, 140.53, 140.32, 136.47, 132.26, 131.43, 131.32, 128.29, 127.90, 126.64, 126.32, 125.56, 124.53, 119.98, 117.75, 110.96, 108.96, 19.21. ESI-HRMS (m/z): [M +H]$^+$ calcd. for C$_{26}$H$_{17}$NO$_5$S: 456.0906; observed, 456.0893 | 32.3 +/− 0.19 (52% Emax) | No Inhibition |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 11 | 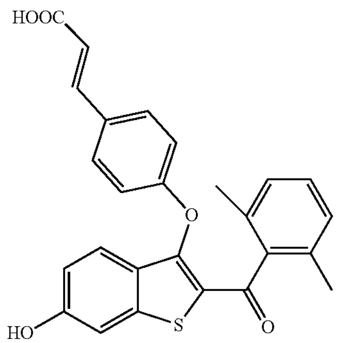 [SMILES: Cc1cccc(C)c1C(=O)c1sc2cc(O)ccc2c1Oc1ccc(/C=C/C(=O)O)cc1] | (E)-3-(4-((2-(2,6-Dimethylbenzoyl)-6-hydroxybenzo[b]thiophen-3-yl)oxy)phenyl) acrylic acid<br>$^1$H NMR (400 MHz, MeOD) δ 7.55 (d, J = 16.0 Hz, 1H), 7.32 (d, J = 8.7 Hz, 2H), 7.27-7.19 (m, 2H), 7.01 (t, J = 7.6 Hz, 1H), 6.87-6.77 (m, 3H), 6.43 (d, J = 8.6 Hz, 2H), 6.31 (d, J = 16.0 Hz, 1H), 2.04 (s, 6H). $^{13}$C NMR (100 MHz, MeOD) δ 194.06, 170.40, 160.93, 160.50, 150.47, 145.38, 143.86, 141.47, 134.76, 130.48, 130.35, 129.90, 128.44, 126.74, 125.99, 117.97, 117.55, 116.38, 109.04, 19.35. | 0.5 +/− 0.04 | 0.1 +/− 0.07 |
| 12 | 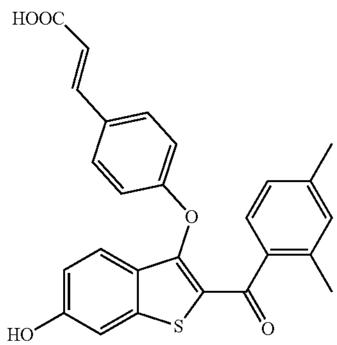 [SMILES: Cc1ccc(C(=O)c2sc3cc(O)ccc3c2Oc2ccc(/C=C/C(=O)O)cc2)c(C)c1] | (E)-3-(4-((2-(2,4-Dimethylbenzoyl)-6-hydroxybenzo[b]thiophen-3-yl)oxy)phenyl) acrylic acid<br>$^1$H NMR (400 MHz, Acetone) δ 7.58 (d, J = 16.0 Hz, 1H), 7.50-7.38 (m, 4H), 7.25 (d, J = 7.7 Hz, 1H), 7.01 (dd, J = 8.8, 2.1 Hz, 1H)), 6.96-6.86 (m, 2H), 6.57 (d, J = 8.7 Hz, 2H), 6.38 (d, J = 16.0 Hz, 1H), 2.29 (s, 3H), 2.07 (s, 3H). $^{13}$C NMR (100 MHz, Acetone) δ 190.44, 167.80, 160.72, 159.80, 148.66, 144.67, 142.52, 141.14, 137.47, 136.47, 131.96, 130.35, 130.01, 128.72, 127.86, 126.99, 126.55, 125.39, 117.81, 117.15, 116.34, 108.90, 21.31, 19.33. | 0.4 +/− 0.04 | 0.1 +/− 0.08 |
| 13 | 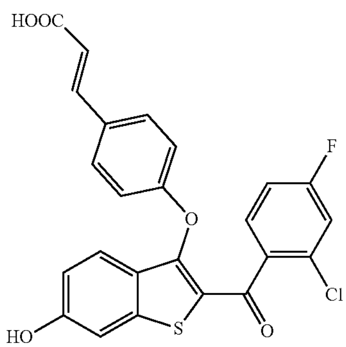 [SMILES: O=C(O)/C=C/c1ccc(Oc2c(C(=O)c3ccc(F)cc3Cl)sc3cc(O)ccc23)cc1] | (E)-3-(4-((2-(2-Chloro-4-fluorobenzoyl)-6-hydroxybenzo[b]thiophen-3-yl)oxy)phenyl) acrylic acid<br>LC-MS M/Z (M − H)$^-$: 467.9 | 2.2 +/− 0.12 | 0.4 +/− 0.13 |
| 14 | 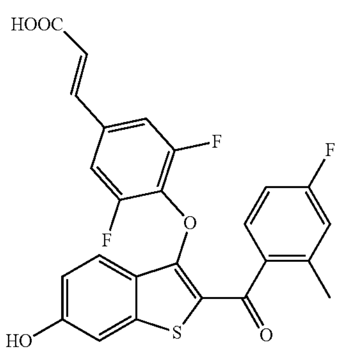 [SMILES: Cc1cc(F)ccc1C(=O)c1sc2cc(O)ccc2c1Oc1c(F)cc(/C=C/C(=O)O)cc1F] | (E)-3-(3,5-Difluoro-4-((2-(4-fluoro-2-methylbenzoyl)-6-hydroxybenzo[b]thiophen-3-yl)oxy)phenyl) acrylic acid<br>LC-MS M/Z (M − H)$^-$: 483.4 | >10 | >10 |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 15 | 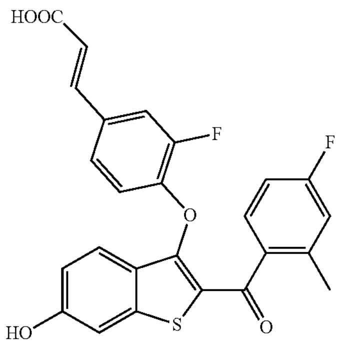 [SMILES: Cc1cc(F)ccc1C(=O)c1sc2cc(O)ccc2c1Oc1ccc(/C=C/C(=O)O)cc1F] | (E)-3-(3-Fluoro-4-((2-(4-fluoro-2-methylbenzoyl)-6-hydroxybenzo[b]thiophen-3-yl)oxy)phenyl) acrylic acid<br>LC-MS M/Z (M − H)⁻: 465.4 | <10 | <10 |
| 16 | 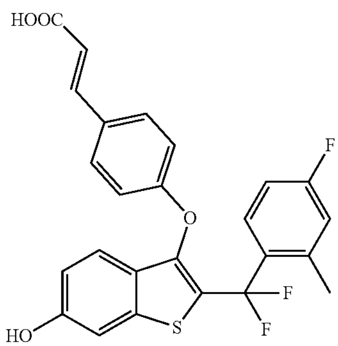 [SMILES: Cc1cc(F)ccc1C(F)(F)c1sc2cc(O)ccc2c1Oc1ccc(/C=C/C(=O)O)cc1] | (E)-3-(4-((2-(Difluoro(4-fluoro-2-methylphenyl)methyl)-6-hydroxybenzo[b]thiophen-3-yl)oxy)phenyl)acrylic acid<br>LC-MS M/Z (M − H)⁻: 469.5 | <100 | <100 |
| 17 | 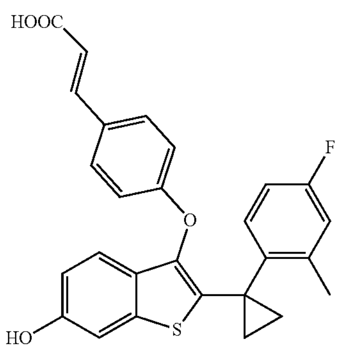 [SMILES: Cc1cc(F)ccc1C1(c2sc3cc(O)ccc3c2Oc2ccc(/C=C/C(=O)O)cc2)CC1] | (E)-3-(4-((2-(1-(4-Fluoro-2-methylphenyl)cyclopropyl)-6-hydroxybenzo[b]thiophen-3-yl)oxy)phenyl) acrylic acid<br>LC-MS M/Z (M − H)⁻: 459.5 | <100 | <100 |
| 18 | 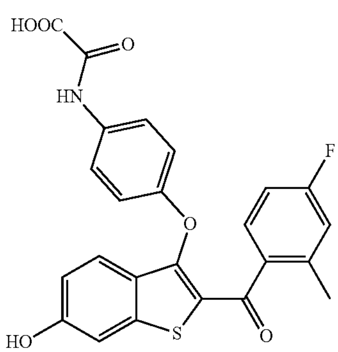 [SMILES: Cc1cc(F)ccc1C(=O)c1sc2cc(O)ccc2c1Oc1ccc(NC(=O)C(=O)O)cc1] | 2-((4-((2-(4-Fluoro-2-methylbenzoyl)-6-hydroxybenzo[b]thiophen-3-yl)oxy)phenyl) amino)-2-oxoacetic acid<br>¹H NMR (400 MHz, MeOD) δ 7.46 (d, J = 8.3 Hz, 2H), 7.38-7.27 (m, 2H), 7.24 (s, 1H), 6.90-6.77 (m, 3H), 6.46 (d, J = 8.2 Hz, 2H), 2.11 (s, 3H). ¹³C NMR (100 MHz, MeOD) δ 191.26, 164.87 (d, J = 248.6 Hz), 160.76, 156.78, 150.82, 143.70, 140.40 (d, J = 8.6 Hz), 136.90, 136.87, 133.35, 131.10 (d, J = 9.1 Hz), 127.30, 127.03, 125.84, 123.09, 118.11 (d, J = 21.7 Hz), 117.38, 116.16, 113.05 (d, J = 21.9 Hz), 108.85, 19.46. | 1.7 +/− 0.07 (64% Emax) | No Inhibition |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 19 | 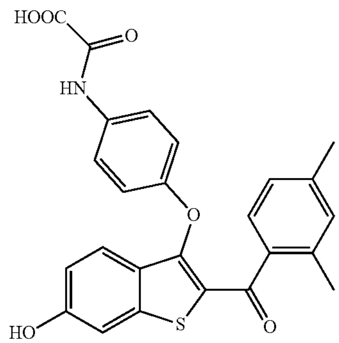 [SMILES: Cc1ccc(C(=O)c2sc3cc(O)ccc3c2Oc2ccc(NC(=O)C(=O)O)cc2)c(C)c1] | 2-((4((2-(2,4-Dimethylbenzoyl)-6-hydroxybenzo[b]thiophen-3-yl)oxy)phenyl) amino)-2-oxoacetic acid<br>LC-MS M/Z (M − H)⁻: 460.1 | >10 | No inhibition |
| 20 | 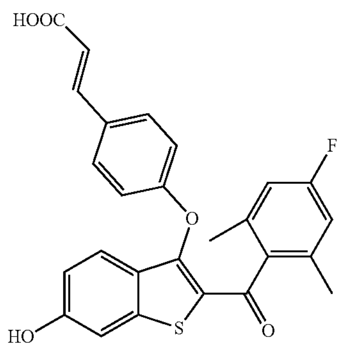 [SMILES: Cc1cc(F)cc(C)c1C(=O)c1sc2cc(O)ccc2c1Oc1ccc(/C=C/C(=O)O)cc1] | (E)-3-(4-((2-(4-Fluoro-2,6-dimethylbenzoyl)-6-hydroxybenzo[b]thiophen-3-yl)oxy)phenyl) acrylic acid<br>$^1$H NMR (400 MHz, Acetone-d6) δ 7.60 (d, J = 16.0 Hz, 1H), 7.51 (d, J = 8.7 Hz, 2H), 7.44 (d, J = 1.7 Hz, 1H), 7.37 (d, J = 8.8 Hz, 1H), 6.99 (dd, J = 8.8, 1.9 Hz, 1H), 6.66 (d, J = 9.8 Hz, 2H), 6.60 (d, J = 8.6 Hz, 2H), 6.40 (d, J = 16.0 Hz, 1H), 2.10 (s, 6H). $^{13}$C NMR (100 MHz, Acetone-d6) δ 191.13, 167.89, 163.21 (d, J = 244.9 Hz), 160.08, 149.15, 144.65, 142.99, 137.66, 137.58 (d, J = 8.8 Hz), 130.34, 130.13, 128.63, 126.65, 125.79, 117.89, 117.34, 115.99, 114.64(d, J = 21.5 Hz), 109.12, 19.34, 19.32. | 0.4 +/− 0.03 | <0.1 |
| 21 | 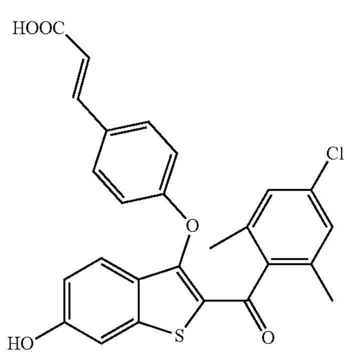 [SMILES: Cc1cc(Cl)cc(C)c1C(=O)c1sc2cc(O)ccc2c1Oc1ccc(/C=C/C(=O)O)cc1] | (E)-3-(4-((2-(4-Chloro-2,6-dimethylbenzoyl)-6-hydroxybenzo[b]thiophen-3-yl)oxy)phenyl) acrylic acid<br>$^1$H NMR (400 MHz, Acetone-d6) δ 7.60 (d, J = 16.0 Hz, 1H), 7.51 (d, J = 8.6 Hz, 2H), 7.45 (d, J = 1.7 Hz, 1H), 7.39 (d, J = 8.8 Hz, 1H), 7.00 (dd, J = 8.8, 1.9 Hz, 1H), 6.91 (s, 2H), 6.58 (d, J = 8.6 Hz, 2H), 6.40 (d, J = 16.0 Hz, 1H), 2.09 (s, 6H). $^{13}$C NMR (100 MHz, Acetone-d6) δ 190.91, 167.77, 160.17, 160.00, 149.30, 144.62, 143.07, 139.99, 136.85, 134.53, 130.26, 130.17, 128.40, 127.88, 126.67, 125.82, 117.94, 117.38, 115.91, 109.13, 19.12. | 0.3 +/− 0.04 | <0.1 |

TABLE 1-continued

Characterization and Biological Data of Compounds 1-24

| Cmpd # | Structure | Name/Physical Data | MCF-7:5C IC$_{50}$ (nM) | MCF-7WS8 IC$_{50}$ (nM) |
|---|---|---|---|---|
| 22 | [Structure: benzo[b]thiophene with HOOC-vinyl-phenyl-oxy, trimethylbenzoyl, and HO groups] | (E)-3-(4-((6-Hydroxy-2-(2,4,6-trimethylbenzoyl)benzo[b]thiophen-3-yl)oxy)phenyl) acrylic acid <br> $^1$H NMR (400 MHz, MeOD) δ 7.55 (d, J = 15.9 Hz, 1H), 7.34 (d, J = 8.7 Hz, 2H), 7.29 (d, J = 8.9 Hz, 1H), 7.26 (d, J = 1.9 Hz, 1H), 6.86 (dd, J = 8.8, 2.1 Hz, 1H), 6.63 (s, 2H), 6.44 (d, J = 8.6 Hz, 2H), 6.32 (d, J = 15.9 Hz, 1H), 2.18 (s, 3H), 2.01 (s, 6H). $^{13}$C NMR (100 MHz, MeOD) δ 194.48, 160.95, 160.62, 150.30, 145.28, 143.76, 139.89, 138.64, 134.74, 130.39, 130.27, 129.13, 128.72, 126.95, 125.91, 118.20, 117.55, 116.26, 109.00, 21.13, 19.30. | 0.5 +/− 0.03 | <0.1 |

Assays:
Cell Viability of MCF7:WS8 and Cell Viability of MCF7:5C (Tamoxifen Resistant)

The DNA content of the cells was determined as previously described using a Fluorescent DNA Quantitation kit (cat. No. 170-2480; Bio-Rad Laboratories, Hercules, Calif.). Briefly, five thousand cells were plated per well in 96-well plates, and treatment with indicated concentrations of compounds was started at the same time in each well. On day 4 or 6, for MCF7:WS8 or MCF7:5C respectively, the cells in the plates were lysed and frozen at −80° C. To measure the total DNA in each well, the plates were allowed to warm to room temperature, incubated with Hoechst dye, and mixed well. The fluorescence was measured using a Synergy H4 Hybrid Multi-Mode Microplate Reader. For each analysis, six replicate wells were used and at least three independent experiments were performed.

Cell Viability of 3D Spheroids

Spheroids were plated at a concentration of 1000 cells per well in Corning® 96-well clear black round-bottom ultra-low attachment spheroid microplate and allowed to grow in the absence of treatment for 48 hours. 100 μL media was removed from each well and 100 μL 2X concentration of the treatment was added. This procedure was repeated every 2-3 days for 12 days. Analysis occurred on day 15 after plating. CellTiter-Glo® 3D Cell Viability Assay protocol was used to determine growth inhibition of the spheroids. The plates and reagent were allowed to warm to room temperature for 30 minutes. During this time, the spheroids were washed with PBS 2 times by removing 100 μL media and replacing with PBS. 100 μL from each well was then removed and replaced with 100 μL CellTiter-Glo® 3D reagent and spheroids were disrupted by pipetting. The plates were placed on a shaker for 5 minutes before allowing to equilibrate in the dark for 25 minutes. 125 μL from each well was then transferred to a white 96-well plate before recording luminescence.

Western Blot:

Whole-cell extracts of cultured cells were prepared in lysis buffer (200 mmol/L Tris, 1% Triton X-100, 5 mmol/L EDTA) with protease and phosphatase inhibitor cocktails (1:50, both from Sigma-Aldrich) after scraping from the culture plates. Protein concentration was measured using the Bradford method (Bio-Rad). Proteins were separated under denaturing conditions and blotted onto nitrocellulose membrane (Bio-Rad) using a wet transfer system (Bio-Rad). Images of blots were acquired on a Bio-Rad ChemiDoc System following incubation with SuperSignal West Dura luminol solution (Thermo Fisher Scientific).

Figure 1B:
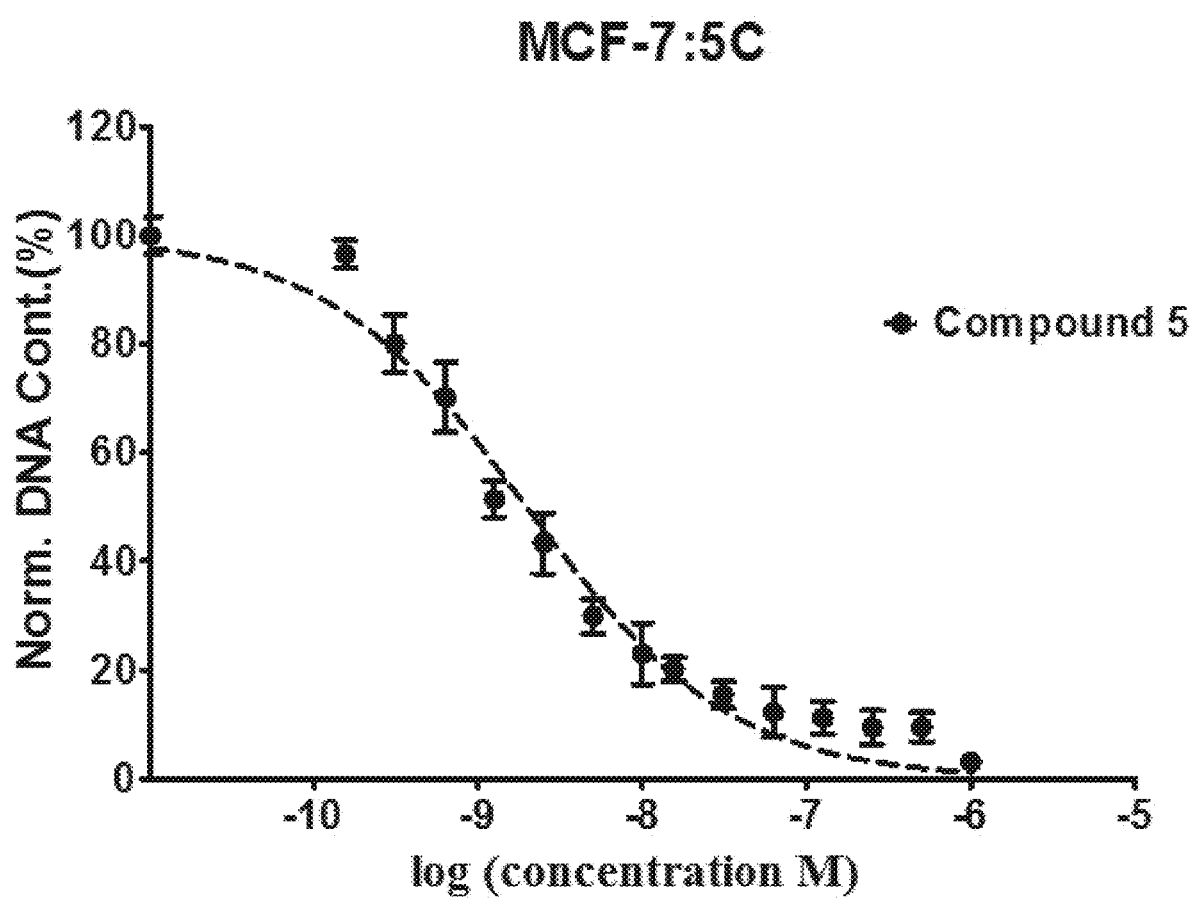
Figure 1C:
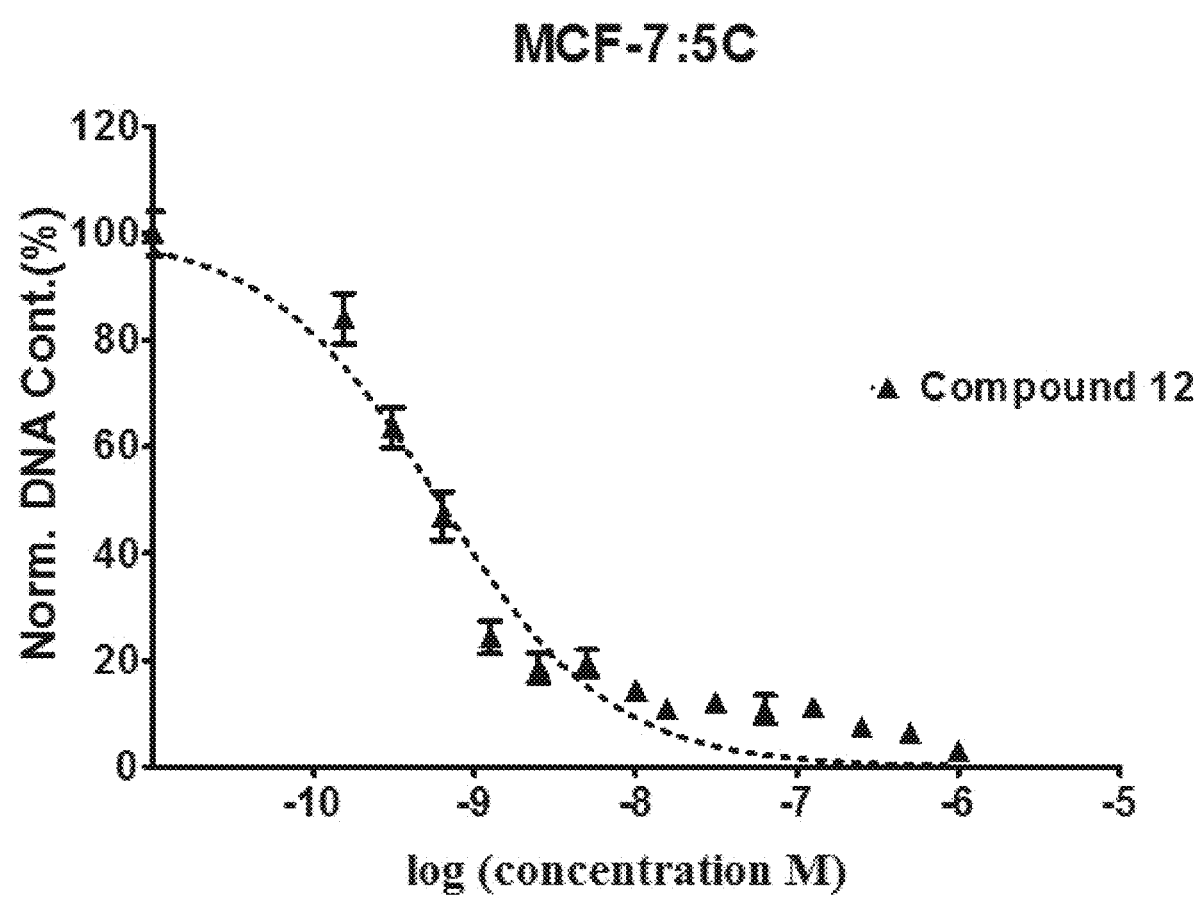
Figure 1D:
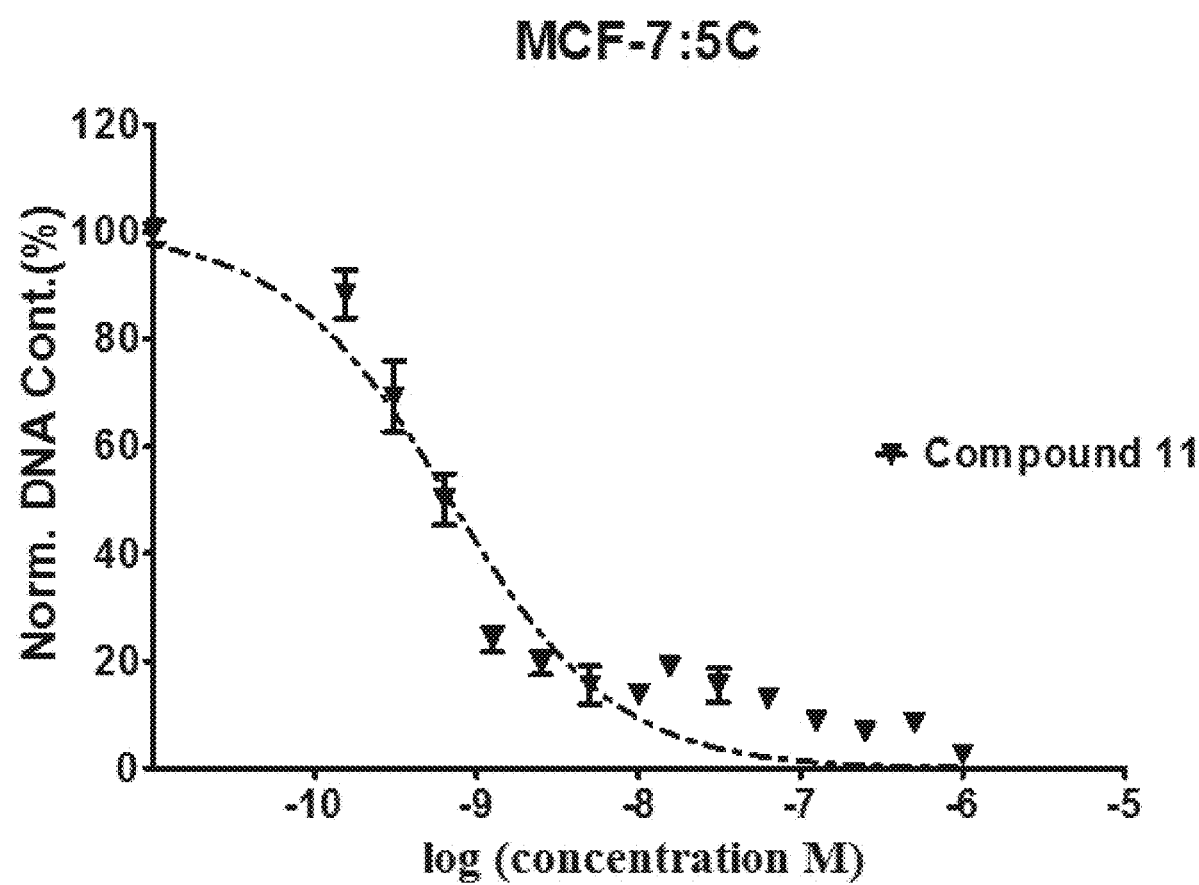
Figure 1E:
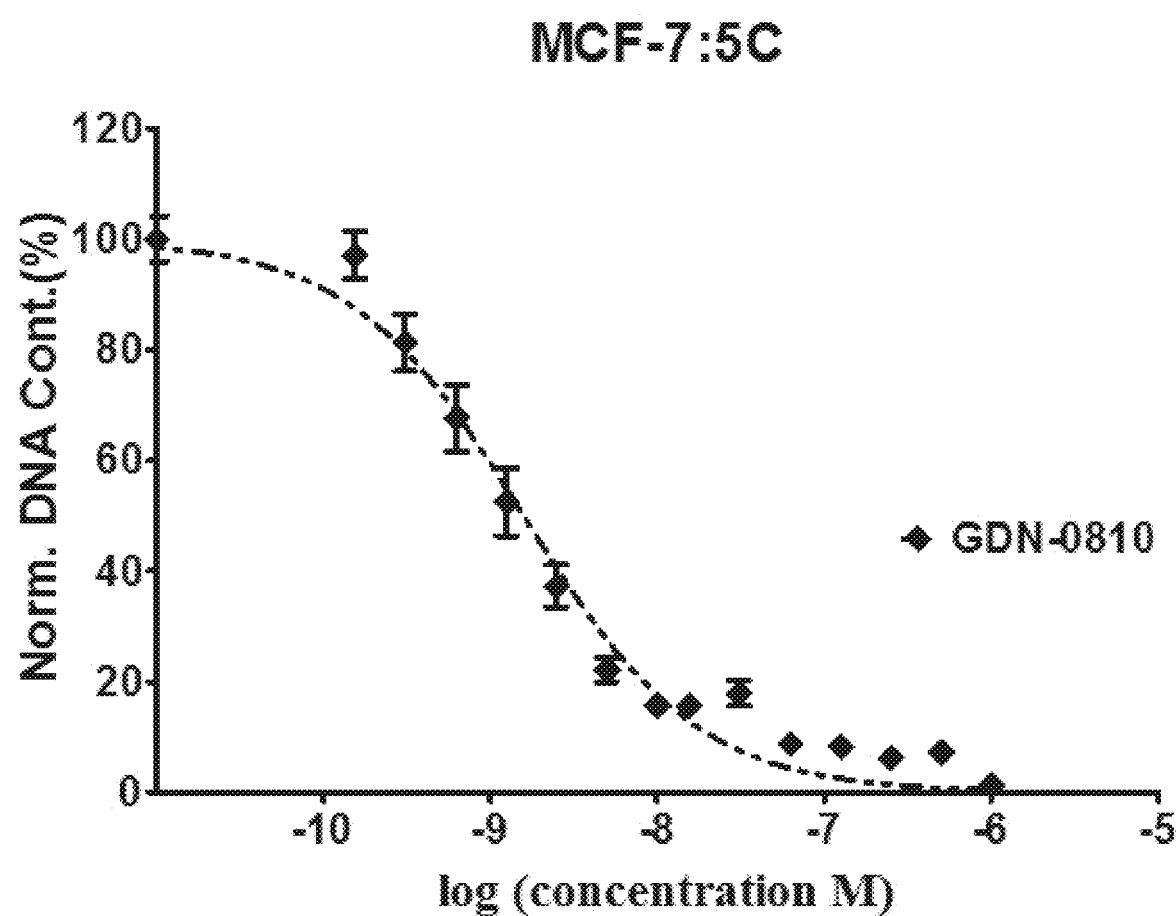
Figure 2A:
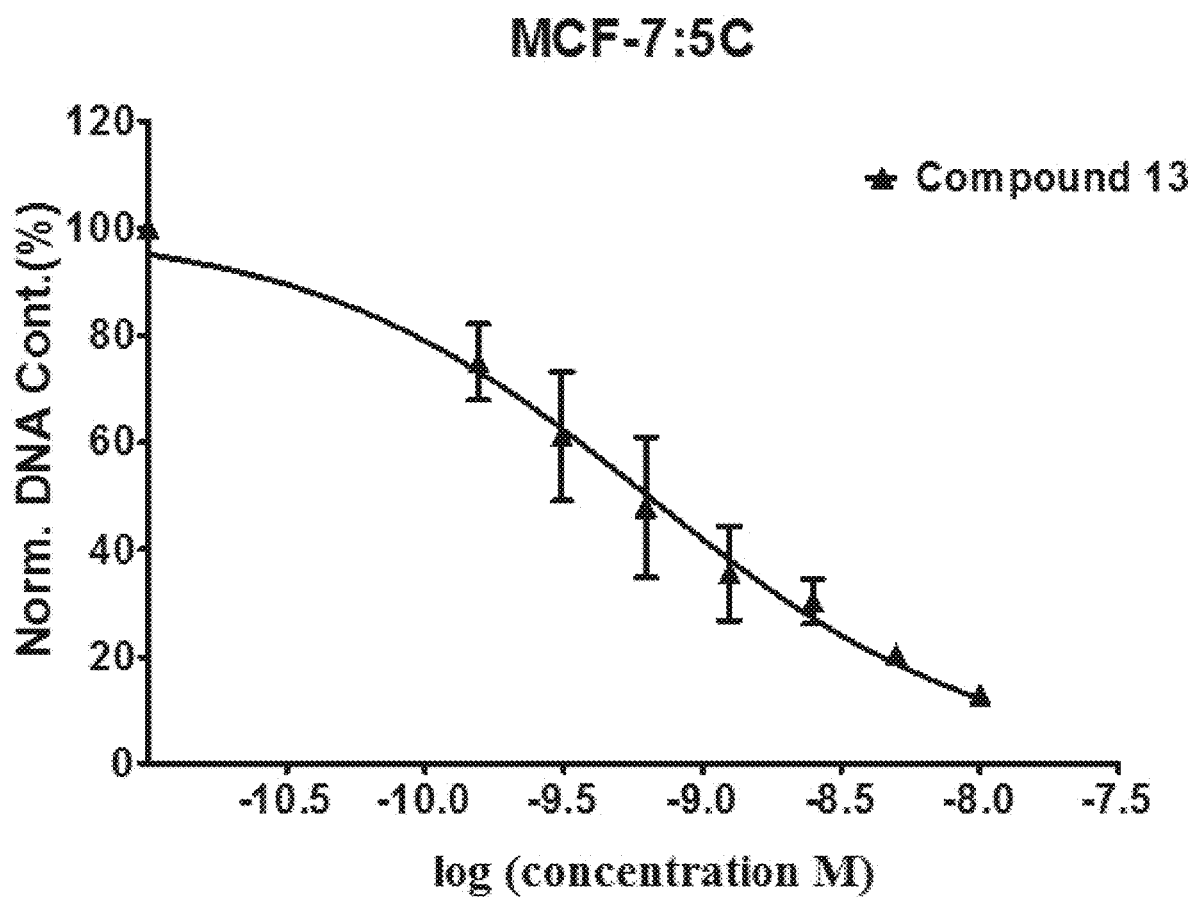
FIG. 2A, FIG. 2B, FIG. 2C, and FIG. 2D are graphs of the efficacy of Compounds 11, 12, and 13 compared to known compound GDN-0810 against tamoxifen-resistant MCF-7:WS8 cells. The y-axis is normalized DNA content in percent and the x-axis is the concentration of compound measured in log(molar) units. The graph shows that representative compounds have sub-nanomolar efficacy in tamoxifen-resistant MCF-7:WS8 cells using DNA content assay.
Figure 2B:
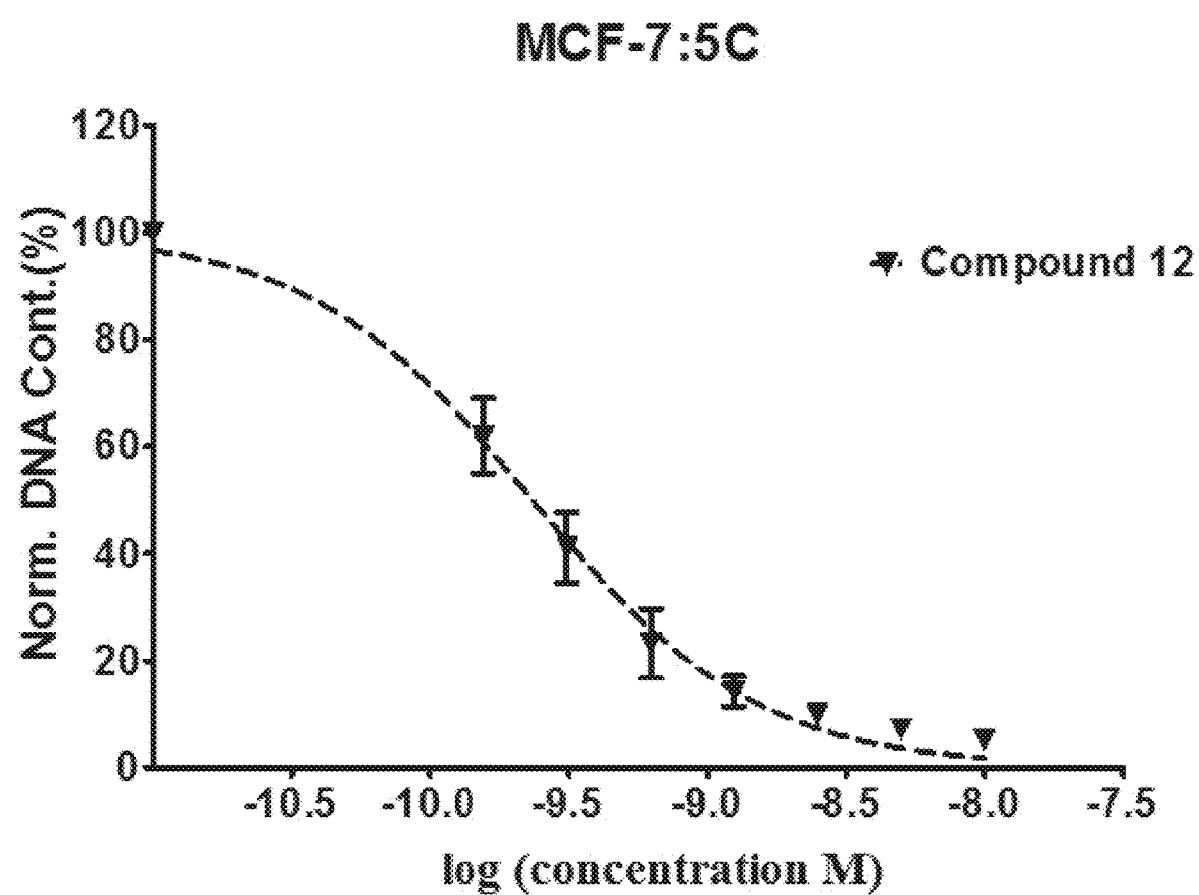
Figure 2C:
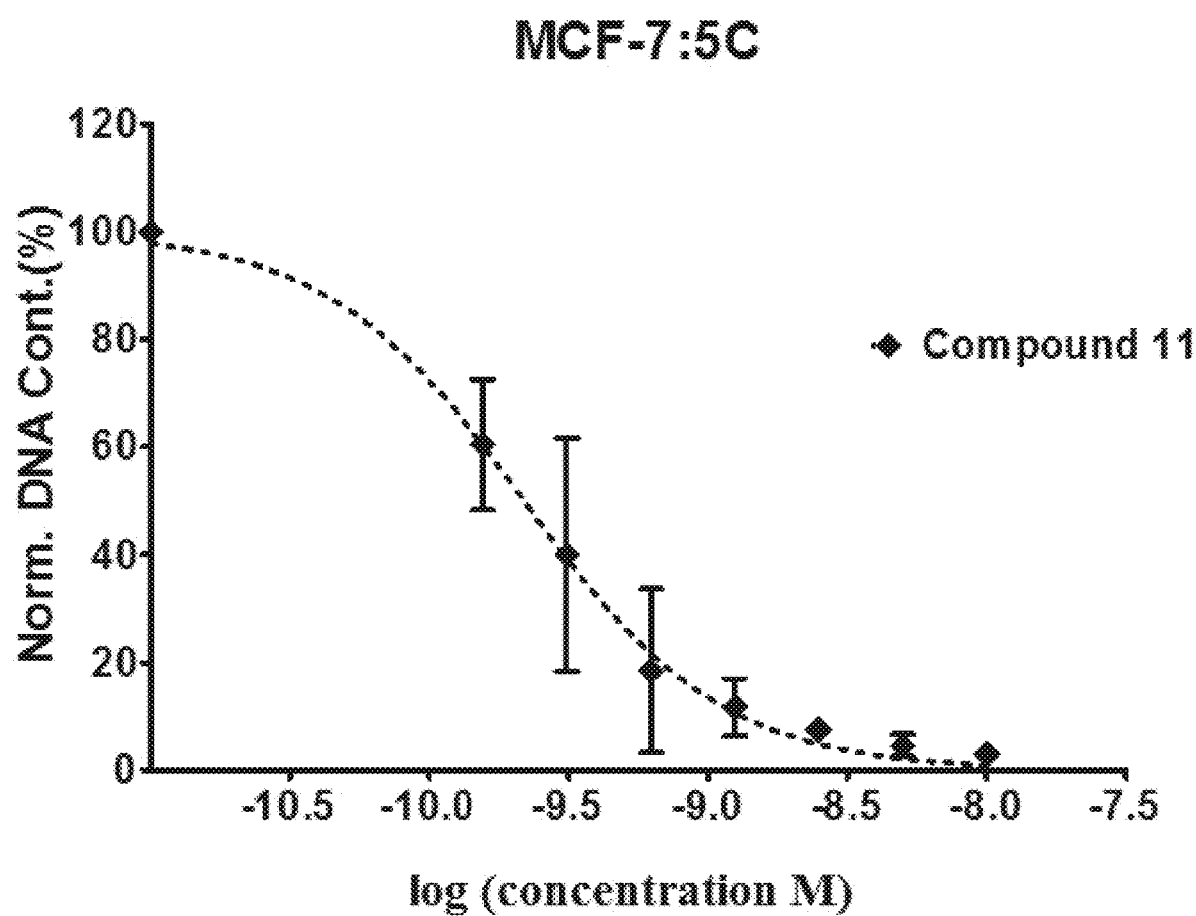
Figure 2D:
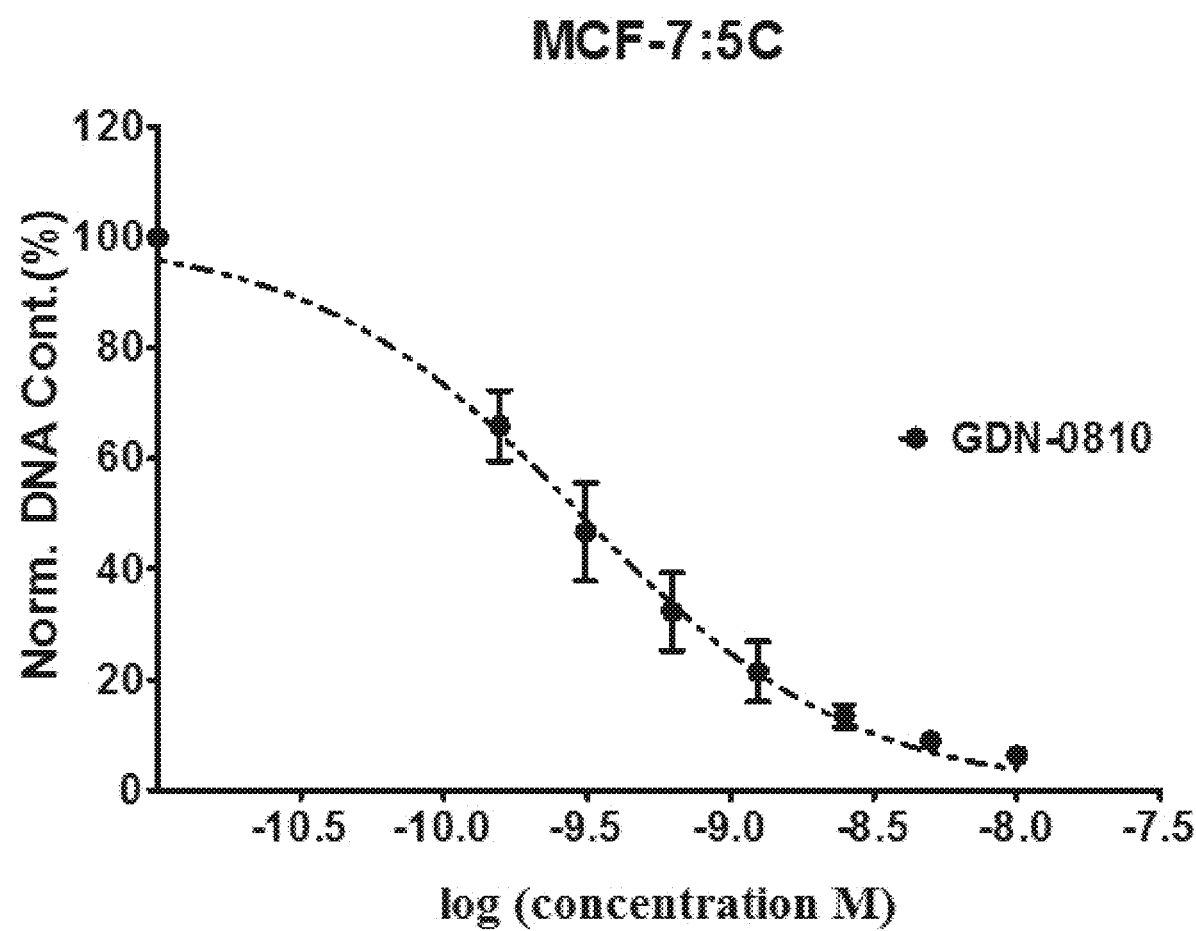
Figure 3:
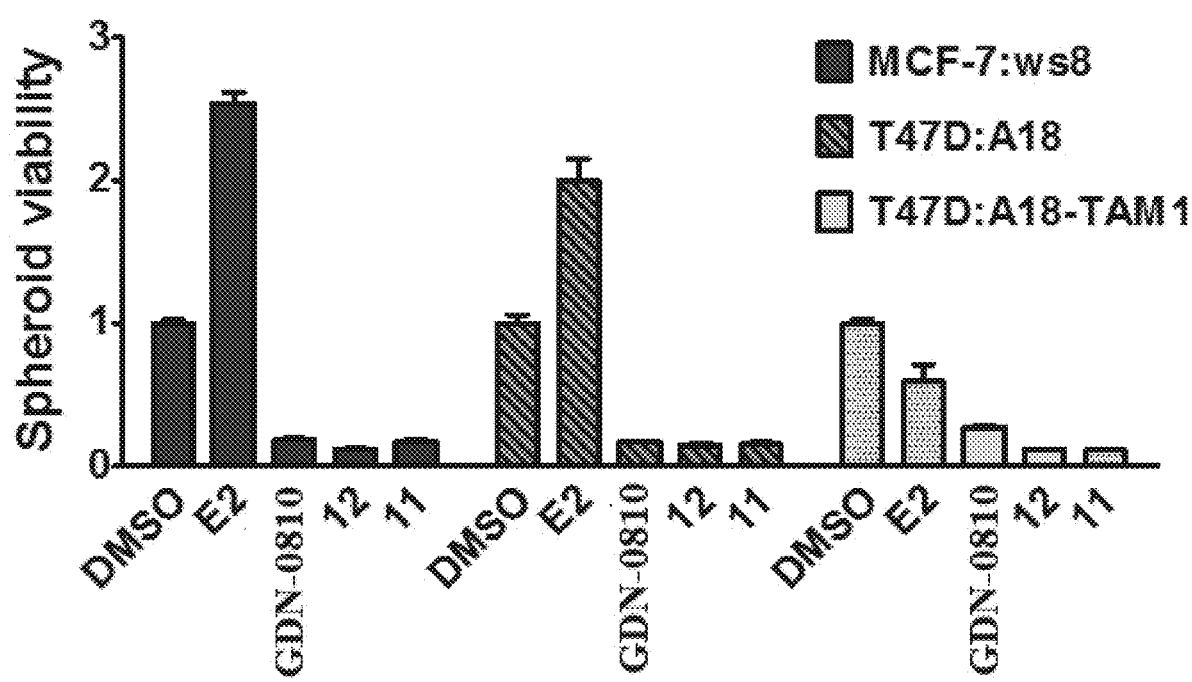
FIG. 3 is a graph of the efficacy of Compounds 11 and 12 compared to known compound GDN-0810 GDN-0810 GDN-0810 GDN-0810 and prostaglandin E2 against MCF-7:ws8, T47D:A18, and T47D:A18-TAM1 tamoxifen resistant spheroid cells. The y-axis is normalized spheroid cell population where 1 is the population exposed to 100 nM DMSO (the control) and the x-axis is compound dosed at 100 nM concentrations. The graph shows that representative compounds of the invention have efficacy at 100 nM in multiple tamoxifen resistant and sensitive 3D cells.
Figure 4:
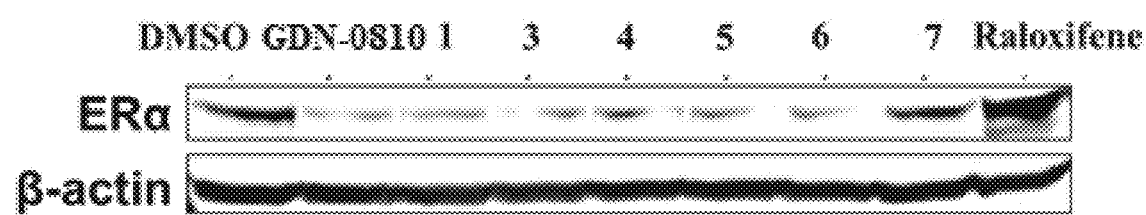
FIG. 4 is a western blot analysis that shows the estrogen receptor downregulation at 10 nM concentrations of Compounds 1, 3, 4, 5, 6, and 7 compared to the known compounds GDN-0810 and Raloxifene. The western blot shows that Compound 1, 3, 4, 5, 6, and 7 all downregulate the estrogen receptor at 10 nM concentrations.
Figure 5A:
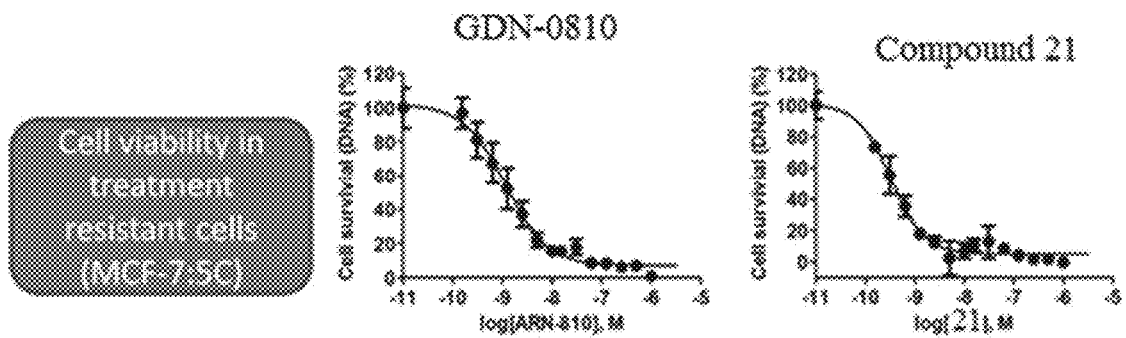
FIG. 5A is a graph demonstrating the cell viability of treatment resistance MCF-7:5C breast cancer cells. The y-axis is cell survival measured in percent and normalized to baseline measurements and the x-axis is concentration of GDN-0810 or Compound 21 measured in log(molar) units. The measurements were taken 4 days after treatment and normalized to 100% vehicle dosing.
Figure 5B:
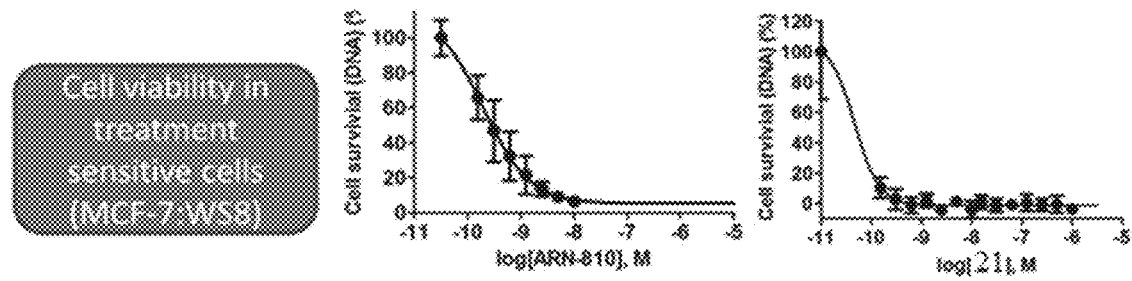
FIG. 5B is a graph demonstrating the cell viability of treatment sensitive MCF-7:WS8 breast cancer cells. The y-axis is cell survival measured in percent and normalized to baseline measurements and the x-axis is concentration of GDN-0810 or Compound 21 measured in log(molar) units. The measurements were taken 4 days after treatment and normalized to 100% vehicle dosing.
Figure 5C:
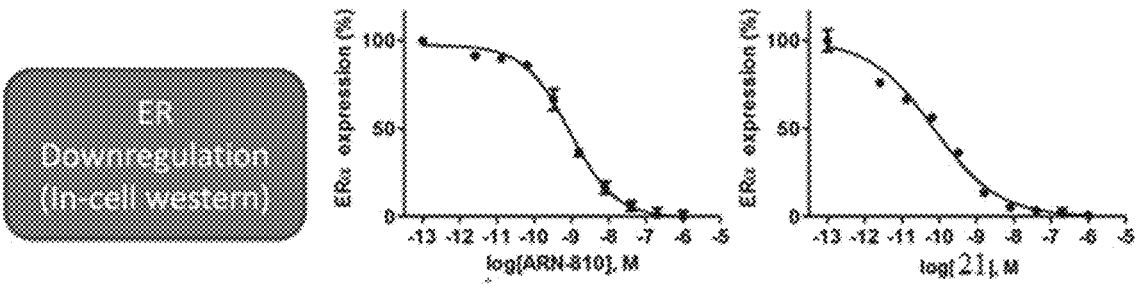
FIG. 5C is a graph demonstrating the level of estrogen receptor downregulation measured in western blot experiments. The y-axis is estrogen receptor expression level measured in percent and normalized to baseline measurements and the x-axis is concentration of GDN-0810 or Compound 21 measured in log(molar) units. Data was normalized to 1 μM GDN-0810 as 0% and DMSO control as 100%.
Figure 5D:
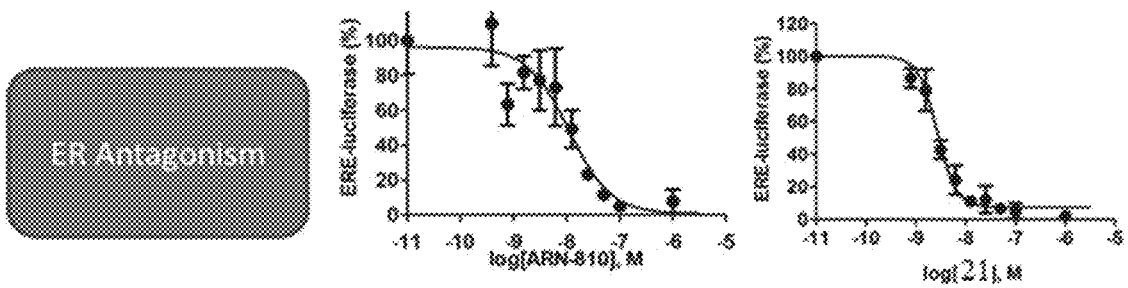
FIG. 5D is a graph demonstrating the level of estrogen receptor antagonism measured in an ERE luciferase assay in MCF-7:WS8 cells. The y-axis is ERE luciferase level measured in percent and normalized to baseline measurements and the-x axis is concentration of GDN-0810 or Compound 21 measured in log(molar) units. Data was normalized to 1 uM GDN-0810 as 0% and 0.1 nM $E_2$ as 100%. Data show mean and s.e.m. from at least 3 cell passages.
Figure 6:
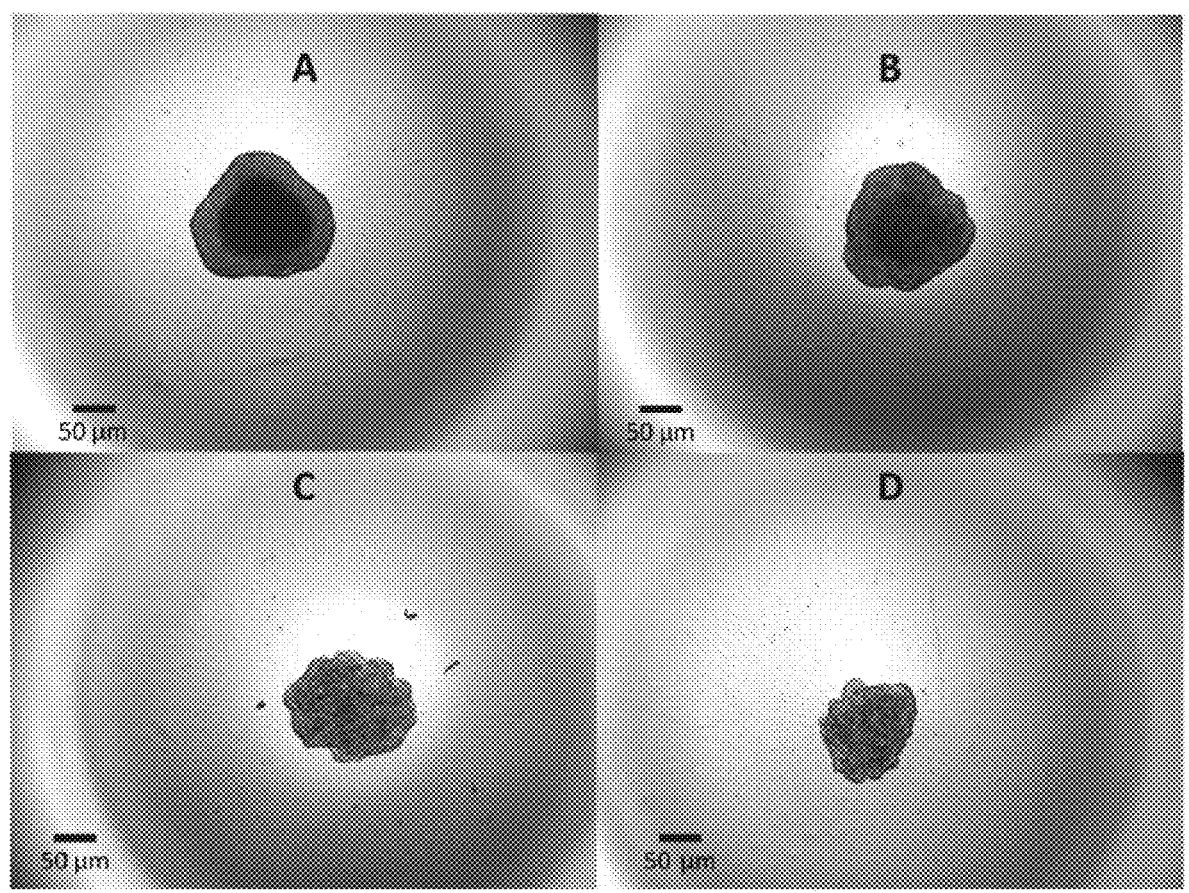
FIG. 6 is cell microscopy images showing that SERDs inhibit growth of MCF-7:TAM1 spheroids after 10 days of treatment. Image A is spheroids in DMSO. Image B is spheroids in the presence of 1 nM concentration of GDN-0810. Image C is spheroids in the presence of 1 nM concentration of Compound 21. Image D is spheroids in the presence of 10 nM concentration of Compound 21.
Figure 7A:
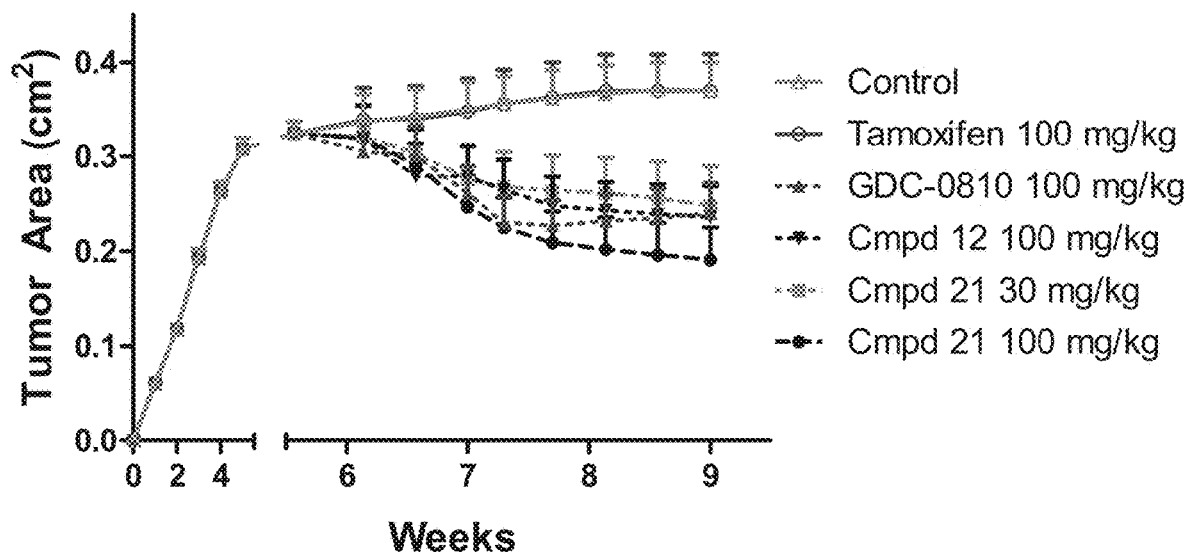
FIG. 7A is a graph of tumor area using MCF7:TAM1 tumors that were grown to an average section area of 0.32 $cm^2$. The y-axis is tumor area measured in $cm^2$ and the x-axis is time measured in weeks. For the study, mice were randomized into six treatment groups: control, tamoxifen (100 mg/kg), GDN-0810 (100 mg/kg), Compound 12 (10 mg/kg), and two doses of Compound 21 (30 mg/kg and 100 mg/kg). Compounds were administrated by oral gavage daily.
Figure 7B:
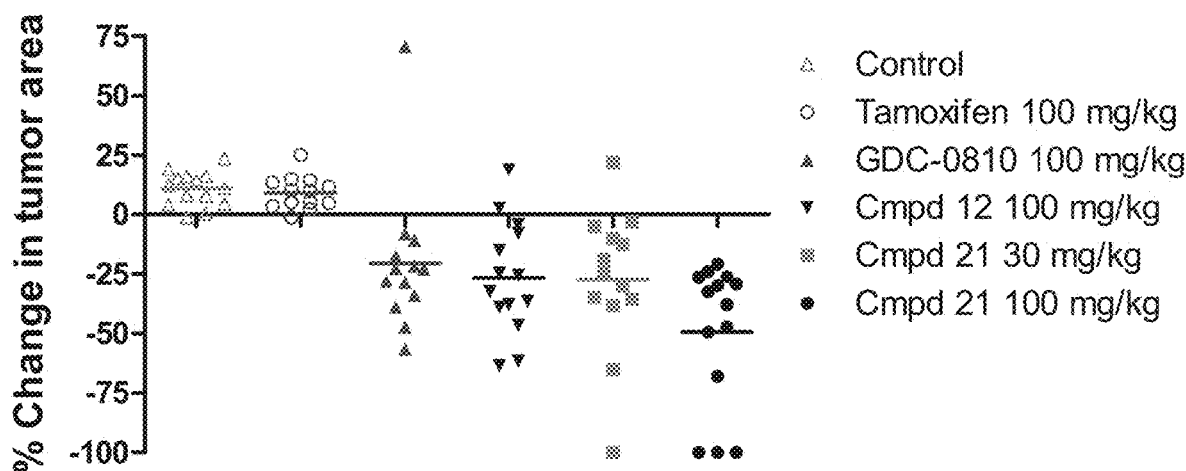
FIG. 7B is a graph of tumor area using MCF7:TAM1 tumors that were grown to an average section area of 0.32 $cm^2$. The y-axis is change in tumor area measured as percent change at day 23 and the x-axis is compound identity. For the study, mice were randomized into six treatment groups: control, tamoxifen (100 mg/kg), GDN-0810 (100 mg/kg), Compound 12 (10 mg/kg), and two doses of Compound 21 (30 mg/kg and 100 mg/kg). Compounds were administrated by oral gavage daily.
Figure 8A:
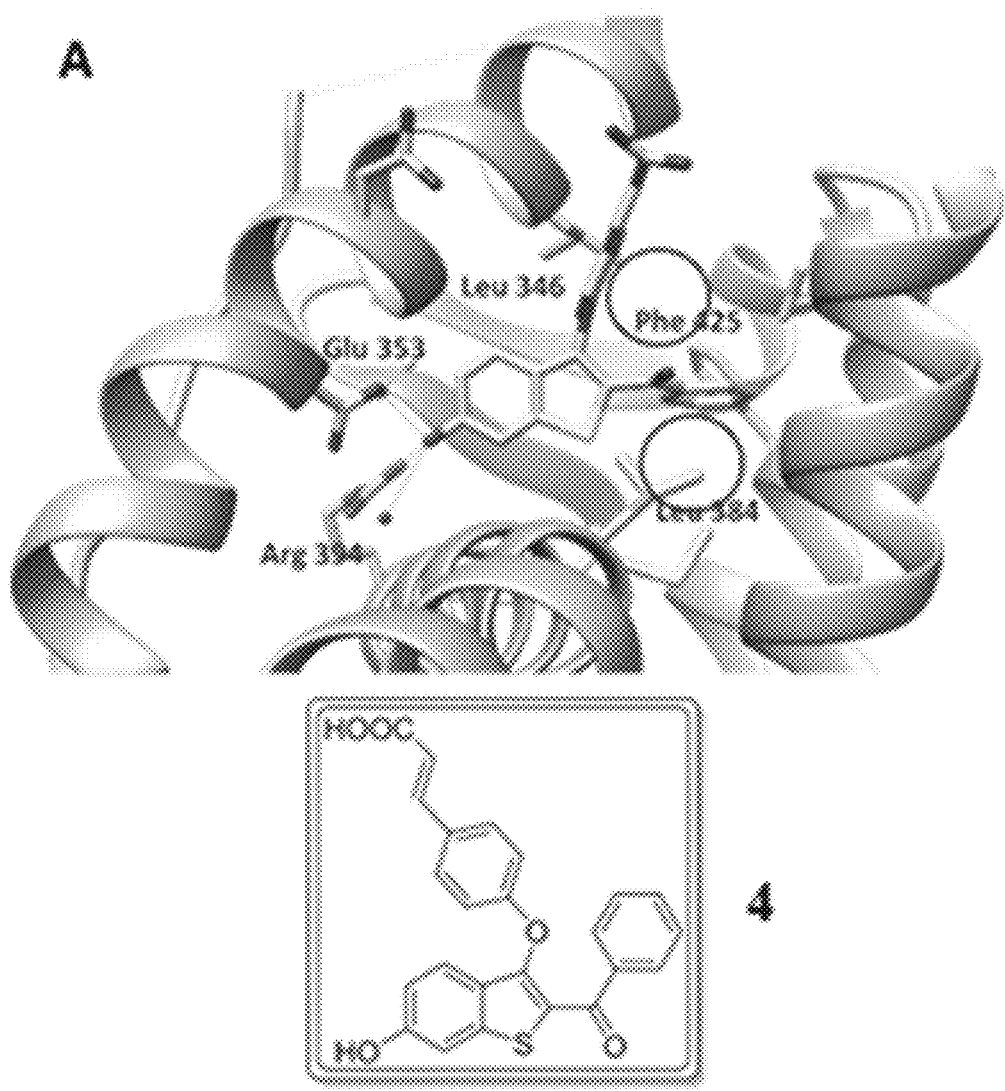
FIG. 8A, FIG. 8B, and FIG. 8C are docketing images of Compounds 4, 5, and 21. Compound 4 (A), 5 (B), and 21 (C) were docked to ER LBD (pdb ID: 5ak2). Compound 4 has minimum contacts with hydrophobic pockets (close to Phe 425 and Leu 384), while compound 5 and 21 have methyl groups that tightly fit into the hydrophobic cavity and correspond to better potency in cell viability assays.
Figure 8B:
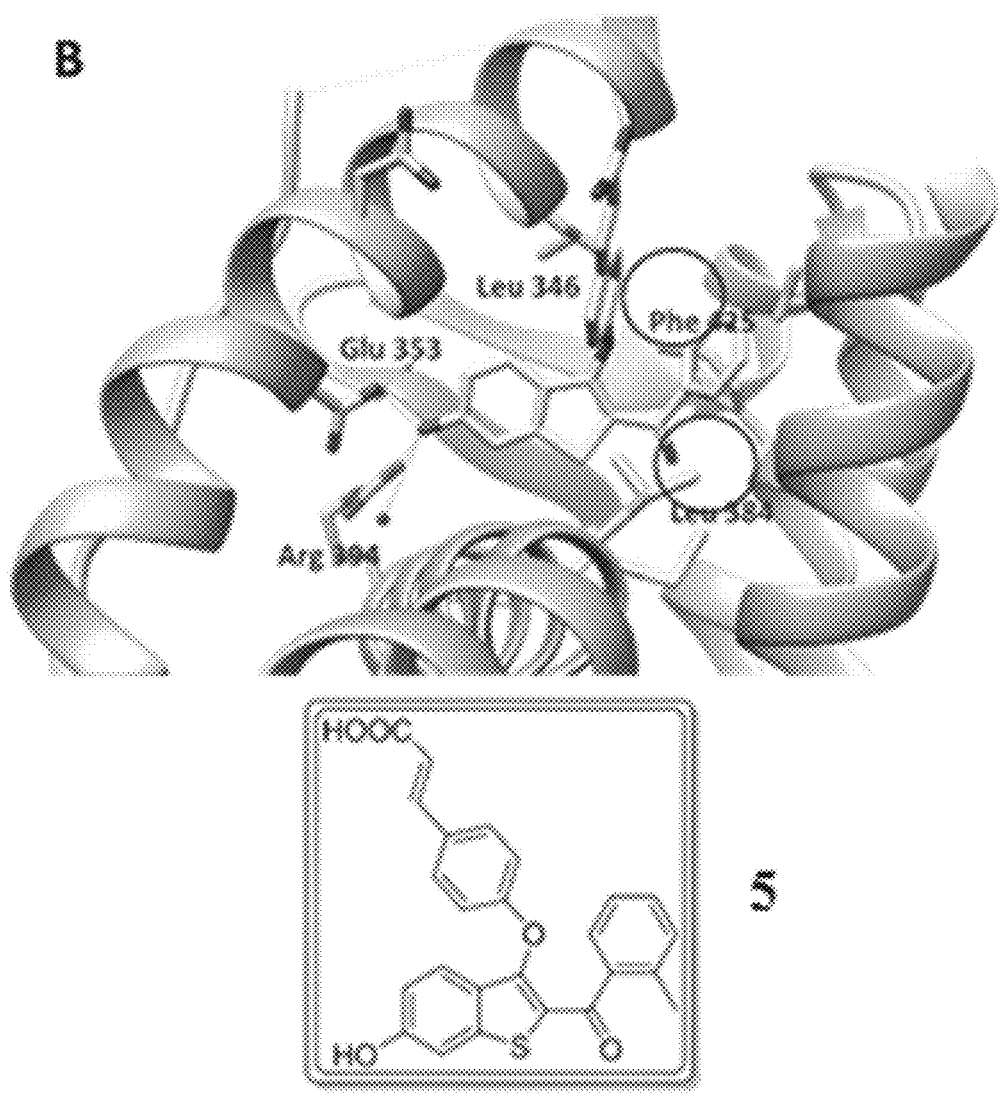
Figure 8C:
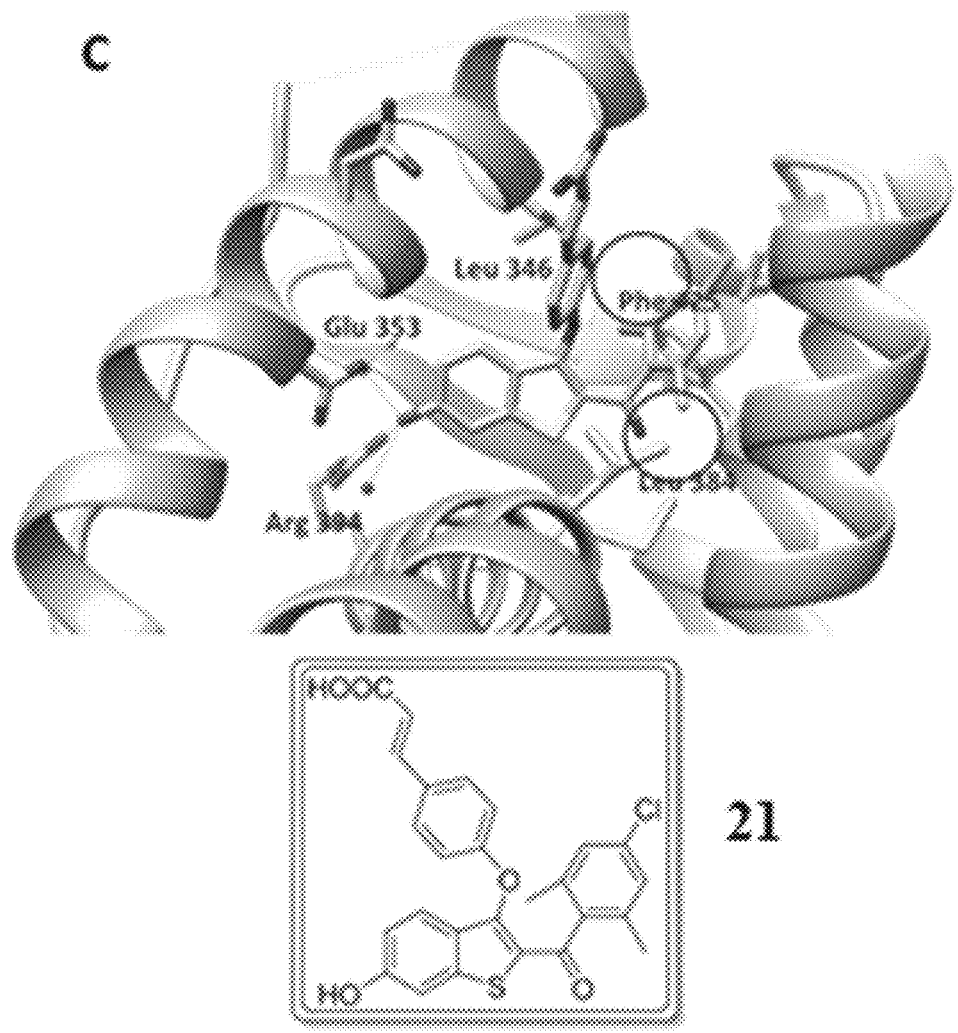
Figure 9:
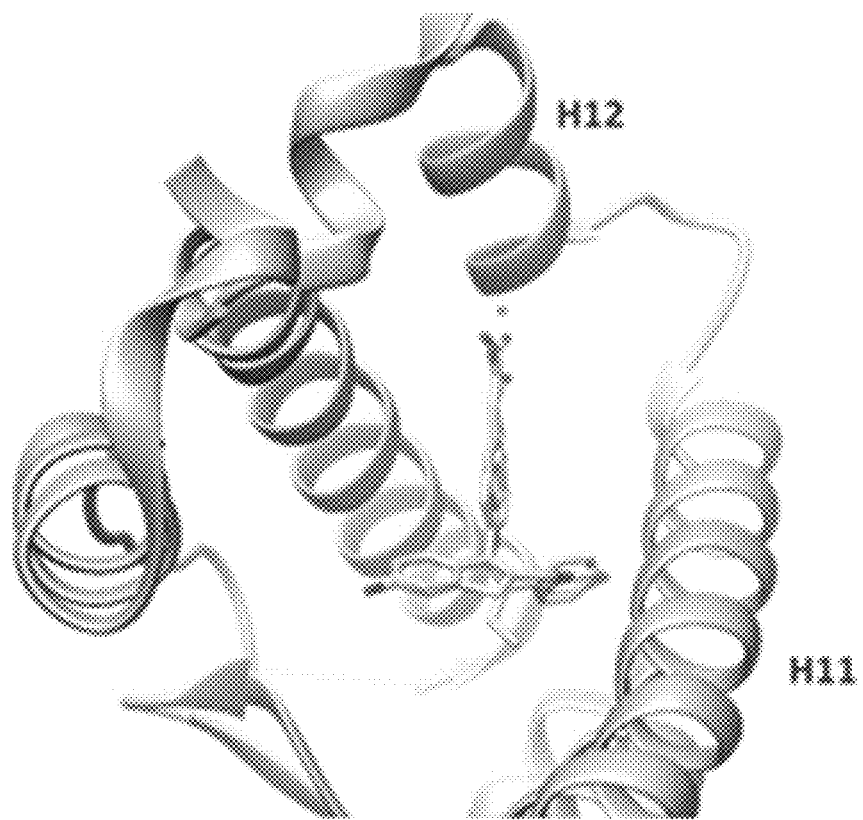
FIG. 9 is the docked pose of Compound 4 docked to ERα LBD (pdb ID: 1R5K), showing similar global topology compared to the GW5638-ER complex. The acrylate side chain interaction with helix 12 is a key structural feature of SERD-ER complexes.
Figure 10:
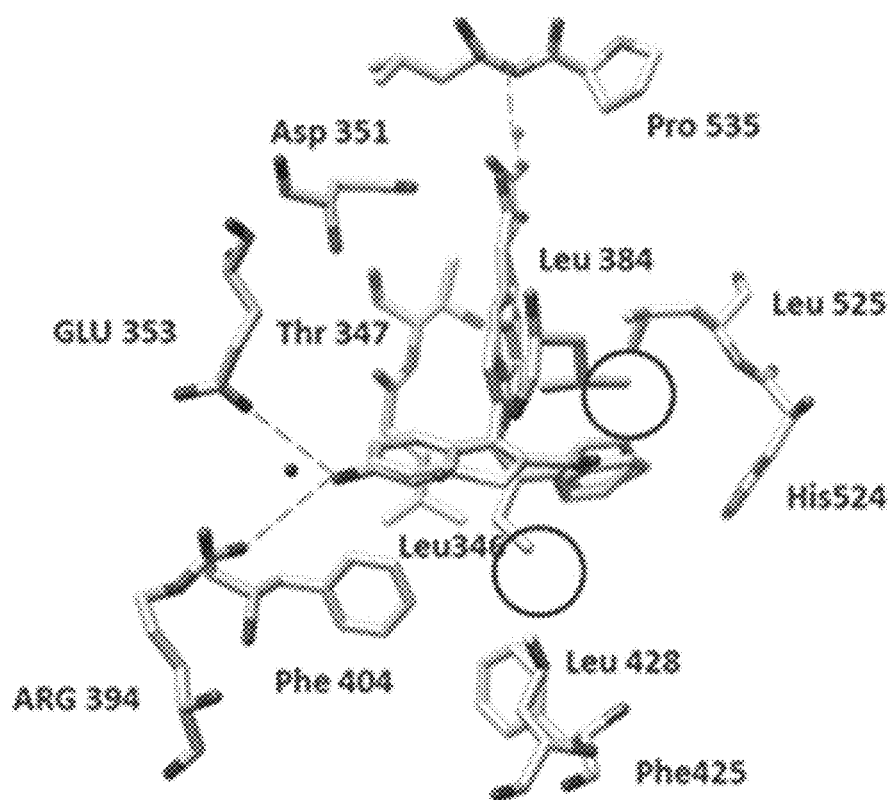
FIG. 10 is the docked pose of Compound 4 docked to ERα LBD (pdb ID: 1R5K). Residues within 5 Å of Compound 12 are highlighted and two hydrophobic cavities in the vicinity of Leu384 and Phe 425 are circled.

The results of the foregoing are shown in FIGS. 1-4 and Table 2.

TABLE 2

IC$_{50}$ of ER downregulation from in-cell western blot experiments

| Compound | IC50 (nM) |
|---|---|
| 1 | 0.7 |
| 3 | 1.2 |
| 4 | 5.0 |
| 5 | 1.1 |
| 6 | 1.1 |
| 7 | 4.6 |

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

A selection of compounds of the current invention were further characterized by their estrogen receptor degradation, estrogen receptor binding efficacy, and inhibition of 3D spheroid growth.

TABLE 3

ERα degradation, antagonism of E₂ signaling, ERα relative binding affinity, and inhibition of growth of ER+ cells cultured in 3D spheroids

| Compounds | R₁ | ERα ICW EC$_{50}$ (nM)[a] | ERE luciferase IC$_{50}$ (nM)[b] | % growth of MCF-7:ws8 3D spheroids (rel. to vehicle)[c] | ERα binding Ki (nM)[d] | RBA % (relative to E$_2$)[e] |
|---|---|---|---|---|---|---|
| GDN-0810 | | 0.8 ± 0.07 | 11.1 ± 0.14 | 15 ± 3.00 | 0.37 ± 0.1 | 53.4 ± 15.0 |
| 5 | 2-Me phenyl | 1.1 ± 0.05 | 16.7 ± 0.07 | 12 ± 0.02 | 1.29 ± 0.4 | 15.5 ± 4.2 |
| 1 | 4-F, 3-Me phenyl | 0.71 ± 0.05 | 8.8 ± 0.11 | 3.3 ± 0.01 | 0.65 ± 0.2 | 30.6 ± 8.7 |
| 12 | 2,3-diMe phenyl | 0.92 ± 0.05 | 4.5 ± 0.07 | 12 ± 0.01 | 0.50 ± 0.1 | 40.3 ± 4.8 |
| 11 | 2,5-diMe phenyl | 0.65 ± 0.06 | 4.2 ± 0.05 | 14 ± 1.00 | 2.0 ± 0.2 | 9.8 ± 0.7 |
| 21 | 4-Cl, 3,5-diMe phenyl | 0.07 ± 0.13 | 2.4 ± 0.10 | 1.3 ± 0.01 | 0.57 ± 0.1 | 34.8 ± 6.2 |
| 20 | 4-F, 3,5-diMe phenyl | 0.24 ± 0.16 | 3.1 ± 0.07 | 2.1 ± 0.01 | 0.73 ± 0.2 | 27.5 ± 7.0 |

[a] Potency for induction of ER degradation measured at 10 concentrations using in-cell westerns (ICW).
[b] Potency of antagonism of ERE-luciferase reporter.
[c] Spheroid growth inhibition after SERD treatment (100 nM) expressed as % of growth of DMSO vehicle control. Data show mean and s.e.m.
[d] Binding affinities calculated by the formula: Ki = (Kd[estradiol]/RBA) * 100, where the Kd for estradiol is 0.2 nM.
[e] Relative binding affinity (RBA) values, determined by radioligand displacement assays expressed as IC$_{50}$ estradiol/IC$_{50}$ compound × 100 (RBA, estradiol = 100%).

Mouse PK and Animal Data

The plasma concentrations of Compounds 1, 5, 11, 12, 20, and 21, at 0.5 hours and 4 hours (100 mg/kg in a 0.5% CMC suspension p.o.) were measured to select a BT-SERD for study in an ectopic xenograft mouse model of endocrine-resistant ER+ breast cancer (Table 4). The oral bioavailability of Compounds 20 and 21 were further studied by measuring plasma concentrations at multiple time points. The MCF-7:TAM1 xenograft model was allowed to proceed for 5.5 weeks prior to treatment and was randomized to six treatment groups with an average tumor area of 0.325 cm². Tamoxifen (100 mg/kg) was entirely without effect, demonstrating the anticipated resistance of this tumorigenic TR breast cancer cell line to tamoxifen. GDN-0810 at a dose of 100 mg/kg, used previously in the literature, caused regression of tumor size by 21% at day 23 after treatment. Compound 12 (100 mg/kg) also caused tumor regression similar to GDN-0810 (26.7% in tumor area reduction at day 20), whereas Compound 21 showed the best efficacy in tumor regression (49% reduction) at a dose of 100 mg/kg.

Regression was dose-dependent for Compound 21: at 30 mg/kg average tumor area was reduced 27%. Injection of tumorigenic cells into mammary fat pads of nude mice produces distinct mammary tumors allowing assessment of individual tumor response, again demonstrating the efficacy of SERD Compound 21. No weight loss was observed during the course of the animal study.

TABLE 4

Plasma concentration of benzothiophene analogs after oral administration

| Compound/Time | 1 (nM) | 11 (nM) | 12 (nM) | 5 (nM) | 21 (nM) | 20 (nM) |
|---|---|---|---|---|---|---|
| 0.5 h | 1238 | 1006 | 3874 | 5575 | 10183 | 9723 |
| 4 h | 145 | 0.5 | 432 | 47 | 858 | 164 |

[a]All compounds administered by oral gavage at 100 mg/kg in PEG400/PVP/TW80/CMC in water, 9:0.5:0.5:90. Data was the average plasma concentration of three mice at 0.5 h and 4 h.

Animal Experiments

MCF-7:Tam1 tumors were grown in 4-6 week old ovariectomized athymic nude mice (Harlan Laboratories) and E2 was administered via silastic capsules (1.0 cm) implanted subcutaneously between the scapulae as previously described. The compound was administered at a dose of 100 mg/kg or 30 mg/kg daily for 3.5 weeks in a formulation of 0.5% CMC:PEG-400:Tween-80:PVP (90:9:05:0.5) solution. Tumor cross-sectional area was determined weekly using Vernier calipers and calculated using the formula (length/2)×(width/2)×π. Mean tumor area was plotted against time (in weeks) to monitor tumor growth.

Cell Lines and Culture Conditions

MCF-7:WS8 is hormone-dependent human breast cancer cell clones maintained in phenol red containing RPMI-1640 medium supplemented with 10% FBS at 37° C., 5% $CO_2$ that have been previously described. MCF-7:5C cells were maintained in phenol-red free RPMI 1640 medium supplemented with 10% charcoal-dextran treated fetal bovine serum at 37° C., 5% $CO_2$ as previously described. The MCF-7:5C cells served as AI resistant cells and were generated from MCF-7:WS8 cells by long-term estrogen deprivation.

Cell Growth Assay

Cells were grown in phenol red-free media for 2 days prior to each experiment. On the day of the experiment, cells were seeded in 96-well plate at a density of 5000 cells/well and treated with either 0.1% (v/v) DMSO, 1 nM $E_2$, or compounds prepared in phenol red free media. All compounds were dissolved in DMSO and added to the medium at a final 1:1000 dilution. DNA content was determined on Day 5 (WS8) or Day 6 (5C) by Hoechst 33258 dye. Fluorescence signals were read by the Synergy H4 (BioTek).

In-Cell Western Analysis

MCF-7:WS8 cells were kept in stripped medium 2 days, and 2.0×104/well of the cells were plated in clear bottom 96-well black plates for 48 hours prior to addition of compounds for 24 hours. Fixation, detection of ESR1 (sc-8002) and analysis were performed per LI-COR manufacturer's protocol using the In-Cell Western™ Assay Kits and LI-COR ODYSSEY infra-red imaging system. Data was normalized to CellTag 700 stain.

3D-Spheroid Growth Assay

Spheroids were plated at 1000 cells/well in Corning® 96-well black clear round-bottom, ultra-low attachment spheroid microplates and grown in the absence of treatment for 24 hours. Spheroids were then treated with 2X treatment media following the removal of 100 μL media from each well. Treatment was repeated every 2-3 days for 14 days. CellTiter-Glo® 3D Cell Viability Assay protocol was used to determine growth inhibition of the spheroids. On day 15, spheroid plates and reagent (CellTiter-Glo® 3D Reagent) were allowed to come to room temperature for 30 minutes. During this time, the spheroids were washed with PBS by removing 100 μL media and replacing with PBS. 100 μL from each well was then removed and replaced with 100 μL of the reagent and spheroids were disrupted by pipetting. The plates were then placed on a shaker for 5 minutes before equilibrating in dark for 25 minutes. 125 μL from each well was then transferred to a white 96-well plate before recording luminescence using an empty well for the background reading.

Binding Affinity Studies

Binding affinities were also determined by a competitive radiometric binding assay using 2 nM [$^3$H]estradiol as tracer (PerkinElmer, Waltham, Mass.) and full-length purified human ERα (Pan Vera/Invitrogen, Carlsbad, Calif.), as reported previously. The RBA values were calculated using the following equation: $IC_{50}$ estradiol/$IC_{50}$ compound×100.

Estrogen Response Elements (ERE) Luciferase Assay in MCF-7 Cells.

MCF-7:WS8 cells were kept in stripped medium 3 days prior to treatment. Cells were plated at a density of 2×10$^4$ cells/well in 96-well plates and were co-transfected with 5 μg of the pERE-luciferase plasmid per plate, which contained three copies of the *Xenopus laevis* vitellogenin A2 ERE upstream of firefly luciferase and 0.5 μg of pRL-TK plasmid (Promega, Madison, Wis.) containing a cDNA encoding *Renilla* luciferase. Transfection was performed for 6 hours using the Lipofectamine 2000 transfection reagent (Invitrogen) in Opti-MEM medium according to the manufacturer's instructions. Cells were treated with test compounds after 6 hours, and the luciferase activity was measured after 18 hours of treatment using the dual luciferase assay system (Promega) with Synergy H4 (Bio Tek).

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A compound, or a pharmaceutically acceptable salt thereof of Formula

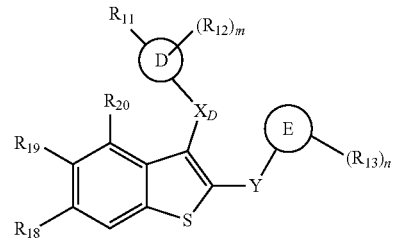

wherein:
m is 0, 1, 2, 3, or 4;
n is 0, 1, 2, 3, or 4;
$X_D$ is selected from —O—, —$CH_2$—, —S—, —$NR_{17}$—, —CHF—, —$CF_2$—, and cycloalkyl;

Y is selected from —C(O)—, —O—, —CF$_2$—, or C$_3$cycloalkyl, —CH$_2$—, —S—, —NH—, and —NMe;

Ring D is phenyl, naphthyl, quinolinyl, 5- or 6-membered monocyclic heteroaryl, cycloalkyl, or 7-, 8-, 9- or 10 membered bicyclic heterocyclyl;

Ring E is phenyl, heteroaryl, 5- or 6-membered monocyclic heteroaryl, cycloalkyl or 7-, 8-, 9- or 10-membered bicyclic heterocyclyl;

$R_{19}$ is selected from $R_{14}$;

$R_{18}$ is hydroxyl;

$R_{20}$ is hydrogen;

$R_{11}$ is selected from —CH=CHCOOR$_{17}$, —NR$_{17}$(CO)COOR$_{17}$, —COOR$_{17}$, cycloalkyl-COOR$_{17}$, —C$_2$-C$_6$alkenylene-COOR$_{17}$, —C$_2$-C$_6$alkynylene-COOR$_{17}$, —CH=CHC(O)R$_{16}$, —NR$_{17}$(CO)C(O)R$_{16}$, —C(O)R$_{16}$, -cycloalkyl-C(O)R$_{16}$, —C$_2$-C$_6$alkenylene-C(O)R$_{16}$ and —C$_2$-C$_6$alkynylene-C(O)R$_{16}$;

$R_{12}$, $R_{13}$, and $R_{14}$ are independently selected at each occurrence from —OR$_{15}$, —SR$_{15}$, —N(R$_{15}$)$_2$, aryl, heteroaryl, halogen, —CN, —NO$_2$, haloalkyl, cycloalkyl, thiol, C$_1$-C$_6$alkyl, —O(C$_1$-C$_6$fluoroalkyl), —C(O)R$_{16}$, —C(S)R$_{16}$, —OSO$_2$R$_{16}$, —NHSO$_2$R$_{16}$, —N(alkyl)SO$_2$R$_{16}$, —OP(O)(R$_{16}$)$_2$, —P(O)(R$_{16}$)$_3$, —P(O)R$_{16}$, —S$_2$R$_{16}$, alkyne, alkene, arylalkyl, aryloxy, heteroarylalkyl, and C$_1$-C$_6$fluoroalkyl;

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, and —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

2. The compound of claim 1, wherein X$_D$ is —O—.

3. The compound of claim 1, wherein X$_D$ is —S—.

4. The compound of claim 1, wherein R$_{11}$ is selected from COOH, —NH(CO)COOH and —CH=CHCOOH.

5. The compound of claim 4, wherein Ring D is phenyl, naphthyl or quinolinyl and Ring E is phenyl or thienyl.

6. The compound of claim 1, wherein R$_{12}$ is independently selected at each occurrence from halogen and C$_1$-C$_6$alkyl, wherein C$_1$-C$_6$alkyl is methyl.

7. The compound of claim 1, wherein R$_{12}$ is independently selected at each occurrence from halogen.

8. A compound, or a pharmaceutically acceptable salt thereof of Formula

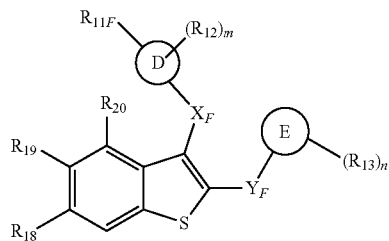

wherein:
m is 0, 1, 2, 3, or 4;
n is 0, 1, 2, 3, or 4;
$R_{19}$ is selected from $R_{14}$;

$R_{18}$ is hydroxyl;

$R_{20}$ is hydrogen;

$X_F$ is selected from —O—, —C(O), —CH$_2$—, —S—, —NR$_{17}$—, —CHF—, —CF$_2$—, and cycloalkyl;

$Y_F$ is selected from —C(O)—, —O, —S, —NR$_{17}$—, CF$_2$—, cycloalkyl, —CH$_2$—, and —CHF—;

Ring D is phenyl, naphthyl, quinolinyl, 5- or 6-membered monocyclic heteroaryl, cycloalkyl, or 7-, 8-, 9- or 10 membered bicyclic heterocyclyl;

Ring E is phenyl, heteroaryl, 5- or 6-membered monocyclic heteroaryl, cycloalkyl or 7-, 8-, 9- or 10-membered bicyclic heterocyclyl;

$R_{11F}$ is selected from —CH=CHCOOR$_{17}$, —NR$_{17}$(CO)COOR$_{17}$, cycloalkyl-COOR$_{17}$, —C$_2$-C$_6$alkenylene-COOR$_{17}$, —C$_2$-C$_6$alkynylene-COOR$_{17}$, —CH=CHC(O)R$_{16}$, —NR$_{17}$(CO)C(O)R$_{16}$, -cycloalkyl-C(O)R$_{16}$,—C$_2$-C$_6$alkenylene-C(O)R$_{16}$ and —C$_2$-C$_6$alkynylene-C(O)R$_{16}$;

$R_{12}$, $R_{13}$, and $R_{14}$ are independently selected at each occurrence from —OR$_{15}$, —SR$_{15}$, —N(R$_{15}$)$_2$, aryl, heteroaryl, halogen, —CN, —NO$_2$, haloalkyl, cycloalkyl, thiol, C$_1$-C$_6$alkyl, —O(C$_1$-C$_6$fluoroalkyl), —C(O)R$_{16}$, —C(S)R$_{16}$, —OSO$_2$R$_{16}$, —NHSO$_2$R$_{16}$, —N(alkyl)SO$_2$R$_{16}$, —OP(O)(R$_{16}$)$_2$, —P(O)(R$_{16}$)$_3$, —P(O)R$_{16}$, —SO$_2$R$_{16}$, alkyne, alkene, arylalkyl, aryloxy, heteroarylalkyl, and C$_1$-C$_6$fluoroalkyl;

$R_{15}$ is independently selected at each occurrence from hydrogen, alkyl, alkenyl, alkynyl, cycloalkyl, aryl, arylalkyl, heteroaryl, and heteroarylalkyl;

$R_{16}$ is independently selected at each occurrence from —N(R$_{15}$)$_2$, —SR$_{15}$, and —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

9. A pharmaceutical composition comprising a compound according to claim 1 and a pharmaceutically acceptable carrier or excipient.

10. A method of treating an estrogen-related disorder in a subject comprising administering to a subject in need thereof a therapeutically effective amount of a compound or pharmaceutical composition according to claim 1 or a pharmaceutically acceptable salt thereof.

11. The method of claim 10, wherein the estrogen-related disorder is a cancer.

12. The method of claim 11, wherein the cancer is selected from the group consisting of breast cancer, ovarian cancer, endometrial cancer, prostate cancer, and lung cancer.

13. The method of claim 11, wherein the cancer is selected from the group consisting of breast cancer, ovarian cancer, and endometrial cancer.

14. The method of claim 11, wherein the cancer is breast cancer.

15. The method of claim 14, wherein the breast cancer is hormone receptor positive metastatic breast cancer.

16. The method of claim 14, wherein the breast cancer is a tamoxifen resistant breast cancer.

17. The method of claim 14, wherein the breast cancer is a triple negative breast cancer.

18. The method of claim 10, wherein the estrogen-related disorder is bone loss.

19. The method of claim 18, wherein the bone loss is caused by osteoporosis.

20. The method of claim 10, wherein the estrogen-related disorder is a tumor.

* * * * *